United States Patent
Nabel et al.

(10) Patent No.: US 12,121,562 B2
(45) Date of Patent: *Oct. 22, 2024

(54) ANTIGENIC EPSTEIN BARR VIRUS POLYPEPTIDES

(71) Applicant: SANOFI, Paris (FR)

(72) Inventors: Gary J. Nabel, Bridgewater, NJ (US); Chih-Jen Wei, Bridgewater, NJ (US); Laura Nguyen, Bridgewater, NJ (US); Kurt Swanson, Bridgewater, NJ (US); Te-Hui Chou, Bridgewater, NJ (US)

(73) Assignee: Sanofi, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/067,940

(22) Filed: Dec. 19, 2022

(65) Prior Publication Data

US 2023/0277619 A1    Sep. 7, 2023

Related U.S. Application Data

(63) Continuation of application No. 17/061,146, filed on Oct. 1, 2020, now Pat. No. 11,617,780, and a continuation of application No. PCT/US2019/025419, filed on Apr. 2, 2019.

(60) Provisional application No. 62/652,201, filed on Apr. 3, 2018.

(51) Int. Cl.
*A61K 39/245* (2006.01)
*A61K 38/16* (2006.01)
*A61K 39/12* (2006.01)
*A61K 47/00* (2006.01)
*C07K 14/05* (2006.01)

(52) U.S. Cl.
CPC ............ *A61K 38/162* (2013.01); *A61K 47/00* (2013.01); *C07K 14/05* (2013.01); *C07K 2319/00* (2013.01)

(58) Field of Classification Search
None
See application file for complete search history.

(56) References Cited

U.S. PATENT DOCUMENTS

| | | |
|---|---|---|
| 6,194,388 B1 | 2/2001 | Krieg et al. |
| 6,207,646 B1 | 3/2001 | Krieg et al. |
| 6,214,806 B1 | 4/2001 | Krieg et al. |
| 6,218,371 B1 | 4/2001 | Krieg et al. |
| 6,239,116 B1 | 5/2001 | Krieg et al. |
| 6,339,068 B1 | 1/2002 | Krieg et al. |
| 6,406,705 B1 | 6/2002 | Davis et al. |
| 6,429,199 B1 | 8/2002 | Krieg et al. |
| 7,951,770 B2 | 5/2011 | Kirschner et al. |
| 8,562,996 B2 | 10/2013 | Spits et al. |
| 9,703,095 B2 | 7/2017 | Pakhchyan |
| 9,962,436 B2 | 5/2018 | Mond et al. |
| 10,961,283 B2 | 3/2021 | Kwong et al. |
| 2009/0074719 A1 | 3/2009 | Kirschner et al. |
| 2012/0267258 A1 | 10/2012 | Uraoka et al. |
| 2014/0072958 A1 | 3/2014 | Nabel et al. |
| 2014/0348865 A1 | 11/2014 | Kwong et al. |
| 2016/0303224 A1 | 10/2016 | Kanekiyo et al. |
| 2020/0276295 A1 | 9/2020 | Ogembo et al. |
| 2020/0282047 A1* | 9/2020 | Ciaramella .......... A61K 9/0019 |
| 2021/0038711 A1 | 2/2021 | Weiner et al. |

FOREIGN PATENT DOCUMENTS

| | | |
|---|---|---|
| CA | 2485363 C | 10/2014 |
| EP | 2515112 B1 | 8/2015 |
| JP | 2011506565 A | 3/2011 |
| JP | 2012225885 A | 11/2012 |
| JP | 2013529078 A | 7/2013 |
| JP | 2014513678 A | 6/2014 |
| JP | 2015530369 A | 10/2015 |
| JP | 2020520674 A | 7/2020 |
| JP | 2021504445 A | 2/2021 |
| WO | 2002016421 A2 | 2/2002 |
| WO | 2007097820 A2 | 8/2007 |
| WO | 2009080719 A1 | 7/2009 |
| WO | 2009126816 A1 | 10/2009 |
| WO | 2011143623 A1 | 11/2011 |
| WO | 2012006180 A1 | 1/2012 |
| WO | 2012025603 A1 | 3/2012 |
| WO | 2012139069 A2 | 10/2012 |
| WO | 2013039792 A1 | 3/2013 |
| WO | 2013044203 A2 | 3/2013 |
| WO | 2014018858 A2 | 1/2014 |
| WO | 2014160463 A1 | 10/2014 |
| WO | 2015054639 A1 | 4/2015 |
| WO | 2015089340 A1 | 6/2015 |
| WO | 2015169271 A1 | 11/2015 |
| WO | 2015183969 A1 | 12/2015 |
| WO | 2016109792 A2 | 7/2016 |

(Continued)

OTHER PUBLICATIONS

Alvarez-Cienfuegos et al., "Intramolecular trimerization, a novel strategy for making multispecific antibodies with controlled orientation of the antigen binding domains", Scientific Reports 2016; 6:28643 (Jun. 2016).

Aslam et al., "The accuracy of protein structure alignment servers", Electronic Journal of Biotechnology, 20, pp. 9-13 (2016).

Balfour Jr., Henry, "Progress, prospects, and problems in Epstein-Barr virus vaccine development", Current Opinion in Virology, 6, pp. 1-5 (2014).

(Continued)

*Primary Examiner* — Nianxiang Zou
(74) *Attorney, Agent, or Firm* — McNeill PLLC

(57) ABSTRACT

This disclosure relates to antigenic EBV polypeptides and their use in eliciting antibodies against EBV. Also disclosed are antigenic polypeptides comprising an EBV polypeptide and a ferritin protein.

35 Claims, 58 Drawing Sheets

Specification includes a Sequence Listing.

(56) References Cited

FOREIGN PATENT DOCUMENTS

| | | | |
|---|---|---|---|
| WO | 2016116904 | A1 | 7/2016 |
| WO | 2016138160 | A1 | 9/2016 |
| WO | 2017096374 | A1 | 6/2017 |
| WO | 2017172890 | A1 | 10/2017 |
| WO | 2017211886 | A1 | 12/2017 |
| WO | 2017218819 | A1 | 12/2017 |
| WO | 2018005558 | A1 | 1/2018 |
| WO | 2018140733 | A1 | 8/2018 |
| WO | 2018193063 | A2 | 10/2018 |
| WO | 2019014569 | A1 | 1/2019 |
| WO | 2019055887 | A1 | 3/2019 |
| WO | 2019103993 | A1 | 5/2019 |
| WO | 2019161163 | A1 | 8/2019 |
| WO | 2019195276 | A1 | 10/2019 |
| WO | 2019195284 | A1 | 10/2019 |
| WO | 2019195291 | A1 | 10/2019 |
| WO | 2019195314 | A2 | 10/2019 |
| WO | 2019195316 | A1 | 10/2019 |
| WO | 2022074358 | A1 | 4/2022 |
| WO | 2023288090 | A1 | 1/2023 |

OTHER PUBLICATIONS

Bordoli et al., "Protein structure homology modeling using Swiss-Model workspace", Nature Protocols, 4(1), pp. 1-13 (2009).

Bu et al., "Immunization with Components of the Viral Fusion Apparatus Elicits Antibodies That Neutralize Epstein-Barr Virus in B Cells and Epithelial Cells", Immunity, 50, pp. 1305-1316 (2019).

Calisti et al., "Probing bulky ligand entry in engineered archaeal ferritins", Biochimica et Biophysica Acta 1861, pp. 450-455 (2017).

Carter et al., "Design and Characterization of a Computationally Optimized Broadly Reactive Hemagglutinin Vaccine for H1N1 Influenza Viruses", J Virol, 90(9), pp. 4720-4734 (May 1, 2016).

Chapter 4 of Holtzhauer, M., Basic Methods for the Biochemical Lab, Springer 2006, ISBN 978-3-540-32785-1, available from www.springer.com.

Cui et al., "Rabbits immunized with Epstein-Barr virus gH/gL or GB recombinant proteins elicit higher serum virus neutralizing activity than gp350" Vaccine, 34(34), pp. 4050-4055 (Jul. 25, 2016).

Danilchanka et al., "Cyclic Dinucleotides and the Innate Immune Response", Cell, 154, pp. 962-970 (Aug. 29, 2013).

DiLillo et al., "Broadly neutralizing hemagglutinin stalk-specific antibodies require FcγR interactions for protection against influenza virus in vivo", Nature Medicine 20(2), pp. 143-151 (2014).

Faloon et al., "An Adjuvanted, Postfusion F Protein-Based Vaccine Did Not Prevent Respiratory Syncytial Virus Illness In Older Adults", J Infect Dis., 216, pp. 1362-1370 (Dec. 1, 2017).

Gaydos et al., "Swine Influenza A Outbreak, Fort Dix, New Jersey, 1976", Emerg Infect Dis, 12(1), pp. 23-28 (1976).

GenBank Accession Nos. CEQ35765.1 (Sep. 24, 2015) (2 pages).

GenBank Accession Nos. YP_001129472.1 (Aug. 13, 2018) (2 pages).

Gomes et al., "Harnessing Nanoparticles for Immunomodulation and Vaccines", Vaccines, 5(1), p. 6, (Feb. 14, 2017).

Gross et al., "Identification of LFA-1 as a candidate autoantigen in treatment-resistant Lyme arthritis", Science, 281 (5377), pp. 703-706 (1998).

Hein et al., "Click Chemistry, a Powerful Tool for Pharmaceutical Sciences", Pharm Res, 25(10), pp. 2216-2230 (Oct. 2008).

Hu et al., "Towards the next generation of biomedicines by site-selective conjugation", Chemical Society Reviews, 45 (6), pp. 1691-1719 (Mar. 21, 2016).

Hurwitz, J., "Respiratory syncytial virus vaccine development", Expert Rev Vaccines, 10(10), pp. 1415-1433 (Oct. 2011).

International Search Report issued in PCT Application No. PCT/US2019/025422 on Sep. 4, 2019 (8 pages).

Kanekiyo et al., "Rational Design of an Epstein-Barr Virus Vaccine Targeting the Receptor-Binding Site", Cell, 162(5), pp. 1090-1100 (Aug. 27, 2015).

Kanekiyo et al., "Self-assembling influenza nanoparticle vaccines elicit broadly neutralizing H1N1 antibodies", Nature, 499(7456), pp. 102-106 (Jul. 4, 2013).

Khazina et al., "Non-LTR retrotransposons encode noncanonical RRMdomains in their first open reading frame", Proc Natl Acad Sci U S A; 106(3), pp. 731-736 (Jan. 20, 2009).

Khoshnejad et al., "Ferritin-based drug delivery systems; Hybrid nanocarriers for vascular immunotargeting", J. Control Release, vol. 282, p. 13-24 (Mar. 6, 2018).

Kim et al., "Efficient Site-Specific Labeling of Proteins via Cysteines", Bioconjugate Chemistry, 19(3), pp. 786-791 (Mar. 1, 2008).

Kitahara, et al., "A Delicate Interplay of Structure, Dynamics, and Thermodynamics for Function: A High Pressure NMR Study of Outer Surface Protein A", Biophys J 102(4), pp. 916-926 (2012).

Klucker et al., "AF03, An Alternative Squalene Emulsion-Based Vaccine Adjuvant Prepared by a Phase Inversion Temperature Method", J Pharm Sci., 101(12), pp. 4490-4500 (Dec. 2012).

Lander, et al., "Appion: an integrated, database-driven pipeline to facilitate EM image processing", J Struct Biol, 166(1), pp. 95-102 (2009).

Lawson et al., "Solving the structure of human H ferritin by genetically engineering intermolecular crystal contacts", Nature, 349, pp. 541-544 (1991).

Li et al., "Ferritin nanoparticle technology . . . A new platform for antigen presentation and vaccine development", Industrial Biotechnology, 2(2), pp. 143-147 (Jul. 17, 2006).

Livey et al., "A New Approach to a Lyme Disease Vaccine", Clinical Infectious Diseases, vol. 52, Supplement 3, pp. S266-S270 (Feb. 1, 2011).

Lopez-Sagaseta et al., "Self-assembling protein nanoparticles in the design of vaccines", Computational and Structural Biotechnology Journal, vol. 14, pp. 58-68 (Jan. 1, 2016).

Lynn et al., "In vivo characterization of the physicochemical properties of polymer-linked TLR agonists that enhance vaccine immunogenicity", Nat Biotechnol., 33(11), pp. 1201-1210 (Nov. 2015).

McLellan et al., "Structure-Based Design of a Fusion Glycoprotein Vaccine for Respiratory Syncytial Virus", Science, 342(6158), pp. 592-598 (Nov. 1, 2013).

McLellan et al., "Structure of RSV Fusion Glycoprotein Trimer Bound to a Prefusion-Specific Neutralizing Antibody", Science, 340(6136), pp. 1113-1117 (2013).

McLellan, et al., "Structure of Respiratory Syncytial Virus Fusion Glycoprotein in the Postfusion Conformation Reveals Preservation of Neutralizing Epitopes", J Virol 85(15), pp. 7788-7796 (2011).

Moyle et al., "Site-Specific Incorporation of Three Toll-Like Receptor 2 Targeting Adjuvants into Semisynthetic, Molecularly Defined Nanoparticles: Application to Group A Streptococcal Vaccines", Bioconjugate Chem., 25, pp. 965-978 (2014).

Notification of Transmittal of The International Search Report and The Written Opinion of The International Searching Authority, or the Declaration, issued in PCT Application No. PCT/US2019/025377 on Jul. 10, 2019 (16 pages).

Notification of Transmittal of The International Search Report and The Written Opinion of The International Searching Authority, or the Declaration, issued in PCT Application No. PCT/US2019/025387 on Jul. 9, 2019 (20 pages).

Notification of Transmittal of The International Search Report and The Written Opinion of The International Searching Authority, or the Declaration, issued in PCT Application No. PCT/US2019/025419 on Oct. 18, 2019 (21 pages).

Notification of Transmittal of The International Search Report and The Written Opinion of The International Searching Authority, or the Declaration, issued in PCT Application No. PCT/US2019/025367 on Jul. 9, 2019 (20 pages).

Perez et al., "Novel Epstein-Barr virus-like particles incorporating gH/gL-EBNA1 or GB-LMP2 induce high neutralizing antibody titers and EBV-specific T-cell responses in immunized mice", Oncotarget, 8(12), (Mar. 21, 2017).

Ra et al., "Lumazine synthase protein cage nanoparticles as antigen delivery nanoplatforms for dendritic cell-based vaccine development", Clin Exp Vaccine Res, 3, pp. 227-234 (2014).

(56) References Cited

OTHER PUBLICATIONS

Rosa et al. "The burgeoning molecular genetics of the Lyme disease spirochaete", Nat Rev Microbiol 3(2), pp. 129-143 (2005).
Sashihara et al., "Human Antibody Titers to Epstein-Barr Virus (EBV) gp350 Correlate with Neutralization of Infectivity Better than Antibody Titers to EBV gp42 Using a Rapid Flow Cytometry-Based EBV Neutralization Assay", Virology, 391(2), pp. 249-256 (Sep. 1, 2009).
Sequence #206 from U.S. Appl. No. 17/061,136, accessed on Mar. 24, 2023 (1 page).
Sliepen et al., "Presenting native-like HIV-1 envelope trimers on ferritin nanoparticles improves their immunogenicity", Retrovirology, 11(1), p. e1004767 (Sep. 26, 2015).
Sorzano et al., XMIPP: a new generation of an open-source image processing package for electron microscopy, J Struct Biol, 148(2), pp. 194-204 (2004).
Steff et al., "Pre-fusion RSV F strongly boosts pre-fusion specific neutralizing responses in cattle pre-exposed to bovine RSV", Nature Communications, 8(1) (Oct. 20, 2017) (abstract).
Swanson et al., "Structural basis for immunization with postfusion respiratory syncytial virus fusion F glycoprotein (RSV F) to elicit high neutralizing antibody titers", Proc Natl Acad Sci, 108(23), pp. 9619-9624 (2011).
Trikha, J., et al. "High Resolution Crystal Structures of Amphibian Red-Cell L Ferritin: Potential Roles for Structural Plasticity and Solvation in Function", J Mol Biol, 248(5), pp. 949-967 (1995).
Tripp et al., "Respiratory Syncytial Virus: Targeting the G Protein Provides a New Approach for an Old Problem", Journal of Virology, 92(3), pp. 1-8 (Nov. 8, 2017).
Uchida et al., "Targeting of Cancer Cells with Ferrimagnetic Ferritin Cage Nanoparticles", Journal of the American Chemical Society, 128(51), pp. 16626-16633 (Dec. 1, 2006).
Van Geel et al., "Chemoenzymatic Conjugation of Toxic Payloads to the Globally Conserved N-Glycan of Native mAbs Provides Homogeneous and Highly Efficacious Antibody-Drug Conjugates", Bioconjugate Chem., 26, pp. 2233-2242 (2015).
Villar et al., "Reconstituted B cell receptor signaling reveals carbohydrate-dependent mode of activation", Scientific Reports, 6:36298, 11 pages (2016).
Wang et al., "Functional ferritin nanoparticles for biomedical applications", Frontiers of Chemical Science and Engineering, 11(4), pp. 633-646 (Feb. 15, 2017).
Wille-Reece et al., "HIV Gag protein conjugated to a Toll-like receptor 7/8 agonist improves the magnitude and quality of Th1 and CD8+ T cell responses in nonhuman primates", Proc Natl Acad Sci, 102(42), pp. 15190-15194 (2005).
Wilske et al., "An OspA Serotyping System for Borrelia burgdorferi Based on Reactivity with Monoclonal Antibodies and OspA Sequence Analysis", J Clin Microbio, 31(2), pp. 340-350 (1993).
Wressnigg et al., "A Novel Multivalent OspA Vaccine against Lyme Borreliosis Is Safe and Immunogenic in an Adult Population Previously Infected with Borrelia burgdorferi Sensu Lato", Clinical and Vaccine Immunology, 21(11), pp. 1490-1499 (Nov. 2014).
Written Opinion of the International Searching Authority issued in PCT Application No. PCT/US2019/025422 on Sep. 4, 2019 (13 pages).
Wu, Tom Y.-H., "Strategies for designing synthetic immune agonists", Immunology, 148(4), pp. 315-325 (Jul. 11, 2016).
Xu et al., "Trispecific broadly neutralizing HIV antibodies mediate potent SHIV protection in macaques", Science 358(6359), pp. 85-90 (2017).
Yassine et al., "Hemagglutinin-stem nanoparticles generate heterosubtypic influenza protection", Nature Medicine 21(9), pp. 1065-1071 (2015).
Zhang et al., "Challenges of glycosylation analysis and control: an integrated approach to producing optimal and consistent therapeutic drugs", Drug Discovery Today, 21(5), pp. 740-765 (May 2016).
Zhen et al., "Ferritins as nanoplatforms for imaging and drug delivery", Expert Opin. Drug Deliv, 11(12), pp. 1913-1922 (2014).

\* cited by examiner

Negative stain EM image of gL and gH nanoparticle

ELISA binding assay against gp220

ELISA binding assay against gp220

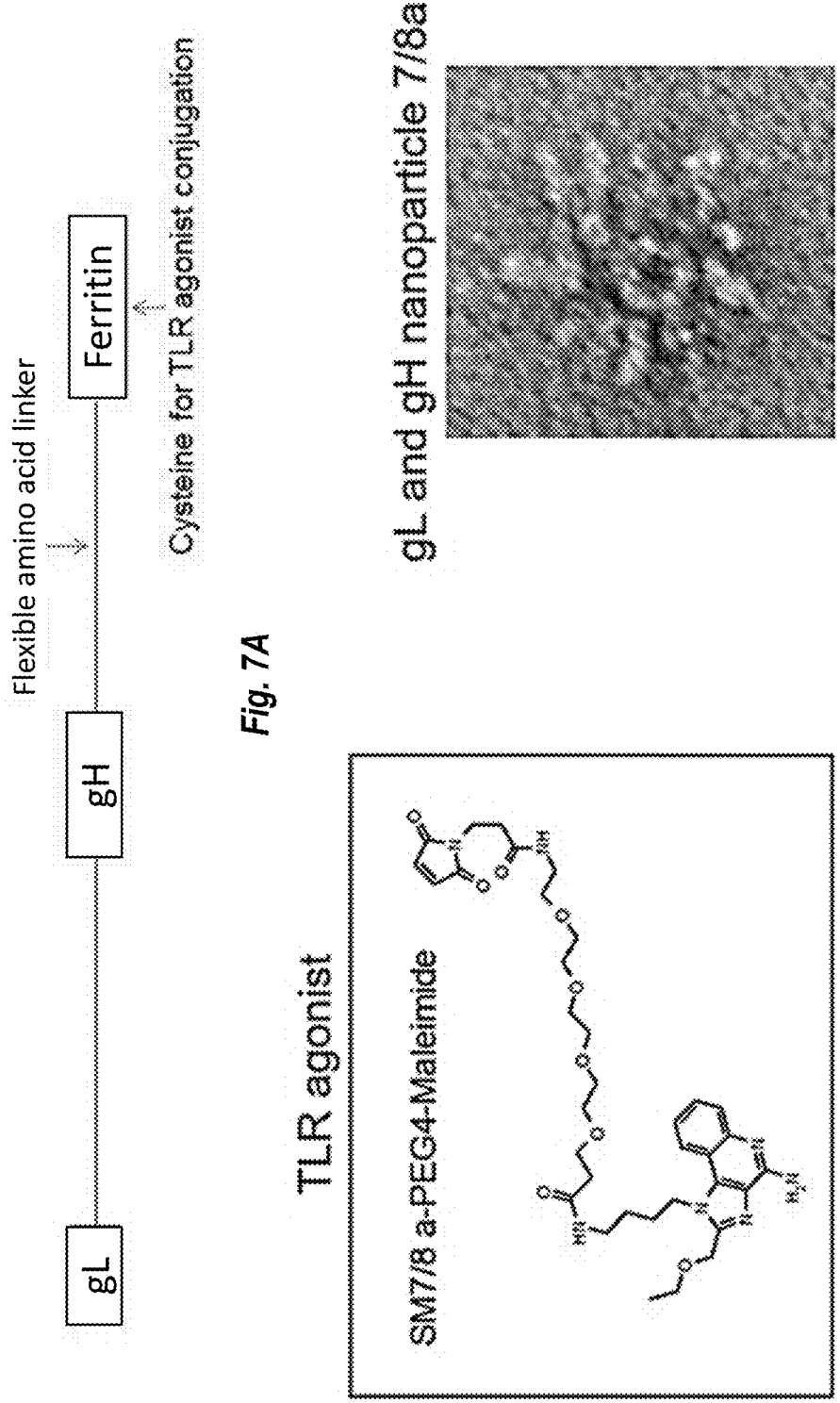

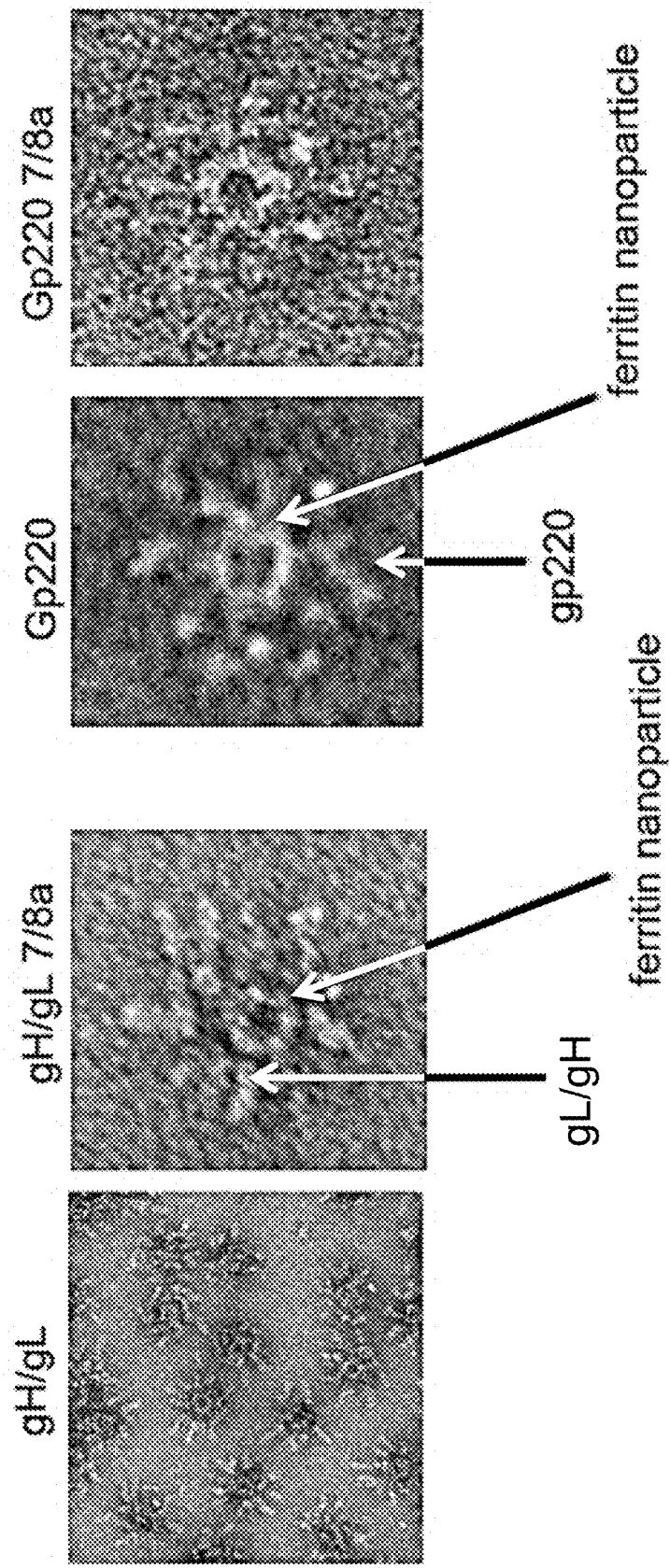

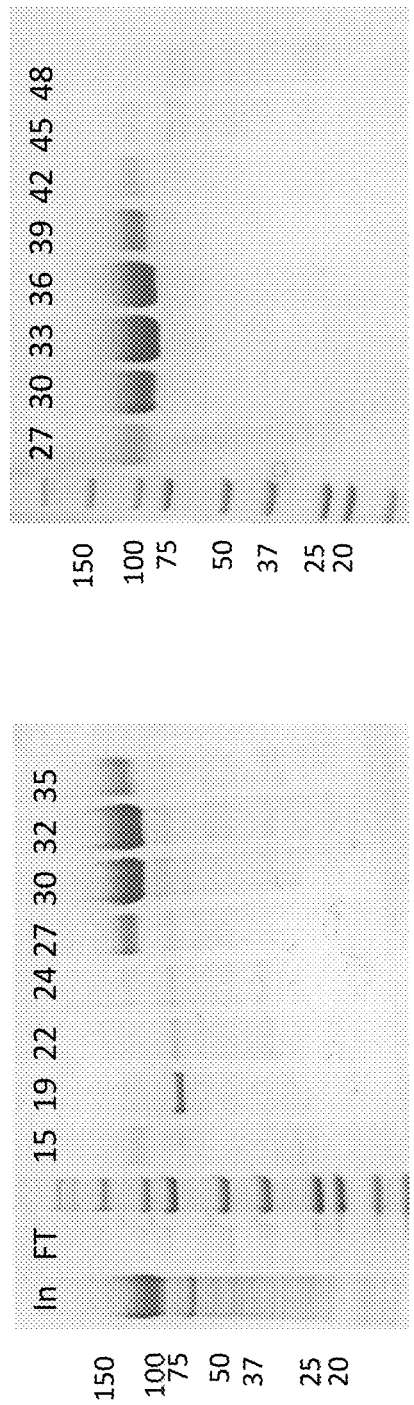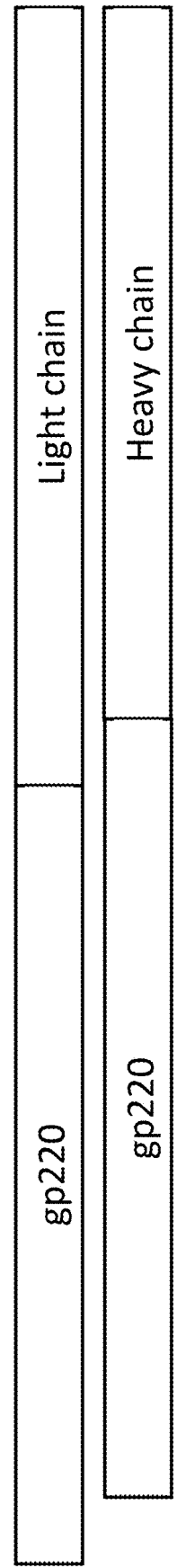
Fig. 24D
Fig. 24C
Fig. 24E

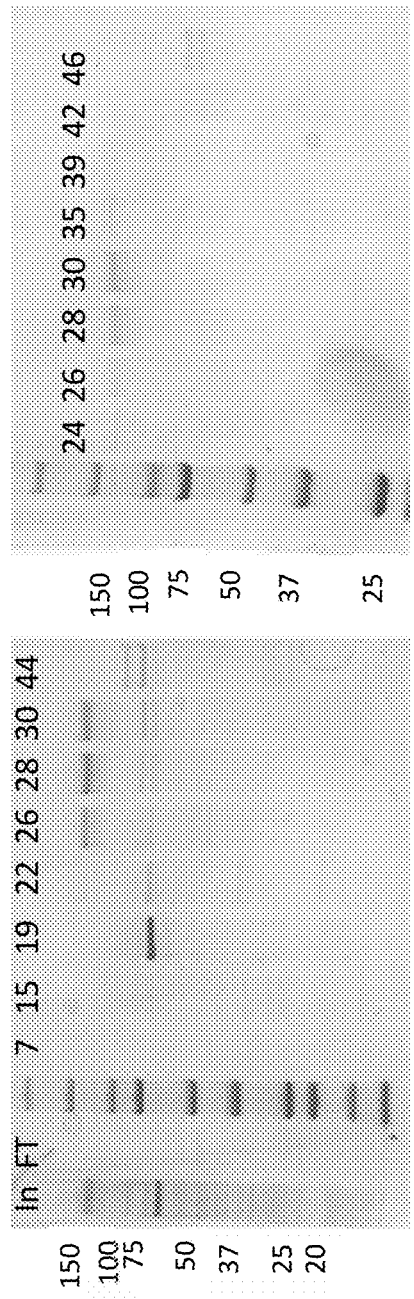
Fig. 25D
Fig. 25C
Light chain
Heavy chain
Fig. 25E
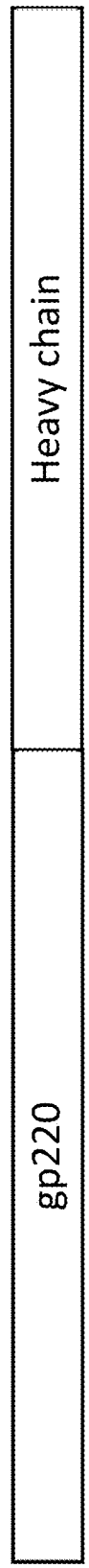
gH_gL
gp220

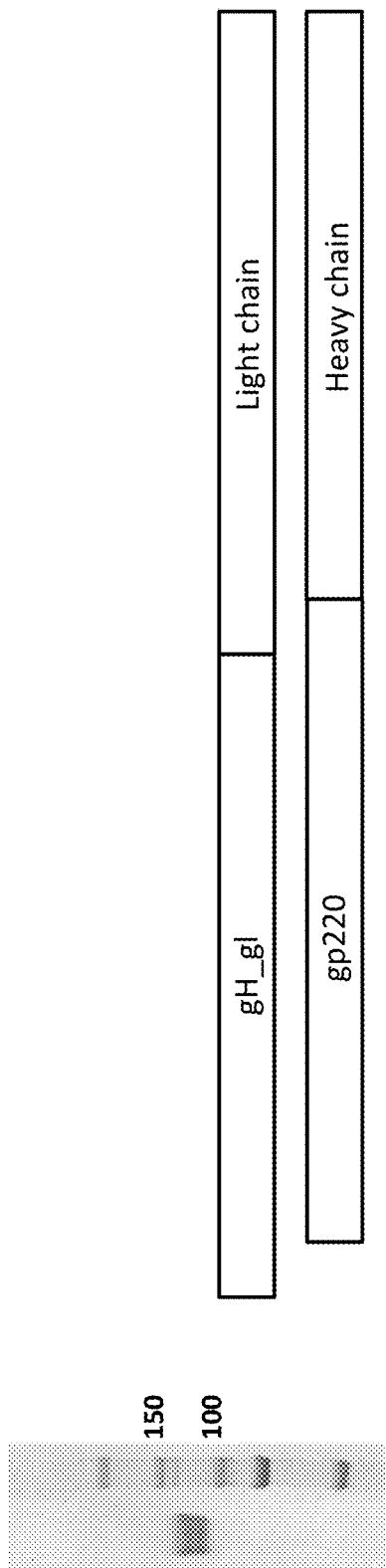
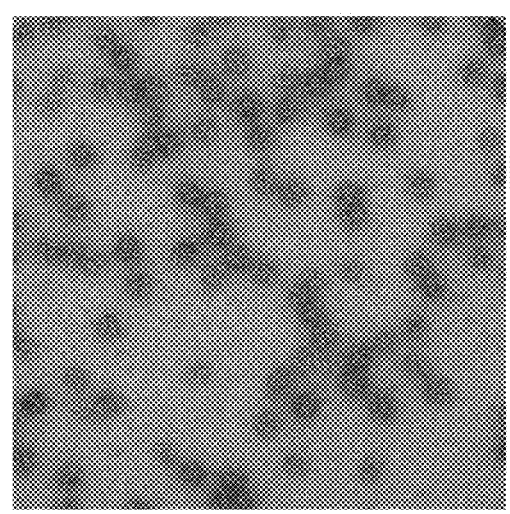
Fig. 26E
Fig. 26F
Fig. 26G

Ferret sera binding to gHgL monomer

*Fig. 30C*

Ferret sera binding to gp220 monomer

*Fig. 30D*

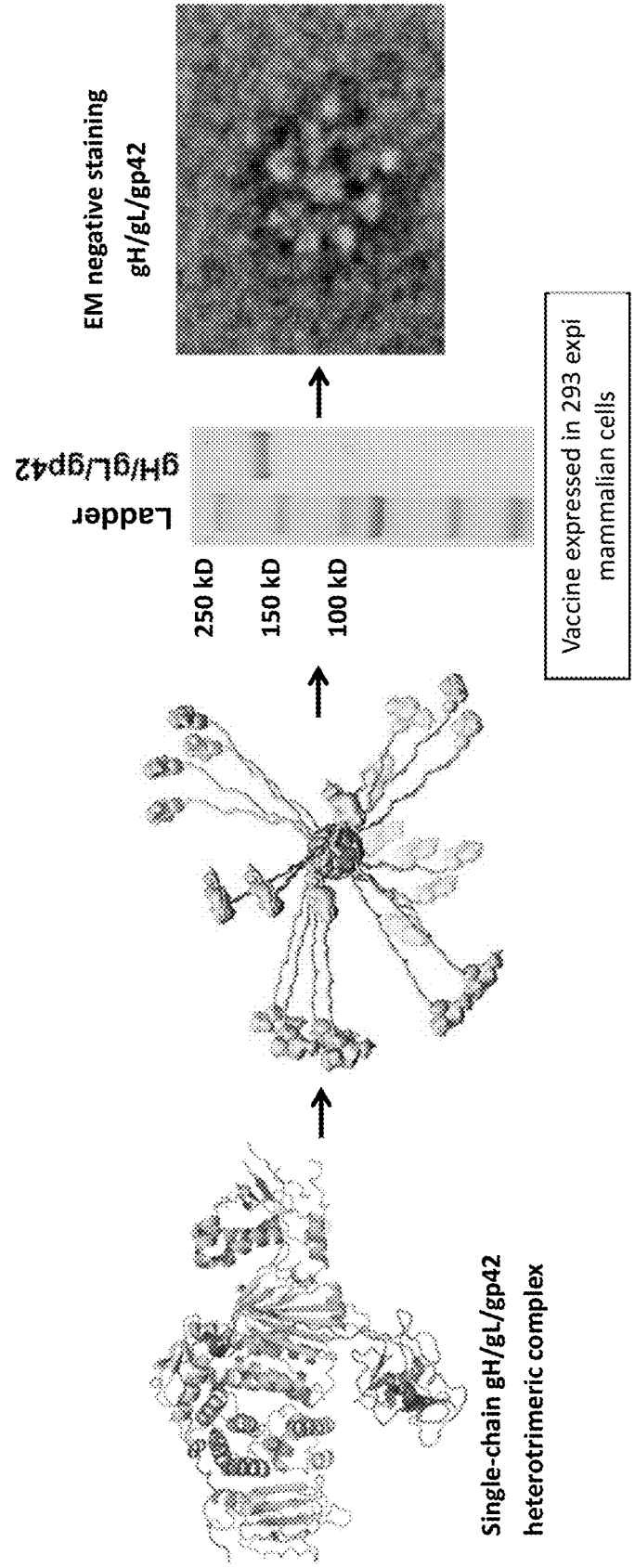
Fig. 35A
Fig. 35B
Fig. 35C
Fig. 35D
Fig. 35E

SEQUENCE LISTING

```
Sequence total quantity: 247
SEQ ID NO: 1              moltype = AA   length = 630
FEATURE                   Location/Qualifiers
REGION                    1..630
                          note = Synthetic polypeptide
source                    1..630
                          mol_type = protein
                          organism = synthetic construct
SEQUENCE: 1
MDSKGSSQKG SRLLLLLVVS NLLLPQGVLA EAALLVCQYT IQSLIHLTGE DPGFFNVEIP  60
EPPFYPTCNV CTADVNVTIN FDVGGKKHQL DLDFGQLTPH TKAVYQPRGA FGGSENATNL  120
FLLELLGAGE LALTMRSKKL PINVTTGEEQ QVSLESVDVY FQDVFGTMWC HHAEMQNPVY  180
LIPETVPYIK WDNCNSTNIT AVVRAQGLDV TLPLSLPTSA QDSNFSVKTE MLGNEIDIEC  240
IMEDGEISQV LPGDNKFNIT CSGYESHVPS GGILTSTSPV ATPIPGTGYA YSLRLTPRPV  300
SRFLGNNSIL YVFYSGNGPK ASGGDYCIQS NIVFSDEIPA SQDMPTNTTD ITYVGDNATY  360
SVPMVTSEDA NSPNVTVTAF WAWPNNTETD FKCKWTLTSG TPSGCENISG AFASNRTFDI  420
TVSGLGTAPK TLIITRTATN ATTTTHKVIF SKAPEGSESQ VRQQFSKDIE KLLNEQVNKE  480
MQSSNLYMSM SSWSYTHSLD GAGLFLFDHA AEEYEHAKKL IIFLNENNVP VQLTSISAPE  540
HKFEGLTQIF QKAYEHEQHI SESINNIVDH AIKCKDHATF NFLQWYVAEQ HEEEVLFKDI  600
LDKIELIGNE NHGLYLADQY VKGIAKSRKS                                  630

SEQ ID NO: 2              moltype = AA   length = 1032
FEATURE                   Location/Qualifiers
REGION                    1..1032
                          note = Synthetic polypeptide
source                    1..1032
                          mol_type = protein
                          organism = synthetic construct
SEQUENCE: 2
MRAVGVFLAI CLVTIFVLPT WGNWAYPCCH VTQLRAQHLL ALENISDIYL VSNQTCDGFS  60
LASLNSPKNG SNQLVISRCA NGLNVVSFFI SILKRSSSAL TGHLRELLTT LETLYGSFSV  120
EDLFGANLNR GGSGSASSGA SASGSSNGSG SGSGSNSSAS SGASSGGASG GSGGSGAASL  180
SEVKLHLDIE GHASHYTIPW TELMAKVPGL SPEALWREAN VTEDLASMLN RYKLIYKTSG  240
TLGIALAEPV DIPAVSEGSM QVDASKVHPG VISGLNSPAC MLSAPLEKQL FYYIGTMLPN  300
TRPHSYVFYQ LRCHLSYVAL SINGDKFQYT GAMTSKFLMG TYKRVTEKGD EHVLSLVFGK  360
TKDLPDLRGP FSYPSLTSAQ SGDYSLVIVT TFVHYANFHN YFVPNLKDMF SRAVTMTAAS  420
YARYVLQKLV LLEMKGGCRE PELDTETLTT MFEVSVAFFK VGHAVGETGN GCVDLRWLAK  480
SFFFELTVLKD IIGICYGATV KGMQSYGLER LAAMLMATVK MEELGHLTTE KQEYALRLAT  540
VGYPKAGVYS GLIGGATSVL LSAYNRHPLF QPLHTVMRET LFIGSHVVLR ELRLNVTTQG  600
PNLALYQLLS TALCSALEIG EVLRGLALGT ESGLFSPCYL SLRFDLTRDK LLSMAPQEAT  660
LDQAAVSNAV DGFLGRLSLE REDRDAWHLP AYKCVDRLDK VLMIIPLINV TFIISSDREV  720
RGSALYEAST TYLSSSLFLS PVIMNKCSQG AVAGEPRQIP KIQNFTRTQK SCIFCGFALL  780
SYDEKEGLET TTYITSQEVQ NSILSSNYFD FDNLHVHYLL LTTNGTVMEI AGLYEERASG  840
GGSGGSGGGG SGGGSGGGSE SQVRQQFSKD IEKLLNEQVN KEMQSSNLYM SMSSWSYTHS  900
LDGAGLFLFD HAAEEYEHAK KLIIFLNENN VPVQLTSISA PEHKFEGLTQ IFQKAYEHEQ  960
HISESINNIV DHAIKCKDHA TFNFLQWYVA EQHEEEVLFK DILDKIELIG NENHGLYLAD  1020
QYVKGIAKSR KS                                                     1032

SEQ ID NO: 3              moltype = AA   length = 1001
FEATURE                   Location/Qualifiers
REGION                    1..1001
                          note = Synthetic polypeptide
source                    1..1001
                          mol_type = protein
                          organism = synthetic construct
SEQUENCE: 3
METDTLLLWV LLLWVPGSTG NWAYPCCHVT QLRAQHLLAL ENISDIYLVS NQTCDGFSLA  60
SLNSPKNGSN QLVISRCANG LNVVSFFISI LKRSSSALTG HLRELLTTLE TLYGSFSVED  120
LFGANLNRGG GSGGGSGGGS GGGSGAASLS EVKLHLDIEG HASHYTIPWT ELMAKVPGLS  180
PEALWREANV TEDLASMLNR YKLIYKTSGT LGIALAEPVD IPAVSEGSMQ VDASKVHPGV  240
ISGLNSPACM LSAPLEKQLF YYIGTMLPNT RPHSYVFYQL RCHLSYVALS INGDKFQYTG  300
AMTSKFLMGT YKRVTEKGDE HVLSLVFGKT KDLPDLRGPF SYPSLTSAQS GDYSLVIVTT  360
FVHYANFHNY FVPNLKDMFS RAVTMTAASY ARYVLQKLVL LEMKGGCREP ELDTETLTTM  420
FEVSVAFFKV GHAVGETGNG CVDLRWLAKS FFELTVLKDI IGICYGATVK GMQSYGLERL  480
AAMLMATVKM EELGHLTTEK QEYALRLATV GYPKAGVYSG LIGGATSVLL SAYNRHPLFQ  540
PLHTVMRETL FIGSHVVLRE LRLNVTTQGP NLALYQLLST ALCSALEIGE VLRGLALGTE  600
SGLFSPCYLS LRFDLTRDKL LSMAPQEATL DQAAVSNAVD GFLGRLSLER EDRDAWHLPA  660
YKCVDRLDKV LMIIPLINVT FIISSDREVR GSALYEASTT YLSSSLFLSP VIMNKCSQGA  720
VAGEPRQIPK IQNFTRTQKS CIFCGFALLS YDEKEGLETT TYITSQEVQN SILSSNYFDF  780
DNLHVHYLLL TTNGTVMEIA GLYEERASGG GSGGSGGGGS GGGSGGGSES QVRQQFSKDI  840
EKLLNEQVNK EMQSSNLYMS MSSWSYTHSL DGAGLFLFDH AAEEYEHAKK LIIFLNENNV  900
PVQLTSISAP EHKFEGLTQI FQKAYEHEQH ISESINNIVD HAIKCKDHAT FNFLQWYVAE  960
QHEEEVLFKD ILDKIELIGN ENHGLYLADQ YVKGIAKSRK S                     1001

SEQ ID NO: 4              moltype = AA   length = 892
FEATURE                   Location/Qualifiers
REGION                    1..892
                          note = Synthetic polypeptide
```

```
                        -continued source                  1..892
                        mol_type = protein
                        organism = synthetic construct
SEQUENCE: 4
MRAVGVFLAI CLVTIFVLPT WGNWAYPCCH VTQLRAQHLL ALENISDIYL VSNQTCDGFS    60
LASLNSPKNG SNQLVISRCA NGLNVVSFFI SILKRSSSAL TGHLRELLTT LETLYGSFSV   120
EDLFGANLNR GGSGSASSGA SASGSSNGSG SGSGSNSSAS SGASSGGASG GSGGSGAASL   180
SEVKLHLDIE GHASHYTIPW TELMAKVPGL SPEALWREAN VTEDLASMLN RYKLIYKTSG   240
TLGIALAEPV DIPAVSEGSM QVDASKVHPG VISGLNSPAC MLSAPLEKQL FYYIGTMLPN   300
TRPHSYVFYQ LRCHLSYVAL SINGDKFQYT GAMTSKFLMG TYKRVTEKGD EHVLSLVFGK   360
TKDLPDLRGP FSYPSLTSAQ SGDYSLVIVT TFVHYANFHN YFVPNLKDMF SRAVTMTAAS   420
YARYVLQKLV LLEMKGGCRE PELDTETLTT MFEVSVAFFK VGHAVGETGN GCVDLRWLAK   480
SFFELTVLKD IIGICYGATV KGMQSYGLER LAAMLMATVK MEELGHLTTE KQEYALRLAT   540
VGYPKAGVYS GLIGGATSVL LSAYNRHPLF QPLHTVMRET LFIGSHVVLR ELRLNVTTQG   600
PNLALYQLLS TALCSALEIG EVLRGLALGT ESGLFSPCYL SLRFDLTRDK LLSMAPQEAT   660
LDQAAVSNAV DGFLGRLSLE REDRDAWHLP AYKCVDRLDK VLMIIPLINV TFIISSDREV   720
RGSALYEAST TYLSSSLFLS PVIMNKCSQG AVAGEPRQIP KIQNFTRTQK SCIFCGFALL   780
SYDEKEGLET TTYITSQEVQ NSILSSNYFD FDNLHVHYLL LTTNGTVMEI AGLYEERASG   840
SGYIPEAPRD GQAYVRKDGE WVLLSTFLGS GSGSGLVPRG SGAGGGHHHH HH           892

SEQ ID NO: 5            moltype = AA  length = 861
FEATURE                 Location/Qualifiers
REGION                  1..861
                        note = Synthetic polypeptide
source                  1..861
                        mol_type = protein
                        organism = synthetic construct
SEQUENCE: 5
METDTLLLWV LLLWVPGSTG NWAYPCCHVT QLRAQHLLAL ENISDIYLVS NQTCDGFSLA    60
SLNSPKNGSN QLVISRCANG LNVVSFFISI LKRSSSALTG HLRELLTTLE TLYGSFSVED   120
LFGANLNRGG GSGGGSGGGS GGGSGAASLS EVKLHLDIEG HASHYTIPWT ELMAKVPGLS   180
PEALWREANV TEDLASMLNR YKLIYKTSGT LGIALAEPVD IPAVSEGSMQ VDASKVHPGV   240
ISGLNSPACM LSAPLEKQLF YYIGTMLPNT RPHSYVFYQL RCHLSYVALS INGDKFQYTG   300
AMTSKFLMGT YKRVTEKGDE HVLSLVFGKT KDLPDLRGPF SYPSLTSAQS GDYSLVIVTT   360
FVHYANFHNY FVPNLKDMFS RAVTMTAASY ARYVLQKLVL LEMKGGCREP ELDTETLTTM   420
FEVSVAFFKV GHAVGETGNG CVDLRWLAKS FFELTVLKDI IGICYGATVK GMQSYGLERL   480
AAMLMATVKM EELGHLTTEK QEYALRLATV GYPKAGVYSG LIGGATSVLL SAYNRHPLFQ   540
PLHTVMRETL FIGSHVVLRE LRLNVTTQGP NLALYQLLST ALCSALEIGE VLRGLALGTE   600
SGLFSPCYLS LRFDLTRDKL LSMAPQEATL DQAAVSNAVD GFLGRLSLER EDRDAWHLPA   660
YKCVDRLDKV LMIIPLINVT FIISSDREVR GSALYEASTT YLSSSLFLSP VIMNKCSQGA   720
VAGEPRQIPK IQNFTRTQKS CIFCGFALLS YDEKEGLETT TYITSQEVQN SILSSNYFDF   780
DNLHVHYLLL TTNGTVMEIA GLYEERASGS GYIPEAPRDG QAYVRKDGEW VLLSTFLGSG   840
SGSGLVPRGS GAGGGHHHHH H                                             861

SEQ ID NO: 6            moltype = AA  length = 863
FEATURE                 Location/Qualifiers
REGION                  1..863
                        note = Synthetic polypeptide
source                  1..863
                        mol_type = protein
                        organism = synthetic construct
SEQUENCE: 6
MRAVGVFLAI CLVTIFVLPT WGNWAYPCCH VTQLRAQHLL ALENISDIYL VSNQTCDGFS    60
LASLNSPKNG SNQLVISRCA NGLNVVSFFI SILKRSSSAL TGHLRELLTT LETLYGSFSV   120
EDLFGANLNR GGSGSASSGA SASGSSNGSG SGSGSNSSAS SGASSGGASG GSGGSGAASL   180
SEVKLHLDIE GHASHYTIPW TELMAKVPGL SPEALWREAN VTEDLASMLN RYKLIYKTSG   240
TLGIALAEPV DIPAVSEGSM QVDASKVHPG VISGLNSPAC MLSAPLEKQL FYYIGTMLPN   300
TRPHSYVFYQ LRCHLSYVAL SINGDKFQYT GAMTSKFLMG TYKRVTEKGD EHVLSLVFGK   360
TKDLPDLRGP FSYPSLTSAQ SGDYSLVIVT TFVHYANFHN YFVPNLKDMF SRAVTMTAAS   420
YARYVLQKLV LLEMKGGCRE PELDTETLTT MFEVSVAFFK VGHAVGETGN GCVDLRWLAK   480
SFFELTVLKD IIGICYGATV KGMQSYGLER LAAMLMATVK MEELGHLTTE KQEYALRLAT   540
VGYPKAGVYS GLIGGATSVL LSAYNRHPLF QPLHTVMRET LFIGSHVVLR ELRLNVTTQG   600
PNLALYQLLS TALCSALEIG EVLRGLALGT ESGLFSPCYL SLRFDLTRDK LLSMAPQEAT   660
LDQAAVSNAV DGFLGRLSLE REDRDAWHLP AYKCVDRLDK VLMIIPLINV TFIISSDREV   720
RGSALYEAST TYLSSSLFLS PVIMNKCSQG AVAGEPRQIP KIQNFTRTQK SCIFCGFALL   780
SYDEKEGLET TTYITSQEVQ NSILSSNYFD FDNLHVHYLL LTTNGTVMEI AGLYEERASG   840
SGSGSGLVPR GSGAGGGHHH HHH                                           863

SEQ ID NO: 7            moltype = AA  length = 832
FEATURE                 Location/Qualifiers
REGION                  1..832
                        note = Synthetic polypeptide
source                  1..832
                        mol_type = protein
                        organism = synthetic construct
SEQUENCE: 7
METDTLLLWV LLLWVPGSTG NWAYPCCHVT QLRAQHLLAL ENISDIYLVS NQTCDGFSLA    60
SLNSPKNGSN QLVISRCANG LNVVSFFISI LKRSSSALTG HLRELLTTLE TLYGSFSVED   120
LFGANLNRGG GSGGGSGGGS GGGSGAASLS EVKLHLDIEG HASHYTIPWT ELMAKVPGLS   180
```

```
PEALWREANV TEDLASMLNR YKLIYKTSGT LGIALAEPVD IPAVSEGSMQ VDASKVHPGV  240
ISGLNSPACM LSAPLEKQLF YYIGTMLPNT RPHSYVFYQL RCHLSYVALS INGDKFQYTG  300
AMTSKFLMGT YKRVTEKGDE HVLSLVFGKT KDLPDLRGPF SYPSLTSAQS GDYSLVIVTT  360
FVHYANFHNY FVPNLKDMFS RAVTMTAASY ARYVLQKLVL LEMKGGCREP ELDTETLTTM  420
FEVSVAFFKV GHAVGETGNG CVDLRWLAKS FFELTVLKDI IGICYGATVK GMQSYGLERL  480
AAMLMATVKM EELGHLTTEK QEYALRLATV GYPKAGVYSG LIGGATSVLL SAYNRHPLFQ  540
PLHTVMRETL FIGSHVVLRE LRLNVTTQGP NLALYQLLST ALCSALEIGE VLRGLALGTE  600
SGLFSPCYLS LRFDLTRDKL LSMAPQEATL DQAAVSNAVD GFLGRLSLER EDRDAWHLPA  660
YKCVDRLDKV LMIIPLINVT FIISSDREVR GSALYEASTT YLSSSLFLSP VIMNKCSQGA  720
VAGEPRQIPK IQNFTRTQKS CIFCGFALLS YDEKEGLETT TYITSQEVQN SILSSNYFDF  780
DNLHVHYLLL TTNGTVMEIA GLYEERASGS GSGSGLVPRG SGAGGGHHHH HH         832

SEQ ID NO: 8           moltype = AA  length = 870
FEATURE                Location/Qualifiers
REGION                 1..870
                       note = Synthetic polypeptide
source                 1..870
                       mol_type = protein
                       organism = synthetic construct
SEQUENCE: 8
MRAVGVFLAI CLVTIFVLPT WGNWAYPCCH VTQLRAQHLL ALENISDIYL VSNQTCDGFS   60
LASLNSPKNG SNQLVISRCA NGLNVVSFFI SILKRSSSAL TGHLRELLTT LETLYGSFSV  120
EDLFGANLNR YAWHRGGGGS GSASSGASAS GSSNGSGSGS GSNSSASSGA SSGGASGGSG  180
GSGAASLSEV KLHLDIEGHA SHYTIPWTEL MAKVPGLSPE ALWREANVTE DLASMLNRYK  240
LIYKTSGTLG IALAEPVDIP AVSEGSMQVD ASKVHPGVIS GLNSPACMLS APLEKQLFYY  300
IGTMLPNTRP HSYVFYQLRC HLSYVALSIN GDKFQYTGAM TSKFLMGTYK RVTEKGDEHV  360
LSLVFGKTKD LPDLRGPFSY PSLTSAQSGD YSLVIVTTFV HYANFHNYFV PNLKDMFSRA  420
VTMTAASYAR YVLQKLVLLE MKGGCREPEL DTETLTTMFE VSVAFFKVGH AVGETGNGCV  480
DLRWLAKSFF ELTVLKDIIG ICYGATVKGM QSYGLERLAA MLMATVKMEE LGHLTTEKQE  540
YALRLATVGY PKAGVYSGLI GGATSVLLSA YNRHPLFQPL HTVMRETLFI GSHVVLRELR  600
LNVTTQGPNL ALYQLLSTAL CSALEIGEVL RGLALGTESG LFSPCYLSLR FDLTRDKLLS  660
MAPQEATLDQ AAVSNAVDGF LGRLSLERED RDAWHLPAYK CVDRLDKVLM IIPLINVTFI  720
ISSDREVRGS ALYEASTTYL SSSLFLSPVI MNKCSQGAVA GEPRQIPKIQ NFTRTQKSCI  780
FCGFALLSYD EKEGLETTTY ITSQEVQNSI LSSNYFDFDN LHVHYLLLTT NGTVMEIAGL  840
YEERASGSGS GSGLVPRGSG AGGGHHHHHH                                  870

SEQ ID NO: 9           moltype = AA  length = 852
FEATURE                Location/Qualifiers
REGION                 1..852
                       note = Synthetic polypeptide
source                 1..852
                       mol_type = protein
                       organism = synthetic construct
SEQUENCE: 9
MRAVGVFLAI CLVTIFVLPT WGNWAYPCCH VTQLRAQHLL ALENISDIYL VSNQTCDGFS   60
LASLNSPKNG SNQLVISRCA NGLNVVSFFI SILKRSSSAL TGHLRELLTT LETLYGSFSV  120
EDLFGANLNR YAWHRGGGGS GSGSNSSASS GASSGGASGS GSGSGAASLS EVKLHLDIEG  180
HASHYTIPWT ELMAKVPGLS PEALWREANV TEDLASMLNR YKLIYKTSGT LGIALAEPVD  240
IPAVSEGSMQ VDASKVHPGV ISGLNSPACM LSAPLEKQLF YYIGTMLPNT RPHSYVFYQL  300
RCHLSYVALS INGDKFQYTG AMTSKFLMGT YKRVTEKGDE HVLSLVFGKT KDLPDLRGPF  360
SYPSLTSAQS GDYSLVIVTT FVHYANFHNY FVPNLKDMFS RAVTMTAASY ARYVLQKLVL  420
LEMKGGCREP ELDTETLTTM FEVSVAFFKV GHAVGETGNG CVDLRWLAKS FFELTVLKDI  480
IGICYGATVK GMQSYGLERL AAMLMATVKM EELGHLTTEK QEYALRLATV GYPKAGVYSG  540
LIGGATSVLL SAYNRHPLFQ PLHTVMRETL FIGSHVVLRE LRLNVTTQGP NLALYQLLST  600
ALCSALEIGE VLRGLALGTE SGLFSPCYLS LRFDLTRDKL LSMAPQEATL DQAAVSNAVD  660
GFLGRLSLER EDRDAWHLPA YKCVDRLDKV LMIIPLINVT FIISSDREVR GSALYEASTT  720
YLSSSLFLSP VIMNKCSQGA VAGEPRQIPK IQNFTRTQKS CIFCGFALLS YDEKEGLETT  780
TYITSQEVQN SILSSNYFDF DNLHVHYLLL TTNGTVMEIA GLYEERASGS GSGSGLVPRG  840
SGAGGGHHHH HH                                                     852

SEQ ID NO: 10          moltype = AA  length = 1007
FEATURE                Location/Qualifiers
REGION                 1..1007
                       note = Synthetic polypeptide
source                 1..1007
                       mol_type = protein
                       organism = synthetic construct
SEQUENCE: 10
METDTLLLWV LLLWVPGSTG NWAYPCCHVT QLRAQHLLAL ENISDIYLVS NQTCDGFSLA   60
SLNSPKNGSN QLVISRCANG LNVVSFFISI LKRSSSALTG HLRELLTTLE TLYGSFSVED  120
LFGANLNRYA WHRGGGGGGS GGGGSGGGGS GAASLSEVKL HLDIEGHASH YTIPWTELMA  180
KVPGLSPEAL WREANVTEDL ASMLNRYKLI YKTSGTLGIA LAEPVDIPAV SEGSMQVDAS  240
KVHPGVISGL NSPACMLSAP LEKQLFYYIG TMLPNTRPHS YVFYQLRCHL SYVALSINGD  300
KFQYTGAMTS KFLMGTYKRV TEKGDEHVLS LVFGKTKDLP DLRGPFSYPS LTSAQSGDYS  360
LVIVTTFVHY ANFHNYFVPN LKDMFSRAVT MTAASYARYV LQKLVLLEMK GGCREPELDT  420
ETLTTMFEVS VAFFKVGHAV GETGNGCVDL RWLAKSFFEL TVLKDIIGIC YGATVKGMQS  480
YGLERLAAML MATVKMEELG HLTTEKQEYA LRLATVGYPK AGVYSGLIGG ATSVLLSAYN  540
RHPLFQPLHT VMRETLFIGS HVVLRELRLN VTTQGPNLAL YQLLSTALCS ALEIGEVLRG  600
LALGTESGLF SPCYLSLRFD LTRDKLLSMA PQEATLDQAA VSNAVDGFLG RLSLEREDRD  660
```

```
AWHLPAYKCV DRLDKVLMII PLINVTFIIS SDREVRGSAL YEASTTYLSS SLFLSPVIMN    720
KCSQGAVAGE PRQIPKIQNF TRTQKSCIFC GFALLSYDEK EGLETTTYIT SQEVQNSILS    780
SNYFDFDNLH VHYLLLTTNG TVMEIAGLYE ERASGGGSGG GSGGGSGGGS GGGSESQVRQ    840
QFSKDIEKLL NEQVNKEMQS SNLYMSMSSW SYTHSLDGAG LFLFDHAAEE YEHAKKLIIF    900
LNENNVPVQL TSISAPEHKF EGLTQIFQKA YEHEQHISES INNIVDHAIK CKDHATFNFL    960
QWYVAEQHEE EVLFKDILDK IELIGNENHG LYLADQYVKG IAKSRKS                 1007

SEQ ID NO: 11           moltype = AA  length = 881
FEATURE                 Location/Qualifiers
REGION                  1..881
                        note = Synthetic polypeptide
source                  1..881
                        mol_type = protein
                        organism = synthetic construct
SEQUENCE: 11
MRAVGVFLAI CLVTIFVLPT WGNWAYPCCH VTQLRAQHLL ALENISDIYL VSNQTCDGFS    60
LASLNSPKNG SNQLVISRCA NGLNVVSFFI SILKRSSSAL TGHLRELLTT LETLYGSFSV   120
EDLFGANLNR YAWHRGGGGS GSGSNSSASS GASSGGASGG SGGSGAASLS EVKLHLDIEG   180
HASHYTIPWT ELMAKVPGLS PEALWREANV TEDLASMLNR YKLIYKTSGT LGIALAEPVD   240
IPAVSEGSMQ VDASKVHPGV ISGLNSPACM LSAPLEKQLF YYIGTMLPNT RPHSYVFYQL   300
RCHLSYVALS INGDKFQYTG AMTSKFLMGT YKRVTEKGDE HVLSLVFGKT KDLPDLRGPF   360
SYPSLTSAQS GDYSLVIVTT FVHYANFHNY FVPNLKDMFS RAVTMTAASY ARYVLQKLVL   420
LEMKGGCREP ELDTETLTTM FEVSAFFKV GHAVGETGNG CVDLRWLAKS FFELTVLKDI    480
IGICYGATVK GMQSYGLERL AAMLMATVKM EELGHLTTEK QEYALRLATV GYPKAGVYSG   540
LIGGATSVLL SAYNRHPLFQ PLHTVMRETL FIGSHVVLRE LRLNVTTQGP NLALYQLLST   600
ALCSALEIGE VLRGLALGTE SGLFSPCYLS LRFDLTRDKL LSMAPQEATL DQAAVSNAVD   660
GFLGRLSLER EDRDAWHLPA YKCVDRLDKV LMIIPLINVT FIISSDREVR GSALYEASTT   720
YLSSSLFLSP VIMNKCSQGA VAGEPRQIPK IQNFTRTQKS CIFCGFALLS YDEKEGLETT   780
TYIITSQEVQN SILSSNYFDF DNLHVHYLLL TTNGTVMEIA GLYEERASGS GYIPEAPRDG  840
QAYVRKDGEW VLLSTFLGSG SGSGLVPRGS GAGGGHHHHH H                       881

SEQ ID NO: 12           moltype = AA  length = 899
FEATURE                 Location/Qualifiers
REGION                  1..899
                        note = Synthetic polypeptide
source                  1..899
                        mol_type = protein
                        organism = synthetic construct
SEQUENCE: 12
MRAVGVFLAI CLVTIFVLPT WGNWAYPCCH VTQLRAQHLL ALENISDIYL VSNQTCDGFS    60
LASLNSPKNG SNQLVISRCA NGLNVVSFFI SILKRSSSAL TGHLRELLTT LETLYGSFSV   120
EDLFGANLNR YAWHRGGGGS GSASSGASAS GSSNGSGSGS GSNSSASSGA SSGGASGGSG   180
GSGAASLSEV KLHLDIEGHA SHYTIPWTEL MAKVPGLSPE ALWREANVTE DLASMLNRYK   240
LIYKTSGTLG IALAEPVDIP AVSEGSMQVD ASKVHPGVIS GLNSPACMLS APLEKQLFYY   300
IGTMLPNTRP HSYVFYQLRC HLSYVALSIN GDKFQYTGAM TSKFLMGTYK RVTEKGDEHV   360
LSLVFGKTKD LPDLRGPFSY PSLTSAQSGD YSLVIVTTFV HYANFHNYFV PNLKDMFSRA   420
VTMTAASYAR YVLQKLVLLE MKGGCREPEL DTETLTTMFE VSAFFKVGH AVGETGNGCV    480
DLRWLAKSFF ELTVLKDIIG ICYGATVKGM QSYGLERLAA MLMATVKMEE LGHLTTEKQE   540
YALRLATVGY PKAGVYSGLI GGATSVLLSA YNRHPLFQPL HTVMRETLFI GSHVVLRELR   600
LNVTTQGPNL ALYQLLSTAL CSALEIGEVL RGLALGTESG LFSPCYLSLR FDLTRDKLLS   660
MAPQEATLDQ AAVSNAVDGF LGRLSLERED RDAWHLPAYK CVDRLDKVLM IIPLINVTFI   720
ISSDREVRGS ALYEASTTYL SSSLFLSPVI MNKCSQGAVA GEPRQIPKIQ NFTRTQKSCI   780
FCGFALLSYD EKEGLETTTY ITSQEVQNSI LSSNYFDFDN LHVHYLLLTT NGTVMEIAGL   840
YEERASGSGY IPEAPRDGQA YVRKDGEWVL LSTFLGSGSG SGLVPRGSGA GGGHHHHHH    899

SEQ ID NO: 13           moltype = AA  length = 1021
FEATURE                 Location/Qualifiers
REGION                  1..1021
                        note = Synthetic polypeptide
source                  1..1021
                        mol_type = protein
                        organism = synthetic construct
SEQUENCE: 13
MRAVGVFLAI CLVTIFVLPT WGNWAYPCCH VTQLRAQHLL ALENISDIYL VSNQTCDGFS    60
LASLNSPKNG SNQLVISRCA NGLNVVSFFI SILKRSSSAL TGHLRELLTT LETLYGSFSV   120
EDLFGANLNR YAWHRGGGGS GSGSNSSASS GASSGGASGG SGGSGAASLS EVKLHLDIEG   180
HASHYTIPWT ELMAKVPGLS PEALWREANV TEDLASMLNR YKLIYKTSGT LGIALAEPVD   240
IPAVSEGSMQ VDASKVHPGV ISGLNSPACM LSAPLEKQLF YYIGTMLPNT RPHSYVFYQL   300
RCHLSYVALS INGDKFQYTG AMTSKFLMGT YKRVTEKGDE HVLSLVFGKT KDLPDLRGPF   360
SYPSLTSAQS GDYSLVIVTT FVHYANFHNY FVPNLKDMFS RAVTMTAASY ARYVLQKLVL   420
LEMKGGCREP ELDTETLTTM FEVSAFFKV GHAVGETGNG CVDLRWLAKS FFELTVLKDI    480
IGICYGATVK GMQSYGLERL AAMLMATVKM EELGHLTTEK QEYALRLATV GYPKAGVYSG   540
LIGGATSVLL SAYNRHPLFQ PLHTVMRETL FIGSHVVLRE LRLNVTTQGP NLALYQLLST   600
ALCSALEIGE VLRGLALGTE SGLFSPCYLS LRFDLTRDKL LSMAPQEATL DQAAVSNAVD   660
GFLGRLSLER EDRDAWHLPA YKCVDRLDKV LMIIPLINVT FIISSDREVR GSALYEASTT   720
YLSSSLFLSP VIMNKCSQGA VAGEPRQIPK IQNFTRTQKS CIFCGFALLS YDEKEGLETT   780
TYIITSQEVQN SILSSNYFDF DNLHVHYLLL TTNGTVMEIA GLYEERASGG GSGGGSGGGS  840
GGGSGGGSES QVRQQFSKDI EKLLNEQVNK EMQSSNLYMS MSSWSYTHSL DGAGLFLFDH   900
AAEEYEHAKK LIIFLNENNV PVQLTSISAP EHKFEGLTQI FQKAYEHEQH ISESINNIVD   960
```

-continued

```
HAIKCKDHAT FNFLQWYVAE QHEEEVLFKD ILDKIELIGN ENHGLYLADQ YVKGIAKSRK  1020
S                                                                 1021

SEQ ID NO: 14           moltype = AA  length = 1039
FEATURE                 Location/Qualifiers
REGION                  1..1039
                        note = Synthetic polypeptide
source                  1..1039
                        mol_type = protein
                        organism = synthetic construct
SEQUENCE: 14
MRAVGVFLAI CLVTIFVLPT WGNWAYPCCH VTQLRAQHLL ALENISDIYL VSNQTCDGFS   60
LASLNSPKNG SNQLVISRCA NGLNVVSFFI SILKRSSSAL TGHLRELLTT LETLYGSFSV  120
EDLFGANLNR YAWHRGGGGS GSASSGASAS GSSNGSGSGS GSNSSASSGA SSGGASGGSG  180
GSGAASLSEV KLHLDIEGHA SHYTIPWTEL MAKVPGLSPE ALWREANVTE DLASMLNRYK  240
LIYKTSGTLG IALAEPVDIP AVSEGSMQVD ASKVHPGVIS GLNSPACMLS APLEKQLFYY  300
IGTMLPNTRP HSYVFYQLRC HLSYVALSIN GDKFQYTGAM TSKFLMGTYK RVTEKGDEHV  360
LSLVFGKTKD LPDLRGPFSY PSLTSAQSGD YSLVIVTTFV HYANFHNYFV PNLKDMFSRA  420
VTMTAASYAR YVLQKLVLLE MKGGCREPEL DTETLTTMFE VSVAFFKVGH AVGETGNGCV  480
DLRWLAKSFF ELTVLKDIIG ICYGATVKGM QSYGLERLAA MLMATVKMEE LGHLTTEKQE  540
YALRLATVGY PKAGVYSGLI GGATSVLLSA YNRHPLFQPL HTVMRETLFI GSHVVLRELR  600
LNVTTQGPNL ALYQLLSTAL CSALEIGEVL RGLALGTESG LFSPCYLSLR FDLTRDKLLS  660
MAPQEATLDQ AAVSNAVDGF LGRLSLERED RDAWHLPAYK CVDRLDKVLM IIPLINVTFI  720
ISSDREVRGS ALYEASTTYL SSSLFLSPVI MNKCSQGAVA GEPRQIPKIQ NFTRTQKSCI  780
FCGFALLSYD EKEGLETTTY ITSQEVQNSI LSSNYFDFDN LHVHYLLLTT NGTVMEIAGL  840
YEERASGGGS GGGSGGGSGG GSGGGSESQV RQQFSKDIEK LLNEQVNKEM QSSNLYMSMS  900
SWSYTHSLDG AGLFLFDHAA EEYEHAKKLI IFLNENNVPV QLTSISAPEH KFEGLTQIFQ  960
KAYEHEQHIS ESINNIVDHA IKCKDHATFN FLQWYVAEQH EEEVLFKDIL DKIELIGNEN  1020
HGLYLADQYV KGIAKSRKS                                             1039

SEQ ID NO: 15           moltype = AA  length = 838
FEATURE                 Location/Qualifiers
REGION                  1..838
                        note = Synthetic polypeptide
source                  1..838
                        mol_type = protein
                        organism = synthetic construct
SEQUENCE: 15
METDTLLLWV LLLWVPGSTG NWAYPCCHVT QLRAQHLLAL ENISDIYLVS NQTCDGFSLA   60
SLNSPKNGSN QLVISRCANG LNVVSFFISI LKRSSSALTG HLRELLTTLE TLYGSFSVED  120
LFGANLNRYA WHRGGGGGS GGGGSGGGGS GAASLSEVKL HLDIEGHASH YTIPWTELMA  180
KVPGLSPEAL WREANVTEDL ASMLNRYKLI YKTSGTLGIA LAEPVDIPAV SEGSMQVDAS  240
KVHPGVISGL NSPACMLSAP LEKQLFYYIG TMLPNTRPHS YVFYQLRCHL SYVALSINGD  300
KFQYTGAMTS KFLMGTYKRV TEKGDEHVLS LVFGKTKDLP DLRGPFSYPS LTSAQSGDYS  360
LVIVTTFVHY ANFHNYFVPN LKDMFSRAVT MTAASYARYV LQKLVLLEMK GGCREPELDT  420
ETLTTMFEVS VAFFKVGHAV GETGNGCVDL RWLAKSFFEL TVLKDIIGIC YGATVKGMQS  480
YGLERLAAML MATVKMEELG HLTTEKQEYA LRLATVGYPK AGVYSGLIGG ATSVLLSAYN  540
RHPLFQPLHT VMRETLFIGS HVVLRELRLN VTTQGPNLAL YQLLSTALCS ALEIGEVLRG  600
LALGTESGLF SPCYLSLRFD LTRDKLLSMA PQEATLDQAA VSNAVDGFLG RLSLEREDRD  660
AWHLPAYKCV DRLDKVLMII PLINVTFIIS SDREVRGSAL YEASTTYLSS SLFLSPVIMN  720
KCSQGAVAGE PRQIPKIQNF TRTQKSCIFC GFALLSYDEK EGLETTTYIT SQEVQNSILS  780
SNYFDFDNLH VHYLLLTTNG TVMEIAGLYE ERASGSGSGS GLVPRGSGAG GGHHHHHH    838

SEQ ID NO: 16           moltype = AA  length = 867
FEATURE                 Location/Qualifiers
REGION                  1..867
                        note = Synthetic polypeptide
source                  1..867
                        mol_type = protein
                        organism = synthetic construct
SEQUENCE: 16
METDTLLLWV LLLWVPGSTG NWAYPCCHVT QLRAQHLLAL ENISDIYLVS NQTCDGFSLA   60
SLNSPKNGSN QLVISRCANG LNVVSFFISI LKRSSSALTG HLRELLTTLE TLYGSFSVED  120
LFGANLNRYA WHRGGGGGS GGGGSGGGGS GAASLSEVKL HLDIEGHASH YTIPWTELMA  180
KVPGLSPEAL WREANVTEDL ASMLNRYKLI YKTSGTLGIA LAEPVDIPAV SEGSMQVDAS  240
KVHPGVISGL NSPACMLSAP LEKQLFYYIG TMLPNTRPHS YVFYQLRCHL SYVALSINGD  300
KFQYTGAMTS KFLMGTYKRV TEKGDEHVLS LVFGKTKDLP DLRGPFSYPS LTSAQSGDYS  360
LVIVTTFVHY ANFHNYFVPN LKDMFSRAVT MTAASYARYV LQKLVLLEMK GGCREPELDT  420
ETLTTMFEVS VAFFKVGHAV GETGNGCVDL RWLAKSFFEL TVLKDIIGIC YGATVKGMQS  480
YGLERLAAML MATVKMEELG HLTTEKQEYA LRLATVGYPK AGVYSGLIGG ATSVLLSAYN  540
RHPLFQPLHT VMRETLFIGS HVVLRELRLN VTTQGPNLAL YQLLSTALCS ALEIGEVLRG  600
LALGTESGLF SPCYLSLRFD LTRDKLLSMA PQEATLDQAA VSNAVDGFLG RLSLEREDRD  660
AWHLPAYKCV DRLDKVLMII PLINVTFIIS SDREVRGSAL YEASTTYLSS SLFLSPVIMN  720
KCSQGAVAGE PRQIPKIQNF TRTQKSCIFC GFALLSYDEK EGLETTTYIT SQEVQNSILS  780
SNYFDFDNLH VHYLLLTTNG TVMEIAGLYE ERASGSGYIP EAPRDGQAYV RKDGEWVLLS  840
TFLGSGSGSG LVPRGSGAGG GHHHHHH                                      867

SEQ ID NO: 17           moltype = AA  length = 1019
FEATURE                 Location/Qualifiers
```

```
REGION                      1..1019
                            note = Synthetic polypeptide
source                      1..1019
                            mol_type = protein
                            organism = synthetic construct
SEQUENCE: 17
MRAVGVFLAI CLVTIFVLPT WGNWAYPCCH VTQLRAQHLL ALENISDIYL VSNQTCDGFS    60
LASLNSPKNG SNQLVISRCA NGLNVVSFFI SILKRSSSAL TGHLRELLTT LETLYGSFSV   120
EDLFGANLNR YAWHRGGGGS GSASAEAAAK EAAAKAGGSG GSGAASLSEV KLHLDIEGHA   180
SHYTIPWTEL MAKVPGLSPE ALWREANVTE DLASMLNRYK LIYKTSGTLG IALAEPVDIP   240
AVSEGSMQVD ASKVHPGVIS GLNSPACMLS APLEKQLFYY IGTMLPNTRP HSYVFYQLRC   300
HLSYVALSIN GDKFQYTGAM TSKFLMGTYK RVTEKGDEHV LSLVFGKTKD LPDLRGPFSY   360
PSLTSAQSGD YSLVIVTTFV HYANFHNYFV PNLKDMFSRA VTMTAASYAR YVLQKLVLLE   420
MKGGCREPEL DTETLTTMFE VSVAFFKVGH AVGETGNGCV DLRWLAKSFF ELTVLKDIIG   480
ICYGATVKGM QSYGLERLAA MLMATVKMEE LGHLTTEKQE YALRLATVGY PKAGVYSGLI   540
GGATSVLLSA YNRHPLFQPL HTVMRETLFI GSHVVRELR LNVTTQGPNL ALYQLLSTAL    600
CSALEIGEVL RGLALGTESG LFSPCYLSLR FDLTRDKLLS MAPQEATLDQ AAVSNAVDGF   660
LGRLSLERED RDAWHLPAYK CVDRLDKVLM IIPLINVTFI ISSDREVRGS ALYEASTTYL   720
SSSLFLSPVI MNKCSQGAVA GEPRQIPKIQ NFTRTQKSCI FCGFALLSYD EKEGLETTTY   780
ITSQEVQNSI LSSNYFDFDN LHVHYLLLTT NGTVMEIAGL YEERASGGGS GGGSGGGSGG   840
GSGGGSESQV RQQFSKDIEK LLNEQVNKEM QSSNLYMSMS SWSYTHSLDG AGLFLFDHAA   900
EEYEHAKKLI IFLNENNVPV QLTSISAPEH KFEGLTQIFQ KAYEHEQHIS ESINNIVDHA   960
IKCKDHATFN FLQWYVAEQH EEEVLFKDIL DKIELIGNEN HGLYLADQYV KGIAKSRKS   1019

SEQ ID NO: 18               moltype = AA   length = 1025
FEATURE                     Location/Qualifiers
REGION                      1..1025
                            note = Synthetic polypeptide
source                      1..1025
                            mol_type = protein
                            organism = synthetic construct
SEQUENCE: 18
MRAVGVFLAI CLVTIFVLPT WGNWAYPCCH VTQLRAQHLL ALENISDIYL VSNQTCDGFS    60
LASLNSPKNG SNQLVISRCA NGLNVVSFFI SILKRSSSAL TGHLRELLTT LETLYGSFSV   120
EDLFGANLNR YAWHRGGGGS GSASAEAAAK EAAAKEAAAK ASGGSGGSGA ASLSEVKLHL   180
DIEGHASHYT IPWTELMAKV PGLSPEALWR EANVTEDLAS MLNRYKLIYK TSGTLGIALA   240
EPVDIPAVSE GSMQVDASKV HPGVISGLNS PACMLSAPLE KQLFYYIGTM LPNTRPHSYV   300
FYQLRCHLSY VALSINGDKF QYTGAMTSKF LMGTYKRVTE KGDEHVLSLV FGKTKDLPDL   360
RGPFSYPSLT SAQSGDYSLV IVTTFVHYAN FHNYFVPNLK DMFSRAVTMT AASYARYVLQ   420
KLVLLEMKGG CREPELDTET LTTMFEVSVA FFKVGHAVGE TGNGCVDLRW LAKSFFELTV   480
LKDIIGICYG ATVKGMQSYG LERLAAMLMA TVKMEELGHL TTEKQEYALR LATVGYPKAG   540
VYSGLIGGAT SVLLSAYNRH PLFQPLHTVM RETLFIGSHV VRELRLNVT TQGPNLALYQ    600
LLSTALCSAL EIGEVLRGLA LGTESGLFSP CYLSLRFDLT RDKLLSMAPQ EATLDQAAVS   660
NAVDGFLGRL SLEREDRDAW HLPAYKCVDR LDKVLMIIPL INVTFIISSD REVRGSALYE   720
ASTTYLSSSL FLSPVIMNKC SQGAVAGEPR QIPKIQNFTR TQKSCIFCGF ALLSYDEKEG   780
LETTTYITSQ EVQNSILSSN YFDFDNLHVH YLLLTTNGTV MEIAGLYEER ASGGGSGGGS   840
GGGSGGGGEG GSESQVRQQF SKDIEKLLNE QVNKEMQSSN LYMSMSSWSY THSLDGAGLF   900
LFDHAAEEYE HAKKLIIFLN ENNVPVQLTS ISAPEHKFEG LTQIFQKAYE HEQHISESIN   960
NIVDHAIKCK DHATFNFLQW YVAEQHEEEV LFKDILDKIE LIGNENHGLY LADQYVKGIA  1020
KSRKS                                                              1025

SEQ ID NO: 19               moltype = AA   length = 1065
FEATURE                     Location/Qualifiers
REGION                      1..1065
                            note = Synthetic polypeptide
source                      1..1065
                            mol_type = protein
                            organism = synthetic construct
SEQUENCE: 19
MRAVGVFLAI CLVTIFVLPT WGNWAYPCCH VTQLRAQHLL ALENISDIYL VSNQTCDGFS    60
LASLNSPKNG SNQLVISRCA NGLNVVSFFI SILKRSSSAL TGHLRELLTT LETLYGSFSV   120
EDLFGANLNR YAWHRGGGGS GSASSGASAS GSSNGSGSGS GSNSSASSGA SSGGASGGSG   180
GSGAASLSEV KLHLDIEGHA SHYTIPWTEL MAKVPGLSPE ALWREANVTE DLASMLNRYK   240
LIYKTSGTLG IALAEPVDIP AVSEGSMQVD ASKVHPGVIS GLNSPACMLS APLEKQLFYY   300
IGTMLPNTRP HSYVFYQLRC HLSYVALSIN GDKFQYTGAM TSKFLMGTYK RVTEKGDEHV   360
LSLVFGKTKD LPDLRGPFSY PSLTSAQSGD YSLVIVTTFV HYANFHNYFV PNLKDMFSRA   420
VTMTAASYAR YVLQKLVLLE MKGGCREPEL DTETLTTMFE VSVAFFKVGH AVGETGNGCV   480
DLRWLAKSFF ELTVLKDIIG ICYGATVKGM QSYGLERLAA MLMATVKMEE LGHLTTEKQE   540
YALRLATVGY PKAGVYSGLI GGATSVLLSA YNRHPLFQPL HTVMRETLFI GSHVVRELR   600
LNVTTQGPNL ALYQLLSTAL CSALEIGEVL RGLALGTESG LFSPCYLSLR FDLTRDKLLS   660
MAPQEATLDQ AAVSNAVDGF LGRLSLERED RDAWHLPAYK CVDRLDKVLM IIPLINVTFI   720
ISSDREVRGS ALYEASTTYL SSSLFLSPVI MNKCSQGAVA GEPRQIPKIQ NFTRTQKSCI   780
FCGFALLSYD EKEGLETTTY ITSQEVQNSI LSSNYFDFDN LHVHYLLLTT NGTVMEIAGL   840
YEERASGGGS GSASSGASAS GSSGSGSGSG SSSASSGASS GGASGGGSGG SGESQVRQQF   900
SKDIEKLLNE QVNKEMQSSN LYMSMSSWSY THSLDGAGLF LFDHAAEEYE HAKKLIIFLN   960
ENNVPVQLTS ISAPEHKFEG LTQIFQKAYE HEQHISESIN NIVDHAIKCK DHATFNFLQW  1020
YVAEQHEEEV LFKDILDKIE LIGNENHGLY LADQYVKGIA KSRKS                  1065

SEQ ID NO: 20               moltype = AA   length = 1065
```

```
FEATURE              Location/Qualifiers
REGION               1..1065
                     note = Synthetic polypeptide
source               1..1065
                     mol_type = protein
                     organism = synthetic construct
SEQUENCE: 20
MRAVGVFLAI CLVTIFVLPT WGNWAYPCCH VTQLRAQHLL ALENISDIYL VSNQTCDGFS   60
LASLNSPKNG SNQLVISRCA NGLNVVSFFI SILKRSSSAL TGHLRELLTT LETLYGSFSV  120
EDLFGANLNR YAWHRGGGGS GSASSGASAS GSSNGSGSGS GSNSSASSGA SSGGASGGSG  180
GSGAASLSEV KLHLDIEGHA SHYTIPWTEL MAKVPGLSPE ALWREANVTE DLASMLNRYK  240
LIYKTSGTLG IALAEPVDIP AVSEGSMQVD ASKVHPGVIS GLNSPACMLS APLEKQLFYY  300
IGTMLPNTRP HSYVFYQLRC HLSYVALSIN GDKFQYTGAM TSKFLMGTYK RVTEKGDEHV  360
LSLVFGKTKD LPDLRGPFSY PSLTSAQSGD YSLVIVTTFV HYANFHNYFV PNLKDMFSRA  420
VTMTAASYAR YVLQKLVLLE MKGGCREPEL DTETLTTMFE VSVAFFKVGH AVGETGNGCV  480
DLRWLAKSFF ELTVLKDIIG ICYGATVKGM QSYGLERLAA MLMATVKMEE LGHLTTEKQE  540
YALRLATVGY PKAGVYSGLI GGATSVLLSA YNRHPLFQPL HTVMRETLFI GSHVVLRELR  600
LNVTTQGPNL ALYQLLSTAL CSALEIGEVL RGLALGTESG LFSPCYLSLR FDLTRDKLLS  660
MAPQEATLDQ AAVSNAVDGF LGRLSLERED RDAWHLPAYK CVDRLDKVLM IIPLINVTFI  720
ISSDREVRGS ALYEASTTYL SSSLFLSPVI MNKCSQGAVA GEPRQIPKIQ NFTRTQKSCI  780
FCGFALLSYD EKEGLETTTY ITSQEVQNSI LSSNYFDFDN LHVHYLLLTT NGTVMEIAGL  840
YEERASGGGS GSASSGASAS GSSCASSGSG SSSASSGASS GGASGGGSGG SGESQVRQQF  900
SKDIEKLLNE QVNKEMQSSN LYMSMSSWSY THSLDGAGLF LFDHAAEEYE HAKKLIIFLN  960
ENNVPVQLTS ISAPEHKFEG LTQIFQKAYE HEQHISESIN NIVDHAIKSK DHATFNFLQW 1020
YVAEQHEEEV LFKDILDKIE LIGNENHGLY LADQYVKGIA KSRKS               1065

SEQ ID NO: 21        moltype = AA   length = 1366
FEATURE              Location/Qualifiers
REGION               1..1366
                     note = Synthetic polypeptide
source               1..1366
                     mol_type = protein
                     organism = synthetic construct
SEQUENCE: 21
MRAVGVFLAI CLVTIFVLPT WGNWAYPCCH VTQLRAQHLL ALENISDIYL VSNQTCDGFS   60
LASLNSPKNG SNQLVISRCA NGLNVVSFFI SILKRSSSAL TGHLRELLTT LETLYGSFSV  120
EDLFGANLNR YAWHRGGGGS GSASSGASAS GSSNGSGSGS GSNSSASSGA SSGGASGGSG  180
GSGAASLSEV KLHLDIEGHA SHYTIPWTEL MAKVPGLSPE ALWREANVTE DLASMLNRYK  240
LIYKTSGTLG IALAEPVDIP AVSEGSMQVD ASKVHPGVIS GLNSPACMLS APLEKQLFYY  300
IGTMLPNTRP HSYVFYQLRC HLSYVALSIN GDKFQYTGAM TSKFLMGTYK RVTEKGDEHV  360
LSLVFGKTKD LPDLRGPFSY PSLTSAQSGD YSLVIVTTFV HYANFHNYFV PNLKDMFSRA  420
VTMTAASYAR YVLQKLVLLE MKGGCREPEL DTETLTTMFE VSVAFFKVGH AVGETGNGCV  480
DLRWLAKSFF ELTVLKDIIG ICYGATVKGM QSYGLERLAA MLMATVKMEE LGHLTTEKQE  540
YALRLATVGY PKAGVYSGLI GGATSVLLSA YNRHPLFQPL HTVMRETLFI GSHVVLRELR  600
LNVTTQGPNL ALYQLLSTAL CSALEIGEVL RGLALGTESG LFSPCYLSLR FDLTRDKLLS  660
MAPQEATLDQ AAVSNAVDGF LGRLSLERED RDAWHLPAYK CVDRLDKVLM IIPLINVTFI  720
ISSDREVRGS ALYEASTTYL SSSLFLSPVI MNKCSQGAVA GEPRQIPKIQ NFTRTQKSCI  780
FCGFALLSYD EKEGLETTTY ITSQEVQNSI LSSNYFDFDN LHVHYLLLTT NGTVMEIAGL  840
YEERASGGGS GSASSGASAS GSSGSGSGSG SSSASSGDSK GSSQKGSRLL LLLVVSNLLL  900
PQGVLAYFLP PRVRGGGRVA AAAITWVPKP NVEVWPVDPP PPVNFNKTAE QEYGDKEVKL  960
PHWTPTLHTF QVPQNYTKAN CTYCNTREYT FSYKGCCFYP TKKKHTWNGC FQACAELYPC 1020
TYFYGPTPDI LPVVTRNLNA IESLWVGVYR VGEGNWTSLD GGTFKVYQIF GSHCTYVSKF 1080
STVPVSHHEC SFLKPCLCVS QRSNGGSGSS ASSGASASGS SGSGSGSGSS SASSGASSGG 1140
ASGGSGGSGG GSGSASSGAS ASGSSGSGSG SGSSSASSGA SSGGASGGSG GSGESQVRQQ 1200
FSKDIEKLLN EQVNKEMQSS NLYMSMSSWS YTHSLDGAGL LFDHAAEEY EHAKKLIIFL 1260
NENNVPVQLT SISAPEHKFE GLTQIFQKAY EHEQHISESI NNIVDHAIKC KDHATFNFLQ 1320
WYVAEQHEEE VLFKDILDKI ELIGNENHGL YLADQYVKGI AKSRKS               1366

SEQ ID NO: 22        moltype = AA   length = 1065
FEATURE              Location/Qualifiers
REGION               1..1065
                     note = Synthetic polypeptide
source               1..1065
                     mol_type = protein
                     organism = synthetic construct
SEQUENCE: 22
MRAVGVFLAI CLVTIFVLPT WGNWAYPCCH VTQLRAQHLL ALENISDIYL VSNQTCDGFS   60
LASLNSPKNG SNQLVISRCA NGLNVVSFFI SILKRSSSAL TGHLRELLTT LETLYGSFSV  120
EDLFGANLNR YAWHRGGGGS GSASSGASAS GSSNGSGSGS GSNSSASSGA SSGGASGGSG  180
GSGAASLSEV KLHLDIEGHA SHYTIPWTEL MAKVPGLSPE ALWREANVTE DLASMLNRYK  240
LIYKTSGTLG IALAEPVDIP AVSEGSMQVD ASKVHPGVIS GLNSPACMLS APLEKQLFYY  300
IGTMLPNTRP HSYVFYQLRA HLSYVALSIN GDKFQYTGAM TSKFLMGTYK RVTEKGDEHV  360
LSLVFGKTKD LPDLRGPFSY PSLTSAQSGD YSLVIVTTFV HYANFHNYFV PNLKDMFSRA  420
VTMTAASYAR YVLQKLVLLE MKGGCREPEL DTETLTTMFE VSVAFFKVGH AVGETGNGCV  480
DLRWLAKSFF ELTVLKDIIG ICYGATVKGM QSYGLERLAA MLMATVKMEE LGHLTTEKQE  540
YALRLATVGY PKAGVYSGLI GGATSVLLSA YNRHPLFQPL HTVMRETLFI GSHVVLRELR  600
LNVTTQGPNL ALYQLLSTAL CSALEIGEVL RGLALGTESG LFSPCYLSLR FDLTRDKLLS  660
MAPQEATLDQ AAVSNAVDGF LGRLSLERED RDAWHLPAYK CVDRLDKVLM IIPLINVTFI  720
ISSDREVRGS ALYEASTTYL SSSLFLSPVI MNKCSQGAVA GEPRQIPKIQ NFTRTQKSCI  780
```

```
FCGFALLSYD EKEGLETTTY ITSQEVQNSI LSSNYFDFDN LHVHYLLLTT NGTVMEIAGL    840
YEERASGGGS GSASSGASAS GSSGSGSGSG SSSASSGASS GGASGGGSGG SGESQVRQQF    900
SKDIEKLLNE QVNKEMQSSN LYMSMSSWSY THSLDGAGLF LFDHAAEEYE HAKKLIIFLN    960
ENNVPVQLTS ISAPEHKFEG LTQIFQKAYE HEQHISESIN NIVDHAIKCK DHATFNFLQW   1020
YVAEQHEEEV LFKDILDKIE LIGNENHGLY LADQYVKGIA KSRKS                  1065

SEQ ID NO: 23           moltype = AA   length = 1065
FEATURE                 Location/Qualifiers
REGION                  1..1065
                        note = Synthetic polypeptide
source                  1..1065
                        mol_type = protein
                        organism = synthetic construct
SEQUENCE: 23
MRAVGVFLAI CLVTIFVLPT WGNWAYPCCH VTQLRAQHLL ALENISDIYL VSNQTCDGFS     60
LASLNSPKNG SNQLVISRCA NGLNVVSFFI SILKRSSSAL TGHLRELLTT LETLYGSFSV    120
EDLFGANLNR YAWHRGGGGS GSASSGASAS GSSNGSGSGS GSNSSASSGA SSGGASGGSG    180
GSGAASLSEV KLHLDIEGHA SHYTIPWTEL MAKVPGLSPE ALWREANVTE DLASMLNRYK    240
LIYKTSGTLG IALAEPVDIP AVSEGSMQVD ASKVHPGVIS GLNSPACMLS APLEKQLFYY    300
IGTMLPNTRP HSYVFYQLRA HLSYVALSIN GDKFQYTGAM TSKFLMGTYK RVTEKGDEHV    360
LSLVFGKTKD LPDLRGPFSY PSLTSAQSGD YSLVIVTTFV HYANFHNYFV PNLKDMFSRA    420
VTMTAASYAR YVLQKLVLLE MKGGCREPEL DTETLTTMFE VSVAFFKVGH AVGETGNGCV    480
DLRWLAKSFF ELTVLKDIIG ICYGATVKGM QSYGLERLAA MLMATVKMEE LGHLTTEKQE    540
YALRLATVGY PKAGVYSGLI GGATSVLLSA YNRHPLFQPL HTVMRETLFI GSHVVLRELR    600
LNVTTQGPNL ALYQLLSTAL CSALEIGEVL RGLALGTESG LFSPCYLSLR FDLTRDKLLS    660
MAPQEATLDQ AAVSNAVDGF LGRLSLERED RDAWHLPAYK CVDRLDKVLM IIPLINVTFI    720
ISSDREVRGS ALYEASTTYL SSSLFLSPVI MNKCSQGAVA GEPRQIPKIQ NFTRTQKSCI    780
FCGFALLSYD EKEGLETTTY ITSQEVQNSI LSSNYFDFDN LHVHYLLLTT NGTVMEIAGL    840
YEERASGGGS GSASSGASAS GSSCSGSGSG SSSASSGASS GGASGGGSGG SGESQVRQQF    900
SKDIEKLLNE QVNKEMQSSN LYMSMSSWSY THSLDGAGLF LFDHAAEEYE HAKKLIIFLN    960
ENNVPVQLTS ISAPEHKFEG LTQIFQKAYE HEQHISESIN NIVDHAIKSK DHATFNFLQW   1020
YVAEQHEEEV LFKDILDKIE LIGNENHGLY LADQYVKGIA KSRKS                  1065

SEQ ID NO: 24           moltype = AA   length = 648
FEATURE                 Location/Qualifiers
REGION                  1..648
                        note = Synthetic polypeptide
source                  1..648
                        mol_type = protein
                        organism = synthetic construct
SEQUENCE: 24
MDSKGSSQKG SRLLLLLVVS NLLLPQGVLA EAALLVCQYT IQSLIHLTGE DPGFFNVEIP     60
EFPFYPTCNV CTADVNVTIN FDVGKKHQL DLDFGQLTPH TKAVYQPRGA FGGSENATNL    120
FLLELLGAGE LALTMRSKKL PINVTTGEEQ QVSLESVDVY FQDVFGTMWC HHAEMQNPVY    180
LIPETVPYIK WDNCNSTNIT AVVRAQGLDV TLPLSLPTSA QDSNFSVKTE MLGNEIDIEC    240
IMEDGEISQV LPGDNKFNIT CSGYESHVPS GGILTSTSPV ATPIPGTGYA YSLRLTPRPV    300
SRFLGNNSIL YVFYSGNGPK ASGGDYCIQS NIVFSDEIPA SQDMPTNTTD ITYVGDNATY    360
SVPMVTSEDA NSPNVTVTAF WAWPNNTETD FKCKWTLTSG TPSGCENISG AFASNRTFDI    420
TVSGLGTAPK TLIITRTATN ATTTTHKVIF SKAPEGSTQC NVNPVQIPKD WITMHRSCRN    480
SMRQQIQMEV GASLQYLAMG AHFSKDVVNR PGFAQLFFDA ASEEREHAMK LIEYLLMRGE    540
LTNDVSSLLQ VRPPTRSSWK GGVEALEHAL SMESDVTKSI RNVIKACEDD SEFNDYHLVD    600
YLTGDFLEEQ YKGQRDLAGK ASTLKKLMDR HEALGEFIFD KKLLGIDV                648

SEQ ID NO: 25           moltype = AA   length = 1039
FEATURE                 Location/Qualifiers
REGION                  1..1039
                        note = Synthetic polypeptide
source                  1..1039
                        mol_type = protein
                        organism = synthetic construct
SEQUENCE: 25
MRAVGVFLAI CLVTIFVLPT WGNWAYPCCH VTQLRAQHLL ALENISDIYL VSNQTCDGFS     60
LASLNSPKNG SNQLVISRCA NGLNVVSFFI SILKRSSSAL TGHLRELLTT LETLYGSFSV    120
EDLFGANLNR YAWHRGGGGS GSASSGASAS GSSNGSGSGS GSNSSASSGA SSGGASGGSG    180
GSGAASLSEV KLHLDIEGHA SHYTIPWTEL MAKVPGLSPE ALWREANVTE DLASMLNRYK    240
LIYKTSGTLG IALAEPVDIP AVSEGSMQVD ASKVHPGVIS GLNSPACMLS APLEKQLFYY    300
IGTMLPNTRP HSYVFYQLRC HLSYVALSIN GDKFQYTGAM TSKFLMGTYK RVTEKGDEHV    360
LSLVFGKTKD LPDLRGPFSY PSLTSAQSGD YSLVIVTTFV HYANFHNYFV PNLKDMFSRA    420
VTMTAASYAR YVLQKLVLLE MKGGCREPEL DTETLTTMFE VSVAFFKVGH AVGETGNGCV    480
DLRWLAKSFF ELTVLKDIIG ICYGATVKGM QSYGLERLAA MLMATVKMEE LGHLTTEKQE    540
YALRLATVGY PKAGVYSGLI GGATSVLLSA YNRHPLFQPL HTVMRETLFI GSHVVLRELR    600
LNVTTQGPNL ALYQLLSTAL CSALEIGEVL RGLALGTESG LFSPCYLSLR FDLTRDKLLS    660
MAPQEATLDQ AAVSNAVDGF LGRLSLERED RDAWHLPAYK CVDRLDKVLM IIPLINVTFI    720
ISSDREVRGS ALYEASTTYL SSSLFLSPVI MNKCSQGAVA GEPRQIPKIQ NFTRTQKSCI    780
FCGFALLSYD EKEGLETTTY ITSQEVQNSI LSSNYFDFDN LHVHYLLLTT NGTVMEIAGL    840
YEERASGSTQ CNVNPVQIPK DWITMHRSCR NSMRQQIQME VGASLQYLAM GAHFSKDVVN    900
RPGFAQLFFD AASEEREHAM KLIEYLLMRG ELTNDVSSLL QVRPPTRSSW KGGVEALEHA    960
LSMESDVTKS IRNVIKACED DSEFNDYHLV DYLTGDFLEE QYKGQRDLAG KASTLKKLMD   1020
RHEALGEFIF DKKLLGIDV                                                1039
```

```
SEQ ID NO: 26            moltype = AA  length = 669
FEATURE                  Location/Qualifiers
REGION                   1..669
                         note = Synthetic polypeptide
source                   1..669
                         mol_type = protein
                         organism = synthetic construct
SEQUENCE: 26
MDSKGSSQKG SRLLLLLVVS NLLLPQGVLA EAALLVCQYT IQSLIHLTGE DPGFFNVEIP    60
EPFYPTCNV  CTADVNVTIN  FDVGGKKHQL DLDFGQLTPH TKAVYQPRGA FGGSENATNL  120
FLLELLGAGE LALTMRSKKL  PINVTTGEEQ QVSLESVDVY FQDVFGTMWC HHAEMQNPVY  180
LIPETVPYIK WDNCSTNIT   AVVRAQGLDV TLPLSLPTSA QDSNFSVKTE MLGNEIDIEC  240
IMEDGEISQV LPGDNKFNIT  CSGYESHVPS GGILTSTSPV ATPIPGTGYA YSLRLTPRPV  300
SRFLGNNSIL YVFYSGNGPK  ASGGDYCIQS NIVFSDEIPA SQDMPTNTTD ITYVGDNATY  360
SVPMVTSEDA NSPNVTVTAF  WAWPNNTETD FKCKWTLTSG TPSGCENISG AFASNRTFDI  420
TVSGLGTAPK TLIITRTATN  ATTTTHKVIF SKAPEGSADT CYNDVALDCG ITSNSLALPR  480
CNAVYGEYGS HGNVATELQA  YAKLHLERSY DYLLSAAYFN NYQTNRAGFS KLFKKLSDEA  540
WSKTIDIIKH VTKRGDKMNF  DQHSTMKTER KNYTAENHEL EALAKALDTQ KELAERAFYI  600
HREATRNSQH LHDPEIAQYL  EEEFIEDHAE KIRTLAGHTS DLKKFITANN GHDLSLALYV  660
FDEYLQKTV                                                           669

SEQ ID NO: 27            moltype = AA  length = 1060
FEATURE                  Location/Qualifiers
REGION                   1..1060
                         note = Synthetic polypeptide
source                   1..1060
                         mol_type = protein
                         organism = synthetic construct
SEQUENCE: 27
MRAVGVFLAI CLVTIFVLPT  WGNWAYPCCH VTQLRAQHLL ALENISDIYL VSNQTCDGFS    60
LASLNSPKNG SNQLVISRCA  NGLNVVSFFI SILKRSSSAL TGHLRELLTT LETLYGSFSV  120
EDLFGANLNR YAWHRGGGGS  GSASSGASAS GSSNGSGSGS GSNSSASSGA SSGGASGGSG  180
GSGAASLSEV KLHLDIEGHA  SHYTIPWTEL MAKVPGLSPE ALWREANVTE DLASMLNRYK  240
LIYKTSGTLG IALAEPVDIP  AVSEGSMQVD ASKVHPGVIS GLNSPACMLS APLEKQLFYY  300
IGTMLPNTRP HSYVFYQLRC  HLSYVALSIN GDKFQYTGAM TSKFLMGTYK RVTEKGDEHV  360
LSLVFGKTKD LPDLRGPFSY  PSLTSAQSGD YSLVIVTTFV HYANFHNYFV PNLKDMFSRA  420
VTMTAASYAR YVLQKLVLLE  MKGGCREPEL DTETLTTMFE VSVAFFKVGH AVGETGNGCV  480
DLRWLAKSFF ELTVLKDIIG  ICYGATVKGM QSYGLERLAA MLMATVKMEE LGHLTTEKQE  540
YALRLATVGY PKAGVYSGLI  GGATSVLLSA YNRHPLFQPL HTVMRETLFI GSHVVLRELR  600
LNVTTQGPNL ALYQLLSTAL  CSALEIGEVL RGLALGTESG LFSPCYLSLR FDLTRDKLLS  660
MAPQEATLDQ AAVSNAVDGF  LGRLSLERED RDAWHLPAYK CVDRLDKVLM IIPLINVTFI  720
ISSDREVRGS ALYEASTTYL  SSSLFLSPVI MNKCSQGAVA GEPRQIPKIQ NFTRTQKSCI  780
FCGFALLSYD EKEGLETTTY  ITSQEVQNSI LSSNYFDFDN LHVHYLLLTT NGTVMEIAGL  840
YEEERASGSAD TCYNDVALDC GITSNSLALP RCNAVYGEYG SHGNVATELQ AYAKLHLERS  900
YDYLLSAAYF NNYQTNRAGF  SKLFKKLSDE AWSKTIDIIK HVTKRGDKMN FDQHSTMKTE  960
RKNYTAENHE LEALAKALDT  QKELAERAFY IHREATRNSQ HLHDPEIAQY LEEEFIEDHA  1020
EKIRTLAGHT SDLKKFITAN  NGHDLSLALY VFDEYLQKTV                        1060

SEQ ID NO: 28            moltype = AA  length = 16
FEATURE                  Location/Qualifiers
REGION                   1..16
                         note = Synthetic polypeptide
source                   1..16
                         mol_type = protein
                         organism = synthetic construct
SEQUENCE: 28
GGGGSGGGGS GGGGSG                                                    16

SEQ ID NO: 29            moltype = AA  length = 28
FEATURE                  Location/Qualifiers
REGION                   1..28
                         note = Synthetic polypeptide
source                   1..28
                         mol_type = protein
                         organism = synthetic construct
SEQUENCE: 29
GGSGSGSNSS ASSGASSGGA SGGSGGSG                                       28

SEQ ID NO: 30            moltype = AA  length = 46
FEATURE                  Location/Qualifiers
REGION                   1..46
                         note = Synthetic polypeptide
source                   1..46
                         mol_type = protein
                         organism = synthetic construct
SEQUENCE: 30
GGSGSASSGA SASGSSNGSG SGSGSNSSAS SGASSGGASG GSGGGSG                  46
```

```
SEQ ID NO: 31              moltype = AA   length = 26
FEATURE                    Location/Qualifiers
REGION                     1..26
                           note = Synthetic polypeptide
source                     1..26
                           mol_type = protein
                           organism = synthetic construct
SEQUENCE: 31
GGSGSASAEA AAKEAAAKAG GSGGSG                                          26

SEQ ID NO: 32              moltype = AA   length = 32
FEATURE                    Location/Qualifiers
REGION                     1..32
                           note = Synthetic polypeptide
source                     1..32
                           mol_type = protein
                           organism = synthetic construct
SEQUENCE: 32
GGSGSASAEA AAKEAAAKEA AAKASGGSGG SG                                   32

SEQ ID NO: 33              moltype = AA   length = 47
FEATURE                    Location/Qualifiers
REGION                     1..47
                           note = Synthetic polypeptide
source                     1..47
                           mol_type = protein
                           organism = synthetic construct
SEQUENCE: 33
SGGGSGSASS GASASGSSCS GSGSGSSSAS SGASSGGASG GGSGGSG                   47

SEQ ID NO: 34              moltype = AA   length = 228
FEATURE                    Location/Qualifiers
source                     1..228
                           mol_type = protein
                           organism = Human herpesvirus 4
SEQUENCE: 34
DSKGSSQKGS RLLLLLVVSN LLLPQGVLAY FLPPRVRGGG RVAAAAITWV PKPNVEVWPV     60
DPPPPVNFNK TAEQEYGDKE VKLPHWTPTL HTFQVPQNYT KANCTYCNTR EYTFSYKGCC    120
FYFTKKKHTW NGCFQACAEL YPCTYFYGPT PDILPVVTRN LNAIESLWVG VYRVGEGNWT    180
SLDGGTFKVY QIFGSHCTYV SKFSTVPVSH HECSFLKPCL CVSQRSNS                 228

SEQ ID NO: 35              moltype = DNA   length = 22
FEATURE                    Location/Qualifiers
misc_feature               1..22
                           note = Synthetic oligonucleotide
source                     1..22
                           mol_type = other DNA
                           organism = synthetic construct
SEQUENCE: 35
tgactgtgaa cgttcgagat ga                                             22

SEQ ID NO: 36              moltype = AA   length = 115
FEATURE                    Location/Qualifiers
source                     1..115
                           mol_type = protein
                           organism = Human herpesvirus 4
SEQUENCE: 36
NWAYPCCHVT QLRAQHLLAL ENISDIYLVS NQTCDGFSLA SLNSPKNGSN QLVISRCANG     60
LNVVSFFISI LKRSSSALTG HLRELLTTLE TLYGSFSVED LFGANLNRYA WHRGG         115

SEQ ID NO: 37              moltype = AA   length = 662
FEATURE                    Location/Qualifiers
source                     1..662
                           mol_type = protein
                           organism = Human herpesvirus 4
SEQUENCE: 37
AASLSEVKLH LDIEGHASHY TIPWTELMAK VPGLSPEALW REANVTEDLA SMLNRYKLIY     60
KTSGTLGIAL AEPVDIPAVS EGSMQVDASK VHPGVISGLN SPACMLSAPL EKQLFYYIGT    120
MLPNTRPHSY VFYQLRCHLS YVALSINGDK FQYTGAMTSK FLMGTYKRVT EKGDEHVLSL    180
VFGKTKDLPD LRGPFSYPSL TSAQSGDYSL VIVTTFVHYA NFHNYFVPNL KDMFSRAVTM    240
TAASYARYVL QKLVLLEMKG GCREPELDTE TLTTMFEVSV AFFKVGHAVG ETGNGCVDLR    300
WLAKSFFELT VLKDIIGICY GATVKGMQSY GLERLAAMLM ATVKMEELGH LTTEKQEYAL    360
RLATVGYPKA GVYSGLIGGA TSVLLSAYNR HPLFQPLHTV MRETLFIGSH VVLRELRLNV    420
TTQGPNLALY QLLSTALCSA LEIGEVLRGL ALGTESGLFS PCYLSLRFDL TRDKLLSMAP    480
QEATLDQAAV SNAVDGFLGR LSLEREDRDA WHLPAYKCVD RLDKVLMIIP LINVTFIISS    540
DREVRGSALY EASTTYLSSS LFLSPVIMNK CSQGAVAGEP RQIPKIQNFT RTQKSCIFCG    600
FALLSYDEKE GLETTTYITS QEVQNSILSS NYFDFDNLHV HYLLLTTNGT VMEIAGLYEE    660
RA                                                                  662
```

```
SEQ ID NO: 38            moltype = AA  length = 425
FEATURE                  Location/Qualifiers
source                   1..425
                         mol_type = protein
                         organism = Human herpesvirus 4
SEQUENCE: 38
EAALLVCQYT IQSLIHLTGE DPGFFNVEIP EFPFYPTCNV CTADVNVTIN FDVGGKKHQL   60
DLDFGQLTPH TKAVYQPRGA FGGSENATNL FLLELLGAGE LALTMRSKKL PINVTTGEEQ  120
QVSLESVDVY PQDVFGTMWC HHAEMQNPVY LIPETVPYIK WDNCNSTNIT AVVRAQGLDV  180
TLPLSLPTSA QDSNFSVKTE MLGNEIDIEC IMEDGEISQV LPGDNKFNIT CSGYESHVPS  240
GGILTSTSPV ATPIPGTGYA YSLRLTPRPV SRFLGNNSIL YVFYSGNGPK ASGGDYCIQS  300
NIVFSDEIPA SQDMPTNTTD ITYVGDNATY SVPMVTSEDA NSPNVTVTAF WAWPNNTETD  360
FKCKWTLTSG TPSGCENISG AFASNRTFDI TVSGLGTAPK TLIITRTATN ATTTTHKVIF  420
SKAPE                                                              425

SEQ ID NO: 39            moltype = AA  length = 15
FEATURE                  Location/Qualifiers
REGION                   1..15
                         note = Synthetic polypeptide
source                   1..15
                         mol_type = protein
                         organism = synthetic construct
SEQUENCE: 39
CLVPRGSLEH HHHHH                                                   15

SEQ ID NO: 40            moltype = AA  length = 154
FEATURE                  Location/Qualifiers
source                   1..154
                         mol_type = protein
                         organism = Aquifex aeolicus
SEQUENCE: 40
MQIYEGKLTA EGLRFGIVAS RFNHALVDRL VEGAIDCIVR HGGREEDITL VRVPGSWEIP   60
VAAGELARKE DIDAVIAIGV LIRGATPHFD YIASEVSKGL ANLSLELRKP ITFGVITADT  120
LEQAIERAGT KHGNKGWEAA LSAIEMANLF KSLR                              154

SEQ ID NO: 41            moltype = AA  length = 156
FEATURE                  Location/Qualifiers
source                   1..156
                         mol_type = protein
                         organism = Escherichia coli
SEQUENCE: 41
MNIIEANVAT PDARVAITIA RFNNFINDSL LEGAIDALKR IGQVKDENIT VVWVPGAYEL   60
PLAAGALAKT GKYDAVIALG TVIRGGTAHF EYVAGGASNG LAHVAQDSEI PVAFGVLTTE  120
SIEQAIERAG TKAGNKGAEA ALTALEMINV LKAIKA                            156

SEQ ID NO: 42            moltype =     length =
SEQUENCE: 42
000

SEQ ID NO: 43            moltype =     length =
SEQUENCE: 43
000

SEQ ID NO: 44            moltype =     length =
SEQUENCE: 44
000

SEQ ID NO: 45            moltype =     length =
SEQUENCE: 45
000

SEQ ID NO: 46            moltype =     length =
SEQUENCE: 46
000

SEQ ID NO: 47            moltype =     length =
SEQUENCE: 47
000

SEQ ID NO: 48            moltype =     length =
SEQUENCE: 48
000

SEQ ID NO: 49            moltype =     length =
SEQUENCE: 49
000

SEQ ID NO: 50            moltype =     length =
SEQUENCE: 50
```

000

SEQ ID NO: 51        moltype =    length =
SEQUENCE: 51
000

SEQ ID NO: 52        moltype =    length =
SEQUENCE: 52
000

SEQ ID NO: 53        moltype =    length =
SEQUENCE: 53
000

SEQ ID NO: 54        moltype =    length =
SEQUENCE: 54
000

SEQ ID NO: 55        moltype =    length =
SEQUENCE: 55
000

SEQ ID NO: 56        moltype =    length =
SEQUENCE: 56
000

SEQ ID NO: 57        moltype =    length =
SEQUENCE: 57
000

SEQ ID NO: 58        moltype =    length =
SEQUENCE: 58
000

SEQ ID NO: 59        moltype =    length =
SEQUENCE: 59
000

SEQ ID NO: 60        moltype =    length =
SEQUENCE: 60
000

SEQ ID NO: 61        moltype =    length =
SEQUENCE: 61
000

SEQ ID NO: 62        moltype =    length =
SEQUENCE: 62
000

SEQ ID NO: 63        moltype =    length =
SEQUENCE: 63
000

SEQ ID NO: 64        moltype =    length =
SEQUENCE: 64
000

SEQ ID NO: 65        moltype =    length =
SEQUENCE: 65
000

SEQ ID NO: 66        moltype =    length =
SEQUENCE: 66
000

SEQ ID NO: 67        moltype =    length =
SEQUENCE: 67
000

SEQ ID NO: 68        moltype =    length =
SEQUENCE: 68
000

SEQ ID NO: 69        moltype =    length =
SEQUENCE: 69
000

SEQ ID NO: 70        moltype =    length =

| | | |
|---|---|---|
| SEQUENCE: 70 000 | | |
| SEQ ID NO: 71 SEQUENCE: 71 000 | moltype = | length = |
| SEQ ID NO: 72 SEQUENCE: 72 000 | moltype = | length = |
| SEQ ID NO: 73 SEQUENCE: 73 000 | moltype = | length = |
| SEQ ID NO: 74 SEQUENCE: 74 000 | moltype = | length = |
| SEQ ID NO: 75 SEQUENCE: 75 000 | moltype = | length = |
| SEQ ID NO: 76 SEQUENCE: 76 000 | moltype = | length = |
| SEQ ID NO: 77 SEQUENCE: 77 000 | moltype = | length = |
| SEQ ID NO: 78 SEQUENCE: 78 000 | moltype = | length = |
| SEQ ID NO: 79 SEQUENCE: 79 000 | moltype = | length = |
| SEQ ID NO: 80 SEQUENCE: 80 000 | moltype = | length = |
| SEQ ID NO: 81 SEQUENCE: 81 000 | moltype = | length = |
| SEQ ID NO: 82 SEQUENCE: 82 000 | moltype = | length = |
| SEQ ID NO: 83 SEQUENCE: 83 000 | moltype = | length = |
| SEQ ID NO: 84 SEQUENCE: 84 000 | moltype = | length = |
| SEQ ID NO: 85 SEQUENCE: 85 000 | moltype = | length = |
| SEQ ID NO: 86 SEQUENCE: 86 000 | moltype = | length = |
| SEQ ID NO: 87 SEQUENCE: 87 000 | moltype = | length = |
| SEQ ID NO: 88 SEQUENCE: 88 000 | moltype = | length = |
| SEQ ID NO: 89 SEQUENCE: 89 000 | moltype = | length = |

| | | |
|---|---|---|
| SEQ ID NO: 90<br>SEQUENCE: 90<br>000 | moltype = | length = |
| SEQ ID NO: 91<br>SEQUENCE: 91<br>000 | moltype = | length = |
| SEQ ID NO: 92<br>SEQUENCE: 92<br>000 | moltype = | length = |
| SEQ ID NO: 93<br>SEQUENCE: 93<br>000 | moltype = | length = |
| SEQ ID NO: 94<br>SEQUENCE: 94<br>000 | moltype = | length = |
| SEQ ID NO: 95<br>SEQUENCE: 95<br>000 | moltype = | length = |
| SEQ ID NO: 96<br>SEQUENCE: 96<br>000 | moltype = | length = |
| SEQ ID NO: 97<br>SEQUENCE: 97<br>000 | moltype = | length = |
| SEQ ID NO: 98<br>SEQUENCE: 98<br>000 | moltype = | length = |
| SEQ ID NO: 99<br>SEQUENCE: 99<br>000 | moltype = | length = |
| SEQ ID NO: 100<br>SEQUENCE: 100<br>000 | moltype = | length = |
| SEQ ID NO: 101<br>SEQUENCE: 101<br>000 | moltype = | length = |
| SEQ ID NO: 102<br>SEQUENCE: 102<br>000 | moltype = | length = |
| SEQ ID NO: 103<br>SEQUENCE: 103<br>000 | moltype = | length = |
| SEQ ID NO: 104<br>SEQUENCE: 104<br>000 | moltype = | length = |
| SEQ ID NO: 105<br>SEQUENCE: 105<br>000 | moltype = | length = |
| SEQ ID NO: 106<br>SEQUENCE: 106<br>000 | moltype = | length = |
| SEQ ID NO: 107<br>SEQUENCE: 107<br>000 | moltype = | length = |
| SEQ ID NO: 108<br>SEQUENCE: 108<br>000 | moltype = | length = |
| SEQ ID NO: 109<br>SEQUENCE: 109<br>000 | moltype = | length = |

| | | |
|---|---|---|
| SEQ ID NO: 110 SEQUENCE: 110 000 | moltype = | length = |
| SEQ ID NO: 111 SEQUENCE: 111 000 | moltype = | length = |
| SEQ ID NO: 112 SEQUENCE: 112 000 | moltype = | length = |
| SEQ ID NO: 113 SEQUENCE: 113 000 | moltype = | length = |
| SEQ ID NO: 114 SEQUENCE: 114 000 | moltype = | length = |
| SEQ ID NO: 115 SEQUENCE: 115 000 | moltype = | length = |
| SEQ ID NO: 116 SEQUENCE: 116 000 | moltype = | length = |
| SEQ ID NO: 117 SEQUENCE: 117 000 | moltype = | length = |
| SEQ ID NO: 118 SEQUENCE: 118 000 | moltype = | length = |
| SEQ ID NO: 119 SEQUENCE: 119 000 | moltype = | length = |
| SEQ ID NO: 120 SEQUENCE: 120 000 | moltype = | length = |
| SEQ ID NO: 121 SEQUENCE: 121 000 | moltype = | length = |
| SEQ ID NO: 122 SEQUENCE: 122 000 | moltype = | length = |
| SEQ ID NO: 123 SEQUENCE: 123 000 | moltype = | length = |
| SEQ ID NO: 124 SEQUENCE: 124 000 | moltype = | length = |
| SEQ ID NO: 125 SEQUENCE: 125 000 | moltype = | length = |
| SEQ ID NO: 126 SEQUENCE: 126 000 | moltype = | length = |
| SEQ ID NO: 127 SEQUENCE: 127 000 | moltype = | length = |
| SEQ ID NO: 128 SEQUENCE: 128 000 | moltype = | length = |
| SEQ ID NO: 129 SEQUENCE: 129 | moltype = | length = |

000

SEQ ID NO: 130          moltype =      length =
SEQUENCE: 130
000

SEQ ID NO: 131          moltype =      length =
SEQUENCE: 131
000

SEQ ID NO: 132          moltype =      length =
SEQUENCE: 132
000

SEQ ID NO: 133          moltype =      length =
SEQUENCE: 133
000

SEQ ID NO: 134          moltype =      length =
SEQUENCE: 134
000

SEQ ID NO: 135          moltype =      length =
SEQUENCE: 135
000

SEQ ID NO: 136          moltype =      length =
SEQUENCE: 136
000

SEQ ID NO: 137          moltype =      length =
SEQUENCE: 137
000

SEQ ID NO: 138          moltype =      length =
SEQUENCE: 138
000

SEQ ID NO: 139          moltype =      length =
SEQUENCE: 139
000

SEQ ID NO: 140          moltype =      length =
SEQUENCE: 140
000

SEQ ID NO: 141          moltype =      length =
SEQUENCE: 141
000

SEQ ID NO: 142          moltype =      length =
SEQUENCE: 142
000

SEQ ID NO: 143          moltype =      length =
SEQUENCE: 143
000

SEQ ID NO: 144          moltype =      length =
SEQUENCE: 144
000

SEQ ID NO: 145          moltype =      length =
SEQUENCE: 145
000

SEQ ID NO: 146          moltype =      length =
SEQUENCE: 146
000

SEQ ID NO: 147          moltype =      length =
SEQUENCE: 147
000

SEQ ID NO: 148          moltype =      length =
SEQUENCE: 148
000

SEQ ID NO: 149          moltype =      length =

| | | |
|---|---|---|
| SEQUENCE: 149 000 | | |
| SEQ ID NO: 150 SEQUENCE: 150 000 | moltype = | length = |
| SEQ ID NO: 151 SEQUENCE: 151 000 | moltype = | length = |
| SEQ ID NO: 152 SEQUENCE: 152 000 | moltype = | length = |
| SEQ ID NO: 153 SEQUENCE: 153 000 | moltype = | length = |
| SEQ ID NO: 154 SEQUENCE: 154 000 | moltype = | length = |
| SEQ ID NO: 155 SEQUENCE: 155 000 | moltype = | length = |
| SEQ ID NO: 156 SEQUENCE: 156 000 | moltype = | length = |
| SEQ ID NO: 157 SEQUENCE: 157 000 | moltype = | length = |
| SEQ ID NO: 158 SEQUENCE: 158 000 | moltype = | length = |
| SEQ ID NO: 159 SEQUENCE: 159 000 | moltype = | length = |
| SEQ ID NO: 160 SEQUENCE: 160 000 | moltype = | length = |
| SEQ ID NO: 161 SEQUENCE: 161 000 | moltype = | length = |
| SEQ ID NO: 162 SEQUENCE: 162 000 | moltype = | length = |
| SEQ ID NO: 163 SEQUENCE: 163 000 | moltype = | length = |
| SEQ ID NO: 164 SEQUENCE: 164 000 | moltype = | length = |
| SEQ ID NO: 165 SEQUENCE: 165 000 | moltype = | length = |
| SEQ ID NO: 166 SEQUENCE: 166 000 | moltype = | length = |
| SEQ ID NO: 167 SEQUENCE: 167 000 | moltype = | length = |
| SEQ ID NO: 168 SEQUENCE: 168 000 | moltype = | length = |

| | | |
|---|---|---|
| SEQ ID NO: 169 SEQUENCE: 169 | moltype = | length = 000 |
| SEQ ID NO: 170 SEQUENCE: 170 | moltype = | length = 000 |
| SEQ ID NO: 171 SEQUENCE: 171 | moltype = | length = 000 |
| SEQ ID NO: 172 SEQUENCE: 172 | moltype = | length = 000 |
| SEQ ID NO: 173 SEQUENCE: 173 | moltype = | length = 000 |
| SEQ ID NO: 174 SEQUENCE: 174 | moltype = | length = 000 |
| SEQ ID NO: 175 SEQUENCE: 175 | moltype = | length = 000 |
| SEQ ID NO: 176 SEQUENCE: 176 | moltype = | length = 000 |
| SEQ ID NO: 177 SEQUENCE: 177 | moltype = | length = 000 |
| SEQ ID NO: 178 SEQUENCE: 178 | moltype = | length = 000 |
| SEQ ID NO: 179 SEQUENCE: 179 | moltype = | length = 000 |
| SEQ ID NO: 180 SEQUENCE: 180 | moltype = | length = 000 |
| SEQ ID NO: 181 SEQUENCE: 181 | moltype = | length = 000 |
| SEQ ID NO: 182 SEQUENCE: 182 | moltype = | length = 000 |
| SEQ ID NO: 183 SEQUENCE: 183 | moltype = | length = 000 |
| SEQ ID NO: 184 SEQUENCE: 184 | moltype = | length = 000 |
| SEQ ID NO: 185 SEQUENCE: 185 | moltype = | length = 000 |
| SEQ ID NO: 186 SEQUENCE: 186 | moltype = | length = 000 |
| SEQ ID NO: 187 SEQUENCE: 187 | moltype = | length = 000 |
| SEQ ID NO: 188 SEQUENCE: 188 | moltype = | length = 000 |

```
SEQ ID NO: 189        moltype =    length =
SEQUENCE: 189
000

SEQ ID NO: 190        moltype =    length =
SEQUENCE: 190
000

SEQ ID NO: 191        moltype =    length =
SEQUENCE: 191
000

SEQ ID NO: 192        moltype =    length =
SEQUENCE: 192
000

SEQ ID NO: 193        moltype =    length =
SEQUENCE: 193
000

SEQ ID NO: 194        moltype =    length =
SEQUENCE: 194
000

SEQ ID NO: 195        moltype =    length =
SEQUENCE: 195
000

SEQ ID NO: 196        moltype =    length =
SEQUENCE: 196
000

SEQ ID NO: 197        moltype =    length =
SEQUENCE: 197
000

SEQ ID NO: 198        moltype =    length =
SEQUENCE: 198
000

SEQ ID NO: 199        moltype =    length =
SEQUENCE: 199
000

SEQ ID NO: 200        moltype =    length =
SEQUENCE: 200
000

SEQ ID NO: 201        moltype = AA   length = 173
FEATURE               Location/Qualifiers
REGION                1..173
                      note = Synthetic polypeptide
source                1..173
                      mol_type = protein
                      organism = synthetic construct
SEQUENCE: 201
ESQVRQQFSK DIEKLLNEQV NKEMQSSNLY MCMSSWSYTH SLDGAGLFLF DHAAEEYEHA    60
KKLIIFLNEN NVPVQLTSIS APEHKFEGLT QIFQKAYEHE QHISESINNI VDHAIKSKDH   120
ATFNFLQWYV AEQHEEEVLF KDILDKIELI GNENHGLYLA DQYVKGIAKS RKS          173

SEQ ID NO: 202        moltype = AA   length = 173
FEATURE               Location/Qualifiers
REGION                1..173
                      note = Synthetic polypeptide
source                1..173
                      mol_type = protein
                      organism = synthetic construct
SEQUENCE: 202
ESQVRQQFSK DIEKLLNEQV NKEMQSSNLY MSMSSWSYTH SLDGAGLFLF DHAAEEYEHA    60
KKLIIFLNEN NVPVQLTCIS APEHKFEGLT QIFQKAYEHE QHISESINNI VDHAIKSKDH   120
ATFNFLQWYV AEQHEEEVLF KDILDKIELI GNENHGLYLA DQYVKGIAKS RKS          173

SEQ ID NO: 203        moltype = AA   length = 173
FEATURE               Location/Qualifiers
REGION                1..173
                      note = Synthetic polypeptide
source                1..173
                      mol_type = protein
```

```
                       organism = synthetic construct
SEQUENCE: 203
ESQVRQQFSK DIEKLLNEQV NKEMQSSNLY MSMSSWSYTH SLDGAGLFLF DHAAEEYEHA    60
KKLIIFLNEN NVPVQLTSIS CPEHKFEGLT QIFQKAYEHE QHISESINNI VDHAIKSKDH   120
ATFNFLQWYV AEQHEEEVLF KDILDKIELI GNENHGLYLA DQYVKGIAKS RKS          173

SEQ ID NO: 204         moltype = AA  length = 173
FEATURE                Location/Qualifiers
REGION                 1..173
                       note = Synthetic polypeptide
source                 1..173
                       mol_type = protein
                       organism = synthetic construct
SEQUENCE: 204
ESQVRQQFSK DIEKLLNEQV NKEMQSSNLY MSMSSWSYTH SLDGAGLFLF DHAAEEYEHA    60
KKLIIFLNEN NVPVQLTSIS APEHCFEGLT QIFQKAYEHE QHISESINNI VDHAIKSKDH   120
ATFNFLQWYV AEQHEEEVLF KDILDKIELI GNENHGLYLA DQYVKGIAKS RKS          173

SEQ ID NO: 205         moltype = AA  length = 173
FEATURE                Location/Qualifiers
REGION                 1..173
                       note = Synthetic polypeptide
source                 1..173
                       mol_type = protein
                       organism = synthetic construct
SEQUENCE: 205
ESQVRQQFSK DIEKLLNEQV NKEMQSSNLY MSMSSWSYTH SLDGAGLFLF DHAAEEYEHA    60
KKLIIFLNEN NVPVQLTSIS APEHKFEGLT QIFQKAYEHE QHISECINNI VDHAIKSKDH   120
ATFNFLQWYV AEQHEEEVLF KDILDKIELI GNENHGLYLA DQYVKGIAKS RKS          173

SEQ ID NO: 206         moltype = AA  length = 173
FEATURE                Location/Qualifiers
REGION                 1..173
                       note = Synthetic polypeptide
source                 1..173
                       mol_type = protein
                       organism = synthetic construct
SEQUENCE: 206
ESQVRQQFSK DIEKLLNEQV NKEMQSSNLY MSMSSWSYTH SLDGAGLFLF DHAAEEYEHA    60
KKLIIFLNEN NVPVQLTSIS APEHKFEGLT QIFQKAYEHE QHISESINNI VDHAIKCKDH   120
ATFNFLQWYV AEQHEEEVLF KDILDKIELI GNENHGLYLA DQYVKGIAKS RKS          173

SEQ ID NO: 207         moltype = AA  length = 173
FEATURE                Location/Qualifiers
REGION                 1..173
                       note = Synthetic polypeptide
source                 1..173
                       mol_type = protein
                       organism = synthetic construct
SEQUENCE: 207
ESQVRQQFSK DIEKLLNCQV NKEMQSSNLY MSMSSWSYTH SLDGAGLFLF DHAAEEYEHA    60
KKLIIFLNEN NVPVQLTSIS APEHKFEGLT QIFQKAYEHE QHISESINNI VDHAIKSKDH   120
ATFNFLQWYV AEQHEEEVLF KDILDKIELI GNENHGLYLA DQYVKGIAKS RKS          173

SEQ ID NO: 208         moltype = AA  length = 173
FEATURE                Location/Qualifiers
REGION                 1..173
                       note = Synthetic polypeptide
source                 1..173
                       mol_type = protein
                       organism = synthetic construct
SEQUENCE: 208
ESQVRQQFSK DIEKLLNEQV NKEMNSSNLY MSMSSWCYTH SLDGAGLFLF DHAAEEYEHA    60
KKLIIFLNEN NVPVQLTSIS APEHKFEGLT QIFQKAYEHE QHISESINNI VDHAIKSKDH   120
ATFNFLQWYV AEQHEEEVLF KDILDKIELI GNENHGLYLA DQYVKGIAKS RKS          173

SEQ ID NO: 209         moltype = AA  length = 166
FEATURE                Location/Qualifiers
source                 1..166
                       mol_type = protein
                       organism = Helicobacter pylori
SEQUENCE: 209
LSKDIIKLLN EQVNKEMNSS NLYMSMSSWC YTHSLDGAGL FLFDHAAEEY EHAKKLIIFL    60
NENNVPVQLT SISAPEHKFE GLTQIFQKAY EHEQHISESI NNIVDHAIKS KDHATFNFLQ   120
WYVAEQHEEE VLFKDILDKI ELIGNENHGL YLADQYVKGI AKSRKS                  166

SEQ ID NO: 210         moltype = DNA  length = 22
FEATURE                Location/Qualifiers
misc_feature           1..22
```

```
                        note = Synthetic oligonucleotide
source                  1..22
                        mol_type = other DNA
                        organism = synthetic construct
SEQUENCE: 210
tgactgtgaa cgttcgagat ga                                              22

SEQ ID NO: 211          moltype = AA  length = 191
FEATURE                 Location/Qualifiers
source                  1..191
                        mol_type = protein
                        organism = Trichoplusia ni
SEQUENCE: 211
TQCNVNPVQI PKDWITMHRS CRNSMRQQIQ MEVGASLQYL AMGAHFSKDV VNRPGFAQLF      60
FDAASEEREH AMKLIEYLLM RGELTNDVSS LLQVRPPTRS SWKGGVEALE HALSMESDVT     120
KSIRNVIKAC EDDSEFNDYH LVDYLTGDFL EEQYKGQRDL AGKASTLKKL MDRHEALGEF     180
IFDKKLLGID V                                                         191

SEQ ID NO: 212          moltype = AA  length = 212
FEATURE                 Location/Qualifiers
source                  1..212
                        mol_type = protein
                        organism = Trichoplusia ni
SEQUENCE: 212
ADTCYNDVAL DCGITSNSLA LPRCNAVYGE YGSHGNVATE LQAYAKLHLE RSYDYLLSAA      60
YFNNYQTNRA GFSKLFKKLS DEAWSKTIDI IKHVTKRGDK MNFDQHSTMK TERKNYTAEN     120
HELEALAKAL DTQKELAERA FYIHREATRN SQHLHDPEIA QYLEEEFIED HAEKIRTLAG     180
HTSDLKKFIT ANNGHDLSLA LYVFDEYLQK TV                                  212

SEQ ID NO: 213          moltype = AA  length = 174
FEATURE                 Location/Qualifiers
source                  1..174
                        mol_type = protein
                        organism = Pyrococcus furiosus
SEQUENCE: 213
MLSERMLKAL NDQLNRELYS AYLYFAMAAY FEDLGLEGFA NWMKAQAEEE IGHALRFYNY      60
IYDRNGRVEL DEIPKPPKEW ESPLKAFEAA YEHEKFISKS IYELAALAEE EKDYSTRAFL     120
EWFINEQVEE EASVKKILDK LKFAKDSPQI LFMLDKELSA RAPKLPGLLM QGGE           174

SEQ ID NO: 214          moltype = AA  length = 183
FEATURE                 Location/Qualifiers
source                  1..183
                        mol_type = protein
                        organism = Homo sapiens
SEQUENCE: 214
MTTASTSQVR QNYHQDSEAA INRQINLELY ASYVYLSMSY YFDRDDVALK NFAKYFLHQS      60
HEEREHAEKL MKLQNQRGGR IFLQDIKKPD CDDWESGLNA MECALHLEKN VQQSLLELHK     120
LATDKNDPHL CDFIETHYLN EQVKAIKELG DHVTNLRKMG APESGLAEYL FDKHTLGDSD     180
QES                                                                  183

SEQ ID NO: 215          moltype = AA  length = 204
FEATURE                 Location/Qualifiers
source                  1..204
                        mol_type = protein
                        organism = Homo sapiens
SEQUENCE: 215
MDSKGSSQKG SRLLLLLVVS NLLLPQGVLA SSQIRQNYST DVEAAVNSLV NLYLQASYTY      60
LSLGFYFDRD DVALEGVSHF FRELAEEKRE GYERLLKMQN QRGGRALFQD IKKPAEDEWG     120
KTPDAMKAAM ALEKKLNQAL LDLHALGSAR TDPHLCDFLE THFLDEEVKL IKKMGDHLTN     180
LHRLGGPEAG LGEYLFERLT LKHD                                           204

SEQ ID NO: 216          moltype = AA  length = 154
FEATURE                 Location/Qualifiers
source                  1..154
                        mol_type = protein
                        organism = Aquifex aeolicus
SEQUENCE: 216
MQIYEGKLTA EGLRFGIVAS RFNHALVDRL VEGAIDCIVR HGGREEDITL VRVPGSWEIP      60
VAAGELARKE DIDAVIAIGV LIRGATPHFD YIASEVSKGL ANLSLELRKP ITFGVITADT     120
LEQAIERAGT KHGNKGWEAA LSAIEMANLF KSLR                                154

SEQ ID NO: 217          moltype = AA  length = 8
FEATURE                 Location/Qualifiers
REGION                  1..8
                        note = Bullfrog linker sequence
source                  1..8
                        mol_type = protein
                        organism = unidentified
SEQUENCE: 217
```

```
ESQVRQQF                                                                   8

SEQ ID NO: 218            moltype = AA   length = 15
FEATURE                   Location/Qualifiers
REGION                    1..15
                          note = Synthetic polypeptide
source                    1..15
                          mol_type = protein
                          organism = synthetic construct
SEQUENCE: 218
CLVPRGSLEH HHHHH                                                          15

SEQ ID NO: 219            moltype = AA   length = 156
FEATURE                   Location/Qualifiers
source                    1..156
                          mol_type = protein
                          organism = Escherichia coli
SEQUENCE: 219
MNIIEANVAT PDARVAITIA RFNNFINDSL LEGAIDALKR IGQVKDENIT VVWVPGAYEL          60
PLAAGALAKT GKYDAVIALG TVIRGGTAHF EYVAGGASNG LAHVAQDSEI PVAFGVLTTE         120
SIEQAIERAG TKAGNKGAEA ALTALEMINV LKAIKA                                  156

SEQ ID NO: 220            moltype = AA   length = 16
FEATURE                   Location/Qualifiers
REGION                    1..16
                          note = Synthetic polypeptide
source                    1..16
                          mol_type = protein
                          organism = synthetic construct
SEQUENCE: 220
GGGGSGGGGS GGGGSG                                                         16

SEQ ID NO: 221            moltype = AA   length = 28
FEATURE                   Location/Qualifiers
REGION                    1..28
                          note = Synthetic polypeptide
source                    1..28
                          mol_type = protein
                          organism = synthetic construct
SEQUENCE: 221
GGSGSGSNSS ASSGASSGGA SGGSGGSG                                            28

SEQ ID NO: 222            moltype = AA   length = 46
FEATURE                   Location/Qualifiers
REGION                    1..46
                          note = Synthetic polypeptide
source                    1..46
                          mol_type = protein
                          organism = synthetic construct
SEQUENCE: 222
GGSGSASSGA SASGSSNGSG SGSGSNSSAS SGASSGGASG GSGGSG                         46

SEQ ID NO: 223            moltype = AA   length = 26
FEATURE                   Location/Qualifiers
REGION                    1..26
                          note = Synthetic polypeptide
source                    1..26
                          mol_type = protein
                          organism = synthetic construct
SEQUENCE: 223
GGSGSASAEA AAKEAAAKAG GSGGSG                                              26

SEQ ID NO: 224            moltype = AA   length = 32
FEATURE                   Location/Qualifiers
REGION                    1..32
                          note = Synthetic polypeptide
source                    1..32
                          mol_type = protein
                          organism = synthetic construct
SEQUENCE: 224
GGSGSASAEA AAKEAAAKEA AAKASGGSGG SG                                       32

SEQ ID NO: 225            moltype = AA   length = 47
FEATURE                   Location/Qualifiers
REGION                    1..47
                          note = Synthetic polypeptide
source                    1..47
                          mol_type = protein
                          organism = synthetic construct
```

```
SEQUENCE: 225
SGGGSGSASS GASASGSSCS GSGSGSSSAS SGASSGGASG GGSGGSG                    47

SEQ ID NO: 226           moltype = AA  length = 1086
FEATURE                  Location/Qualifiers
REGION                   1..1086
                         note = Synthetic polypeptide
source                   1..1086
                         mol_type = protein
                         organism = synthetic construct
SEQUENCE: 226
MRAVGVFLAI CLVTIFVLPT WGNWAYPCCH VTQLRAQHLL ALENISDIYL VSNQTCDGFS      60
LASLNSPKNG SNQLVISRCA NGLNVVSFFI SILKRSSSAL TGHLRELLTT LETLYGSFSV     120
EDLFGANLNR YAWHRGGGGS GSASSGASAS GSSNGSGSGS GSNSSASSGA SSGGASGGSG     180
GSGAASLSEV KLHLDIEGHA SHYTIPWTEL MAKVPGLSPE ALWREANVTE DLASMLNRYK     240
LIYKTSGTLG IALAEPVDIP AVSEGSMQVD ASKVHPGVIS GLNSPACMLS APLEKQLFYY     300
IGTMLPNTRP HSYVFYQLRA HLSYVALSIN GDKFQYTGAM TSKFLMGTYK RVTEKGDEHV     360
LSLVFGKTKD LPDLRGPFSY PSLTSAQSGD YSLVIVTTFV HYANFHNYFV PNLKDMFSRA     420
VTMTAASYAR YVLQKLVLLE MKGGCREPEL DTETLTTMFE VSVAFFKVGH AVGETGNGCV     480
DLRWLAKSFF ELTVLKDIIG ICYGATVKGM QSYGLERLAA MLMATVKMEE LGHLTTEKQE     540
YALRLATVGY PKAGVYSGLI GGATSVLLSA YNRHPLFQPL HTVMRETLFI GSHVVLRELR     600
LNVTTQGPNL ALYQLLSTAL CSALEIGEVL RGLALGTESG LFSPCYLSLR FDLTRDKLLS     660
MAPQEATLDQ AAVSNAVDGF LGRLSLERED RDAWHLPAYK CVDRLDKVLM IIPLINVTFI     720
ISSDREVRGS ALYEASTTYL SSSLFLSPVI MNKCSQGAVA GEPRQIPKIQ NFTRTQKSCI     780
FCGFALLSYD EKEGLETTTY ITSQEVQNSI LSSNYFDFDN LHVHYLLLTT NGTVMEIAGL     840
YEERASGGGS GSASSGASAS GSSSGSGSGS SSSASSGLAY FLPPRVRGGG RVAAAAITWV     900
PKPNVEVWPV DPPPPVNFNK TAEQEYGDKE VKLPHWTPTL HTFQVPQNYT KANCTYCNTR     960
EYTFSYKGCC FYFTKKKHTW NGCFQACAEL YPCTYFYGPT PDILPVVTRN LNAIESLWVG    1020
VYRVGEGNWT SLDGGTFKVY QIFGSHCTYV SKFSTVPVSH HECSFLKPCL CVSQRSNSGS    1080
HHHHHH                                                               1086

SEQ ID NO: 227           moltype = AA  length = 1339
FEATURE                  Location/Qualifiers
REGION                   1..1339
                         note = Synthetic polypeptide
source                   1..1339
                         mol_type = protein
                         organism = synthetic construct
SEQUENCE: 227
MRAVGVFLAI CLVTIFVLPT WGNWAYPCCH VTQLRAQHLL ALENISDIYL VSNQTCDGFS      60
LASLNSPKNG SNQLVISRCA NGLNVVSFFI SILKRSSSAL TGHLRELLTT LETLYGSFSV     120
EDLFGANLNR YAWHRGGGGS GSASSGASAS GSSNGSGSGS GSNSSASSGA SSGGASGGSG     180
GSGAASLSEV KLHLDIEGHA SHYTIPWTEL MAKVPGLSPE ALWREANVTE DLASMLNRYK     240
LIYKTSGTLG IALAEPVDIP AVSEGSMQVD ASKVHPGVIS GLNSPACMLS APLEKQLFYY     300
IGTMLPNTRP HSYVFYQLRA HLSYVALSIN GDKFQYTGAM TSKFLMGTYK RVTEKGDEHV     360
LSLVFGKTKD LPDLRGPFSY PSLTSAQSGD YSLVIVTTFV HYANFHNYFV PNLKDMFSRA     420
VTMTAASYAR YVLQKLVLLE MKGGCREPEL DTETLTTMFE VSVAFFKVGH AVGETGNGCV     480
DLRWLAKSFF ELTVLKDIIG ICYGATVKGM QSYGLERLAA MLMATVKMEE LGHLTTEKQE     540
YALRLATVGY PKAGVYSGLI GGATSVLLSA YNRHPLFQPL HTVMRETLFI GSHVVLRELR     600
LNVTTQGPNL ALYQLLSTAL CSALEIGEVL RGLALGTESG LFSPCYLSLR FDLTRDKLLS     660
MAPQEATLDQ AAVSNAVDGF LGRLSLERED RDAWHLPAYK CVDRLDKVLM IIPLINVTFI     720
ISSDREVRGS ALYEASTTYL SSSLFLSPVI MNKCSQGAVA GEPRQIPKIQ NFTRTQKSCI     780
FCGFALLSYD EKEGLETTTY ITSQEVQNSI LSSNYFDFDN LHVHYLLLTT NGTVMEIAGL     840
YEERASGGGS GSASSGASAS GSSSGSGSGS SSSASSGLAY FLPPRVRGGG RVAAAAITWV     900
PKPNVEVWPV DPPPPVNFNK TAEQEYGDKE VKLPHWTPTL HTFQVPQNYT KANCTYCNTR     960
EYTFSYKGCC FYFTKKKHTW NGCFQACAEL YPCTYFYGPT PDILPVVTRN LNAIESLWVG    1020
VYRVGEGNWT SLDGGTFKVY QIFGSHCTYV SKFSTVPVSH HECSFLKPCL CVSQRSNSGG    1080
SGSSASSGASA SGSSGSGSGS GSSSASSGAS SGGASGGSGG SGGGSGSASS GASASGSSGS    1140
GSGSGSSSAS SGASSGGASG GSGGGSGESQV RQQFSKDIEK LLNEQVNKEM QSSNLYMSMS    1200
SWSYTHSLDG AGLFLFDHAA EEYEHAKKLI IFLNENNVPV QLTSISAPEH KFEGLTQIFQ    1260
KAYEHEQHIS ESINNIVDHA IKCKDHATFN FLQWYVAEQH EEEVLFKDIL DKIELIGNEN    1320
HGLYLADQYV KGIAKSRKS                                                 1339

SEQ ID NO: 228           moltype = AA  length = 1295
FEATURE                  Location/Qualifiers
REGION                   1..1295
                         note = Synthetic polypeptide
source                   1..1295
                         mol_type = protein
                         organism = synthetic construct
SEQUENCE: 228
MRAVGVFLAI CLVTIFVLPT WGNWAYPCCH VTQLRAQHLL ALENISDIYL VSNQTCDGFS      60
LASLNSPKNG SNQLVISRCA NGLNVVSFFI SILKRSSSAL TGHLRELLTT LETLYGSFSV     120
EDLFGANLNR YAWHRGGGGS GSASSGASAS GSSNGSGSGS GSNSSASSGA SSGGASGGSG     180
GSGAASLSEV KLHLDIEGHA SHYTIPWTEL MAKVPGLSPE ALWREANVTE DLASMLNRYK     240
LIYKTSGTLG IALAEPVDIP AVSEGSMQVD ASKVHPGVIS GLNSPACMLS APLEKQLFYY     300
IGTMLPNTRP HSYVFYQLRA HLSYVALSIN GDKFQYTGAM TSKFLMGTYK RVTEKGDEHV     360
LSLVFGKTKD LPDLRGPFSY PSLTSAQSGD YSLVIVTTFV HYANFHNYFV PNLKDMFSRA     420
VTMTAASYAR YVLQKLVLLE MKGGCREPEL DTETLTTMFE VSVAFFKVGH AVGETGNGCV     480
```

```
DLRWLAKSFF ELTVLKDIIG ICYGATVKGM QSYGLERLAA MLMATVKMEE LGHLTTEKQE   540
YALRLATVGY PKAGVYSGLI GGATSVLLSA YNRHPLFQPL HTVMRETLFI GSHVVLRELR   600
LNVTTQGPNL ALYQLLSTAL CSALEIGEVL RGLALGTESG LFSPCYLSLR FDLTRDKLLS   660
MAPQEATLDQ AAVSNAVDGF LGRLSLERED RDAWHLPAYK CVDRLDKVLM IIPLINVTFI   720
ISSDREVRGS ALYEASTTYL SSSLFLSPVI MNKCSQGAVA GEPRQIPKIQ NFTRTQKSCI   780
FCGFALLSYD EKEGLETTTY ITSQEVQNSI LSSNYFDFDN LHVHYLLLTT NGTVMEIAGL   840
YEERASGGGS GSASSGASAS GSSGSGSGSG SSSASSGLAY FLPPRVRGGG RVAAAAITWV   900
PKPNVEVWPV DPPPPVNFNK TAEQEYGDKE VKLPHWTPTL HTFQVPQNYT KANCTYCNTR   960
EYTFSYKGCC FYFTKKKHTW NGCFQACAEL YPCTYFYGPT PDILPVVTRN LNAIESLWVG  1020
VYRVGEGNWT SLDGGTFKVY QIFGSHCTYV SKFSTVPVSH HECSFLKPCL CVSQRSNSGG  1080
SGGSASSGASA SGSSGSGSGS GSSSASSGAS SGGASGGSGG SGESQVRQQF SKDIEKLLNE  1140
QVNKEMQSSN LYMSMSSWSY THSLDGAGLF LFDHAAEEYE HAKKLIIFLN ENNVPVQLTS  1200
ISAPEHKFEG LTQIFQKAYE HEQHISESIN NIVDHAIKCK DHATFNFLQW YVAEQHEEEV  1260
LFKDILDKIE LIGNENHGLY LADQYVKGIA KSRKS                            1295

SEQ ID NO: 229           moltype = AA  length = 1263
FEATURE                  Location/Qualifiers
REGION                   1..1263
                         note = Synthetic polypeptide
source                   1..1263
                         mol_type = protein
                         organism = synthetic construct
SEQUENCE: 229
MRAVGVFLAI CLVTIFVLPT WGNWAYPCCH VTQLRAQHLL ALENISDIYL VSNQTCDGFS    60
LASLNSPKNG SNQLVISRCA NGLNVVSFFI SILKRSSSAL TGHLRELLTT LETLYGSFSV   120
EDLFGANLNR YAWHRGGGGS GSASSGASAS GSSNGSGSGS GSNSSASSGA SSGGASGGSG   180
GSGAASLSEV KLHLDIEGHA SHYTIPWTEL MAKVPGLSPE ALWREANVTE DLASMLNRYK   240
LIYKTSGTLG IALAEPVDIP AVSEGSMQVD ASKVHPGVIS GLNSPACMLS APLEKQLFYY   300
IGTMLPNTRP HSYVFYQLRA HLSYVALSIN GDKFQYTGAM TSKFLMGTYK RVTEKGDEHV   360
LSLVFGKTKD LPDLRGPFSY PSLTSAQSGD YSLVIVTTFV HYANFHNYFV PNLKDMFSRA   420
VTMTAASYAR YVLQKLVLLE MKGGCREPEL DTETLTTMFE VSVAFFKVGH AVGETGNGCV   480
DLRWLAKSFF ELTVLKDIIG ICYGATVKGM QSYGLERLAA MLMATVKMEE LGHLTTEKQE   540
YALRLATVGY PKAGVYSGLI GGATSVLLSA YNRHPLFQPL HTVMRETLFI GSHVVLRELR   600
LNVTTQGPNL ALYQLLSTAL CSALEIGEVL RGLALGTESG LFSPCYLSLR FDLTRDKLLS   660
MAPQEATLDQ AAVSNAVDGF LGRLSLERED RDAWHLPAYK CVDRLDKVLM IIPLINVTFI   720
ISSDREVRGS ALYEASTTYL SSSLFLSPVI MNKCSQGAVA GEPRQIPKIQ NFTRTQKSCI   780
FCGFALLSYD EKEGLETTTY ITSQEVQNSI LSSNYFDFDN LHVHYLLLTT NGTVMEIAGL   840
YEERASGGGS GSASSGASAS GSSGSGSGSG SSSASSGLAY FLPPRVRGGG RVAAAAITWV   900
PKPNVEVWPV DPPPPVNFNK TAEQEYGDKE VKLPHWTPTL HTFQVPQNYT KANCTYCNTR   960
EYTFSYKGCC FYFTKKKHTW NGCFQACAEL YPCTYFYGPT PDILPVVTRN LNAIESLWVG  1020
VYRVGEGNWT SLDGGTFKVY QIFGSHCTYV SKFSTVPVSH HECSFLKPCL CVSQRSNSEP  1080
EPEPEPEPGG ESQVRQQFSK DIEKLLNEQV NKEMQSSNLY MSMSSWSYTH SLDGAGLFLF  1140
DHAAEEYEHA KKLIIFLNEN NVPVQLTSIS APEHKFEGLT QIFQKAYEHE QHISESINNI  1200
VDHAIKCKDH ATFNFLQWYV AEQHEEEVLF KDILDKIELI GNENHGLYLA DQYVKGIAKS  1260
RKS                                                               1263

SEQ ID NO: 230           moltype = AA  length = 1255
FEATURE                  Location/Qualifiers
REGION                   1..1255
                         note = Synthetic polypeptide
source                   1..1255
                         mol_type = protein
                         organism = synthetic construct
SEQUENCE: 230
MRAVGVFLAI CLVTIFVLPT WGNWAYPCCH VTQLRAQHLL ALENISDIYL VSNQTCDGFS    60
LASLNSPKNG SNQLVISRCA NGLNVVSFFI SILKRSSSAL TGHLRELLTT LETLYGSFSV   120
EDLFGANLNR YAWHRGGGGS GSASSGASAS GSSNGSGSGS GSNSSASSGA SSGGASGGSG   180
GSGAASLSEV KLHLDIEGHA SHYTIPWTEL MAKVPGLSPE ALWREANVTE DLASMLNRYK   240
LIYKTSGTLG IALAEPVDIP AVSEGSMQVD ASKVHPGVIS GLNSPACMLS APLEKQLFYY   300
IGTMLPNTRP HSYVFYQLRA HLSYVALSIN GDKFQYTGAM TSKFLMGTYK RVTEKGDEHV   360
LSLVFGKTKD LPDLRGPFSY PSLTSAQSGD YSLVIVTTFV HYANFHNYFV PNLKDMFSRA   420
VTMTAASYAR YVLQKLVLLE MKGGCREPEL DTETLTTMFE VSVAFFKVGH AVGETGNGCV   480
DLRWLAKSFF ELTVLKDIIG ICYGATVKGM QSYGLERLAA MLMATVKMEE LGHLTTEKQE   540
YALRLATVGY PKAGVYSGLI GGATSVLLSA YNRHPLFQPL HTVMRETLFI GSHVVLRELR   600
LNVTTQGPNL ALYQLLSTAL CSALEIGEVL RGLALGTESG LFSPCYLSLR FDLTRDKLLS   660
MAPQEATLDQ AAVSNAVDGF LGRLSLERED RDAWHLPAYK CVDRLDKVLM IIPLINVTFI   720
ISSDREVRGS ALYEASTTYL SSSLFLSPVI MNKCSQGAVA GEPRQIPKIQ NFTRTQKSCI   780
FCGFALLSYD EKEGLETTTY ITSQEVQNSI LSSNYFDFDN LHVHYLLLTT NGTVMEIAGL   840
YEERASGGGS GSASSGASAS GSSGSGSGSG SSSASSGLAY FLPPRVRGGG RVAAAAITWV   900
PKPNVEVWPV DPPPPVNFNK TAEQEYGDKE VKLPHWTPTL HTFQVPQNYT KANCTYCNTR   960
EYTFSYKGCC FYFTKKKHTW NGCFQACAEL YPCTYFYGPT PDILPVVTRN LNAIESLWVG  1020
VYRVGEGNWT SLDGGTFKVY QIFGSHCTYV SKFSTVPVSH HECSFLKPCL CVSQRSNSGG  1080
SGESQVRQQF SKDIEKLLNE QVNKEMQSSN LYMSMSSWSY THSLDGAGLF LFDHAAEEYE  1140
HAKKLIIFLN ENNVPVQLTS ISAPEHKFEG LTQIFQKAYE HEQHISESIN NIVDHAIKCK  1200
DHATFNFLQW YVAEQHEEEV LFKDILDKIE LIGNENHGLY LADQYVKGIA KSRKS       1255

SEQ ID NO: 231           moltype = AA  length = 1329
FEATURE                  Location/Qualifiers
REGION                   1..1329
```

```
                           note = Synthetic polypeptide
source                     1..1329
                           mol_type = protein
                           organism = synthetic construct
SEQUENCE: 231
MDSKGSSQKG SRLLLLLVVS NLLLPQGVLA NWAYPCCHVT QLRAQHLLAL ENISDIYLVS    60
NQTCDAFSLA SLNSPKQGSN QLVISRCANG LNVVSFFISI LKRSSSALTG HLRELLTTLE   120
TLYGSFSVED LFGAQLNRYA WHRGGGGSGS ASSGASASGS SGGSGSGSGS GSSASSGASS   180
GGASGGSGGS GAASLSEVKL HLDIEGHASH YTIPWTELLA KVPGLSPEAL WREANVTEDL   240
ASMLNRYKLI YKTSGTLGIA LAEPVDIPAV SEGSMQVDAS KVHPGVISGL NSPACMLSAP   300
LEKQLFYYIG TMLPNTRPHS YVFYQLRCHL SYVALSINGD KFQYTGAMTS KFLMGTYKRV   360
TEKGDEHVLS LVFGKTKDLP DLRGPFSYPS LTSAQSGEYS LVIVTTFVHY ANFHNYFVPN   420
LKDMFSRAVT MTAASYARYV LQKLVLLEMK GGCREPELET ETLTTMFEVS VAFFKVGHAV   480
GETGNGCVDL RWLAKSFFEL TVLKDIIGIC YGATVKGMQS YGLERLAAIL MATVKMEELG   540
HLTTEKQEYA LRLATVGYPK AGVYSGLIGG ATSVLLSAYN RHPLFQPLHT VMRETLFIGS   600
HVVLRELRLN VTTQGPNLAL YQLLSTALCS ALEIGEVLRG LALGTESGLF SPCYLSLRFD   660
LTRDKLLSIA PQEATLDQAA VSQAVDGFLG RLSLEREDRD AWHLPAYKCV DRLDKVLMII   720
PLINVTFIIS SDREVRGSAL YEASTTYLSS SLFLSPVILN KCSQGAVAGE PRQIPKIQNF   780
TRTQKSCIFC GFALLSYDEK EGLETTTYIT SQEVQNSILS SNYFDFDNLH VHYLLLTTNG   840
TVMEIAGLYE ERASGGGSGS ASSGASASGS SGSGSGSGSS SASSGAITWV PKPNVEVWPV   900
DPPPPVNFNK TAEQEYGDKE VKLPHWTPTL HTFQVPQNYT KANCTYCNTR EYTFSYKGCC   960
FYFTKKKHTW QGCFQACAEL YPCTYFYGPT PDILPVVTRS LQAIESLWVG VYRVGEGNWT  1020
SLDGGTFKVY QIFGSHCTYV SKFSTVPVSH HECSFLKPCL CVSQRSNSGG SGSASSGASA  1080
SGSSGSGSGS GSSSASSGAS SGGASGGSGG SGGGSGSASS GASAQRSSGG GSGSGSSSAS  1140
SGASSGGASG GSGGSGESQV RSQFSKDIEK LLNEQVNKEM QSSNLYMSMS SWSYTHSLDG  1200
AGLFLFDHAA EEYEHAKKLI IFLNENNVPV QLTSISAPEH KFEGLTQIFQ KAYEHEQHIS  1260
ESINQIVDHA IKCKDHATFN FLQWYVAEQH EEEVLFKDIL DKIELIGQEN HGLYLADQYV  1320
KGIAKSRKS                                                          1329

SEQ ID NO: 232             moltype = AA   length = 1066
FEATURE                    Location/Qualifiers
REGION                     1..1066
                           note = Synthetic polypeptide
source                     1..1066
                           mol_type = protein
                           organism = synthetic construct
SEQUENCE: 232
MRAVGVFLAI CLVTIFVLPT WGNWAYPCCH VTQLRAQHLL ALENISDIYL VSNQTCDGFS    60
LASLNSPKNG SNQLVISRCA NGLNVVSFFI SILKRSSSAL TGHLRELLTT LETLYGSFSV   120
EDLFGANLNR YAWHRGGGGS GSASSGASAS GSSNGSGSGS GSNSSASSGA SSGGASGGSG   180
GSGAASLSEV KLHLDIEGHA SHYTIPWTEL MAKVPGLSPE ALWREANVTE DLASMLNRYK   240
LIYKTSGTLG IALAEPVDIP AVSEGSMQVD ASKVHPGVIS GLNSPACMLS APLEKQLFYY   300
IGTMLPNTRP HSYVFYQLRA HLSYVALSIN GDKFQYTGAM TSKFLMGTYK RVTEKGDEHV   360
LSLVFGKTKD LPDLRGPFSY PSLTSAQSGD YSLVIVTTFV HYANFHNYFV PNLKDMFSRA   420
VTMTAASYAR YVLQKLVLLE MKGGCREPEL DTETTTMFE VSVAFFKVGH AVGETGNGCV    480
DLRWLAKSFF ELTVLKDIIG ICYGATVKGM QSYGLERLAA MLMATVKMEE LGHLTTEKQE   540
YALRLATVGY PKAGVYSGLI GGATSVLLSA YNRHPLFQPL HTVMRETLFI GSHVVLRELR   600
LNVTTQGPNL ALYQLLSTAL CSALEIGEVL RGLALGTESG LFSPCYLSLR FDLTRDKLLS   660
MAPQEATLDQ AAVSNAVDGF LGRLSLERED RDAWHLPAYK CVDRLDKVLM IIPLINVTFI   720
ISSDREVRGS ALYEASTTYL SSSLFLSPVI MNKCSQGAVA GEPRQIPKIQ NFTRTQKSCI   780
FCGFALLSYD EKEGLETTTY ITSQEVQNSI LSSNYFDFDN LHVHYLLLTT NGTVMEIAGL   840
YEERASGEPE PEPEPEPEPE PEPEPEPEPE PEPEPEPEPE PEPEPEPEPE PESQVRQQ     900
FSKDIEKLLN EQVNKEMQSS NLYMSMSSWS YTHSLDGAGL FLFDHAAEEY EHAKKLIIFL   960
NENNVPVQLT SISAPEHKFE GLTQIFQKAY EHEQHISESI NNIVDHAIKC KDHATFNFLQ  1020
WYVAEQHEEE VLFKDILDKI ELIGNENHGL YLADQYVKGI AKSRKS                 1066

SEQ ID NO: 233             moltype = AA   length = 46
FEATURE                    Location/Qualifiers
REGION                     1..46
                           note = Synthetic polypeptide
source                     1..46
                           mol_type = protein
                           organism = synthetic construct
SEQUENCE: 233
GGSGSASSGA SASGSSGGSG SGSGSGSSAS SGASSGGASG GSGGSG                   46

SEQ ID NO: 234             moltype = AA   length = 32
FEATURE                    Location/Qualifiers
REGION                     1..32
                           note = Synthetic polypeptide
source                     1..32
                           mol_type = protein
                           organism = synthetic construct
SEQUENCE: 234
SGGGSGSASS GASASGSSGS GSGSGSSSAS SG                                  32

SEQ ID NO: 235             moltype = AA   length = 88
FEATURE                    Location/Qualifiers
REGION                     1..88
```

```
                        note = Synthetic polypeptide
source                  1..88
                        mol_type = protein
                        organism = synthetic construct
SEQUENCE: 235
GGSGSASSGA SASGSSGSGS GSGSSSASSG ASSGGASGGS GGSGGGSGSA SSGASASGSS    60
GSGSGSGSSS ASSGASSGGA SGGSGGSG                                      88

SEQ ID NO: 236          moltype = AA   length = 44
FEATURE                 Location/Qualifiers
REGION                  1..44
                        note = Synthetic polypeptide
source                  1..44
                        mol_type = protein
                        organism = synthetic construct
SEQUENCE: 236
GGSGSASSGA SASGSSGSGS GSGSSSASSG ASSGGASGGS GGSG                    44

SEQ ID NO: 237          moltype = AA   length = 12
FEATURE                 Location/Qualifiers
REGION                  1..12
                        note = Synthetic polypeptide
source                  1..12
                        mol_type = protein
                        organism = synthetic construct
SEQUENCE: 237
EPEPEPEPEP GG                                                       12

SEQ ID NO: 238          moltype = AA   length = 48
FEATURE                 Location/Qualifiers
REGION                  1..48
                        note = Synthetic polypeptide
source                  1..48
                        mol_type = protein
                        organism = synthetic construct
SEQUENCE: 238
SGEPEPEPEP EPEPEPEPEP EPEPEPEPEP EPEPEPEPEP EPEPEPEP                48

SEQ ID NO: 239          moltype = AA   length = 201
FEATURE                 Location/Qualifiers
REGION                  1..201
                        note = Synthetic polypeptide
source                  1..201
                        mol_type = protein
                        organism = synthetic construct
SEQUENCE: 239
LAYFLPPRVR GGGRVAAAAI TWVPKPNVEV WPVDPPPPVN FNKTAEQEYG DKEVKLPHWT    60
PTLHTFQVPQ NYTKANCTYC NTREYTFSYK GCCFYFTKKK HTWNGCFQAC AELYPCTYFY   120
GPTPDILPVV TRNLNAIESL WVGVYRVGEG NWTSLDGGTF KVYQIFGSHC TYVSKFSTVP   180
VSHHECSFLK PCLCVSQRSN S                                            201

SEQ ID NO: 240          moltype = AA   length = 183
FEATURE                 Location/Qualifiers
REGION                  1..183
                        note = Synthetic polypeptide
source                  1..183
                        mol_type = protein
                        organism = synthetic construct
SEQUENCE: 240
AITWVPKPNV EVWPVDPPPP VNFNKTAEQE YGDKEVKLPH WTPTLHTFQV PQNYTKANCT    60
YCNTREYTFS YKGCCFYFTK KKHTWQGCFQ ACAELYPCTY FYGPTPDILP VVTRSLQAIE   120
SLWVGVYRVG EGNWTSLDGG TFKVYQIFGS HCTYVSKFST VPVSHHECSF LKPCLCVSQR   180
SNS                                                                183

SEQ ID NO: 241          moltype = AA   length = 1329
FEATURE                 Location/Qualifiers
REGION                  1..1329
                        note = Synthetic polypeptide
source                  1..1329
                        mol_type = protein
                        organism = synthetic construct
SEQUENCE: 241
MDSKGSSQKG SRLLLLLVVS NLLLPQGVLA NWAYPCCHVT QLRAQHLLAL ENISDIYLVS    60
NQTCDAFSLA SLNSPKQGSN QLVISRCANG LNVVSFFISI LKRSSSALTG HLRELLTTLE   120
TLYGSFSVED LFGAQLNRYA WHRGGGGSGS ASSGASASGS SGGSGSGSGS GSSASSGASS   180
GGASGGSGGS GAASLSEVKL HLDIEGHASH YTIPWTELLA KVPGLSPEAL WREANVTEDL   240
ASMLNRYKLI YKTSGTLGIA LAEPVDIPAV SEGSMQVDAS KVHPGVISGL NSPACMLSAP   300
LEKQLFYYIG TMLPNTRPHS YVFYQLRCHL SYVALSINGD KFQYTGAMTS KFLMGTYKRV   360
TEKGDEHVLS LVFGKTKDLP DLRGPFSYPS LTSAQSGEYS LVIVTTFVHY ANFHNYFVPN   420
```

```
LKDMFSRAVT MTAASYARYV LQKLVLLEMK GGCREPELET ETLTTMFEVS VAFFKVGHAV        480
GETGNGCVDL RWLAKSFFEL TVLKDIIGIC YGATVKGMQS YGLERLAAIL MATVKMEELG        540
HLTTEKQEYA LRLATVGYPK AGVYSGLIGG ATSVLLSAYN RHPLFQPLHT VMRETLFIGS        600
HVVLRELRLN VTTQGPNLAL YQLLSTALCS ALEIGEVLRG LALGTESGLF SPCYLSLRFD        660
LTRDKLLSIA PQEATLDQAA VSQAVDGFLG RLSLEREDRD AWHLPAYKCV DRLDKVLMII        720
PLINVTFIIS SDREVRGSAL YEASTTYLSS SLFLSPVIMN KCSQGAVAGE PRQIPKIQNF        780
TRTQKSCIFC GFALLSYDEK EGLETTTYIT SQEVQNSILS SNYFDFDNLH VHYLLLTTNG        840
TVMEIAGLYE ERASGGGSGS ASSGASASGS SGSGSGSGSS SASSGAITWV PKPNVEVWPV        900
DPPPPVNFNK TAEQEYGDKE VKLPHWTPTL HTFQVPQNYT KANCTYCNTR EYTFSYKGCC        960
FYFTKKKHTW QGCFQACAEL YPCTYFYGPT PDILPVVTRN LNAIESLWVG VYRVGEGNWT       1020
SLDGGTFKVY QIFGSHCTYV SKFSTVPVSH HECSFLKPCL CVSQRSNSGG SGSASSGASA       1080
SGSSSGSGSG GSSSASSGAS SGGASGGSGG SGGGSGSASS GASASGSSGS GSGSGSSSAS       1140
SGASSGGASG GSGGSGESQV RSQFSKDIEK LLNEQVNKEM QSSNLYMSMS SWSYTHSLDG       1200
AGLFLFDHAA EEYEHAKKLI IFLNENNVPV QLTSISAPEH KFEGLTQIFQ KAYEHEQHIS       1260
ESINQIVDHA IKCKDHATFN FLQWYVAEQH EEEVLFKDIL DKIELIGQEN HGLYLADQYV       1320
KGIAKSRKS                                                              1329

SEQ ID NO: 242           moltype = AA   length = 1329
FEATURE                  Location/Qualifiers
REGION                   1..1329
                         note = Synthetic polypeptide
source                   1..1329
                         mol_type = protein
                         organism = synthetic construct
SEQUENCE: 242
MDSKGSSQKG SRLLLLLVVS NLLLPQGVLA NWAYPCCHVT QLRAQHLLAL ENISDIYLVS         60
NQTCDAFSLA SLNSPKQGSN QLVISRCANG LNVVSFFISI LKRSSSALTG HLRELLTTLE        120
TLYGSFSVED LFGAQLNRYA WHRGGGGSGS ASSGASASGS SGSGSGSGSG GSSASSGASS        180
GGASGGSGGS GAASLSEVKL HLDIEGHASH YTIPWTELLA KVPGLSPEAL WREANVTEDL        240
ASMLNRYKLI YKTSGTLGIA LAEPVDIPAV SEGSMQVDAS KVHPGVISGL NSPACMLSAP        300
LEKQLFYYIG TMLPNTRPHS YVFYQLRCHL SYVALSINGD KFQYTGAMTS KFLMGTYKRV        360
TEKGDEHVLS LVFGKTKDLP DLRGPFSYPS LTSAQSGEYS LVIVTTFVHY ANFHNYFVPN        420
LKDMFSRAVT MTAASYARYV LQKLVLLEMK GGCREPELET ETLTTMFEVS VAFFKVGHAV        480
GETGNGCVDL RWLAKSFFEL TVLKDIIGIC YGATVKGMQS YGLERLAAML MATVKMEELG        540
HLTTEKQEYA LRLATVGYPK AGVYSGLIGG ATSVLLSAYN RHPLFQPLHT VMRETLFIGS        600
HVVLRELRLN VTTQGPNLAL YQLLSTALCS ALEIGEVLRG LALGTESGLF SPCYLSLRFD        660
LTRDKLLSMA PQEATLDQAA VSNAVDGFLG RLSLEREDRD AWHLPAYKCV DRLDKVLMII        720
PLINVTFIIS SDREVRGSAL YEASTTYLSS SLFLSPVIMN KCSQGAVAGE PRQIPKIQNF        780
TRTQKSCIFC GFALLSYDEK EGLETTTYIT SQEVQNSILS SNYFDFDNLH VHYLLLTTNG        840
TVMEIAGLYE ERASGGGSGS ASSGASASGS SGSGSGSGSS SASSGAITWV PKPNVEVWPV        900
DPPPPVNFNK TAEQEYGDKE VKLPHWTPTL HTFQVPQNYT KANCTYCNTR EYTFSYKGCC        960
FYFTKKKHTW NGCFQACAEL YPCTYFYGPT PDILPVVTRN LNAIESLWVG VYRVGEGNWT       1020
SLDGGTFKVY QIFGSHCTYV SKFSTVPVSH HECSFLKPCL CVSQRSNSGG SGSASSGASA       1080
SGSSSGSGSG GSSSASSGAS SGGASGGSGG SGGGSGSASS GASASGSSGS GSGSGSSSAS       1140
SGASSGGASG GSGGSGESQV RSQFSKDIEK LLNEQVNKEM QSSNLYMSMS SWSYTHSLDG       1200
AGLFLFDHAA EEYEHAKKLI IFLNENNVPV QLTSISAPEH KFEGLTQIFQ KAYEHEQHIS       1260
ESINQIVDHA IKCKDHATFN FLQWYVAEQH EEEVLFKDIL DKIELIGQEN HGLYLADQYV       1320
KGIAKSRKS                                                              1329

SEQ ID NO: 243           moltype = AA   length = 6
FEATURE                  Location/Qualifiers
REGION                   1..6
                         note = 6xHis tag
source                   1..6
                         mol_type = protein
                         organism = synthetic construct
SEQUENCE: 243
HHHHHH                                                                    6

SEQ ID NO: 244           moltype = AA   length = 4
FEATURE                  Location/Qualifiers
REGION                   1..4
                         note = Synthetic polypeptide
source                   1..4
                         mol_type = protein
                         organism = synthetic construct
SEQUENCE: 244
GGGS                                                                      4

SEQ ID NO: 245           moltype = AA   length = 8
FEATURE                  Location/Qualifiers
REGION                   1..8
                         note = Synthetic polypeptide
source                   1..8
                         mol_type = protein
                         organism = synthetic construct
SEQUENCE: 245
GGGSGGGS                                                                  8
```

```
SEQ ID NO: 246          moltype = AA  length = 20
FEATURE                 Location/Qualifiers
REGION                  1..20
                        note = Synthetic polypeptide
source                  1..20
                        mol_type = protein
                        organism = synthetic construct
SEQUENCE: 246
GGGSGGGSGG GSGGGSGGGS                                                    20

SEQ ID NO: 247          moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 247
tccatgacgt tcctgacgtt                                                    20
```

ANTIGENIC EPSTEIN BARR VIRUS POLYPEPTIDES

This application is a continuation of U.S. application Ser. No. 17/061,146, filed Oct. 1, 2020, which is a continuation of International Application No. PCT/US2019/025419, filed Apr. 2, 2019, which claims the benefit of priority of U.S. Provisional Patent Application No. 62/652,201, filed Apr. 3, 2018, the entire contents of which are incorporated herein by reference.

This invention was created in the performance of a Cooperative Research and Development Agreement (CRADA) with the National Institutes of Health, an Agency of the Department of Health and Human Services. The Government of the United States has certain rights in this invention.

The present application contains a Sequence Listing which has been submitted electronically in XML format. Said XML copy, created on Nov. 28, 2022, is named 2022-11-28_01121-0032-01US_SL_ST26.txt and is 178,732 bytes in size. The information in the electronic format of the sequence listing is incorporated herein by reference in its entirety.

Even with many successes in the field of vaccinology, new breakthroughs are needed to protect humans against many life-threatening infectious diseases. Many currently licensed vaccines rely on decade-old technologies to produce live-attenuated or inactivated killed pathogens, which carry inherent safety concerns and in many cases, stimulate only short-lived, weak immune responses that require the administration of multiple doses. While advances in genetic and biochemical engineering have made it possible to develop therapeutic agents to challenging disease targets, these applications to the field of vaccinology have not been fully realized. Recombinant protein technologies now allow the design of optimal antigens. Additionally, nanoparticles have increasingly demonstrated the potential for optimal antigen presentation and targeted drug delivery. Nanoparticles with multiple attached antigens have been shown to have increased binding avidity afforded by the multivalent display of their molecular cargos, and an ability to cross biological barriers more efficiently due to their nanoscopic size. *Helicobacter pylori* (*H. pylori*) ferritin nanoparticles fused to influenza virus haemagglutinin (HA) protein has allowed improved antigen stability and increased immunogenicity in mouse influenza models (see Kanekiyo et al., Nature 499:102-106 (2013)). This fusion protein self-assembled into an octahedrally-symmetric nanoparticle and presented 8 trimeric HA spikes to give a robust immune response in various pre-clinical models when used with an adjuvant.

Epstein Barr virus (EBV) infects about 95% of the adult population worldwide and has been known to be associated with two B-cell lymphomas, Burkitt's and Hodgkin's lymphomas. The virus can also infect epithelial cells and is associated with nasopharyngeal cancer. Furthermore, EBV causes most cases of infectious mononucleosis in developed countries, affecting mainly children and young adults. Infectious mononucleosis can result in a long recovery period of up to one month. There are currently no approved vaccines on the market, so there is a strong need for a preventive vaccine.

Here, a set of new polypeptides, nanoparticles, compositions, methods, and uses involving EBV polypeptides is presented. Novel EBV single-chain gL and gH (sometimes depicted as gL/gH or gH/gL) polypeptides were generated, as were antigenic polypeptides comprising these novel EBV polypeptides and ferritin. Antigenic polypeptides and nanoparticles comprising the single-chain gL and gH polypeptides can comprise a relatively long linker between the gL and gH sequences, which was observed to provide an increase in immunogenicity. Antigenic ferritin polypeptides and nanoparticles comprising EBV gp220 polypeptides were also generated. Furthermore, self-adjuvanting antigenic polypeptides comprising the described EBV polypeptides and ferritin were developed wherein immune-stimulatory moieties, such as adjuvants, were directly, chemically attached to the antigenic polypeptide. The direct conjugation of an immune-stimulatory moiety to the antigenic polypeptide allows for targeted co-delivery of the immune-stimulatory moiety and EBV polypeptide in a single macromolecular entity, which can greatly decrease the potential for systemic toxicity that is feared with traditional vaccines that comprise antigens and immune-stimulatory molecules such as adjuvants as separate molecules. The co-delivery of immune-stimulatory moieties together with EBV polypeptides in a macromolecular entity and their multivalent presentation may also reduce the overall dose needed to elicit protection, reducing manufacturing burdens and costs.

SUMMARY

It is an object of this disclosure to provide compositions, kits, methods, and uses that can provide one or more of the advantages discussed above, or at least provide the public with a useful choice. Accordingly, the following embodiments are disclosed herein.

Embodiment 1 is an antigenic EBV polypeptide comprising an Epstein Barr Virus (EBV) gL polypeptide and an EBV gH polypeptide, wherein a linker having a length of at least 15 amino acids separates the EBV gL polypeptide and the EBV gH polypeptide.

Embodiment 2 is an antigenic EBV polypeptide comprising an Epstein Barr Virus (EBV) gL polypeptide, an EBV gH polypeptide, and an EBV gp42 polypeptide, wherein a linker having a length of at least 15 amino acids separates the EBV gL polypeptide and the EBV gH polypeptide.

Embodiment 3 is the antigenic EBV polypeptide of embodiment 1 or embodiment 2, further comprising a ferritin.

Embodiment 4 is an antigenic EBV polypeptide comprising an EBV polypeptide and a ferritin protein, wherein the ferritin protein comprises a mutation replacing a surface-exposed amino acid with a cysteine.

Embodiment 5 is the antigenic EBV polypeptide of embodiment 4, wherein the EBV polypeptide comprises an EBV gL polypeptide, an EBV gH polypeptide, or an EBV gp220 polypeptide.

Embodiment 6 is the antigenic EBV polypeptide of embodiment 5, wherein the EBV polypeptide comprises a gL polypeptide and the polypeptide further comprises an EBV gH polypeptide.

Embodiment 7 is the antigenic EBV polypeptide of any one of embodiments 1 or 3-6, wherein the polypeptide further comprises an EBV gp42 polypeptide.

Embodiment 8 is a composition comprising a first antigenic EBV polypeptide and a second antigenic EBV polypeptide, wherein the first antigenic EBV polypeptide comprises a ferritin heavy chain and a first EBV polypeptide, the second antigenic EBV polypeptide comprises a ferritin light chain and a second EBV polypeptide, and the first and second EBV polypeptides are different.

Embodiment 9 is the composition of embodiment 8, wherein the first EBV polypeptide or the second EBV polypeptide comprises a gp220 polypeptide.

Embodiment 10 is the composition of any one of embodiments 8 to 9, wherein (i) the first antigenic EBV polypeptide comprises one or both of a gL polypeptide and a gH polypeptide and the second antigenic EBV polypeptide comprises a gp220 polypeptide, or (ii) the first antigenic EBV polypeptide comprises a gp220 polypeptide and the second antigenic EBV polypeptide comprises one or both of a gL polypeptide and a gH polypeptide.

Embodiment 11 is the composition of any one of embodiments 8 to 10, wherein the first antigenic EBV polypeptide comprises a gL polypeptide and a gH polypeptide; or the second antigenic EBV polypeptide comprises a gL polypeptide and an EBV gH polypeptide.

Embodiment 12 is the composition of embodiment 10 or 11, wherein the antigenic EBV polypeptide comprising a gL polypeptide and/or a gH polypeptide further comprises a gp42 polypeptide.

Embodiment 13 is the antigenic EBV polypeptide or composition of any one of embodiments 1-12, comprising a gH and gL polypeptide, wherein the gH polypeptide is C-terminal to the gL polypeptide, optionally comprising a gp42 polypeptide, wherein the gp42 polypeptide is C-terminal to the gH polypeptide.

Embodiment 14 is the antigenic EBV polypeptide or composition of any one of embodiments 1-13, comprising a gp42 polypeptide, wherein the gp42 polypeptide comprises an amino acid sequence with at least 80%, 85%, 90%, 95%, 97%, 98%, 99%, or 100% identity to SEQ ID NO: 239 or 240.

Embodiment 15 is the antigenic EBV polypeptide or composition of any one of embodiments 1-14, comprising an EBV gH polypeptide and an EBV gp42 polypeptide, wherein a linker having a length of at least 15 amino acids separates the EBV gH polypeptide and the EBV gp42 polypeptide, optionally wherein the linker has a length of 15 to 60 amino acids, 20 to 60 amino acids, 30 to 60 amino acids, 40 to 60 amino acids, 30 to 50 amino acids, or 40 to 50 amino acids, further optionally wherein the linker comprises an amino acid sequence with at least 80%, 85%, 90%, 95%, 97%, 98%, 99%, or 100% identity to SEQ ID NO: 234.

Embodiment 16 is the antigenic EBV polypeptide or composition of any one of the preceding embodiments, comprising a linker, wherein the linker has a length of at least 15 amino acids, optionally wherein the linker separates a first EBV polypeptide and a second EBV polypeptide.

Embodiment 17 is the antigenic EBV polypeptide or composition of embodiment 16, wherein the linker has a length of 15 to 60 amino acids, 20 to 60 amino acids, 30 to 60 amino acids, 40 to 60 amino acids, 30 to 50 amino acids, or 40 to 50 amino acids.

Embodiment 18 is the antigenic EBV polypeptide or composition of any one of the preceding embodiments, wherein the EBV polypeptide comprises an amino acid sequence with at least 80%, 85%, 90%, 95%, 97%, 98%, 99%, or 100% identity to SEQ ID NO: 36.

Embodiment 19 is the antigenic EBV polypeptide or composition of any one of the preceding embodiments, wherein the EBV polypeptide comprises an amino acid sequence with at least 80%, 85%, 90%, 95%, 97%, 98%, 99%, or 100% identity to SEQ ID NO: 37.

Embodiment 20 is the antigenic EBV polypeptide or composition of any one of the preceding embodiments, wherein the polypeptide comprises a linker comprising an amino acid sequence with at least 80%, 85%, 90%, 95%, 97%, 98%, 99%, or 100% identity to SEQ ID NO: 30, optionally wherein the linker separates a first EBV polypeptide and a second EBV polypeptide.

Embodiment 21 is the antigenic EBV polypeptide or composition of any one of the preceding embodiments, wherein the EBV polypeptide comprises an amino acid sequence with at least 80%, 85%, 90%, 95%, 97%, 98%, 99%, or 100% identity to SEQ ID NO: 38.

Embodiment 22 is the antigenic EBV polypeptide or composition of any one of embodiments 3-21, further comprising a further linker that separates the EBV polypeptide and the ferritin.

Embodiment 23 is the antigenic EBV polypeptide or composition of any one of embodiments 3-22, comprising an EBV gp42 polypeptide located N-terminal to the ferritin and C-terminal to the gH polypeptide, wherein a linker separates the EBV gp42 polypeptide and the ferritin, optionally wherein the linker has a length of at least 15 amino acids or has a length of 15 to 60 amino acids, 20 to 60 amino acids, 30 to 60 amino acids, 40 to 60 amino acids, 30 to 50 amino acids, or 40 to 50 amino acids, further optionally wherein the linker comprises an amino acid sequence with at least 80%, 85%, 90%, 95%, 97%, 98%, 99%, or 100% identity to any one of SEQ ID NOs: 233, 234, 235, 236, 237, or 238.

Embodiment 24 is the antigenic EBV polypeptide or composition of embodiments 22 or 23, wherein the linker comprises a cysteine.

Embodiment 25 is the antigenic EBV polypeptide or composition of any one of embodiments 22-24, wherein the linker comprises an amino acid sequence with at least 80%, 85%, 90%, 95%, 97%, 98%, 99%, or 100% identity to SEQ ID NO: 33.

Embodiment 26 is the antigenic EBV polypeptide or composition of embodiments 24-25, wherein the cysteine is conjugated to an immune-stimulatory moiety, optionally wherein the immune-stimulatory moiety is an agonist of TLR2, TLR7/8, TLR9, or STING.

Embodiment 27 is the antigenic EBV polypeptide or composition of any one of embodiments 3-26, wherein the ferritin comprises one or more of E12C, S26C, S72C, A75C, K79C, S100C, and S111C mutations of H. pylori ferritin or one or more corresponding mutations in a non-H. pylori ferritin as determined by pairwise or structural alignment.

Embodiment 28 is the antigenic EBV polypeptide or composition of any one of embodiments 3-27, wherein the ferritin comprises a mutation replacing a surface-exposed asparagine with a non-asparagine amino acid, optionally wherein the asparagine is at position 19 of H. pylori ferritin, or an analogous position in a non-H. pylori ferritin as determined by pairwise or structural alignment.

Embodiment 29 is the antigenic EBV polypeptide or composition of any one of embodiments 3-28, wherein the ferritin comprises a mutation replacing an internal cysteine with a non-cysteine amino acid, optionally wherein the internal cysteine is at position 31 of H. pylori ferritin, or a position that corresponds to position 31 of H. pylori ferritin as determined by pair-wise or structural alignment.

Embodiment 30 is the antigenic EBV polypeptide or composition of any one of embodiments 3-29, wherein the ferritin comprises an amino acid sequence with 80%, 85%, 90%, 95%, 98%, or 99% identity to any one of SEQ ID NOs: 201-207 or 211-215.

Embodiment 31 is the antigenic EBV polypeptide or composition of any one of embodiments 1-31, wherein the antigenic EBV polypeptide comprises a sequence with at least 80%, 85%, 90%, 95%, 98%, or 99% identity to amino acids 23-1078 of SEQ ID NO: 226.

Embodiment 32 is the antigenic EBV polypeptide or composition of any one of embodiments 1-31, wherein the antigenic EBV polypeptide comprises a sequence with at least 80%, 85%, 90%, 95%, 98%, or 99% identity to any one of SEQ ID NOs: 226-231 or 241-242, optionally lacking the leader sequence.

Embodiment 33 is a ferritin particle comprising the antigenic EBV polypeptide or the first and second polypeptides of any one of embodiments 3-32.

Embodiment 34 is a composition comprising the antigenic EBV polypeptide(s) or ferritin particle of any one of the preceding embodiments and a pharmaceutically acceptable carrier.

Embodiment 35 is the composition of embodiment 34, wherein the ferritin particle comprises an EBV gL polypeptide and an EBV gH polypeptide, and the composition further comprises a second ferritin particle comprising a gp220 polypeptide.

Embodiment 36 is the antigenic EBV polypeptide, ferritin particle, or composition of any one of the preceding embodiments for use in a method of eliciting an immune response to influenza or in protecting a subject against infection with EBV.

Embodiment 37 is a method of eliciting an immune response to EBV or protecting a subject against infection with EBV comprising administering any one or more antigenic EBV polypeptide, ferritin particle, or composition of any one of the preceding embodiments to a subject.

Embodiment 38 is the antigenic EBV polypeptide, ferritin particle, composition, or method of any one of embodiments 36-37, wherein the subject is human.

Embodiment 39 is a nucleic acid encoding the antigenic EBV polypeptide of any one of embodiments 1-32, optionally wherein the nucleic acid is an mRNA.

Additional objects and advantages will be set forth in the description which follows, and/or will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate certain embodiments and together with the description, serve to explain the principles described herein.

BRIEF DESCRIPTION OF THE DRAWINGS

FIG. 1B also presents the UV absorbance trace of fractions from a size exclusion column (Superose® 6) purification.

FIG. 7A shows the design of a nanoparticle comprising an EBV polypeptide and ferritin comprising a mutation replacing a surface-exposed amino acid with a cysteine for conjugation to an immune-stimulatory moiety such as a toll-like receptor (TLR) agonist. For an exemplary sequence corresponding to this design, see SEQ ID NO: 14, in which a single-chain gL/gH antigen is linked to ferritin by a flexible 46 amino acid linker. FIG. 7B shows a representative toll-like receptor (TLR) agonist (SM7/8a with a PEG4-maleimide linker) suitable for conjugation to a construct according to FIG. 7A. FIG. 7C shows an electron micrograph (EM) image of a gL/gH nanoparticle with SM7/8a conjugated thereto via the cysteine on the ferritin surface and a PEG4-maleimide linker.

FIGS. 11A-11D show electron microscopy (EM) images of unconjugated (FIGS. 11A, C) and conjugated (FIGS. 11B, D) single-chain gL/gH (FIGS. 11A, B) and gp220 (FIGS. 11C, D) ferritin nanoparticles, indicating that conjugation of SM7/8a to these nanoparticles did not disrupt nanoparticle structure.

FIGS. 30A-E show endpoint binding titers against the indicated antigens.

FIG. 31A shows purification of gH/gL/gp42_NP_C12 (SEQ ID NO: 228) using Superose 6 size exclusion chromatography. The arrow depicts the fractions collected from the peak with a denaturing coomassie gel analysis and a western blot analysis using anti-ferritin antibodies. FIG. 31B is a dynamic light scattering analysis of the sample in FIG. 31A, which shows the particle size radius of 20.6 nm.

FIG. 32A shows purification of gH/gL/gp42_NP_C13 (SEQ ID NO: 229) using the Superose 6 size exclusion chromatography. The arrow depicts the fractions collected from the peak with a denaturing coomassie gel analysis and a western blot analysis using anti-ferritin antibodies. FIG. 32B is a dynamic light scattering analysis of the sample in FIG. 32A, which shows the particle size radius of 17.1 nm.

FIG. 33A shows purification of gH/gL/gp42_NP_C14 (SEQ ID NO: 230) using the Superose 6 size exclusion chromatography. The arrow depicts the fractions collected from the peak with a denaturing coomassie gel analysis and a western blot analysis using anti-ferritin antibodies. FIG. 33B is a dynamic light scattering analysis of the sample in FIG. 33A, which shows the particle size radius of 16.9 nm.

FIG. 35A-E: A cartoon of a single-chain construct of gH/gL/gp42 fused to ferritin (as in each of SEQ ID NOs: 227-231) is shown in FIG. 35A. The fusion between each protein is via a flexible amino acid linker or a rigid amino acid linker specified above. The single-chain gH/gL/gp42 molecule will assure a 1:1:1 ratio of heterotrimer formation on the nanoparticle. The crystal structure of this heterotrimer has been solved to show that the single-chain gH/gL/gp42 can adopt a heterotrimer formation similar to wild-type gH, gL, and gp42 proteins found in nature (FIG. 35B; see also FIG. 34). FIG. 35C is a model of how this single-chain gH/gL/gp42 heterotrimer is displayed on the nanoparticle through the fusion with ferritin. There are twenty-four copies of the single-chain gH/gL/gp42 displayed on a single nanoparticle. FIG. 35D shows the purification after expression of SEQ ID NOs: 227 in 293Expi cells. A denaturing SDS Coomassie gel shows the gH/gL/gp42 fused to ferritin to be above 150 kD with glycosylation. FIG. 35E shows negative stain electron microscopy analysis of the purified product, indicating that the single-chain gH/gL/gp42 fused to ferritin can successfully form nanoparticles displaying the gH/gL/gp42 antigens on the surface.

DETAILED DESCRIPTION

Figure 1A:
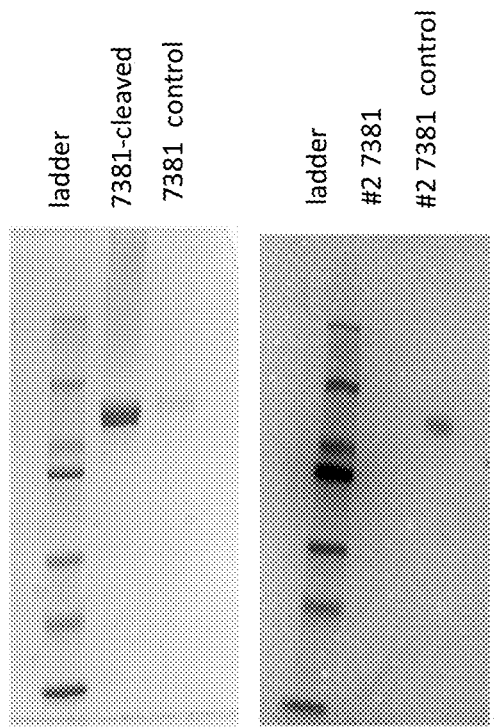
FIGS. 1A-1B show purified single-chain gL and gH monomer (FIG. 1A) (SEQ ID NO: 6) and trimer (FIG. 1B) (SEQ ID NO: 11) with and without removal of the His-tag by Coomassie and Western blot analysis.

EBV polypeptides are provided, which can be antigenic when administered alone, with adjuvant as a separate molecule, and/or as part of a nanoparticle (e.g., ferritin particle or lumazine synthase particle), which can be self-adjuvanting. Such polypeptides and compositions comprising such polypeptides can be used to elicit antibody responses against Epstein Barr virus (EBV). The EBV polypeptide can comprise a gL, gH, gL/gH, gp220, or gp42 polypeptide, or combinations thereof, and a multimerization domain such as a ferritin. The ferritin may comprise a mutation replacing a surface-exposed amino acid with a cysteine, which can facilitate conjugating immune-stimulatory moieties to the ferritin via the cysteine. Such conjugation may eliminate or reduce the need for separately administered adjuvant, and may also potentially reduce the amount of adjuvant/immune-stimulatory moiety needed to elicit an immune response to the EBV polypeptide. In some embodiments, an antigenic EBV polypeptide comprising (i) an EBV polypeptide, and (ii-a) a ferritin comprising a surface-exposed cysteine, or (ii-b) a ferritin and an N- or C-terminal linker comprising a cysteine is provided. Any of the EBV polypeptides described herein can be combined with any of the ferritins described below. Nucleic acids that encode the polypeptides described herein are also provided.

A. Definitions

As used herein, an "EBV polypeptide" refers to a polypeptide comprising all or part of an amino acid sequence encoded by EBV. Similarly, gL, gH, gp42, and gp220 polypeptides refer to polypeptides comprising all or part of a gL, gH, gp42, or gp220 amino acid sequence, respectively, encoded by EBV. Polypeptides with, e.g., at least 80% identity to an EBV-encoded polypeptide will necessarily comprise part of the EBV-encoded polypeptide. The terms "gL polypeptide," "gH polypeptide," "gp42 polypeptide," and "gp220 polypeptide" are used interchangeably with "EBV gL polypeptide," "EBV gH polypeptide," "EBV gp42 polypeptide," and "EBV gp220 polypeptide," respectively. Immunization with an EBV polypeptide as part or all of an antigenic polypeptide may confer protection from infection with EBV. Unless the context dictates otherwise, any polypeptide disclosed herein comprising an EBV polypeptide can comprise all or part of multiple sequences encoded by EBV (for example, all or part of gL and gH of EBV, or all or part of gL, gH, and gp42 of EBV).

As used herein, a "monomer," or "monomer construct" refers to a construct expressed as a single-chain protein. A monomer may comprise gL and gH of EBV expressed in a single chain, or gL, gH, and gp42 of EBV expressed in a single chain.

As used herein, a "trimer," or "trimer construct" refers to a construct comprising gL and/or gH of EBV together with a trimerization domain, such as a foldon trimerization domain derived from T4 phage fibritin. Other trimerization domains, such as the human collagen XVIII trimerization domain (see, e.g., Alvarez-Cienfuegos et al., Scientific Reports 2016; 6:28643) and the L1ORF1p trimerization domain (see, e.g., Khazina et al., Proc Natl Acad Sci USA 2009 Jan. 12; 106(3):731-36) are also known in the art and can be used in trimeric constructs.

"Ferritin" or "ferritin protein," as used herein, refers to a protein with detectable sequence identity to *H. pylori* ferritin (SEQ ID NO: 208 or 209) or another ferritin discussed herein, such as *P. furiosus* ferritin, *Trichoplusia ni* ferritin, or human ferritin, that serves to store iron, e.g., intracellularly or in tissues or to carry iron in the bloodstream. Such exemplary ferritins, including those that occur as two polypeptide chains, known as the heavy and light chains (e.g., *T. ni* and human ferritin), are discussed in detail below. In some embodiments, a ferritin comprises a sequence with at least 15%, 20%, 30%, 40%, 50%, 60%, 70%, 75%, 80%, 85%, 90%, 95%, 97%, 98%, 99%, or 99.5% identity to a ferritin sequence disclosed herein, e.g., in Table 2 (Sequence Table). A ferritin may be a fragment of a full-length naturally-occurring sequence.

"Wild-type ferritin," as used herein, refers to a ferritin whose sequence consists of a naturally-occurring sequence. Ferritins also include full-length ferritin or a fragment of ferritin with one or more differences in its amino acid sequence from a wild-type ferritin.

As used herein, a "ferritin monomer" refers to a single ferritin molecule (or, where applicable, a single ferritin heavy or light chain) that has not assembled with other ferritin molecules. A "ferritin multimer" comprises multiple associated ferritin monomers. A "ferritin protein" includes monomeric ferritin and multimeric ferritin.

As used herein, "ferritin particle," refers to ferritin that has self-assembled into a globular form. Ferritin particles are sometimes referred to as "ferritin nanoparticles" or simply "nanoparticles". In some embodiments, a ferritin particle comprises 24 ferritin monomers (or, where applicable, 24 total heavy and light chains).

"Hybrid ferritin," as used herein, refers to ferritin comprising H. pylori ferritin with an amino terminal extension of bullfrog ferritin. An exemplary sequence used as an amino terminal extension of bullfrog ferritin appears as SEQ ID NO: 217. In hybrid ferritin, the amino terminal extension of bullfrog ferritin can be fused to H. pylori ferritin such that immune-stimulatory moiety attachment sites are distributed evenly on the ferritin particle surface. "Bullfrog linker" as used herein is a linker comprising the sequence of SEQ ID NO: 217. Hybrid ferritin is also sometimes referred to as "bfpFerr" or "bfp ferritin." Any of the constructs comprising a bullfrog sequence can be provided without the bullfrog sequence, such as, for example, without a linker or with an alternative linker. Exemplary bullfrog linker sequences are provided in Table 2. Where Table 2 shows a bullfrog linker, the same construct may be made without a linker or with an alternative linker.

"N-glycan," as used herein, refers to a saccharide chain attached to a protein at the amide nitrogen of an N (asparagine) residue of the protein. As such, an N-glycan is formed by the process of N-glycosylation. This glycan may be a polysaccharide.

"Glycosylation," as used herein, refers to the addition of a saccharide unit to a protein.

"Immune response," as used herein, refers to a response of a cell of the immune system, such as a B cell, T cell, dendritic cell, macrophage or polymorphonucleocyte, to a stimulus such as an antigen or vaccine. An immune response can include any cell of the body involved in a host defense response, including for example, an epithelial cell that secretes an interferon or a cytokine. An immune response includes, but is not limited to, an innate and/or adaptive immune response. As used herein, a "protective immune response" refers to an immune response that protects a subject from infection (e.g., prevents infection or prevents the development of disease associated with infection). Methods of measuring immune responses are well known in the art and include, for example, by measuring proliferation and/or activity of lymphocytes (such as B or T cells), secretion of cytokines or chemokines, inflammation, antibody production and the like. An "antibody response" is an immune response in which antibodies are produced.

As used herein, an "antigen" refers to an agent that elicits an immune response, and/or an agent that is bound by a T cell receptor (e.g., when presented by an WIC molecule) or to an antibody (e.g., produced by a B cell) when exposed or administered to an organism. In some embodiments, an antigen elicits a humoral response (e.g., including production of antigen-specific antibodies) in an organism. Alternatively, or additionally, in some embodiments, an antigen elicits a cellular response (e.g., involving T-cells whose receptors specifically interact with the antigen) in an organism. A particular antigen may elicit an immune response in one or several members of a target organism (e.g., mice, rabbits, primates, humans), but not in all members of the target organism species. In some embodiments, an antigen elicits an immune response in at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the members of a target organism species. In some embodiments, an antigen binds to an antibody and/or T cell receptor, and may or may not induce a particular physiological response in an organism. In some embodiments, for example, an antigen may bind to an antibody and/or to a T cell receptor in vitro, whether or not such an interaction occurs in vivo. In some embodiments, an antigen reacts with the products of specific humoral or cellular immunity, including those induced by heterologous immunogens. Antigens include antigenic ferritin proteins comprising ferritin (e.g., comprising one or more mutations) and a non-ferritin polypeptide as described herein.

An "immune-stimulatory moiety," as used herein, refers to a moiety that is covalently attached to a ferritin or antigenic ferritin polypeptide and that can activate a component of the immune system (either alone or when attached to ferritin or antigenic ferritin polypeptide). Exemplary immune-stimulatory moieties include agonists of toll-like receptors (TLRs), e.g., TLR 4, 7, 8, or 9. In some embodiments, an immune-stimulatory moiety is an adjuvant.

"Adjuvant," as used herein, refers to a substance or vehicle that non-specifically enhances the immune response to an antigen. Adjuvants can include, without limitation, a suspension of minerals (e.g., alum, aluminum hydroxide, or phosphate) on which antigen is adsorbed; a water-in-oil or oil-in-water emulsion in which antigen solution is emulsified in mineral oil or in water (e.g., Freund's incomplete adjuvant). Sometimes killed mycobacteria is included (e.g., Freund's complete adjuvant) to further enhance antigenicity. Immuno-stimulatory oligonucleotides (e.g., a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants can also include biological molecules, such as Toll-Like Receptor (TLR) agonists and costimulatory molecules. An adjuvant may be administered as a separate molecule in a composition or covalently bound (conjugated) to ferritin or an antigenic ferritin polypeptide.

An "antigenic EBV polypeptide" is used herein to refer to a polypeptide comprising all or part of an EBV amino acid sequence of sufficient length that the molecule is antigenic with respect to EBV. Antigenicity may be a feature of the EBV sequence as part of a construct further comprising a heterologous sequence, such as a ferritin or lumazine synthase protein and/or immune-stimulatory moiety. That is, if an EBV sequence is part of a construct further comprising a heterologous sequence, then it is sufficient that the construct can serve as an antigen that generates anti-EBV antibodies, regardless of whether the EBV sequence without the heterologous sequence could do so.

"Antigenic ferritin polypeptide" and "antigenic ferritin protein" are used interchangeably herein to refer to a polypeptide comprising a ferritin and a non-ferritin polypeptide (e.g., an EBV polypeptide) of sufficient length that the molecule is antigenic with respect to the non-ferritin polypeptide. The antigenic ferritin polypeptide may further comprise an immune-stimulatory moiety. Antigenicity may be a feature of the non-ferritin sequence as part of the larger construct. That is, it is sufficient that the construct can serve as an antigen against the non-ferritin polypeptide, regardless of whether the non-ferritin polypeptide without the ferritin (and immune-stimulatory moiety if applicable) could do so. In some embodiments, the non-ferritin polypeptide is an EBV polypeptide, in which case the antigenic ferritin polypeptide is also an "antigenic EBV polypeptide." To be clear, however, an antigenic EBV polypeptide does not need to comprise ferritin. "Antigenic polypeptide" is used herein to refer to a polypeptide which is either or both of an antigenic ferritin polypeptide and an antigenic EBV polypeptide.

"Self-adjuvanting," as used herein, refers to a composition or polypeptide comprising a ferritin and an immune-stimulatory moiety directly conjugated to the ferritin so that the ferritin and immune-stimulatory moiety are in the same molecular entity. An antigenic ferritin polypeptide comprising a non-ferritin polypeptide may be conjugated to an immune-stimulatory moiety to generate a self-adjuvanting polypeptide.

A "surface-exposed" amino acid, as used herein, refers to an amino acid residue in a protein (e.g., a ferritin) with a side chain that can be contacted by solvent molecules when the protein is in its native three-dimensional conformation after multimerization, if applicable. Thus, for example, in the case of ferritin that forms a 24-mer, a surface-exposed amino acid residue is one whose side chain can be contacted by solvent when the ferritin is assembled as a 24-mer, e.g., as a ferritin multimer or ferritin particle.

As used herein, a "subject" refers to any member of the animal kingdom. In some embodiments, "subject" refers to humans. In some embodiments, "subject" refers to non-human animals. In some embodiments, subjects include, but are not limited to, mammals, birds, reptiles, amphibians, fish, insects, and/or worms. In certain embodiments, the non-human subject is a mammal (e.g., a rodent, a mouse, a rat, a rabbit, a monkey, a dog, a cat, a sheep, cattle, a primate, and/or a pig). In some embodiments, a subject may be a transgenic animal, genetically-engineered animal, and/or a clone. In certain embodiments of the present invention the subject is an adult, an adolescent or an infant. In some embodiments, terms "individual" or "patient" are used and are intended to be interchangeable with "subject".

As used herein, the term "vaccination" or "vaccinate" refers to the administration of a composition intended to generate an immune response, for example to a disease-causing agent. Vaccination can be administered before, during, and/or after exposure to a disease-causing agent, and/or to the development of one or more symptoms, and in some embodiments, before, during, and/or shortly after exposure to the agent. In some embodiments, vaccination includes multiple administrations, appropriately spaced in time, of a vaccinating composition.

The disclosure describes nucleic acid sequences and amino acid sequences having a certain degree of identity to a given nucleic acid sequence or amino acid sequence, respectively (a references sequence).

"Sequence identity" between two nucleic acid sequences indicates the percentage of nucleotides that are identical between the sequences. "Sequence identity" between two amino acid sequences indicates the percentage of amino acids that are identical between the sequences.

The terms "% identical", "% identity" or similar terms are intended to refer, in particular, to the percentage of nucleotides or amino acids which are identical in an optimal alignment between the sequences to be compared. Said percentage is purely statistical, and the differences between the two sequences may be but are not necessarily randomly distributed over the entire length of the sequences to be compared. Comparisons of two sequences are usually carried out by comparing said sequences, after optimal alignment, with respect to a segment or "window of comparison", in order to identify local regions of corresponding sequences. The optimal alignment for a comparison may be carried out manually or with the aid of the local homology algorithm by Smith and Waterman, 1981, Ads App. Math. 2, 482, with the aid of the local homology algorithm by Needleman and Wunsch, 1970, J. Mol. Biol. 48, 443, with the aid of the similarity search algorithm by Pearson and Lipman, 1988, Proc. Natl Acad. Sci. USA 88, 2444, or with the aid of computer programs using said algorithms (GAP, BESTFIT, FASTA, BLAST P, BLAST N and TFASTA in Wisconsin Genetics Software Package, Genetics Computer Group, 575 Science Drive, Madison, Wis.).

Percentage identity is obtained by determining the number of identical positions at which the sequences to be compared correspond, dividing this number by the number of positions compared (e.g., the number of positions in the reference sequence) and multiplying this result by 100.

In some embodiments, the degree of identity is given for a region which is at least about 50%, at least about 60%, at least about 70%, at least about 80%, at least about 90% or about 100% of the entire length of the reference sequence. For example, if the reference nucleic acid sequence consists of 200 nucleotides, the degree of identity is given for at least about 100, at least about 120, at least about 140, at least about 160, at least about 180, or about 200 nucleotides, in some embodiments in continuous nucleotides. In some embodiments, the degree of identity is given for the entire length of the reference sequence.

Nucleic acid sequences or amino acid sequences having a particular degree of identity to a given nucleic acid sequence or amino acid sequence, respectively, may have at least one functional property of said given sequence, e.g., and in some instances, are functionally equivalent to said given sequence. One important property includes the ability to act as a cytokine, in particular when administered to a subject. In some embodiments, a nucleic acid sequence or amino acid sequence having a particular degree of identity to a given nucleic acid sequence or amino acid sequence is functionally equivalent to said given sequence.

As used herein, the term "kit" refers to a packaged set of related components, such as one or more compounds or compositions and one or more related materials such as solvents, solutions, buffers, instructions, or desiccants.

B. Antigenic EBV Polypeptides Comprising gL and gH Polypeptides

EBV has three glycoproteins, glycoprotein B (gB), gH, and gL, that form the core membrane fusion machinery to allow viral penetration into a cell. gL and gH have been previously described, for example, in Matsuura et al., Proc Natl Acad Sci USA. 2010 Dec. 28; 107(52):22641-6. Monomers and trimers of gL and gH for use as vaccines have been described, for example, in Cui et al., Vaccine. 2016 Jul. 25; 34(34):4050-5. The gH and gL proteins associate to form a heterodimeric complex considered necessary for efficient membrane fusion and binding to epithelial cell receptors required for viral entry.

Disclosed herein are antigenic polypeptides comprising EBV gL and EBV gH. In some embodiments, the polypeptide exists as a single-chain. In some embodiments, the polypeptide forms a trimer, e.g., through trimerization of a trimerization domain, such as a T4 phage fibritin trimerization domain. In some embodiments, the polypeptide forms a nanoparticle (e.g., ferritin or lumazine synthase particle), e.g., through multimerization of a ferritin or lumazine synthase. In some embodiments, an antigenic EBV polypeptide according to this disclosure comprises an EBV gL polypeptide and an EBV gH polypeptide, and a linker having a length of at least 15 amino acids separating the EBV gL polypeptide and the EBV gH polypeptide. It has been found that a relatively long linker can provide benefits such as improved expression and/or immunogenicity.

In some embodiments, the EBV gH and/or gL polypeptides are full-length gH and/or gL (for exemplary full-length sequences, see GenBank Accession Nos. CEQ35765.1 and YP_001129472.1, respectively). In some embodiments, the EBV gH and/or gL polypeptides are fragments of gH and/or gL. In some embodiments, the gL polypeptide is a gL(D7) construct with a 7-amino acid deletion at the end of the gL C terminus. In some embodiments, the gH polypeptide comprises a mutation at C137, such as a C137A mutation. In some embodiments, the C137 mutation removes a native, unpaired cysteine to avoid non-specific conjugation. In some embodiments, the gH polypeptide comprises a mutation to remove a cysteine corresponding to cysteine 137 of SEQ ID NO: 37, such as a C137A mutation. In some embodiments, the C137 mutation removes a native, unpaired cysteine to avoid non-specific conjugation.

In some embodiments, the EBV gL polypeptide comprises an amino acid sequence with at least 80%, 85%, 90%, 95%, 97%, 98%, 99%, or 100% identity to SEQ ID NO: 36. In some embodiments, the EBV gH polypeptide comprises an amino acid sequence with at least 80%, 85%, 90%, 95%, 97%, 98%, 99%, or 100% identity to SEQ ID NO: 37.

In some embodiments, a mammalian leader sequence (also known as a signal sequence) is appended N-terminally to an EBV polypeptide such as a gH or gL polypeptide, e.g., at the N-terminus of the polypeptide. In some embodiments, a mammalian leader sequence results in secretion of a protein when expressed in mammalian cells.

Native EBV gH and/or gL sequences are shown in GenBank Accession No. NC_009334.1 (Human herpesvirus 4, complete genome, dated 26 Mar. 2010). For some of the constructs disclosed herein, amino acids 23-137 of the gL amino acid sequence in NC_009334.1 was used as the gL polypeptide, and the native signal peptide (amino acids 1-22 of the NCBI sequence) was replaced with an IgG K leader sequence. For some of the constructs, amino acids 19-678 of the gH amino acid sequence in NC_009334.1 was used as the gH polypeptide. In some embodiments, the gL and gH were linked via a linker as shown in the table of sequences herein.

In some embodiments, gL and gH polypeptides are expressed as a single-chain monomer. In some embodiments, the monomer composition comprises or consists of a sequence shown in the Sequence Table and denoted in the description as "monomer". A single-chain comprising gL and gH polypeptides may be referred to as "gL/gH," which can be used interchangeably with "gH_gL," "gL_gH," or "gL/gH."

In some embodiments, gL and gH are provided as a trimer. In some embodiments, a trimerization domain is placed after (C-terminal to) the gH sequence and in some embodiments, this is followed by a His6 (SEQ ID NO: 243) sequence. The foldon trimerization domain is exemplary, as any trimerization domain known in the art can be used, such as collagen or L1ORF1p trimerization domains referenced herein. A gL and gH trimer has been shown to induce higher serum neutralization titers relative to a gL and gH monomer using peripheral blood human naïve B cells (see, for example, Cui et al., Vaccine. 2016 Jul. 25; 34(34):4050-5).

In some embodiments, a gL/gH trimer has an amino acid sequence comprising or consisting of a sequence shown in the Sequence Table and denoted in the description as "trimer."

The gL/gH polypeptide can be combined with any of the ferritins or lumazine synthases discussed herein. For example, in some embodiments, an antigenic EBV polypeptide comprises a monomer or trimer gL/gH polypeptide (+/−gp42 and/or gp220) and i) a heavy or light chain ferritin (e.g., *T. ni* heavy or light chain ferritin); or ii) a ferritin, optionally comprising a surface-exposed cysteine.

Additionally, in some embodiments, any antigenic EBV polypeptide comprising an EBV gL/gH polypeptide and a ferritin can be present in a composition comprising another polypeptide disclosed herein.

C. Antigenic EBV Polypeptides Comprising a Gp220 Polypeptide

In some embodiments, an antigenic EBV polypeptide comprises a gp220 polypeptide. A gp220-hybrid bullfrog/*H. pylori* ferritin nanoparticle has been previously described in Kanekiyo Cell. 2015 Aug. 27; 162(5):1090-100. This nanoparticle did not comprise a mutation providing a surface-exposed cysteine or a linker comprising a cysteine, among other differences from certain ferritins described herein.

In some embodiments, the gp220 polypeptide comprises an amino acid sequence with at least 80%, 85%, 90%, 95%, 97%, 98%, 99%, or 100% identity to SEQ ID NO: 38.

In some embodiments, a mammalian leader sequence (also known as a signal sequence) is N-terminally appended to a gp220 polypeptide. In some embodiments, a mammalian leader sequence results in secretion of a protein when expressed in mammalian cells.

The gp220 polypeptide can be combined with any of the ferritins or lumazine synthases discussed herein. For example, in some embodiments, an antigenic EBV polypeptide comprises a gp220 polypeptide (+/−gL/gH and/or gp42) and i) a heavy or light chain ferritin (e.g., *T. ni* heavy or light chain ferritin); or ii) a ferritin, optionally comprising a surface-exposed cysteine as described herein.

Additionally, in some embodiments, any antigenic EBV polypeptide comprising a gp220 polypeptide and a ferritin can be present in a composition comprising another polypeptide disclosed herein.

D. Antigenic EBV Polypeptides Comprising a Gp42 Polypeptide

In some embodiments, an antigenic EBV polypeptide comprises a gp42 polypeptide. An exemplary gp42 sequence is provided as SEQ ID NO: 34. A further exemplary gp42 sequence, suitable for inclusion in fusions e.g. with gL and gH polypeptides, is provided as SEQ ID NO: 239. Another exemplary gp42 sequence, suitable for inclusion in fusions e.g. with gL and gH polypeptides, is provided as SEQ ID NO: 240.

In some embodiments, the gp42 polypeptide comprises an amino acid sequence with at least 80%, 85%, 90%, 95%, 97%, 98%, 99%, or 100% identity to SEQ ID NO: 34. In some embodiments, the gp42 polypeptide comprises an amino acid sequence with at least 80%, 85%, 90%, 95%, 97%, 98%, 99%, or 100% identity to SEQ ID NO: 239. In some embodiments, the gp42 polypeptide comprises an amino acid sequence with at least 80%, 85%, 90%, 95%, 97%, 98%, 99%, or 100% identity to SEQ ID NO: 240.

In some embodiments, a mammalian leader sequence (also known as a signal sequence) is N-terminally appended to a gp42 polypeptide. In some embodiments, a mammalian leader sequence results in secretion of a protein when expressed in mammalian cells. An exemplary leader sequence is amino acids 1-22 of SEQ ID NO: 226.

In some embodiments, an antigenic EBV polypeptide comprising a gH and/or gL polypeptide further comprises a gp42 polypeptide. Any of the EBV polypeptides comprising a gH and/or gL polypeptide described above can further comprise a gp42 polypeptide. In some embodiments, the gp42 polypeptide is located C-terminal to the gH and/or gL polypeptide(s), as exemplified in SEQ ID NOs: 21 and 226-231. In some embodiments, the gp42 polypeptide is located N-terminal to a ferritin, also as exemplified in SEQ ID NOs: 21 and 227-231. Thus, for example, an antigenic EBV polypeptide may comprise, in N- to C-terminal orientation, a gL polypeptide, a gH polypeptide, a gp42 polypeptide, and optionally a ferritin. Linkers such as those described herein can separate the gp42 polypeptide from EBV polypeptides and/or ferritins located N-terminal and/or C-terminal thereto. In some embodiments, a linker separates each EBV polypeptide in an antigenic ferritin polypeptide (e.g., a gL polypeptide, a gH polypeptide, and a gp42 polypeptide), and a further linker may be present between the ferritin if present and the EBV polypeptide proximal thereto (e.g., a gp42 polypeptide).

In some embodiments, a linker having a length of at least 15 amino acids separates the EBV gH polypeptide and the EBV gp42 polypeptide. Such a linker may have a length of 15 to 60 amino acids, 20 to 60 amino acids, 30 to 60 amino acids, 40 to 60 amino acids, 30 to 50 amino acids, or 40 to 50 amino acids. In some embodiments, the linker comprises an amino acid sequence with at least 80%, 85%, 90%, 95%, 97%, 98%, 99%, or 100% identity to SEQ ID NO: 234.

In some embodiments, where gp42 and ferritin are present in a polypeptide, a linker separates the EBV gp42 polypeptide and the ferritin. Such a linker may have a length of at least 15 amino acids or has a length of 15 to 60 amino acids, 20 to 60 amino acids, 30 to 60 amino acids, 40 to 60 amino acids, 30 to 50 amino acids, or 40 to 50 amino acids. In some embodiments, such a linker comprises an amino acid sequence with at least 80%, 85%, 90%, 95%, 97%, 98%, 99%, or 100% identity to any one of SEQ ID NOs: 233, 234, 235, 236, 237, or 238.

The gp42 polypeptide can be combined with any of the ferritins or lumazine synthases discussed herein. For example, in some embodiments, a polypeptide comprises a gp42 polypeptide (+/−gL/gH and/or gp220) and a heavy or light chain ferritin (e.g., T. ni heavy or light chain ferritin); or ii) ferritin, optionally comprising a surface-exposed cysteine as described herein.

In some embodiments, the antigenic EBV polypeptide comprises a sequence with at least 80%, 85%, 90%, 95%, 98%, or 99% identity to amino acids 23-1078 of SEQ ID NO: 226. In some embodiments, the antigenic EBV polypeptide comprises a sequence with 80%, 85%, 90%, 95%, 98%, or 99% identity to amino acids 1-1078 of SEQ ID NO: 226. In some embodiments, the antigenic EBV polypeptide comprises a sequence with at least 80%, 85%, 90%, 95%, 98%, or 99% identity to any one of SEQ ID NOs: 226, 227, 228, 229, 230, or 231, optionally lacking the leader sequence (e.g., lacking any or all of amino acids 1-22 of these sequences).

Additionally, in some embodiments, any antigenic EBV polypeptide comprising a gp42 polypeptide and a ferritin can be present in a composition comprising another polypeptide disclosed herein.

E. Linkers

In some embodiments, an antigenic EBV polypeptide comprises a linker between gL and gH polypeptides. In some embodiments, an antigenic EBV polypeptide comprises a linker between an EBV polypeptide and a ferritin or lumazine synthase. The following features are described with respect to either of such linkers, although the present invention provides that a relatively long linker between the gL and gH sequences may provide an increase in immunogenicity. Any linker may be used; for example, in some embodiments, the linker is 2, 3, 4, 5, 6, 7, 8, 9, or 10 amino acids in length. In some embodiments, the linker is about 2-4, 2-6, 2-8, 2-10, 2-12, or 2-14 amino acids in length. In some embodiments, the linker is a peptide linker, which can facilitate expression of the antigenic ferritin polypeptide as a fusion protein (e.g., from a single open reading frame). In some embodiments, the linker is a glycine-serine linker. In some embodiments, the glycine-serine linker is GS, GGGS (SEQ ID NO: 244), 2XGGGS (i.e., GGGSGGGS) (SEQ ID NO: 245), or 5XGGGS (SEQ ID NO: 246). In some embodiments, the linker between the EBV polypeptide and ferritin is GS, GGGS (SEQ ID NO: 244), 2XGGGS (i.e., GGGSGGGS) (SEQ ID NO: 245), or 5XGGGS (SEQ ID NO: 246).

In some embodiments, the linker is at least 15 amino acids in length. In some embodiments, the linker is at least 25 amino acids in length. In some embodiments, the linker is at least 30 amino acids in length. In some embodiments, the linker is at least 35 amino acids in length. In some embodiments, the linker is at least 40 amino acids in length. In some embodiments, the linker is less than or equal to 60 amino acids in length. In some embodiments, the linker is less than or equal to 50 amino acids in length. In some embodiments, the linker is about 16, 28, 40, 46, or 47 amino acids in length. In some embodiments, the linker is flexible. In some embodiments, the linker comprises a cysteine, e.g., for use as a site for conjugation of an immune-stimulatory moiety (e.g., adjuvant); an exemplary linker comprising a cysteine is provided as SEQ ID NO: 225. In some embodiments, the linker comprises a sequence with at least 75%, 80%, 85%, 90%, or 95% identity to SEQ ID NO: 225, and further comprises a cysteine corresponding to the cysteine in SEQ ID NO: 225. In some embodiments, the linker comprises at least 25 amino acids (e.g., 25 to 60 amino acids), wherein a cysteine is located at a position ranging from the $8^{th}$ amino acid from the N-terminus to the $8^{th}$ amino acid from the C-terminus, or within 10 amino acids of the central residue or bond of the linker.

In some embodiments, the linker comprises glycine (G) and/or serine (S) amino acids. In some embodiments, the linker comprises or consists of glycine (G), serine (S), asparagine (N), and/or alanine (A) amino acids, and optionally a cysteine as discussed above. In some embodiments, the linker comprises an amino acid sequence with at least 80%, 85%, 90%, 95%, 97%, 98%, 99%, or 100% identity to SEQ ID NO: 222. In some embodiments, the linker comprises GGGGSGGGGSGGGGSG (SEQ ID NO: 28), GGSGSGSNSSASSGASSGGASGGSGGSG (SEQ ID NO: 29), GGSGSASSGASASGSSNGSGSGSGSNSSASS-GASSGGASGGSGGSG (SEQ ID NO: 30), or GS. In some embodiments, the linker comprises FR1 (SEQ ID NO: 31) or FR2 (SEQ ID NO: 32). In some embodiments, the linker comprises SEQ ID NO: 233-238.

In some embodiments, a linker comprising a cysteine as a conjugation site for an immune-stimulatory moiety such as an adjuvant is used in a construct comprising a ferritin molecule lacking an unpaired, surface-exposed cysteine, or in a construct comprising a ferritin molecule comprising an unpaired, surface-exposed cysteine.

In some embodiments, the linker is a cysteine-thrombin-histidine linker. In some embodiments, this linker is used to directly conjugate an EBV polypeptide to ferritin via click chemistry. An exemplary sequence comprising a cysteine-thrombin-histidine linker is SEQ ID NO: 39. Click chemistry suitable for conjugation reactions involving the cysteine-thrombin-histidine linker is discussed herein.

In some embodiments, a construct does not comprise a linker. In some embodiments, a construct comprises one linker. In some embodiments, a construct comprises two or more than two linkers.

In some embodiments, the construct comprises a linker between gH and gL but not between the polypeptide and ferritin or vice versa. In some embodiments, the construct only comprises a linker between the polypeptide and ferritin.

F. Antigenic EBV Polypeptides Comprising an EBV Polypeptide and Ferritin or Lumazine Synthase In some embodiments, an antigenic EBV polypeptide is provided, comprising an EBV polypeptide and ferritin. The EBV polypeptide can be any of the EBV polypeptides described herein, such as a gL, gH, gL/gH, gp220, gp42 polypeptide, or combinations thereof. The ferritin component of the polypeptide may be a ferritin from any species, and may or may not have mutations, such as a mutation replacing a surface-exposed amino acid with a cysteine as described herein. In some embodiments, the polypeptide comprises the amino acids of any one of SEQ ID NOS: 1-27.

In some embodiments, the ferritin in the polypeptide is a wild-type ferritin. In some embodiments, the ferritin is bacterial, insect, fungal, bird, or mammalian. In some embodiments, the ferritin is human. In some embodiments, the ferritin is bacterial.

In some embodiments, the ferritin is a light chain and/or heavy chain ferritin. In some embodiments, the ferritin is an insect ferritin, such as Trichoplusia ni heavy chain ferritin (SEQ ID NO: 211) or Trichoplusia ni light chain ferritin (SEQ ID NO: 212). In some embodiments, the ferritin is a human ferritin, such as human heavy chain ferritin (SEQ ID NO: 214 or FTH1, GENE ID No: 2495) or human light chain ferritin (SEQ ID NO: 215 or FTL, GENE ID No: 2512). In some embodiments, a ferritin nanoparticle comprises 24 total subunits of heavy chain ferritin and light chain ferritin, such as in human or Trichoplusia ni ferritin nanoparticles. T. ni ferritin nanoparticles can comprise 12 subunits of heavy chain ferritin and 12 subunits of light chain ferritin.

In some embodiments, an antigenic EBV polypeptide comprises a light chain ferritin and an EBV polypeptide. In some embodiments, an antigenic EBV polypeptide comprises a heavy chain ferritin and an EBV polypeptide. In some embodiments, an antigenic EBV polypeptide comprising a light chain ferritin and an EBV polypeptide can assemble with a heavy chain ferritin that is not linked to an EBV polypeptide. In some embodiments, an antigenic EBV polypeptide comprising a heavy chain ferritin and an EBV polypeptide can assemble with a light chain ferritin that is not linked to an EBV polypeptide. A ferritin not linked to an EBV polypeptide (or, more generally, a non-ferritin polypeptide) may be referred as a "naked ferritin."

In some embodiments, an antigenic polypeptide comprising a heavy chain ferritin and a polypeptide can assemble with an antigenic polypeptide comprising a light chain ferritin and an EBV polypeptide to allow presentation of two of the same or different non-ferritin polypeptides on a single ferritin nanoparticle. In some embodiments, the two different non-ferritin polypeptides are EBV polypeptides. In some embodiments, the two different non-ferritin polypeptides are encoded by EBV and a different infectious agent. In some embodiments, the different non-ferritin polypeptide from a different infectious agent is from a virus or bacterium.

In some embodiments, an antigenic polypeptide comprising a heavy chain ferritin and a non-ferritin polypeptide can assemble with a polypeptide comprising a light chain ferritin and a non-ferritin polypeptide to produce a bivalent composition.

In some embodiments, an antigenic polypeptide comprises a light chain ferritin and a gp220 and/or gp42 polypeptide. In some embodiments, an antigenic polypeptide comprises a heavy chain ferritin and a gp220 and/or gp42 polypeptide.

In some embodiments, an antigenic polypeptide comprises a light chain ferritin and a single-chain gL and gH polypeptide. In some embodiments, an antigenic polypeptide comprises a heavy chain ferritin and a single-chain gL and gH polypeptide.

In some embodiments, an antigenic polypeptide comprising a light chain ferritin and a gp220 and/or gp42 polypeptide assembles with an antigenic polypeptide comprising a heavy chain ferritin and a single-chain gL and gH polypeptide.

In some embodiments, an antigenic polypeptide comprising a heavy chain ferritin and a gp220 and/or gp42 polypeptide assembles with an antigenic polypeptide comprising a light chain ferritin and a single-chain gL and gH polypeptide. In some embodiments, twelve (12) gp220 and/or gp42 polypeptides and twelve (12) single-chain gL and gH polypeptides are comprised in an assembled ferritin nanoparticle, as in the case of an assembled T. ni ferritin nanoparticle.

Any type of ferritin nanoparticle(s) that comprises both gp220 and/or gp42 and single-chain gL and gH polypeptides may be referred to as a "bivalent" or "bivalent EBV" particle or construct. A composition comprising a gL and gH trimer together with a ferritin that comprises gp220 and/or gp42 would also be a bivalent EBV composition.

In some embodiments, the ferritin is H. pylori ferritin (see SEQ ID NO: 208 or 209 for an exemplary H. pylori ferritin sequence), optionally with one or more mutations such as those described herein. In some embodiments, the lower sequence homology between H. pylori ferritin (or other bacterial ferritins) and human ferritin may decrease the potential for autoimmunity when used as a vaccine platform (see Kanekiyo et al., Cell 162, 1090-1100 (2015)).

In some embodiments, a nanoparticle is provided comprising an antigenic EBV polypeptide as disclosed herein comprising an EBV polypeptide and a ferritin.

1. Ferritin Mutations

In some embodiments, the ferritin comprises one or more mutations are disclosed herein. In some embodiments, the one or more mutations comprise changes to the amino acid sequence of a wild-type ferritin and/or an insertion, e.g., at the N- or C-terminus. In some embodiments, one, two, three, four, five, or more different amino acids are mutated in the ferritin as compared to wild-type ferritin (in some embodiments, in addition to any N-terminal insertion). The one or more mutations can change functional properties of the ferritin, e.g., as discussed in detail below. In general, a mutation simply refers to a difference in the sequence (such as a substituted, added, or deleted amino acid residue or residues) relative to the corresponding wild-type ferritin.

2. Cysteine for Conjugation

In some embodiments, ferritin is mutated to provide a chemical handle for conjugation of an immune-stimulatory moiety and/or EBV polypeptide. This can be achieved with a mutation replacing a surface-exposed non-cysteine amino acid with a cysteine. For the avoidance of doubt, language such as "replacing a surface-exposed amino acid with a cysteine" necessarily implies that the surface-exposed amino acid in the wild-type or pre-mutation sequence is not cysteine. Another approach for providing a chemical handle for conjugation of an immune-stimulatory moiety or EBV polypeptide is to include a segment of amino acids, such as a linker, N- or C-terminal to the ferritin, wherein the segment of amino acids comprises a cysteine. In some embodiments, this cysteine (whether replacing a surface-exposed amino acid or in an N- or C-terminal linker) is unpaired, which means that it does not have an appropriate partner cysteine to form a disulfide bond. In some embodiments, this cysteine does not change the secondary structure of ferritin. In some embodiments, this cysteine does not change the tertiary structure of ferritin.

In some embodiments, this cysteine can be used to conjugate agents, such as immune-stimulatory moieties, to ferritin. In some embodiments, this cysteine provides a free thiol group that is reactive. In some embodiments, agents conjugated to this cysteine on ferritin are exposed on the surface of an assembled ferritin particle. In some embodiments, this cysteine can interact with molecules and cells of the subject after administration while the ferritin particle is assembled.

In some embodiments, the presence of this cysteine allows conjugation of one or more immune-stimulatory moieties, e.g., adjuvants. In some embodiments, conjugation of the immune-stimulatory moiety would not occur in the absence of this cysteine.

In some embodiments, the non-cysteine amino acid that is replaced with a cysteine is selected from E12, S72, A75, K79, S100, and S111 of *H. pylori* ferritin. Thus, in some embodiments, the surface-exposed amino acid that is replaced in favor of cysteine is an amino acid residue that corresponds to E12, S26, S72, A75, K79, S100, or S111 of *H. pylori* ferritin. Analogous amino acids can be found in non-*H. pylori* ferritin by pair-wise or structural alignment. In some embodiments, the non-cysteine amino acid that is replaced with a cysteine can be selected from an amino acid that corresponds to S3, S19, S33, I82, A86, A102, and A120 of human light chain ferritin. In some embodiments, the surface-exposed amino acid to be replaced with a cysteine is selected based on the understanding that if the native amino acid were replaced with cysteine, it would be reactive in an assembled ferritin multimer or particle and/or that this cysteine does not disrupt the stability of the ferritin multimer or particle and/or that this cysteine does not lead to reduction in expression levels of ferritin.

In some embodiments, the ferritin comprises an E12C mutation. In some embodiments, the E12C residue can be used to conjugate agents (e.g., immune-stimulatory moieties and/or EBV polypeptides) to ferritin. In some embodiments, the E12C residue provides a free thiol group that is reactive. In some embodiments, agents conjugated to the E12C residue on ferritin monomers are expressed on the surface on an assembled ferritin multimer or particle. In some embodiments, twenty-four E12C residues (one from each monomer) are present on the surface of a ferritin multimer or particle.

In some embodiments, the ferritin comprises an S26C mutation. In some embodiments, the S26C residue can be used to conjugate agents (e.g., immune-stimulatory moieties and/or EBV polypeptides) to ferritin. In some embodiments, the S26C residue provides a free thiol group that is reactive. In some embodiments, agents conjugated to the S26C residue on ferritin monomers are expressed on the surface on an assembled ferritin multimer or particle. In some embodiments, twenty-four S26C residues (one from each monomer) are present on the surface of a ferritin multimer or particle.

In some embodiments, the ferritin comprises an S72C mutation. In some embodiments, the S72C residue can be used to conjugate agents (e.g., immune-stimulatory moieties and/or EBV polypeptides) to ferritin. In some embodiments, the S72C residue provides a free thiol group that is reactive. In some embodiments, agents conjugated to the S72C residue on ferritin monomers are expressed on the surface on an assembled ferritin multimer or particle. In some embodiments, twenty-four S72C residues (one from each monomer) are present on the surface of a ferritin multimer or particle.

In some embodiments, the ferritin comprises an A75C mutation. In some embodiments, the A75C residue can be used to conjugate agents (e.g., immune-stimulatory moieties and/or EBV polypeptides) to ferritin. In some embodiments, the A75C residue provides a free thiol group that is reactive. In some embodiments, agents conjugated to the A75C residue on ferritin monomers are expressed on the surface on an assembled ferritin multimer or particle. In some embodiments, twenty-four A75C residues (one from each monomer) are present on the surface of a ferritin multimer or particle.

In some embodiments, the ferritin comprises an K79C mutation. In some embodiments, the K79C residue can be used to conjugate agents (e.g., immune-stimulatory moieties and/or EBV polypeptides) to ferritin. In some embodiments, the K79C residue provides a free thiol group that is reactive. In some embodiments, agents conjugated to the K79C residue on ferritin monomers are expressed on the surface on an assembled ferritin multimer or particle. In some embodiments, twenty-four K79C residues (one from each monomer) are present on the surface of a ferritin multimer or particle.

In some embodiments, the ferritin comprises an S100C mutation. In some embodiments, the S100C residue can be used to conjugate agents (e.g., immune-stimulatory moieties and/or EBV polypeptides) to ferritin. In some embodiments, the S100C residue provides a free thiol group that is reactive. In some embodiments, agents conjugated to the S100C residue on ferritin monomers are expressed on the surface on an assembled ferritin multimer or particle. In some embodiments, twenty-four S100C residues (one from each monomer) are present on the surface of a ferritin multimer or particle.

In some embodiments, the ferritin comprises an S111C mutation. In some embodiments, the S111C residue can be used to conjugate agents (e.g., immune-stimulatory moieties and/or EBV polypeptides) to ferritin. In some embodiments, the S111C residue provides a free thiol group that is reactive. In some embodiments, agents conjugated to the S111C residue on ferritin monomers are expressed on the surface on an assembled ferritin multimer or particle. In some embodiments, twenty-four S111C residues (one from each monomer) are present on the surface of a ferritin multimer or particle.

3. Removal of Internal Cysteine

In some embodiments, the ferritin comprises a mutation replacing an internal cysteine with a non-cysteine amino acid. Removal of a native internal cysteine residue can ensure that there is only one unpaired cysteine per ferritin monomer and avoid undesired reactions such as disulfide formation and may result in a more stable and efficient result (e.g., adjuvant presentation). In some embodiments, C31 of *H. pylori* ferritin is replaced with a non-cysteine amino acid. In some embodiments, C31 of *H. pylori* ferritin is replaced with a serine (C31S), although any non-cysteine residue may be used, e.g., alanine, glycine, threonine, or asparagine. Analogous amino acids can be found in non-*H. pylori* ferritin by pair-wise or structural alignment. Thus, in some embodiments, the internal cysteine that is replaced in favor of non-cysteine is an amino acid residue that aligns with C31 of *H. pylori* ferritin. Exemplary ferritin sequences showing a C31S mutation are shown in SEQ ID NOS: 201-207. In some embodiments, when more than one internal cysteine is present in ferritin, two or more (e.g., each) internal cysteine is replaced with a non-cysteine amino acid, such as serine or an amino acid selected from serine, alanine, glycine, threonine, or asparagine.

4. Glycosylation

Human-compatible glycosylation can contribute to safety and efficacy in recombinant drug products. Regulatory approval may be contingent on demonstrating appropriate glycosylation as a critical quality attribute (see Zhang et al., Drug Discovery Today 21(5):740-765 (2016)). N-glycans can result from glycosylation of asparagine side chains and can differ in structure between humans and other organisms such as bacteria and yeast. Thus, it may be desirable to reduce or eliminate non-human glycosylation and/or N-glycan formation in ferritin according to the disclosure. In some embodiments, controlling glycosylation of ferritin improves the efficacy and/or safety of the composition, especially when used for human vaccination.

In some embodiments, ferritin is mutated to inhibit formation of an N-glycan. In some embodiments, a mutated ferritin has reduced glycosylation as compared to its corresponding wild type ferritin.

In some embodiments, the ferritin comprises a mutation replacing a surface-exposed asparagine with a non-asparagine amino acid. In some embodiments, the surface-exposed asparagine is N19 of *H. pylori* ferritin or a position that corresponds to position 31 of *H. pylori* ferritin as determined by pair-wise or structural alignment In some embodiments, mutating such an asparagine, e.g., N19 of *H. pylori* ferritin, decreases glycosylation of ferritin. In some embodiments, the mutation replaces the asparagine with a glutamine. In some embodiments, the ferritin is an *H. pylori* ferritin comprising an N19Q mutation. SEQ ID NOS: 201-207 are exemplary ferritin sequences comprising N19Q mutations.

A mammal exposed to a glycosylated protein produced in bacteria or yeast may generate an immune response to the glycosylated protein, because the pattern of glycosylation of a given protein in bacterial or yeast could be different from the pattern of glycosylation of the same protein in a mammal. Thus, some glycosylated therapeutic proteins may not be appropriate for production in bacteria or yeast.

In some embodiments, decreased glycosylation of ferritin by amino acid mutation facilitates protein production in bacteria or yeast. In some embodiments, decreased glycosylation of ferritin reduces the potential for adverse effects in mammals upon administration of mutated ferritin that is expressed in bacteria or yeast. In some embodiments, the reactogenicity in a human subject of a mutated ferritin produced in bacteria or yeast is lower because glycosylation is decreased. In some embodiments, the incidence of hypersensitivity responses in human subjects is lower following treatment with a mutated ferritin with reduced glycosylation compared to wildtype ferritin.

In some embodiments, degradation in a subject of a composition comprising a mutated ferritin with reduced glycosylation is slower compared with a composition comprising a wild-type ferritin, or a composition comprising a corresponding ferritin with wild-type glycosylation. In some embodiments, a composition comprising a mutated ferritin with reduced glycosylation has reduced clearance in a subject compared with a composition comprising a wild-type ferritin, or a composition comprising a corresponding ferritin with wild-type glycosylation. In some embodiments, a composition comprising a mutated ferritin with reduced glycosylation has a longer-serum half-life compared to wild-type ferritin, or a composition comprising a corresponding ferritin with wild-type glycosylation.

5. Combinations of Mutations

In some embodiments, a ferritin comprises more than one type of mutation described herein. In some embodiments, the ferritin comprises one or more mutations independently selected from: a mutation to decrease glycosylation, a mutation to remove an internal cysteine, and a mutation to generate a surface-exposed cysteine. In some embodiments, the ferritin comprises a mutation to decrease glycosylation, a mutation to remove an internal cysteine, and a mutation to generate a surface-exposed cysteine.

In some embodiments, the ferritin comprises an N19Q mutation, a C31S mutation, and a mutation to generate a surface-exposed cysteine. In some embodiments, the ferritin comprises an N19Q mutation, a C31S mutation, and an E12C mutation. In some embodiments, the ferritin comprises an N19Q mutation, a C31S mutation, and an S72C mutation. In some embodiments, the ferritin comprises an N19Q mutation, a C31S mutation, and an A75C mutation. In some embodiments, the ferritin comprises an N19Q mutation, a C31S mutation, and an K79C mutation. In some embodiments, the ferritin comprises an N19Q mutation, a C31S mutation, and an S100C mutation. In some embodiments, the ferritin comprises an N19Q mutation, a C31S mutation, and an S111C mutation. In some embodiments, the ferritin comprises mutations corresponding to any of the foregoing sets of mutations, wherein the corresponding mutations change an N to a Q, a C to an S, and a non-cysteine surface-exposed amino acid to a cysteine at positions determined by pair-wise alignment of the ferritin amino acid sequence to an *H. pylori* ferritin amino acid sequence (SEQ ID NO: 208 OR 209).

Exemplary ferritins comprising more than one type of mutation are provided in SEQ ID NOS: 201-207.

6. Structural Alignment

As discussed herein, positions of mutations corresponding to those described with respect to a given polypeptide (e.g., *H. pylori* ferritin) can be identified by pairwise or structural alignment. Structural alignment is relevant to large protein families such as ferritin where the proteins share similar structures despite considerable sequence variation and many members of the family have been structurally characterized, and can also be used to identify corresponding positions in different versions of other polypeptides described herein, such as EBV polypeptides (e.g., gL, gH, gp220, or gp42). The protein databank (PDB) comprises 3D structures for many ferritins, including those listed below with their accession numbers.

2jd6, 2jd7-PfFR-*Pyrococcus furiosus*. 2jd8-PfFR+Zn. 3a68-soFR from gene SferH4-soybean. 3a9q-soFR from gene SferH4 (mutant). 3egm, 3bvf, 3bvi, 3bvk, 3bv1-HpFR-Heliobacter *pylori*. 5c6f-HpFR (mutant)+Fe. 1z4a, 1vlg-FR-*Thermotoga* maritime. 1s3q, 1sq3, 3kx9-FR-*Archaeoglubus fulgidus*. 1krq-FR-*Campylobacter jejuni*. 1eum-EcFR-*Escherichia coli*. 4reu-EcFR+Fe. 4xgs-EcFR (mutant)+Fe2O2. 4ztt-EcFR (mutant)+Fe2O+Fe2+Fe+O2. 1qgh-LiFR-*Listeria innocua*. 3qz3-VcFR-*Vibrio cholerae*. 3vnx-FR-Ulva pertusa. 4ism, 4isp, 4itt, 4itw, 4iwj, 4iwk, 4ixk, 3e6s-PnmFR-Pseudo-nitschia multiseries. 4zkh, 4zkw, 4zkx, 4zl5, 4zl6, 4zlw, 4zmc-PnmFR (mutant)+Fe. 1z6o-FR-*Trichoplusia ni*. 4cmy-FR+Fe-*Chlorobaculum tepidum*. Ferritin light chain (FTL). 1lb3, 1h96-mFTL-mouse. 1rcc, 1rcd, 1rci-bFTL+tartrate+Mg. 1rce, 1rcg-bFTL+tartrate+Mn. 3noz, 3np0, 3np2, 3o7r-hoFTL (mutant)-horse. 3o7s, 3u90-hoFTL. 4v1w-hoFTL-cryo EM. 3rav, 3rd0-hoFTL+barbiturate. Ferritin light+heavy chains: 5gn8-hFTH+Ca.

Structural alignment involves identifying corresponding residues across two (or more) polypeptide sequences by (i) modeling the structure of a first sequence using the known structure of the second sequence or (ii) comparing the structures of the first and second sequences where both are known, and identifying the residue in the first sequence most similarly positioned to a residue of interest in the second sequence. Corresponding residues are identified in some algorithms based on alpha-carbon distance minimization in the overlaid structures (e.g., what set of paired alpha carbons provides a minimized root-mean-square deviation for the alignment). When identifying positions in a non-*H. pylori* ferritin corresponding to positions described with respect to *H. pylori* ferritin, *H. pylori* ferritin can be the "second" sequence. Where a non-*H. pylori* ferritin of interest does not have an available known structure, but is more closely related to another non-*H. pylori* ferritin that does have a known structure than to *H. pylori* ferritin, it may be most effective to model the non-*H. pylori* ferritin of interest using the known structure of the closely related non-*H. pylori* ferritin, and then compare that model to the *H. pylori* ferritin structure to identify the desired corresponding residue in the ferritin of interest. There is an extensive literature on structural modeling and alignment; representative disclosures include U.S. Pat. Nos. 6,859,736; 8,738,343; and those cited in Aslam et al., Electronic Journal of Biotechnology 20 (2016) 9-13. For discussion of modeling a structure based on a known related structure or structures, see, e.g., Bordoli et al., Nature Protocols 4 (2009) 1-13, and references cited therein.

7. Lumazine Synthase

In some embodiments, the antigenic polypeptide comprises a lumazine synthase protein. Lumazine synthases can form higher-order structures, e.g., a 60-subunit lumazine synthase particle. Exemplary lumazine synthases are *Aquifex aeolicus* lumazine synthase (SEQ ID NO: 40) and *E. coli* lumazine synthase (SEQ ID NO: 41). In some embodiments, the lumazine synthase has at least 85%, 90%, 95%, 97%, 98%, 99%, or 100% identity to the sequence of SEQ ID NOS: 40 or 41. The lumazine synthase can be located C-terminal to the EBV polypeptide and can be separated from the EBV polypeptide by a linker as discussed herein.

G. Mutations in gL, gH, Gp42, Linker, and/or Ferritin Sequences to Eliminate Potential Oxidation, Deamidation, or Isoaspartate Formation Sites In some embodiments, an antigenic EBV polypeptide comprises one or more mutations to eliminate potential oxidation, deamidation, or Isoaspartate formation sites, such as the exemplary mutations set forth in Table 1 below.

For example, in some embodiments, a gL sequence comprises one or more mutations to eliminate a potential succinimide/isoaspartate or deamidation site. For example, a gL sequence can comprise a G to A mutation at a position corresponding to position 36 of SEQ ID NO: 227; an N to Q mutation at a position corresponding to position 47 of SEQ ID NO: 227; or an N to Q mutation at a position corresponding to position 105 of SEQ ID NO: 227. A position in an amino acid sequence "corresponds" to a given position in SEQ ID NO: 227 if it aligns to that position according to a standard sequence alignment algorithm such as the Smith-Waterman algorithm using default parameters.

In some embodiments, a linker comprises one or more mutations to eliminate a potential deamidation site. For example, a linker sequence can comprise an N to G mutation at a position corresponding to position 132 or 141 of SEQ ID NO: 227.

In some embodiments, a gH sequence comprises one or more mutations to eliminate a potential succinimide/isoaspartate or oxidation site. For example, a gH sequence can comprise an M to L mutation at a position corresponding to position 189, 401, or 729 of SEQ ID NO: 227; a D to E mutation at a position corresponding to position 368 of SEQ ID NO: 227; an M to I mutation at a position corresponding to position 499 or 639 of SEQ ID NO: 227; or an N to Q mutation at a position corresponding to position 653 of SEQ ID NO: 227.

In some embodiments, a gp42 sequence comprises one or more mutations to eliminate a potential deamidation site. For example, a gp42 sequence can comprise an N to Q mutation at a position corresponding to position 959 or 990 of SEQ ID NO: 227; or an N to S mutation at a position corresponding to position 988 of SEQ ID NO: 227.

In some embodiments, a ferritin sequence comprises one or more mutations to eliminate a potential deamidation, oxidation, or isoaspartate formation site. For example, a ferritin sequence can comprise a Q to S mutation at a position corresponding to position 1150 of SEQ ID NO: 227; an M to I mutation at a position corresponding to position 1168 of SEQ ID NO: 227; an M to L mutation at a position corresponding to position 1177 of SEQ ID NO: 227; a G to A mutation at a position corresponding to position 1188 of SEQ ID NO: 227; or an N to Q mutation at a position corresponding to position 1253 or 1296 of SEQ ID NO: 227.

Exemplary mutations are shown below in Table 1. The position numbering corresponds to SEQ ID NO: 227.

TABLE 1

Exemplary mutations.

| Location | Modification | START | END | MO-TIF | solvent exposure | Mutation |
|---|---|---|---|---|---|---|
| gL | Succinimide/IsoAsp | 35 | 36 | DG | Exposed | G35A |
| gL | deamidation | 47 | 47 | N | likely exposed | N47Q |
| gL | deamidation | 105 | 105 | N | exposed | N105Q |
| linker | deamidation | 132 | 132 | N | exposed | N132G |
| linker | deamidation | 141 | 141 | N | exposed | N141G |
| gH | oxidation | 189 | 189 | M | exposed | M189L |
| gH | Succinimide/IsoAsp | 368 | 369 | DY | exposed | D368E |
| gH | oxidation | 401 | 401 | M | buried | M401L |
| gH | Succinimide/IsoAsp | 429 | 430 | DT | exposed | D429E |
| gH | oxidation | 499 | 499 | M | exposed | M499I |
| gH | oxidation | 639 | 639 | M | exposed | M639I |
| gH | oxidation | 653 | 653 | N | exposed | N653Q |
| gH | oxidation | 729 | 729 | M | exposed | M729L |
| gp42 | deamidation | 959 | 959 | N | exposed | N959Q |
| gp42 | deamidation | 988 | 988 | N | exposed | N988S |
| gp42 | deamidation | 990 | 990 | N | exposed | N990Q |
| ferritin | deamidation | 1150 | 1150 | Q | exposed | Q1150S |
| ferritin | oxidation | 1168 | 1168 | M | buried | M1168I |
| ferritin | deamidation | 1177 | 1177 | M | buried | M1177L |
| ferritin | IsoAsp | 1187 | 1188 | DG | buried | G1187A |
| ferritin | deamidation | 1253 | 1253 | N | exposed | N1253Q |
| ferritin | deamidation | 1296 | 1296 | N | exposed | N1296Q |

H. Immune-Stimulatory Moieties; Adjuvants; Conjugated EBV Polypeptides

In some embodiments, an EBV polypeptide and/or an immune-stimulatory moiety, such as an adjuvant, is attached to a surface-exposed amino acid. In some embodiments, the surface-exposed amino acid is a cysteine, e.g., resulting from a mutation discussed above. In some embodiments, the surface-exposed amino acid is a lysine, aspartate, or glutamate. Conjugation procedures using glutaraldehyde (for conjugation of a lysine with an amino-bearing linker or moiety) or a carbodiimide (e.g., 1-Cyclohexyl-3-(2-morpholin-4-yl-ethyl) carbodiimide or 1-Ethyl-3-(3-dimethyl-aminopropyl) carbodiimide (EDC; EDAC) for conjugating an aspartate or glutamate to an amino-bearing linker or moiety, or a lysine to a carboxyl-bearing linker or moiety) are described in, e.g., Chapter 4 of Holtzhauer, M., Basic Methods for the Biochemical Lab, Springer 2006, ISBN 978-3-540-32785-1, available from www.springer.com.

In some embodiments, an immune-stimulatory moiety, such as an adjuvant, is attached to a surface-exposed amino acid of ferritin. In some embodiments, more than one immune-stimulatory moiety, such as an adjuvant, is attached to a surface-exposed amino acid of ferritin. In some embodiments, twenty-four immune-stimulatory moieties are attached to a ferritin multimer or particle (e.g., one moiety for each monomer in the H. pylori ferritin particle). In some embodiments with multiple immune-stimulatory moieties attached to a ferritin nanoparticle, all of the immune-stimulatory moieties are identical. In some embodiments with multiple immune-stimulatory moieties attached to a ferritin nanoparticle, all of the immune-stimulatory moieties are not identical.

1. Types of Immune-Stimulatory Moieties; Adjuvants

Any immune-stimulatory moiety that can be attached to a surface-exposed amino acid (e.g., cysteine) can be used in ferritins according to this disclosure. In some embodiments, the immune-stimulatory moiety is a B cell agonist.

In some embodiments, the immune-stimulatory moiety is not hydrophobic. In some embodiments, the immune-stimulatory moiety is hydrophilic. In some embodiments, the immune-stimulatory moiety is polar. In some embodiments, the immune-stimulatory moiety is capable of hydrogen bonding or ionic bonding, e.g., comprises a hydrogen bond donor, hydrogen bond acceptor, cationic moiety, or anionic moiety. A moiety is considered cationic or anionic if it would be ionized in aqueous solution at a physiologically relevant pH, such as pH 6, 7, 7.4, or 8.

In some embodiments, the immune-stimulatory moiety is an adjuvant. In some embodiments, the adjuvant comprises a pathogen associated molecular pattern (PAMP). In some embodiments, the adjuvant is a toll-like receptor (TLR) agonist or stimulator of interferon genes (STING) agonist. In some embodiments, the adjuvant activates TLR signaling in B and/or T cells. In some embodiments, the adjuvant regulates the adaptive immune response.

a) TLR2 Agonists

In some embodiments, the immune-stimulatory moiety is a TLR2 agonist. In some embodiments, the immune-stimulatory moiety stimulates TLR2 signaling. In some embodiments, the immune-stimulatory moiety is a synthetic small molecule ligand of TLR2. In some embodiments, the immune-stimulatory moiety is a synthetic small molecule agonist of TLR2 signaling.

In some embodiments, the TLR2 agonist is PAM2CSK4, FSL-1, or PAM3C SK4.

b) TLR7/8 Agonists

In some embodiments, the immune-stimulatory moiety is a TLR7 and/or TLR8 agonist (i.e., an agonist of at least one of TLR7 and TLR8). In some embodiments, the immune-stimulatory moiety stimulates TLR7 and/or TLR8 signaling. In some embodiments, the immune-stimulatory moiety is a synthetic small molecule ligand of TLR7 and/or TLR8. In some embodiments, the immune-stimulatory moiety is a synthetic small molecule agonist of TLR7 and/or TLR8 signaling.

In some embodiments, the TLR7 and/or TLR8 agonist is single-stranded (ssRNA). In some embodiments, the TLR7 and/or TLR8 agonist is an imidazoquinoline. In some embodiments, the TLR7 and/or TLR8 agonist is a nucleoside analog.

In some embodiments, the TLR7 and/or TLR8 agonist is an imidazoquinolinamine Toll-like receptor (TLR) agonist, such as 3M-012 (3M Pharmaceuticals). The structure of free 3M-012 is:

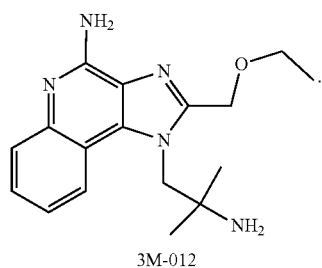 [SMILES: CCOCc1nc2c(N)nc3ccccc3c2n1CC(C)(C)N]

3M-012

It is understood that an immune-stimulatory moiety such as 3M-012 or any moiety discussed herein can be conjugated to a ferritin by substituting an appropriate peripheral atom of the moiety (e.g., a hydrogen) with a bond to a ferritin described herein, e.g., at the sulfur of a surface-exposed cysteine or a linker attached to such a sulfur. Thus, when conjugated to a ferritin, the structure of the immune-stimulatory moiety will differ slightly from the structure of the free molecule.

In some embodiments the TLR7 and/or TLR8 agonist is SM 7/8a. The structure of free SM 7/8a is:

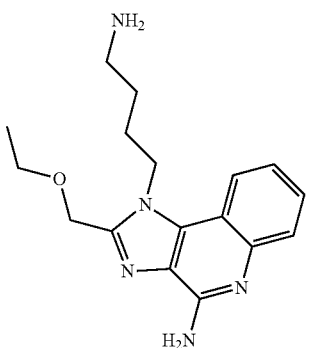

See, e.g., Nat Biotechnol. 2015 November; 33(11):1201-10. doi: 10.1038/nbt.3371.

c) TLR9 Agonists

In some embodiments, the immune-stimulatory moiety is a TLR9 agonist. In some embodiments, the immune-stimulatory moiety stimulates TLR9 signaling. In some embodiments, the immune-stimulatory moiety is a synthetic small molecule ligand of TLR9. In some embodiments, the immune-stimulatory moiety is a synthetic small molecule agonist of TLR9 signaling.

In some embodiments, the TLR9 agonist is a CpG oligodeoxynucleotide (ODN). In some embodiments, the TLR9 agonist is an unmethylated CpG ODN. In some embodiments, the CpG ODN comprises a partial or complete phosphorothioate (PS) backbone instead of the natural phosphodiester (PO) backbone found in ordinary DNA.

In some embodiments, the CpG ODN is a Class B ODN, which comprises one or more 6mer CpG motif comprising 5' Purine (Pu)-Pyrimidine (Py)-C-G-Py-Pu 3'; has a fully phosphorothioated (i.e., PS-modified) backbone; and has a length of 18-28 nucleotides. In some embodiments, the CpG ODN comprises the sequence of SEQ ID NO: 210, optionally comprising phosphorothioate linkages in the backbone.

In some embodiments, the TLR9 agonist comprises an immune-stimulatory sequence (ISS). In some embodiments the TLR9 agonist is ISS-1018 (Dynavax) (SEQ ID NO: 210).

d) STING Agonists

In some embodiments, the immune-stimulatory moiety is a STING (Stimulator of Interferon Genes Protein, also known as Endoplasmic Reticulum IFN Stimulator) agonist. In some embodiments, the immune-stimulatory moiety stimulates STING signaling. In some embodiments, the immune-stimulatory moiety is a synthetic small molecule ligand of STING. In some embodiments, the immune-stimulatory moiety is a synthetic small molecule agonist of STING signaling.

In some embodiments the STING agonist is a cyclic dinucleotide (CDN). See, e.g., Danilchanka et al., Cell 154:962-970 (2013). Exemplary CDNs include cdA, cdG, cAMP-cGMP, and 2'-5',3'-5' cGAMP (see Danilchanka et al. for structures). STING agonists also include synthetic agonists such as DMXAA

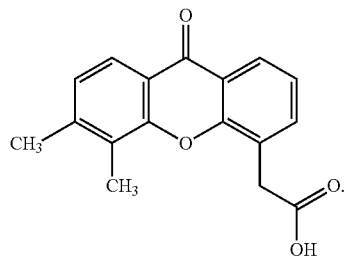 [SMILES: Cc1ccc2c(=O)c3cccc(CC(=O)O)c3oc2c1C]

2. Conjugated EBV Polypeptides

In some embodiments, an EBV polypeptide is conjugated to a surface-exposed amino acid of ferritin. In some embodiments, the EBV polypeptide renders the ferritin protein antigenic. In some embodiments, the EBV polypeptide is antigenic alone, whereas in some embodiments, the EBV polypeptide is antigenic because of its association with ferritin. In some embodiments, the EBV polypeptide is any one of the EBV polypeptides described herein.

3. Conjugation

In some embodiments, a surface-exposed cysteine (e.g., resulting from a mutation described herein) or a cysteine in a peptide linker attached to ferritin (e.g., N-terminally to ferritin) is used to conjugate an immune-stimulatory moiety, such as an adjuvant, or an EBV polypeptide to a ferritin. In some embodiments, a linker is conjugated to such a cysteine, which linker can be subsequently conjugated to an immune-stimulatory moiety, such as an adjuvant, or an EBV polypeptide. In some embodiments, such a cysteine creates a chemical handle for conjugation reactions to attach an adjuvant, linker, or an EBV polypeptide. In some embodiments, bioconjugates are produced, wherein an immune-stimulatory moiety, such as an adjuvant, or an EBV polypeptide is linked to a ferritin after reduction of such a cysteine. In some embodiments, the cysteine is an unpaired surface-exposed cysteine, i.e., that lacks a partner cysteine in an appropriate position to form a disulfide bond. In some embodiments, the cysteine is an unpaired cysteine that comprises a free thiol side chain.

a) Types of Conjugation Chemistries

Any type chemistry can be used to conjugate the immune-stimulatory moiety, such as an adjuvant, or an EBV polypeptide to the ferritin, e.g., via reaction a surface-exposed amino acid such as cysteine or another amino acid such as Lys, Glu, or Asp.

In some embodiments, the conjugation is performed using click chemistry. As used herein, "click chemistry" refers to a reaction between a pair of functional groups that rapidly and selective react (i.e., "click") with each other. In some embodiments, the click chemistry can be performed under mild, aqueous conditions. In some embodiments, a click chemistry reaction takes advantage of a cysteine on the surface of the ferritin, such as a cysteine resulting from mutation of a surface-exposed amino acid, to perform click chemistry using a functional group that can react with the cysteine.

A variety of reactions that fulfill the criteria for click chemistry are known in the field, and one skilled in the art could use any one of a number of published methodologies (see, e.g., Hein et al., Pharm Res 25(10):2216-2230 (2008)). A wide range of commercially available reagents for click chemistry could be used, such as those from Sigma Aldrich, Jena Bioscience, or Lumiprobe. In some embodiments, conjugation is performed using click chemistry as described in the Examples below.

In some embodiments, the click chemistry reaction occurs after reduction of the ferritin.

In some embodiments, the click chemistry may be a 1-step click reaction. In some embodiments, the click chemistry may be a 2-step click reaction.

In some embodiments, the reaction(s) comprises metal-free click chemistry. In some embodiments, the reaction(s) comprise thiol-maleimide and/or disulfide exchange.

Metal-Free Click Chemistry

Metal-free click chemistry can be used for conjugation reactions to avoid potential oxidation of proteins. Metal-free click chemistry has been used to form antibody conjugates (see van Geel et al., Bioconjugate Chem. 2015, 26, 2233-2242).

In some embodiments, metal-free click chemistry is used in reactions to attach adjuvant to ferritin. In some embodiments, copper-free conjugation is used in reactions to attach adjuvant to ferritin. In some embodiments, the metal-free click chemistry uses bicyclo[6.1.0]nonyne (BCN). In some embodiments, the metal-free click chemistry uses dibenzo-azacyclooctyne (DBCO). In some embodiments BCN or DBCO reacts with an azide group.

DBCO has high specificity for azide groups via a strain-promoted click reaction in the absence of a catalyst, resulting in high yield of a stable triazole. In some embodiments, DBCO reacts with azide in the absence of copper catalyst.

In some embodiments, metal-free click chemistry is used in a 1-step click reaction. In some embodiments, metal-free click chemistry is used in a 2-step click reaction.

Thiol-Maleimide and Disulfide Exchange

Ferritins described herein can comprise a cysteine comprising a thiol, also known as a sulfhydryl, which is available for reaction with sulfhydryl-reactive chemical groups (or which can be made available through reduction). Thus, the cysteine allows chemoselective modification to add an immune-stimulatory moiety, such as an adjuvant, to the ferritin. Under basic conditions, the cysteine will be deprotonated to generate a thiolate nucleophile, which can react with soft electrophiles, such as maleimides and iodoacetamides. The reaction of the cysteine with a maleimide or iodoacetamide results in a carbon-sulfur bond.

In some embodiments, a sulfhydryl-reactive chemical group reacts with the surface-exposed cysteine or cysteine in the linker of the ferritin. In some embodiments, the sulfhydryl-reactive chemical group is a haloacetyl, maleimide, aziridine, acryloyl, arylating agent, vinylsulfone, pyridyl disulfide, or TNB-thiol.

In some embodiments, the sulfhydryl-reactive chemical group conjugates to the sulfhydryl of the cysteine by alkylation (i.e., formation of a thioether bond)). In some embodiments, the sulfhydryl-reactive chemical group conjugates to the sulfhydryl of the cysteine by disulfide exchange (i.e., formation of a disulfide bond).

In some embodiments, the reaction to conjugate an immune-stimulatory moiety, such as an adjuvant, to the ferritin is a thiol-maleimide reaction.

In some embodiments, the sulfhydryl-reactive chemical group is a maleimide. In some embodiments, reaction of a maleimide with the cysteine results in formation of a stable thioester linkage, e.g., that is not reversible. In some embodiments, the maleimide does not react with tyrosines, histidines, or methionines in the ferritin. In some embodiments, unreacted maleimides are quenched at the end of the reaction by adding a free thiol, e.g., in excess.

In some embodiments, the reaction to conjugate an immune-stimulatory moiety, such as an adjuvant, to the ferritin is a thiol-disulfide exchange, also known as a disulfide interchange. In some embodiments, the reaction involves formation of a mixed disulfide comprising a portion of the original disulfide. In some embodiments, the original disulfide is the cysteine introduced in the ferritin by mutation of a surface-exposed amino acid or addition of an N-terminal linker.

In some embodiments, the sulfhydryl-reactive chemical group is a pyridyl dithiol. In some embodiments, the sulfhydryl-reactive chemical group is a TNB-thiol group.

b) Linkers

In some embodiments, an immune-stimulatory moiety, such as an adjuvant, or an EBV polypeptide is attached to the ferritin via a linker that is covalently bound to a surface-exposed amino acid such as a cysteine. In some embodiments, the linker comprises a polyethylene glycol, e.g., a PEG linker. In some embodiments, the polyethylene glycol (e.g., PEG) linker increases water solubility and ligation efficiency of the ferritin linked to the immune-stimulatory moiety, such as an adjuvant. The PEG linker is between 2 and 18 PEGs long, e.g., PEG4, PEG5, PEG6, PEG7, PEG8, PEG9, PEG10, PEG11, PEG12, PEG13, PEG14, PEG15, PEG16, PEG17, and PEG18.

In some embodiments, the linker comprises a maleimide. In some embodiments, the linker comprises the components of immune-stimulatory moiety (ISM)-linker-maleimide. In some embodiments, the ISM-linker-maleimide is conjugated to ferritin in a 1-step click chemistry reaction by reaction of the maleimide with a cysteine of the ferritin. In some embodiments, the ISM of the adjuvant-linker-maleimide is SM7/8a. In some embodiments, the linker of the ISM-linker-maleimide is PEG4. In some embodiments, the ISM-linker-maleimide is SM7/8a-PEG4-maleimide.

In some embodiments, a 2-step click chemistry protocol is used with a linker comprising a sulfhydryl-reactive chemical group at one end and an amine-reactive group at the other end. In such a 2-step click chemistry protocol, a sulfhydryl-reactive chemical group reacts with a cysteine of the ferritin, while the amine-reactive group reacts with a reagent attached to the ISM. In this way, the ISM is conjugated to the ferritin via a set of 2 click chemistry reagents.

In some embodiments of the 2-step click chemistry protocol, the sulfhydryl-reactive chemical group is maleimide. In some embodiments of the 2-step click chemistry protocol, the maleimide reacts with the cysteine introduced in the ferritin by mutation of a surface-exposed amino acid or addition of an N-terminal linker.

In some embodiments of the 2-step click chemistry protocol, the amine-reactive group is DBCO. In some embodiments of the 2-step click chemistry protocol, the DBCO reacts with an azide group attached to an ISM.

In some embodiments, a maleimide-linker-DBCO is used. In some embodiments, the maleimide-linker-DBCO is conjugated to ferritin after the ferritin is reduced. In some embodiments, the maleimide-linker-reagent is conjugated to ferritin by reaction of the maleimide with the cysteine of the ferritin in a first step. In some embodiments, the DBCO is used to link to an ISM attached to azide. In some embodiments, the ISM coupled to azide is ISS-1018. In some embodiments, the adjuvant coupled to azide is 3M-012 or CpG.

In some embodiments, a linker with a reactive group is added to the ISM. In some embodiments, the linker is a PEG4-azide linker or a PEG4-maleimide linker.

In some embodiments, a PEG4-azide linker is conjugated to 3M-012. An exemplary structure of 3M-012 conjugated to a PEG4-azide linker is:

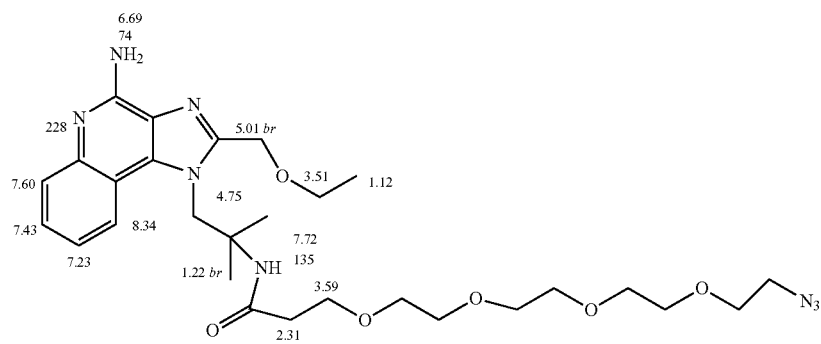 [SMILES: CCOCc1nc2c(N)nc3ccccc3c2n1CC(C)(C)NC(=O)CCOCCOCCOCCOCCN=[N+]=[N-]]

In some embodiments, a PEG4-azide linker is conjugated to SM7/8a. An exemplary structure of SM7/8a conjugated to a PEG4-azide linker is:

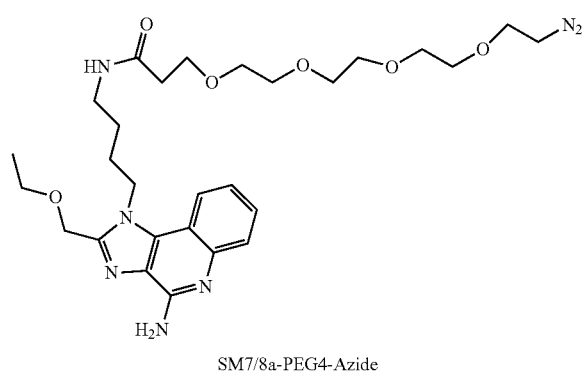

SM7/8a-PEG4-Azide

In some embodiments, a PEG4-maleimide linker is conjugated to SM7/8a. An exemplary structure of SM7/8a conjugated to a PEG4-maleimide linker is:

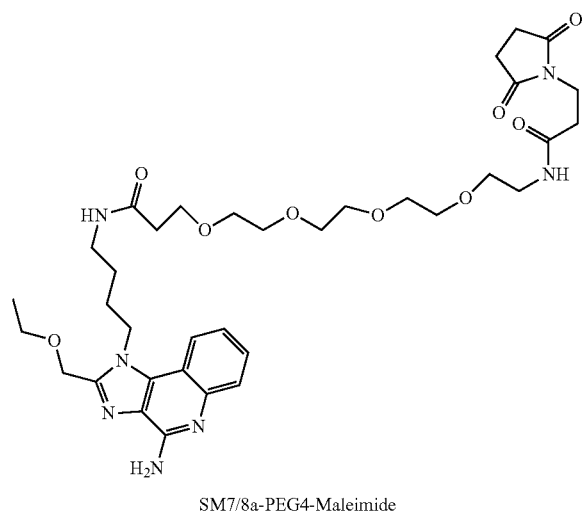 [SMILES: CCOCc1nc2c(N)nc3ccccc3c2n1CCCCNC(=O)CCOCCOCCOCCOCCNC(=O)CCN1C(=O)CCC1=O]

SM7/8a-PEG4-Maleimide

In some embodiments, an azide group is conjugated to ISS-1018. An exemplary structure of ISS-1018 conjugated to an NHS ester-azide linker is:

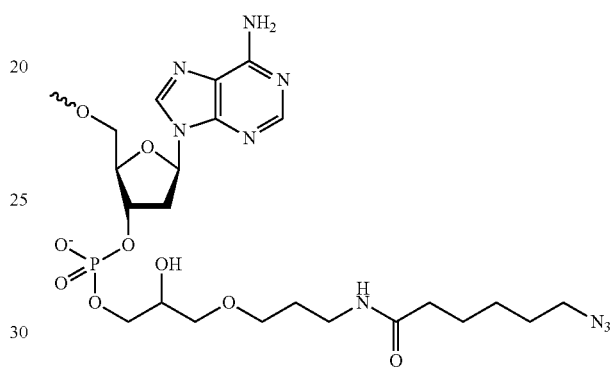

I. Exemplary Compositions, Kits, Nucleic Acids, Uses, and Methods

In some embodiments, the present invention provides methods of immunizing a subject against infection with EBV. The present invention further provides methods of eliciting an immune response against EBV in a subject. In some embodiments, the present methods comprise administering to the subject an effective amount of a pharmaceutical composition described herein to a subject. In some embodiments, the present methods comprises administering to the subject an effective amount of an antigenic EBV polypeptide or nanoparticle described herein to a subject.

In some embodiments, a composition comprising any one or more of the antigenic EBV polypeptides described herein and a pharmaceutically acceptable vehicle, adjuvant, or excipient is provided.

In some embodiments, an antigenic EBV polypeptide, nanoparticle, or composition described herein is administered to a subject, such as a human or any of the subjects discussed below, to immunize against infection caused by EBV. In some embodiments, an antigenic EBV polypeptide or nanoparticle described herein is administered to a subject, such as a human, to produce a protective immune response to future infection with EBV. In some embodiments, an antigenic EBV polypeptide is administered. In some embodiments, an antigenic EBV polypeptide comprising an EBV polypeptide and ferritin is administered, wherein the ferritin can have one or more mutations described herein. In some embodiments, an antigenic EBV polypeptide or nanoparticle comprising any one of SEQ ID NOS: 1-27 is administered.

In some embodiments, the protective immune response decreases the incidence of hospitalization. In some embodiments, the protective immune response decreases the incidence of EBV infection, mononucleosis, complications caused by mononucleosis (e.g. hepatitis, encephalitis, severe hemolytic anemia, or splenomegaly), nasopharyngeal cancer, gastric cancer, or B lymphoma (e.g., Burkitt's or Hodgkin's lymphoma).

In some embodiments, a composition comprises one antigenic EBV polypeptide (e.g., a monovalent composition). In some embodiments, a composition comprises an antigenic EBV polypeptide comprising a gH polypeptide. In some embodiments, a composition comprises an antigenic EBV polypeptide comprising a gL polypeptide. In some embodiments, a composition comprises an antigenic EBV polypeptide comprising a gp220 polypeptide.

In some embodiments, a composition comprises more than one antigenic EBV polypeptide. In some embodiments, a composition comprises one or more antigenic EBV polypeptides comprising more than one polypeptide encoded by EBV (i.e., a multivalent composition). In some embodiments, an EBV vaccine comprises nanoparticles comprising a gp220 polypeptide and, separately, nanoparticles comprising gH and gL polypeptides.

In some embodiments, any one or more of the antigenic EBV polypeptides, nanoparticles, or compositions described herein are provided for use in immunizing against infection caused by EBV. In some embodiments, any one or more of the polypeptides, nanoparticles, or compositions described herein are provided for use in producing a protective immune response to future infection with EBV.

1. Subjects

In some embodiments, the subject is a mammal. In some embodiments, the subject is a human.

In some embodiments, the subject is an adult (greater than or equal to 18 years of age). In some embodiments, the subject is a child or adolescent (less than 18 years of age). In some embodiments, the subject is elderly (greater than 60 years of age). In some embodiments, the subject is a non-elderly adult (greater than or equal to 18 years of age and less than or equal to 60 years of age).

In some embodiments, the composition is suitably formulated for an intended route of administration. Examples of suitable routes of administration include intramuscular, transcutaneous, subcutaneous, intranasal, oral, or transdermal.

In some embodiments, more than one administration of the composition is administered to the subject. In some embodiments, a booster administration improves the immune response.

In some embodiments, any one or more of the antigenic polypeptides, or compositions described herein are for use in a mammal, such as a primate (e.g., non-human primate, such as a monkey (e.g., a macaque, such as rhesus or cynomolgus) or ape), rodent (e.g., mouse or rat), or domesticated mammal (e.g., dog, rabbit, cat, horse, sheep, cow, goat, camel, or donkey).

2. Adjuvants

An adjuvant may be administered together with the antigenic EBV polypeptides and/or nanoparticles described herein to a subject, wherein administration of such a combination may produce a higher titer of antibodies against the EBV polypeptide(s) in the subject as compared to administration of the EBV polypeptide(s) without the adjuvant. An adjuvant may promote earlier, more potent, or more persistent immune response to the EBV polypeptide(s).

In some embodiments, a composition comprises one adjuvant. In some embodiments, a composition comprises more than one adjuvant. In some embodiments, a composition does not comprise an adjuvant.

In some embodiments, an adjuvant comprises aluminum. In some embodiments, an adjuvant is aluminum phosphate. In some embodiments, an adjuvant is Alum (Alyhydrogel '85 2%; Brenntag—Cat #21645-51-2).

In some embodiments, an adjuvant is an organic adjuvant. In some embodiments, an adjuvant is an oil-based adjuvant. In some embodiments, an adjuvant comprises an oil-in-water nanoemulsion.

In some embodiments, an adjuvant comprises squalene. In some embodiments, the adjuvant comprising squalene is Ribi (Sigma adjuvant system Cat #S6322-1v1), Addavax™ MF59, AS03, or AF03 (see U.S. Pat. No. 9,703,095). In some embodiments, the adjuvant comprising squalene is a nanoemulsion.

In some embodiments, an adjuvant comprises a polyacrylic acid polymer (PAA). In some embodiments, the adjuvant comprising PAA is SPA09 (see WO 2017218819).

In some embodiments, an adjuvant comprises non-metabolizable oils. In some embodiments, the adjuvant is Incomplete Freund's Adjuvant (IFA).

In some embodiments, an adjuvant comprises non-metabolizable oils and killed *Mycobacterium tuberculosis*. In some embodiments, the adjuvant is Complete Freund's Adjuvant (CFA).

In some embodiments, an adjuvant is a lipopolysaccharide. In some embodiments, an adjuvant is monophosphoryl A (MPL or MPLA).

3. Pharmaceutical Compositions

In various embodiments, a pharmaceutical composition comprising an antigenic EBV polypeptide described herein and/or related entities is provided. In some embodiments, the pharmaceutical composition is an immunogenic composition (e.g., a vaccine) capable of eliciting an immune response such as a protective immune response against a pathogen.

For example, in some embodiments, the pharmaceutical compositions may comprise one or more of the following: (1) an antigenic EBV polypeptide comprising an EBV polypeptide and a ferritin comprising a mutation replacing a surface-exposed amino acid with a cysteine; (2) an antigenic EBV polypeptide comprising an EBV polypeptide and a ferritin comprising a mutation replacing a surface exposed amino acid with a cysteine and an immune-stimulatory moiety linked to the cysteine; (3) an antigenic EBV polypeptide comprising an EBV polypeptide and a ferritin comprising (i) a surface-exposed cysteine, (ii) a peptide linker N-terminal to the ferritin protein, wherein the EBV polypeptide is N-terminal to the peptide linker; (4) an antigenic EBV polypeptide comprising an EBV polypeptide and a ferritin comprising (i) a mutation replacing a surface exposed amino acid with a cysteine and an immune-stimulatory moiety linked to the cysteine, (ii) a mutation replacing the internal cysteine at position 31 of *H. pylori* ferritin, or a mutation of an internal cysteine at a position that is analogous to position 31 of a non-*H. pylori* ferritin as determined by pair-wise or structural alignment, with a non-cysteine amino acid, and (iii) a mutation replacing a surface-exposed asparagine with a non-asparagine amino acid; or (5) a ferritin particle comprising any of the foregoing polypeptides. In some embodiments, the pharmaceutical compositions may comprise an antigenic EBV gL/gH polypeptide, e.g., wherein the polypeptide comprises a linker of at least 15 amino acids between the gL and gH polypeptide sequences.

In some embodiments, the present invention provides pharmaceutical compositions comprising antibodies or other agents related to the antigenic polypeptides described herein. In an embodiment, the pharmaceutical composition comprises antibodies that bind to and/or compete with an antigenic polypeptide described herein. Alternatively, the antibodies may recognize viral particles or bacteria comprising the non-ferritin polypeptide component of an antigenic polypeptide described herein.

In some embodiments, the pharmaceutical compositions as described herein are administered alone or in combination with one or more agents to enhance an immune response, e.g., an adjuvant described above. In some embodiments, a pharmaceutical composition further comprises an adjuvant described above.

In some embodiments, the pharmaceutical composition further comprises a pharmaceutically acceptable carrier or excipient. As used herein, the term "carrier" refers to a diluent, adjuvant, excipient, or vehicle with which a pharmaceutical composition is administered. In exemplary embodiments, carriers can include sterile liquids, such as, for example, water and oils, including oils of petroleum, animal, vegetable, or synthetic origin, such as, for example, peanut oil, soybean oil, mineral oil, sesame oil and the like. In some embodiments, carriers are or include one or more solid components. Pharmaceutically acceptable carriers can also include, but are not limited to, saline, buffered saline, dextrose, glycerol, ethanol, and combinations thereof. As used herein, an excipient is any non-therapeutic agent that may be included in a pharmaceutical composition, for example to provide or contribute to a desired consistency or stabilizing effect. Suitable pharmaceutical excipients include, but are not limited to, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. In various embodiments, the pharmaceutical composition is sterile.

In some embodiments, the pharmaceutical composition contains minor amounts of wetting or emulsifying agents, or pH buffering agents. In some embodiments, the pharmaceutical compositions of may include any of a variety of additives, such as stabilizers, buffers, or preservatives. In addition, auxiliary, stabilizing, thickening, lubricating, and coloring agents can be included.

In various embodiments, the pharmaceutical composition may be formulated to suit any desired mode of administration. For example, the pharmaceutical composition can take the form of solutions, suspensions, emulsion, drops, tablets, pills, pellets, capsules, capsules containing liquids, gelatin capsules, powders, sustained-release formulations, suppositories, emulsions, aerosols, sprays, suspensions, lyophilized powder, frozen suspension, desiccated powder, or any other form suitable for use. General considerations in the formulation and manufacture of pharmaceutical agents may be found, for example, in Remington's Pharmaceutical Sciences, 19th ed., Mack Publishing Co., Easton, PA, 1995; incorporated herein by reference.

The pharmaceutical composition can be administered via any route of administration. Routes of administration include, for example, oral, intradermal, intramuscular, intraperitoneal, intravenous, subcutaneous, intranasal, mucosal, epidural, sublingual, intranasal, intracerebral, intravaginal, transdermal, rectally, by intratracheal instillation, bronchial instillation, inhalation, or topically. Administration can be local or systemic. In some embodiments, administration is carried out orally. In another embodiment, the administration is by parenteral injection. In some instances, administration results in the release of the antigenic ferritin polypeptide described herein into the bloodstream. The mode of administration can be left to the discretion of the practitioner.

In some embodiments, the pharmaceutical composition is suitable for parenteral administration (e.g. intravenous, intramuscular, intraperitoneal, and subcutaneous). Such compositions can be formulated as, for example, solutions, suspensions, dispersions, emulsions, and the like. They may also be manufactured in the form of sterile solid compositions (e.g. lyophilized composition), which can be dissolved or suspended in sterile injectable medium immediately before use. For example, parenteral administration can be achieved by injection. In such embodiments, injectables are prepared in conventional forms, i.e., either as liquid solutions or suspensions, solid forms suitable for solution or suspension in liquid prior to injection, or as emulsions. In some embodiments, injection solutions and suspensions are prepared from sterile powders, lyophilized powders, or granules.

In a further embodiment, the pharmaceutical composition is formulated for delivery by inhalation (e.g., for direct delivery to the lungs and the respiratory system). For example, the composition may take the form of a nasal spray or any other known aerosol formulation. In some embodiments, preparations for inhaled or aerosol delivery comprise a plurality of particles. In some embodiments, such preparations can have a mean particle size of about 1, about 2, about 3, about 4, about 5, about 6, about 7, about 8, about 9, about 10, about 11, about 12, or about 13 microns. In some embodiments, preparations for inhaled or aerosol delivery are formulated as a dry powder. In some embodiments, preparations for inhaled or aerosol delivery are formulated as a wet powder, for example through inclusion of a wetting agent. In some embodiments, the wetting agent is selected from the group consisting of water, saline, or other liquid of physiological pH.

In some embodiments, the pharmaceutical composition in accordance with the invention are administered as drops to the nasal or buccal cavity. In some embodiments, a dose may comprise a plurality of drops (e.g., 1-100, 1-50, 1-20, 1-10, 1-5, etc.).

The present pharmaceutical composition may be administered in any dose appropriate to achieve a desired outcome. In some embodiments, the desired outcome is the induction of a long-lasting adaptive immune response against a pathogen, such as the source of a non-ferritin polypeptide present in an antigenic ferritin polypeptide present in the composition. In some embodiments, the desired outcome is a reduction in the intensity, severity, frequency, and/or delay of onset of one or more symptoms of infection. In some embodiments, the desired outcome is the inhibition or prevention of infection. The dose required will vary from subject to subject depending on the species, age, weight, and general condition of the subject, the severity of the infection being prevented or treated, the particular composition being used, and its mode of administration.

In some embodiments, pharmaceutical compositions in accordance with the invention are administered in single or multiple doses. In some embodiments, the pharmaceutical compositions are administered in multiple doses administered on different days (e.g., prime-boost vaccination strategies). In some embodiments, the pharmaceutical composition is administered as part of a booster regimen.

In various embodiments, the pharmaceutical composition is co-administered with one or more additional therapeutic agents. Co-administration does not require the therapeutic agents to be administered simultaneously, if the timing of their administration is such that the pharmacological activities of the additional therapeutic agent and the active ingredient(s) in the pharmaceutical composition overlap in time, thereby exerting a combined therapeutic effect. In general, each agent will be administered at a dose and on a time schedule determined for that agent.

4. Nucleic Acid/mRNA

Also provided is a nucleic acid encoding an antigenic EBV polypeptide described herein. In some embodiments, the nucleic acid is an mRNA. Any nucleic acid capable of undergoing translation resulting in a polypeptide is considered an mRNA for purposes of this disclosure.

5. Kits

Also provided herein are kits comprising one or more antigenic EBV polypeptides, nucleic acids, antigenic ferritin particles, antigenic lumazine synthase particles, compositions, or pharmaceutical compositions described herein. In some embodiments, a kit further comprises one or more of a solvent, solution, buffer, instructions, or desiccant.

This description and exemplary embodiments should not be taken as limiting. For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. "About" indicates a degree of variation that does not substantially affect the properties of the described subject matter, e.g., within 10%, 5%, 2%, or 1%. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed considering the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items. The term "or" is used in the inclusive sense, i.e., equivalent to "and/or," unless the context dictates otherwise.

TABLE 2

(SEQUENCE TABLE): DESCRIPTION OF THE SEQUENCES

| Description | Sequences | SEQ ID NO |
|---|---|---|
| SIB 7187 leader sequence gp220 bfpFerr Nanoparticle N19Q/C31S/S111C | MDSKGSSQKGSRLLLLLVVSNLLLPQGVLAEAALLVCQYTIQSLIHLTGEDPGFFNVEIP EFPFYPTCNVCTADVNVTINFDVGGKKHQLDLDFGQLTPHTKAVYQPRGAFGGSENATNL FLLELLGAGELALTMRSKKLPINVTTGEEQQVSLESVDVYFQDVFGTMWCHHAEMQNPVY LIPETVPYIKWDNCNSTNITAVVRAQGLDVTLPLSLPTSAQDSNFSVKTEMLGNEIDIEC IMEDGEISQVLPGDNKFNITCSGYESHVPSGGILTSTSPVATPIPGTGYAYSLRLTPRPV SRFLGNNSILYVFYSGNGPKASGGDYCIQSNIVFSDEIPASQDMPTNTTDITYVGDNATY SVPMVTSEDANSPNVTVTAFWAWPNNTETDFKCKWTLTSGTPSGCENISGAFASNRTFDI TVSGLGTAPKTLIITRTATNATTTTHKVIFSKAPEGSESQVRQQFSKDIEKLLNEQVNKE MQSSNLYMSMSSWSYTHSLDGAGLFLFDHAAEEYEHAKKLIIFLNENNVPVQLTSISAPE HKFEGLTQIFQKAYEHEQHISESINNIVDHAIKCKDHATFNFLQWYVAEQHEEEVLFKDI LDKIELIGNENHGLYLADQYVKGIAKSRKS | 1 |
| SIB 7340 leader sequence gL (D7)_linker_gH bfpFerr Nanoparticle N19Q/C31S/S111C | MRAVGVFLAICLVTIFVLPTWGNWAYPCCHVTQLRAQHLLALENISDIYLVSNQTCDGFSLASLNSPKNGSNQLVISRCA NGLNVVSFFISILKRSSSALTGHLRELLTTLETLYGSFSVEDLFGANLNRGGGSGSASSGASASGSSNGSGSGSNSSAS SGASSGGASGGSGGSGAASLSEVKLHLDIEGHASHYTIPWTELMAKVPGLSPEALWREANVTEDLASMLNRYKLIYKTSG TLGIALAEPVDIPAVSEGSMQVDASKVHPGVISGLNSPACMLSAPLEKQLFYYIGTMLPNTRPHSYVFYQLRCHLSYVAL SINGDKFQYTGAMTSKFLMGTYKRVTEKGDEHVLSLVFGKTKDLPDLRGPFSYPSLTSAQSGDYSLVIVTTFVHYANFHN YFVPNLKDMFSRAVTMTAASYARYVLQKLVLLEMKGGCREPELDTETLTTMFEVSVAFFKVGHAVGETGNGCVDLRWLAK SFFELTVLKDIIGICYGATVKGMQSYGLERLAAMLMATVKMEELGHLTTEKQEYALRLATVGYPKAGVYSGLIGGATSVL LSAYNRHPLFQPLHTVMRETLFIGSHVVLRELRLNVTTQGPNLALYQLLSTALCSALEIGEVLRGLALGTESGLFSPCYL SLRFDLTRDKLLSMAPQEATLDQAAVSNAVDGFLGRLSLEREDRDAWHLPAYKCVDRLDKVLMIIPLINVTFIISSDREV RGSALYEASTTYLSSSLFLSPVIMNKCSQGAVAGEPRQIPKIQNFTRTQKSCIFCGFALLSYDEKEGLETTT YITSQEVQNSILSSNYFDFDNLHVHYLLLTTNGTVMEIAGLYEERASGGGSGGGSGGGSGGGSGGGSESQVRQQFSKDIE KLLNEQVNKEMQSSNLYMSMSSWSYTHSLDGAGLFLFDHAAEEYEHAKKLIIFLNENNVPVQLTSISAPEHKFEGLTQIF QKAYEHEQHISESINNIVDHAIKCKDHATFNFLQWYVAEQHEEEVLFKDILDKIELIGNENHGLYLADQYVKGIAKSRKS | 2 |
| SIB 7342 leader sequence gL (D7)_linker_gH bfpFerr Nanoparticle N19Q/C31S/S111C | METDTLLLWVLLLWVPGSTGNWAYPCCHVTQLRAQHLLALENISDIYLVSNQTCDGFSLASLNSPKNGSNQLVISRCANG LNVVSFFISILKRSSSALTGHLRELLTTLETLYGSFSVEDLFGANLNRGGGSGGGSGGGSGGGSGAASLSEVKLHLDIEG HASHYTIPWTELMAKVPGLSPEALWREANVTEDLASMLNRYKLIYKTSGTLGIALAEPVDIPAVSEGSMQVDASKVHPGV ISGLNSPACMLSAPLEKQLFYYIGTMLPNTRPHSYVFYQLRCHLSYVALSINGDKFQYTGAMTSKFLMGTYKRVTEKGDE HVLSLVFGKTKDLPDLRGPFSYPSLTSAQSGDYSLVIVTTFVHYANFHNYFVPNLKDMFSRAVTMTAASYARYVLQKLVL LEMKGGCREPELDTETLTTMFEVSVAFFKVGHAVGETGNGCVDLRWLAKSFFELTVLKDIIGICYGATVKGMQSYGLERL AAMLMATVKMEELGHLTTEKQEYALRLATVGYPKAGVYSGLIGGATSVLLSAYNRHPLFQPLHTVMRETLFIGSHVVLRE LRLNVTTQGPNLALYQLLSTALCSALEIGEVLRGLALGTESGLFSPCYLSLRFDLTRDKLLSMAPQEATLDQAAVSNAVD | 3 |

TABLE 2-continued (SEQUENCE TABLE): DESCRIPTION OF THE SEQUENCES

| Description | Sequences | SEQ ID NO |
|---|---|---|
| | GFLGRLSLEREDRDAWHLPAYKCVDRLDKVLMIIPLINVTFIISSDREVRGSALYEASTTYLSSSLFLSPVIMNKCSQGA VAGEPRQIPKIQNFTRTQKSCIFCGFALLSYDEKEGLETTTYITSQEVQNSILSSNYFDFDNLHVHYLLLTT NGTVMEIAGLYEERA<u>SGGGSGGGSGGGSGGGSGGGS</u>ESQVRQQFSKDIEKLLNEQVNKEMQSSNLYMSMSSWSYTHSLDG AGLFLFDHAAEEYEHAKKLIIFLNENNVPVQLTSISAPEHKFEGLTQIFQKAYEHEQHISESINNIVDHAIKCKDHATFN FLQWYVAEQHEEEVLFKDILDKIELIGNENHGLYLADQYVKGIAKSRKS | |
| SIB 7379 leader sequence gL (D7)_linker_gH Trimer | <u>MRAVGVFLAICLVTIPVLPTWGN</u>WAYPCCHVTQLRAQHLLALENISDIYLVSNQTCDGFSLASLNSPKNGSNQLVISRCA *NGLNVVSFFISILKRSSSALTGHLRELLTTLETLYGSFSVEDLFGANLNR*<u>GGSGSASSGASASGSSNGSGSGSGSNSSAS SGASSGGASGGSGGGS</u>AASLSEVKLHLDIEGHASHYTIPWTELMAKVPGLSPEALWREANVTEDLASMLNRYKLIYKTSG TLGIALAEPVDIPAVSEGSMQVDASKVHPGVISGLNSPACMLSAPLEKQLFYYIGTMLPNTRPHSYVFYQLRCHLSYVAL SINGDKFQYTGAMTSKFLMGTYKRVTEKGDEHVLSLVFGKTKDLPDLRGPFSYPSLTSAQSGDYSLVIVTTFVHYANFHN YFVPNLKDMFSRAVTMTAASYARYVLQKLVLLEMKGGCREPELDTETLTTMFEVSVAFFKVGHAVGETGNGCVDLRWLAK SFFELTVLKDIIGICYGATVKGMQSYGLERLAAMLMATVKMEELGHLTTEKQEYALRLATVGYPKAGVYSGLIGGATSVL LSAYNRHPLFQPLHTVMRETLFIGSHVVLRELRLNVTTQGPNLALYQLLSTALCSALEIGEVLRGLALGTESGLFSPCYL SLRFDLTRDKLLSMAPQEATLDQAAVSNAVDGFLGRLSLEREDRDAWHLPAYKCVDRLDKVLMIIPLINVTFIISSDREV RGSALYEASTTYLSSSLFLSPVIMNKCSQGAVAGEPRQIPKIQNFTRTQKSCIFCGFALLSYDEKEGLETTTYITSQEVQ NSILSSNYFDFDNLHVHYLLLTTNGTVMEIAGLYEERA<u>SGSGYIPEAPRDGQAYVRKDGEWVLLSTFLGSGSGSLVPRG SGAGGG</u>HHHHHH | 4 |
| SIB 7380 leader sequence gL (D7)_linker_gH Trimer | <u>METDTLLLWVLLLWVPGSTGN</u>WAYPCCHVTQLRAQHLLALENISDIYLVSNQTCDGFSLASLNSPKNGSNQLVISRCANG *LNVVSFFISILKRSSSALTGHLRELLTTLETLYGSFSVEDLFGANLNR*<u>GGGSGGGSGGGSGGGS</u>AASLSEVKLHLDIEG HASHYTIPWTELMAKVPGLSPEALWREANVTEDLASMLNRYKLIYKTSGTLGIALAEPVDIPAVSEGSMQVDASKVHPGV ISGLNSPACMLSAPLEKQLFYYIGTMLPNTRPHSYVFYQLRCHLSYVALSINGDKFQYTGAMTSKFLMGTYKRVTEKGDE HVLSLVFGKTKDLPDLRGPFSYPSLTSAQSGDYSLVIVTTFVHYANFHNYFVPNLKDMFSRAVTMTAASYARYVLQKLVL LEMKGGCREPELDTETLTTMFEVSVAFFKVGHAVGETGNGCVDLRWLAKSFFELTVLKDIIGICYGATVKGMQSYGLERL AAMLMATVKMEELGHLTTEKQEYALRLATVGYPKAGVYSGLIGGATSVLLSAYNRHPLFQPLHTVMRETLFIGSHVVLRE LRLNVTTQGPNLALYQLLSTALCSALEIGEVLRGLALGTESGLFSPCYLSLRFDLTRDKLLSMAPQEATLDQAAVSNAVD GFLGRLSLEREDRDAWHLPAYKCVDRLDKVLMIIPLINVTFIISSDREVRGSALYEASTTYLSSSLFLSPVIMNKCSQGA VAGEPRQIPKIQNFTRTQKSCIFCGFALLSYDEKEGLETTTYITSQEVQNSILSSNYFDFDNLHVHYLLLTT NGTVMEIAGLYEERA<u>SGSGYIPEAPRDGQAYVRKDGEWVLLSTFLGSGSGSLVPRGSGAGGG</u>HHHHHH | 5 |
| SIB 7381 leader sequence gL (D7)_linker_gH Monomer | <u>MRAVGVFLAICLVTIPVLPTWGN</u>WAYPCCHVTQLRAQHLLALENISDIYLVSNQTCDGFSLASLNSPKNGSNQLVISRCA *NGLNVVSFFISILKRSSSALTGHLRELLTTLETLYGSFSVEDLFGANLNR*<u>GGSGSASSGASASGSSNGSGSGSGSNSSAS SGASSGGASGGSGGGS</u>AASLSEVKLHLDIEGHASHYTIPWTELMAKVPGLSPEALWREANVTEDLASMLNRYKLIYKTSG TLGIALAEPVDIPAVSEGSMQVDASKVHPGVISGLNSPACMLSAPLEKQLFYYIGTMLPNTRPHSYVFYQLRCHLSYVAL SINGDKFQYTGAMTSKFLMGTYKRVTEKGDEHVLSLVFGKTKDLPDLRGPFSYPSLTSAQSGDYSLVIVTTFVHYANFHN YFVPNLKDMFSRAVTMTAASYARYVLQKLVLLEMKGGCREPELDTETLTTMFEVSVAFFKVGHAVGETGNGCVDLRWLAK SFFELTVLKDIIGICYGATVKGMQSYGLERLAAMLMATVKMEELGHLTTEKQEYALRLATVGYPKAGVYSGLIGGATSVL LSAYNRHPLFQPLHTVMRETLFIGSHVVLRELRLNVTTQGPNLALYQLLSTALCSALEIGEVLRGLALGTESGLFSPCYL SLRFDLTRDKLLSMAPQEATLDQAAVSNAVDGFLGRLSLEREDRDAWHLPAYKCVDRLDKVLMIIPLINVTFIISSDREV RGSALYEASTTYLSSSLFLSPVIMNKCSQGAVAGEPRQIPKIQNFTRTQKSCIFCGFALLSYDEKEGLETTT YITSQEVQNSILSSNYFDFDNLHVHYLLLTTNGTVMEIAGLYEERA<u>SGSGSGSGLVPRGSGAGGG</u>HHHHHH | 6 |
| SIB 7382 leader sequence gL (D7)_linker_gH Monomer | <u>METDTLLLWVLLLWVPGSTGN</u>WAYPCCHVTQLRAQHLLALENISDIYLVSNQTCDGFSLASLNSPKNGSNQLVISRCANG *LNVVSFFISILKRSSSALTGHLRELLTTLETLYGSFSVEDLFGANLNR*<u>GGGSGGGSGGGSGGGS</u>AASLSEVKLHLDIEG HASHYTIPWTELMAKVPGLSPEALWREANVTEDLASMLNRYKLIYKTSGTLGIALAEPVDIPAVSEGSMQVDASKVHPGV ISGLNSPACMLSAPLEKQLFYYIGTMLPNTRPHSYVFYQLRCHLSYVALSINGDKFQYTGAMTSKFLMGTYKRVTEKGDE HVLSLVFGKTKDLPDLRGPFSYPSLTSAQSGDYSLVIVTTFVHYANFHNYFVPNLKDMFSRAVTMTAASYARYVLQKLVL LEMKGGCREPELDTETLTTMFEVSVAFFKVGHAVGETGNGCVDLRWLAKSFFELTVLKDIIGICYGATVKGMQSYGLERL AAMLMATVKMEELGHLTTEKQEYALRLATVGYPKAGVYSGLIGGATSVLLSAYNRHPLFQPLHTVMRETLFIGSHVVLRE LRLNVTTQGPNLALYQLLSTALCSALEIGEVLRGLALGTESGLFSPCYLSLRFDLTRDKLLSMAPQEATLDQAAVSNAVD GFLGRLSLEREDRDAWHLPAYKCVDRLDKVLMIIPLINVTFIISSDREVRGSALYEASTTYLSSSLFLSPVIMNKCSQGA VAGEPRQIPKIQNFTRTQKSCIFCGFALLSYDEKEGLETTTYITSQEVQNSILSSNYFDFDNLHVHYLLLTT NGTVMEIAGLYEERA<u>SGSGSGSGLVPRGSGAGGG</u>HHHHHH | 7 |
| SIB 7392 leader sequence gL_linker_gH Monomer | <u>MRAVGVFLAICLVTIPVLPTWGN</u>WAYPCCHVTQLRACHLLALENISDIYLVSNQTCDGESLASLNSPKNGSNCLVISRCA *NGLNVVSFFISILKRSSSALTGHLRELLTTLETLYGSFSVEDLFGANLNRYAWHR*<u>GGSGSASSGASASGSSNGSGSGS GSNSSASSGASSGGASGGSGGGS</u>AASLSEVKLHLDIEGHASHYTIPWTELMAKVPGLSPEALWREANVTEDLASMLNRYK LIYKTSGTLGIALAEPVDIPAVSEGSMQVDASKVHPGVISGLNSPACMLSAPLEKQLFYYIGTMLPNTRPHSYVFYQLRC HLSYVALSINGDKFQYTGAMTSKFLMGTYKRVTEKGDEHVLSLVFGKTKDLPDLRGPFSYPSLTSAQSGDYSLVIVTTFV HYANFHNYFVPNLKDMFSRAVTMTAASYARYVLQKLVLLEMKGGCREPELDTETLTTMFEVSVAFFKVGHAVGETGNGCV DLRWLAKSFFELTVLKDIIGICYGATVKGMQSYGLERLAAMLMATVKMEELGHLTTEKQEYALRLATVGYPKAGVYSGLI GGATSVLLSAYNRHPLFQPLHTVMRETLFIGSHVVLRELRLNVTTQGPNLALYQLLSTALCSALEIGEVLRGLALGTESG LFSPCYLSLRFDLTRDKLLSMAPQEATLDQAAVSNAVDGFLGRLSLEREDRDAWHLPAYKCVDRLDKVLMIIPLINVTFI ISSDREVRGSALYEASTTYLSSSLFLSPVIMNKCSQGAVAGEPRQIPKIQNFTRTQKSCIFCGFALLSYDEK EGLETTTYITSQEVQNSILSSNYFDFDNLHVHYLLLTTNGTVMEIAGGLYEERA<u>SGSGSGSGLVPRGSGAGGG</u>HHHHHH | 8 |

TABLE 2-continued (SEQUENCE TABLE): DESCRIPTION OF THE SEQUENCES

| Description | Sequences | SEQ ID NO |
|---|---|---|
| SIB 7397 leader sequence gL_linker_gH Monomer | MRAVGVFLAICLVTIFVLPTWGNWAYPCCHVTQLRACHLLALENISDIYLVSNQTCDGESLASLNSPKNGSNCLVISRCA NGLNVVSFFISILKRSSSALTGHLRELLTTLETLYGSFSVEDLFGANLNRYAWHRGGGGSGSGSNSSASSGASSGGASGG SGGSGAASLSEVKLHLDIEGHASHYTIPWTELMAKVPGLSPEALWREANVTEDLASMLNRYKLIYKTSGTLGIALAEPVD IPAVSEGSMQVDASKVHPGVISGLNSPACMLSAPLEKQLFYYIGTMLPNTRPHSYVFYQLRCHLSYVALSINGDKFQYTG AMTSKFLMGTYKRVTEKGDEHVLSLVFGKTKDLPDLRGPFSYPSLTSAQSGDYSLVIVTTFVHYANFHNYFVPNLKDMFS RAVTMTAASYARYVLQKLVLLEMKGGCREPELDTETLTTMFEVSVAFFKVGHAVGETGNGCVDLRWLAKSFFELTVLKDI IGICYGATVKGMQSYGLERLAAMLMATVKMEELGHLTTEKQEYALRLATVGYPKAGVYSGLIGGATSVLLSAYNRHPLFQ PLHTVMRETLFIGSHVVLRELRLNVTTQGPNLALYQLLSTALCSALEIGEVLRGLALGTESGLFSPCYLSLRFDLTRDKL LSMAPQEATLDQAAVSNAVDGFLGRLSLEREDRDAWHLPAYKCVDRLDKVLMIIPLINVTFIISSDREVRGSALYEASTT YLSSSLFLSPVIMNKCSQGAVAGEPRQIPKIQNFTRTQKSCIFCGFALLSYDEKEGLETTTYITSQEVQNSI LSSNYFDFDLHVHYLLLTTNGTVMEIAGLYEERASGSGSGSGLVPRGSGAGGGHHHHHH | 9 |
| SIB 7400 leader sequence gL_linker_gH bfpFerr Nanoparticle N19Q/C31S/S111C | METDTLLLWVLLLWVPGSTGNWAYPCCHVTQLRACHLLALENISDIYLVSNQTCDGESLASLNSPKNGSNCLVISRCANG LNVVSFFISILKRSSSALTGHLRELLTTLETLYGSFSVEDLFGANLNRYAWHRGGGGGSGGGGSGGGGSGAASLSEVKL HLDIEGHASHYTIPWTELMAKVPGLSPEALWREANVTEDLASMLNRYKLIYKTSGTLGIALAEPVDIPAVSEGSMQVDAS KVHPGVISGLNSPACMLSAPLEKQLFYYIGTMLPNTRPHSYVFYQLRCHLSYVALSINGDKFQYTGAMTSKFLMGTYKRV TEKGDEHVLSLVFGKTKDLPDLRGPFSYPSLTSAQSGDYSLVIVTTFVHYANFHNYFVPNLKDMFSRAVTMTAASYARYV LQKLVLLEMKGGCREPELDTETLTTMFEVSVAFFKVGHAVGETGNGCVDLRWLAKSFFELTVLKDIIGICYGATVKGMQS YGLERLAAMLMATVKMEELGHLTTEKQEYALRLATVGYPKAGVYSGLIGGATSVLLSAYNRHPLFQPLHTVMRETLFIGS HVVLRELRLNVTTQGPNLALYQLLSTALCSALEIGEVLRGLALGTESGLFSPCYLSLRFDLTRDKLLSMAPQEATLDQAA VSNAVDGFLGRLSLEREDRDAWHLPAYKCVDRLDKVLMIIPLINVTFIISSDREVRGSALYEASTTYLSSSLFLSPVIMN KCSQGAVAGEPRQIPKIQNFTRTQKSCIFCGFALLSYDEKEGLETTTYITSQEVQNSILSSNYFDFDNLHVH YLLLTTNGTVMEIAGLYEERASGGGSGGGSGGGSGGGSGGGSESQVRQQFSKDIEKLLNEQVNKEMQSSNLYMSMSSWSY THSLDGAGLFLFDHAAEEYEHAKKLIIFLNENNVPVQLTSISAPEHKFEGLTQIFQKAYEHEQHISESINNIVDHAIKCK DHATFNFLQWYVAEQHEEEVLFKDILDKIELIGNENHGLYLADQYVKGIAKSRKS | 10 |
| SIB 7402 leader sequence gL_linker_gH_ trimer | MRAVGVFLAICLVTIFVLPTWGNWAYPCCHVTQLRACHLLALENISDIYLVSNQTCDGESLASLNSPKNGSNQLVISRCA NGLNVVSFFISILKRSSSALTGHLRELLTTLETLYGSFSVEDLFGANLNRYAWHRGGGSGSGSNSSASSGASSGGASGG SGGSGAASLSEVKLHLDIEGHASHYTIPWTELMAKVPGLSPEALWREANVTEDLASMLNRYKLIYKTSGTLGIALAEPVD IPAVSEGSMQVDASKVHPGVISGLNSPACMLSAPLEKQLFYYIGTMLPNTRPHSYVFYQLRCHLSYVALSINGDKFQYTG AMTSKFLMGTYKRVTEKGDEHVLSLVFGKTKDLPDLRGPFSYPSLTSAQSGDYSLVIVTTFVHYANFHNYFVPNLKDMFS RAVTMTAASYARYVLQKLVLLEMKGGCREPELDTETLTTMFEVSVAFFKVGHAVGETGNGCVDLRWLAKSFFELTVLKDI IGICYGATVKGMQSYGLERLAAMLMATVKMEELGHLTTEKQEYALRLATVGYPKAGVYSGLIGGATSVLLSAYNRHPLFQ PLHTVMRETLFIGSHVVLRELRLNVTTQGPNLALYQLLSTALCSALEIGEVLRGLALGTESGLFSPCYLSLRFDLTRDKL LSMAPQEATLDQAAVSNAVDGFLGRLSLEREDRDAWHLPAYKCVDRLDKVLMIIPLINVTFIISSDREVRGSALYEASTT YLSSSLFLSPVIMNKCSQGAVAGEPRQIPKIQNFTRTQKSCIFCGFALLSYDEKEGLETTTYITSQEVQNSI LSSNYFDFDNLHVHYLLLTTNGTVMEIAGLYEERASGSGYIPEAPRDGQAYVRKDGEWVLLSTFLGSGSGSGLVPRGSGA GGGHHHHHH | 11 |
| SIB 7403 leader sequence gL_linker_gH_ trimer | MRAVGVFLAICLVTIFVLPTWGNWAYPCCHVTQLRACHLLALENISDIYLVSNQTCDGESLASLNSPKNGSNQLVISRCA NGLNVVSFFISILKRSSSALTGHLRELLTTLETLYGSFSVEDLFGANLNRYAWHRGGGSGSASSGASASGSSNGSGSGS GSNSSASSGASGGASGGSGGSGAASLSEVKLHLDIEGHASHYTIPWTELMAKVPGLSPEALWREANVTEDLASMLNRYK LIYKTSGTLGIALAEPVDIPAVSEGSMQVDASKVHPGVISGLNSPACMLSAPLEKQLFYYIGTMLPNTRPHSYVFYQLRC HLSYVALSINGDKFQYTGAMTSKFLMGTYKRVTEKGDEHVLSLVFGKTKDLPDLRGPFSYPSLTSAQSGDYSLVIVTTFV HYANFHNYFVPNLKDMFSRAVTMTAASYARYVLQKLVLLEMKGGCREPELDTETLTTMFEVSVAFFKVGHAVGETGNGCV DLRWLAKSFFELTVLKDIIGICYGATVKGMQSYGLERLAAMLMATVKMEELGHLTTEKQEYALRLATVGYPKAGVYSGLI GGATSVLLSAYNRHPLFQPLHTVMRETLFIGSHVVLRELRLNVTTQGPNLALYQLLSTALCSALEIGEVLRGLALGTESG LFSPCYLSLRFDLTRDKLLSMAPQEATLDQAAVSNAVDGFLGRLSLEREDRDAWHLPAYKCVDRLDKVLMIIPLINVTFI ISSDREVRGSALYEASTTYLSSSLFLSPVIMNKCSQGAVAGEPRQIPKIQNFTRTQKSCIFCGFALLSYDEK EGLETTTYITSQEVQNSILSSNYFDFDNLHVHYLLLTTNGTVMEIAGLYEERASGSGYIPEAPRDGQAYVRKDGEWVLLS TFLGSGSGSGLVPRGSGAGGGHHHHHH | 12 |
| SIB 7404 leader sequence gL_linker_gH bfpFerr Nanoparticle N19Q/C31S/S111C | MRAVGVFLAICLVTIFVLPTWGNWAYPCCHVTQLRACHLLALENISDIYLVSNQTCDGESLASLNSPKNGSNQLVISRCA NGLNVVSFFISILKRSSSALTGHLRELLTTLETLYGSFSVEDLFGANLNRYAWHRGGGGSGSGSNSSASSGASSGGASGG SGGSGAASLSEVKLHLDIEGHASHYTIPWTELMAKVPGLSPEALWREANVTEDLASMLNRYKLIYKTSGTLGIALAEPVD IPAVSEGSMQVDASKVHPGVISGLNSPACMLSAPLEKQLFYYIGTMLPNTRPHSYVFYQLRCHLSYVALSINGDKFQYTG AMTSKFLMGTYKRVTEKGDEHVLSLVFGKTKDLPDLRGPFSYPSLTSAQSGDYSLVIVTTFVHYANFHNYFVPNLKDMFS RAVTMTAASYARYVLQKLVLLEMKGGCREPELDTETLTTMFEVSVAFFKVGHAVGETGNGCVDLRWLAKSFFELTVLKDI IGICYGATVKGMQSYGLERLAAMLMATVKMEELGHLTTEKQEYALRLATVGYPKAGVYSGLIGGATSVLLSAYNRHPLFQ PLHTVMRETLFIGSHVVLRELRLNVTTQGPNLALYQLLSTALCSALEIGEVLRGLALGTESGLFSPCYLSLRFDLTRDKL LSMAPQEATLDQAAVSNAVDGFLGRLSLEREDRDAWHLPAYKCVDRLDKVLMIIPLINVTFIISSDREVRGSALYEASTT YLSSSLFLSPVIMNKCSQGAVAGEPRQIPKIQNFTRTQKSCIFCGFALLSYDEKEGLETTTYITSQEVQNSI | 13 |

TABLE 2-continued

| (SEQUENCE TABLE): DESCRIPTION OF THE SEQUENCES | | |
|---|---|---|
| Description | Sequences | SEQ ID NO |
| | LSSNYFDFDNLHVHYLLLTTNGTVMEIAGLYEERASGGGSGGGSGGGSGGGSGGGSESQVRQQFSKDIEKLLNEQVNKEM<br>QSSNLYMSMSSWSYTHSLDGAGLFLFDHAAEEYEHAKKLIIFLNENNVPVQLTSISAPEHKFEGLTQIFQKAYEHEQHIS<br>ESINNIVDHAIKCKDHATFNFLQWYVAEQHEEEVLFKDILDKIELIGNENHGLYLADQYVKGIAKSRKS | |
| SIB 7406<br>leader sequence<br>gL_linker_gH<br>bfpFerr<br>Nanoparticle<br>N19Q/C31S/S111C | MRAVGVFLAICLVTIFVLPTWG*NWAYPCCHVTQLRACHLLALENISDIYLVSNQTCDGFSLASLNSPKNGSNQLVISRCA*<br>*NGLNVVSFFISILKRSSSALTGHLRELLTTLETLYGSFSVEDLFGANLNRYAWHRGG*GGSGSASSGASASGSSNGSGSGS<br>GSNSSASSGASSGGASGGSGGSGAASLSEVKLHLDIEGHASHYTIPWTELMAKVPGLSPEALWREANVTEDLASMLNRYK<br>LIYKTSGTLGIALAEPVDIPAVSEGSMQVDASKVHPGVISGLNSPACMLSAPLEKQLFYYIGTMLPNTRPHSYVFYQLRC<br>HLSYVALSINGDKFQYTGAMTSKFLMGTYKRVTEKGDEHVLSLVFGKTKDLPDLRGPFSYPSLTSAQSGDYSLVIVTTFV<br>HYANFHNYFVPNLKDMFSRAVTMTAASYARYVLQKLVLLEMKGGCREPELDTETLTTMFEVSVAFFKVGHAVGETGNGCV<br>DLRWLAKSFFELTVLKDIIGICYGATVKGMQSYGLERLAAMLMATVKMEELGHLTTEKQEYALRLATVGYPKAGVYSGLI<br>GGATSVLLSAYNRHPLFQPLHTVMRETLFIGSHVVLRELRLNVTTQGPNLALYQLLSTALCSALEIGEVLRGLALGTESG<br>LFSPCYLSLRFDLTRDKLLSMAPQEATLDQAAVSNAVDGFLGRLSLEREDRDAWHLPAYKCVDRLDKVLMIIPLINVTFI<br>ISSDREVRGSALYEASTTYLSSSLFLSPVIMNKCSQGAVAGEPRQIPKIQNFTRTQKSCIFCGFALLSYDEK<br>EGLETTTYITSQEVQNSILSSNYFDFDNLHVHYLLLTTNGTVMEIAGLYEERASGGGSGGGSGGGSGGGSGGGSESQVRQ<br>QFSKDIEKLLNEQVNKEMQSSNLYMSMSSWSYTHSLDGAGLFLFDHAAEEYEHAKKLIIFLNENNVPVQLTSISAPEHKF<br>EGLTQIFQKAYEHEQHISESINNIVDHAIKCKDHATFNFLQWYVAEQHEEEVLFKDILDKIELIGNENHGLYLADQYVKG<br>IAKSRKS | 14 |
| SIB 7414<br>leader sequence<br>gL_linker_gH<br>Monomer | METDTLLLWVLLLWVPGSTG*NWAYPCCHVTQLRACHLLALENISDIYLVSNQTCDGFSLASLNSPKNGSNQLVISRCANG*<br>*LNVVSFFISILKRSSSALTGHLRELLTTLETLYGSFSVEDLFGANLNRYAWHRGG*GGGGSGGGGSGGGGSGAASLSEVKL<br>HLDIEGHASHYTIPWTELMAKVPGLSPEALWREANVTEDLASMLNRYKLIYKTSGTLGIALAEPVDIPAVSEGSMQVDAS<br>KVHPGVISGLNSPACMLSAPLEKQLFYYIGTMLPNTRPHSYVFYQLRCHLSYVALSINGDKFQYTGAMTSKFLMGTYKRV<br>TEKGDEHVLSLVFGKTKDLPDLRGPFSYPSLTSAQSGDYSLVIVTTFVHYANFHNYFVPNLKDMFSRAVTMTAASYARYV<br>LQKLVLLEMKGGCREPELDTETLTTMFEVSVAFFKVGHAVGETGNGCVDLRWLAKSFFELTVLKDIIGICYGATVKGMQS<br>YGLERLAAMLMATVKMEELGHLTTEKQEYALRLATVGYPKAGVYSGLIGGATSVLLSAYNRHPLFQPLHTVMRETLFIGS<br>HVVLRELRLNVTTQGPNLALYQLLSTALCSALEIGEVLRGLALGTESGLFSPCYLSLRFDLTRDKLLSMAPQEATLDQAA<br>VSNAVDGFLGRLSLEREDRDAWHLPAYKCVDRLDKVLMIIPLINVTFIISSDREVRGSALYEASTTYLSSSLFLSPVIMN<br>KCSQGAVAGEPRQIPKIQNFTRTQKSCIFCGFALLSYDEKEGLETTTYITSQEVQNSILSSNYFDFDNLHVH<br>YLLLTTNGTVMEIAGLYEERASGSGSGSG*LVPRGS*GAGGG***HHHHHH*** | 15 |
| SIB 7429<br>leader sequence<br>gL_linker_gH_<br>trimer | METDTLLLWVLLLWVPGSTG*NWAYPCCHVTQLRACHLLALENISDIYLVSNQTCDGFSLASLNSPKNGSNQLVISRCANG*<br>*LNVVSFFISILKRSSSALTGHLRELLTTLETLYGSFSVEDLFGANLNRYAWHRGG*GGGGSGGGGSGGGGSGAASLSEVKL<br>HLDIEGHASHYTIPWTELMAKVPGLSPEALWREANVTEDLASMLNRYKLIYKTSGTLGIALAEPVDIPAVSEGSMQVDAS<br>KVHPGVISGLNSPACMLSAPLEKQLFYYIGTMLPNTRPHSYVFYQLRCHLSYVALSINGDKFQYTGAMTSKFLMGTYKRV<br>TEKGDEHVLSLVFGKTKDLPDLRGPFSYPSLTSAQSGDYSLVIVTTFVHYANFHNYFVPNLKDMFSRAVTMTAASYARYV<br>LQKLVLLEMKGGCREPELDTETLTTMFEVSVAFFKVGHAVGETGNGCVDLRWLAKSFFELTVLKDIIGICYGATVKGMQS<br>YGLERLAAMLMATVKMEELGHLTTEKQEYALRLATVGYPKAGVYSGLIGGATSVLLSAYNRHPLFQPLHTVMRETLFIGS<br>HVVLRELRLNVTTQGPNLALYQLLSTALCSALEIGEVLRGLALGTESGLFSPCYLSLRFDLTRDKLLSMAPQEATLDQAA<br>VSNAVDGFLGRLSLEREDRDAWHLPAYKCVDRLDKVLMIIPLINVTFIISSDREVRGSALYEASTTYLSSSLFLSPVIMN<br>KCSQGAVAGEPRQIPKIQNFTRTQKSCIFCGFALLSYDEKEGLETTTYITSQEVQNSILSSNYFDFDNLHVH<br>YLLLTTNGTVMEIAGLYEERA*SGSGYIPEAPRDGQAYVRKDGEWVLLSTFL*GSGSGSG*LVPRGS*GAGGG***HHHHHH*** | 16 |
| SIB 15000<br>leader sequence<br>gL_FR1_gH<br>bfpFerr<br>Nanoparticle<br>N19Q/C31S/S111C | MRAVGVFLAICLVTIFVLPTWG*NWAYPCCHVTQLRACHLLALENISDIYLVSNQTCDGESLASLNSPKNGSNQLVISRCA*<br>*NGLNVVSFFISILKRSSSALTGHLRELLTTLETLYGSFSVEDLFGANLNRYAWHRGG*GGSGSASAEAAAKEAAAKAGGSG<br>*GSG***AASLSEVKLHLDIEGHASHYTIPWTELMAKVPGLSPEALWREANVTEDLASMLNRYKLIYKTSGTLGIALAEPVDIP**<br>AVSEGSMQVDASKVHPGVISGLNSPACMLSAPLEKQLFYYIGTMLPNTRPHSYVFYQLRCHLSYVALSINGDKFQYTGAM<br>TSKFLMGTYKRVTEKGDEHVLSLVFGKTKDLPDLRGPFSYPSLTSAQSGDYSLVIVTTFVHYANFHNYFVPNLKDMFSRA<br>VTMTAASYARYVLQKLVLLEMKGGCREPELDTETLTTMFEVSVAFFKVGHAVGETGNGCVDLRWLAKSFFELTVLKDIIG<br>ICYGATVKGMQSYGLERLAAMLMATVKMEELGHLTTEKQEYALRLATVGYPKAGVYSGLIGGATSVLLSAYNRHPLFQPL<br>HTVMRETLFIGSHVVLRELRLNVTTQGPNLALYQLLSTALCSALEIGEVLRGLALGTESGLFSPCYLSLRFDLTRDKLLS<br>MAPQEATLDQAAVSNAVDGFLGRLSLEREDRDAWHLPAYKCVDRLDKVLMIIPLINVTFIISSDREVRGSALYEASTTYL<br>SSSLFLSPVIMNKCSQGAVAGEPRQIPKIQNFTRTQKSCIFCGFALLSYDEKEGLETTTYITSQEVQNSILS<br>SNYFDFDNLHVHYLLLTTNGTVMEIAGLYEERASGGGSGGGSGGGSGGGSGGGSESQVRQQFSKDIEKLLNEQVNKEMQS<br>SNLYMSMSSWSYTHSLDGAGLFLFDHAAEEYEHAKKLIIFLNENNVPVQLTSISAPEHFKEGLTQIFQKAYEHEQHISES<br>INNIVDHAIKCKDHATFNFLQWYVAEQHEEEVLFKDILDKIELIGNENHGLYLADQYVKGIAKSRKS | 17 |

TABLE 2-continued (SEQUENCE TABLE): DESCRIPTION OF THE SEQUENCES

| Description | Sequences | SEQ ID NO |
|---|---|---|
| SIB 15001 leader sequence gL_FR2_gH bfpFerr Nanoparticle N19Q/C31S/S111C | MRAVGVFLAICLVTIFVLPTWGNWAYPCCHVTQLRACHLLALENISDIYLVSNQTCDGESLASLNSPKNGSNQLVISRCA<br>NGLNVVSFFISILKRSSSALTGHLRELLTTLETLYGSFSVEDLFGANLNRYAWHRGGGGSGSASAEAAAKEAAAKEAAAK<br>ASGGSGGSGAASLSEVKLHLDIEGHASHYTIPWTELMAKVPGLSPEALWREANVTEDLASMLNRYKLIYKTSGTLGIALA<br>EPVDIPAVSEGSMQVDASKVHPGVISGLNSPACMLSAPLEKQLFYYIGTMLPNTRPHSYVFYQLRCHLSYVALSINGDKF<br>QYTGAMTSKFLMGTYKRVTEKGDEHVLSLVFGKTKDLPDLRGPFSYPSLTSAQSGDYSLVIVTTFVHYANFHNYFVPNLK<br>DMFSRAVTMTAASYARYVLQKLVLLEMKGGCREPELDTETLTTMFEVSVAFFKVGHAVGETGNGCVDLRWLAKSFFELTV<br>LKDIIGICYGATVKGMQSYGLERLAAMLMATVKMEELGHLTTEKQEYALRLATVGYPKAGVYSGLIGGATSVLLSAYNRH<br>PLFQPLHTVMRETLFIGSHVVLRELRLNVTTQGPNLALYQLLSTALCSALEIGEVLRGLALGTESGLFSPCYLSLRFDLT<br>RDKLLSMAPQEATLDQAAVSNAVDGFLGRLSLEREDRDAWHLPAYKCVDRLDKVLMIIPLINVTFIISSDREVRGSALYE<br>ASTTYLSSSLFLSPVIMNKCSQGAVAGEPRQIPKIQNFTRTQKSCIFCGFALLSYDEKEGLETTTYITSQEV<br>QNSILSSNYFDFDNLHVHYLLLTTNGTVMEIAGLYEERASGGGSGGGSGGGSGGGSGGGSESQVRQQFSKDIEKLLNEQV<br>NKEMQSSNLYMSMSSWSYTHSLDGAGLFLFDHAAEEYEHAKKLIIFLNENNVPVQLTSISAPEHKFEGLTQIFQKAYEHE<br>QHISESINNIVDHAIKCKDHATFNFLQWYVAEQHEEEVLFKDILDKIELIGNENHGLYLADQYVKGIAKSRKS | 18 |
| SIB 15002 leader sequence Construct 5 gL_linker_gH_ linker bfpFerr Nanoparticle N19Q/C31S/S111C | MRAVGVFLAICLVTIFVLPTWGNWAYPCCHVTQLRACHLLALENISDIYLVSNQTCDGESLASLNSPKNGSNQLVISRCA<br>NGLNVVSFFISILKRSSSALTGHLRELLTTLETLYGSFSVEDLFGANLNRYAWHRGGGGSGSASSGASASGSSNGSGSGS<br>GSNSSASSGASSGGASGGSGGSGAASLSEVKLHLDIEGHASHYTIPWTELMAKVPGLSPEALWREANVTEDLASMLNRYK<br>LIYKTSGTLGIALAEPVDIPAVSEGSMQVDASKVHPGVISGLNSPACMLSAPLEKQLFYYIGTMLPNTRPHSYVFYQLRC<br>HLSYVALSINGDKFQYTGAMTSKFLMGTYKRVTEKGDEHVLSLVFGKTKDLPDLRGPFSYPSLTSAQSGDYSLVIVTTFV<br>HYANFHNYFVPNLKDMFSRAVTMTAASYARYVLQKLVLLEMKGGCREPELDTETLTTMFEVSVAFFKVGHAVGETGNGCV<br>DLRWLAKSFFELTVLKDIIGICYGATVKGMQSYGLERLAAMLMATVKMEELGHLTTEKQEYALRLATVGYPKAGVYSGLI<br>GGATSVLLSAYNRHPLFQPLHTVMRETLFIGSHVVLRELRLNVTTQGPNLALYQLLSTALCSALEIGEVLRGLALGTESG<br>LFSPCYLSLRFDLTRDKLLSMAPQEATLDQAAVSNAVDGFLGRLSLEREDRDAWHLPAYKCVDRLDKVLMIIPLINVTFI<br>ISSDREVRGSALYEASTTYLSSSLFLSPVIMNKCSQGAVAGEPRQIPKIQNFTRTQKSCIFCGFALLSYDEKEGLETTTY<br>ITSQEVQNSILSSNYFDFDNLHVHYLLLTTNGTVMEIAGLYEERASGGGSGSASSGASASGSSGSGSGSGSSSASSGASS<br>GGASGGGSGGSGESQVRQQFSKDIEKLLNEQVNKEMQSSNLYMSMSSWSYTHSLDGAGLFLFDHAAEEYEHAKKLIIFLN<br>ENNVPVQLTSISAPEHKFEGLTQIFQKAYEHEQHISESINNIVDHAIKCKDHATFNFLQWYVAEQHEEEVLFKDILDKIE<br>LIGNENHGLYLADQYVKGIAKSRKS | 19 |
| SIB 15003 leader sequence Construct 7 gL_linker_gH_ linker bfpFerr Nanoparticle N19Q/C31S | MRAVGVFLAICLVTIFVLPTWGNWAYPCCHVTQLRACHLLALENISDIYLVSNQTCDGESLASLNSPKNGSNCLVISRCA<br>NGLNVVSFFISILKRSSSALTGHLRELLTTLETLYGSFSVEDLFGANLNRYAWHRGGGGSGSASSGASASGSSNGSGSGS<br>GSNSSASSGASSGGASGGSGGSGAASLSEVKLHLDIEGHASHYTIPWTELMAKVPGLSPEALWREANVTEDLASMLNRYK<br>LIYKTSGTLGIALAEPVDIPAVSEGSMQVDASKVHPGVISGLNSPACMLSAPLEKQLFYYIGTMLPNTRPHSYVFYQLRC<br>HLSYVALSINGDKFQYTGAMTSKFLMGTYKRVTEKGDEHVLSLVFGKTKDLPDLRGPFSYPSLTSAQSGDYSLVIVTTFV<br>HYANFHNYFVPNLKDMFSRAVTMTAASYARYVLQKLVLLEMKGGCREPELDTETLTTMFEVSVAFFKVGHAVGETGNGCV<br>DLRWLAKSFFELTVLKDIIGICYGATVKGMQSYGLERLAAMLMATVKMEELGHLTTEKQEYALRLATVGYPKAGVYSGLI<br>GGATSVLLSAYNRHPLFQPLHTVMRETLFIGSHVVLRELRLNVTTQGPNLALYQLLSTALCSALEIGEVLRGLALGTESG<br>LFSPCYLSLRFDLTRDKLLSMAPQEATLDQAAVSNAVDGFLGRLSLEREDRDAWHLPAYKCVDRLDKVLMIIPLINVTFI<br>ISSDREVRGSALYEASTTYLSSSLFLSPVIMNKCSQGAVAGEPRQIPKIQNFTRTQKSCIFCGFALLSYDEKEGLETTTY<br>ITSQEVQNSILSSNYFDFDNLHVHYLLLTTNGTVMEIAGLYEERASGGGSGSASSGASASGSSCSGSGSGSSSASSGASS<br>GGASGGGSGGSGESQVRQQFSKDIEKLLNEQVNKEMQSSNLYMSMSSWSYTHSLDGAGLFLFDHAAEEYEHAKKLIIFLN<br>ENNVPVQLTSISAPEHKFEGLTQIFQKAYEHEQHISESINNIVDHAIKSKDHATFNFLQWYVAEQHEEEVLFKDILDKIE<br>LIGNENHGLYLADQYVKGIAKSRKS | 20 |
| SIB 15004 leader sequence gL_gH_gp42_ bfpFerr Nanoparticle N19Q/C31S/S111C | MRAVGVFLAICLVTIFVLPTWGNWAYPCCHVTQLRACHLLALENISDIYLVSNQTCDGESLASLNSPKNGSNCLVISRCA<br>NGLNVVSFFISILKRSSSALTGHLRELLTTLETLYGSFSVEDLFGANLNRYAWHRGGGGSGSASSGASASGSSNGSGSGS<br>GSNSASSGASSGGASGGSGGSGAASLSEVKLHLDIEGHASHYTIPWTELMAKVPGLSPEALWREANVTEDLASMLNRYK<br>LIYKTSGTLGIALAEPVDIPAVSEGSMQVDASKVHPGVISGLNSPACMLSAPLEKQLFYYIGTMLPNTRPHSYVFYQLRC<br>HLSYVALSINGDKFQYTGAMTSKFLMGTYKRVTEKGDEHVLSLVFGKTKDLPDLRGPFSYPSLTSAQSGDYSLVIVTTFV<br>HYANFHNYFVPNLKDMFSRAVTMTAASYARYVLQKLVLLEMKGGCREPELDTETLTTMFEVSVAFFKVGHAVGETGNGCV<br>DLRWLAKSFFELTVLKDIIGICYGATVKGMQSYGLERLAAMLMATVKMEELGHLTTEKQEYALRLATVGYPKAGVYSGLI<br>GGATSVLLSAYNRHPLFQPLHTVMRETLFIGSHVVLRELRLNVTTQGPNLALYQLLSTALCSALEIGEVLRGLALGTESG<br>LFSPCYLSLRFDLTRDKLLSMAPQEATLDQAAVSNAVDGFLGRLSLEREDRDAWHLPAYKCVDRLDKVLMIIPLINVTFI<br>ISSDREVRGSALYEASTTYLSSSLFLSPVIMNKCSQGAVAGEPRQIPKIQNFTRTQKSCIFCGFALLSYDEKEGLETTTY<br>ITSQEVQNSILSSNYFDFDNLHVHYLLLTTNGTVMEIAGLYEERASGGGSGSASSGASASGSSGSGSGSGSSSASSGDSK<br>GSSQKGSRLLLLLVVSNLLLPQGVLAYFLPPPRVRGGGRVAAAAITWVPKPNVEVWPVDPPPPVNFNKTAEQEYGDKEVK<br>LPHWTPTLHTFQVPQNYTKANCTYCNTREYTFSYKGCCFYFTKKKHTWNGCFQACAELYPCTYFYGPTPDILPVVTRNLN<br>AIESLWVGVYRVGEGNWTSLDGGTFKVYQIFGSHCTYVSKFSTVPVSHHECSFLKPCLCVSQRSNSGGSGSASSGASASG<br>SSGSGSGSGSSSASSGASSGGASGG<br>SGGSGGGSGSASSGASASGSSGSGSGSGSSSASSGASSGGASGGSGGSGESQVRQQFSKDIEKLLNEQVNKEMQSSNLYM<br>SMSSWSYTHSLDGAGLFLFDHAAEEYEHAKKLIIFLNENNVPVQLTSISAPEHKFEGLTQIFQKAYEHEQHISESINNIV<br>DHAIKCKDHATFNFLQWYVAEQHEEEVLFKDILDKIELIGNENHGLYLADQYVKGIAKSRKS | 21 |

TABLE 2-continued (SEQUENCE TABLE): DESCRIPTION OF THE SEQUENCES

| Description | Sequences | SEQ ID NO |
|---|---|---|
| SIB 15005 leader sequence Construct 5 gL_gH_C137A_ bfpFerr Nanoparticle N19Q/C31S/S111C | MRAVGVFLAICLVTIFVLPTWGNWAYPCCHVTQLRACHLLALENISDIYLVSNQTCDGFSLASLNSPKNGSNQLVISRCA NGLNVVSFFISILKRSSSALTGHLRELLTTLETLYGSFSVEDLFGANLNRYAWHRGGGSGSASSGASASGSSNGSGSGS GSNSSASSGASSGGASGGSGGSGAASLSEVKLHLDIEGHASHYTIPWTELMAKVPGLSPEALWREANVTEDLASMLNRYK LIYKTSGTLGIALAEPVDIPAVSEGSMQVDASKVHPGVISGLNSPACMLSAPLEKQLFYYIGTMLPNTRPHSYVFYQLRA HLSYVALSINGDKFQYTGAMTSKFLMGTYKRVTEKGDEHVLSLVFGKTKDLPDLRGPFSYPSLTSAQSGDYSLVIVTTFV HYANFHNYFVPNLKDMFSRAVTMTAASYARYVLQKLVLLEMKGGCREPELDTETLTTMFEVSAVFFKVGHAVGETGNGCV DLRWLAKSFFELTVLKDIIGICYGATVKGMQSYGLERLAAMLMATVKMEELGHLTTEKQEYALRLATVGYPKAGVYSGLI GGATSVLLSAYNRHPLFQPLHTVMRETLFIGSHVVLRELRLNVTTQGPNLALYQLLSTALCSALEIGEVLRGLALGTESG LFSPCYLSLRFDLTRDKLLSMAPQEATLDQAAVSNAVDGFLGRLSLEREDRDAWHLPAYKCVDRLDKVLMIIPLINVTFI ISSDREVRGSALYEASTTYLSSSLFSPVIMNKCSQGAVAGEPRQIPKIQNFTRTQKSCIFCGFALLSYDEKEGLETTTY ITSQEVQNSILSSNYFDFDNLHVYHLLLLTTNGTVMEIAGLYEERASGGGSGSASSGASASGSSGSGSGSGSSSASSGASS GGASGGGSGGSGESQVRQQFSKDIEKLLNEQVNKEMQSSNLYMSMSSWSYTHSLDGAGLFLFDHAAEEYEHAKKLIIFLN ENNVPVQLTSISAPEHKFEGLTQIFQKAYEHEQHISESINNIVDHAIKCKDHATFNFLQWYVAEQHEEEVLFKDILDKIE LIGNENHGLYLADQYVKGIAKSRKS | 22 |
| SIB 15006 leader sequence Construct 7 gL_gH_C137A_ bfpFerr Nanoparticle N19Q/C31S | MRAVGVFLAICLVTIFVLPTWGNWAYPCCHVTQLRACHLLALENISDIYLVSNQTCDGFSLASLNSPKNGSNQLVISRCA NGLNVVSFFISILKRSSSALTGHLRELLTTLETLYGSFSVEDLFGANLNRYAWHRGGGSGSASSGASASGSSNGSGSGS GSNSSASSGASSGGASGGSGGSGAASLSEVKLHLDIEGHASHYTIPWTELMAKVPGLSPEALWREANVTEDLASMLNRYK LIYKTSGTLGIALAEPVDIPAVSEGSMQVDASKVHPGVISGLNSPACMLSAPLEKQLFYYIGTMLPNTRPHSYVFYQLRA HLSYVALSINGDKFQYTGAMTSKFLMGTYKRVTEKGDEHVLSLVFGKTKDLPDLRGPFSYPSLTSAQSGDYSLVIVTTFV HYANFHNYFVPNLKDMFSRAVTMTAASYARYVLQKLVLLEMKGGCREPELDTETLTTMFEVSAVFFKVGHAVGETGNGCV DLRWLAKSFFELTVLKDIIGICYGATVKGMQSYGLERLAAMLMATVKMEELGHLTTEKQEYALRLATVGYPKAGVYSGLI GGATSVLLSAYNRHPLFQPLHTVMRETLFIGSHVVLRELRLNVTTQGPNLALYQLLSTALCSALEIGEVLRGLALGTESG LFSPCYLSLRFDLTRDKLLSMAPQEATLDQAAVSNAVDGFLGRLSLEREDRDAWHLPAYKCVDRLDKVLMIIPLINVTFI ISSDREVRGSALYEASTTYLSSSLFSPVIMNKCSQGAVAGEPRQIPKIQNFTRTQKSCIFCGFALLSYDEKEGLETTTY ITSQEVQNSILSSNYFDFDNLHVYHLLLLTTNGTVMEIAGLYEERASGGGSGSASSGASASGSSCSGSGSGSSSASSGASS GGASGGGSGGSGESQVRQQFSKDIEKLLNEQVNKEMQSSNLYMSMSSWSYTHSLDGAGLFLFDHAAEEYEHAKKLIIFLN ENNVPVQLTSISAPEHKFEGLTQIFQKAYEHEQHISESINNIVDHAIKSKDHATFNFLQWYVAEQHEEEVLFKDILDKIE LIGNENHGLYLADQYVKGIAKSRKS | 23 |
| SIB 17395 leader sequence gp220-T. ni ferritin heavy chain | MDSKGSSQKGSRLLLLLVVSNLLLPQGVLAEAALLVCQYTIQSLIHLTGEDPGFFNVEIPEFPFYPTCNVCTA DVNVTINFDVGGKKHQLDLDFGQLTPHTKAVYQPRGAFGGSENATNLFLLELLGAGELALTMRSKKLPIN VTTGEEQQVSLESVDVYFQDVFGTMWCHHAEMQNPVYLIPETVPYIKWDNCNSTNITAVVRAQGLDVTL PLSLPTSAQDSNFSVKTEMLGNEIDIECIMEDGEISQVLPGDNKFNITCSGYESHVPSGGILTSTSPVAT PIPGTGYAYSLRLRTPRPVSRFLGNNSILYVFYSGNGPKASGGDYCIQSNIVFSDEIPASQDMPTNTTDIT YVGDNATYSVPMVTSEDANSPNVTVTAFWAWPNNTETDFKCKWTLTSGTPSGCENISGAFASNRTFDI TVSGLGTAPKTLIITRTATNATTTTHKVIFSKAPEGSTQCNVNPVQIPKDWITMHRSCRN SMRQQIQMEVGASLQYLAMGAHFSKDVVNRPGFAQLFFDAASEEREHAMKLIEYLLMRGELTNDVSSLLQVRPPTRSSWK GGVEALEHALSMESDVTKSIRNVIKACEDDSEFNDYHLVDYLTGDFLEEQYKGQRDLAGKASTLKKLMDRHEALGEFIFD KKLLGIDV | 24 |
| SIB 17396 leader sequence gL_linker_gH- T. ni ferritin heavy chain | MRAVGVFLAICLVTIFVLPTWGNWAYPCCHVTQLRACHLLALENISDIYLVSNQTCDGFSLASLNSPKNGSNQLVISRCA NGFLNVVSFISILKRSSSALTGHLRELLTTLETLYGSFSVEDLFGANLNRYAWHRGGGSGSASSGASASGSSNGSGSGS GSNSSASSGASSGGASGGSGGSGAASLSEVKLHLDIEGHASHYTIPWTELMAKVPGLSPEALWREANVTEDLASMLNRYK LIYKTSGTLGIALAEPVDIPAVSEGSMQVDASKVHPGVISGLNSPACMLSAPLEKQLFYYIGTMLPNTRPHSYVFYQLRC HLSYVALSINGDKFQYTGAMTSKFLMGTYKRVTEKGDEHVLSLVFGKTKDLPDLRGPFSYPSLTSAQSGDYSLVIVTTFV HYANFHNYFVPNLKDMFSRAVTMTAASYARYVLQKLVLLEMKGGCREPELDTETLTTMFEVSAVFFKVGHAVGETGNGCV DLRWLAKSFFELTVLKDIIGICYGATVKGMQSYGLERLAAMLMATVKMEELGHLTTEKQEYALRLATVGYPKAGVYSGLI GGATSVLLSAYNRHPLFQPLHTVMRETLFIGSHVVLRELRLNVTTQGPNLALYQLLSTALCSALEIGEVLRGLALGTESG LFSPCYLSLRFDLTRDKLLSMAPQEATLDQAAVSNAVDGFLGRLSLEREDRDAWHLPAYKCVDRLDKVLMIIPLINVTFI ISSDREVRGSALYEASTTYLSSSLFSPVIMNKCSQGAVAGEPRQIPKIQNFTRTQKSCIFCGFALLSYDEK EGLETTTYITSQEVQNSILSSNYFDFDNLHVYHLLLLTTNGTVMEIAGLYEERASGSTQCNVNPVQIPKDWITMHRSCRNS MRQQIQMEVGASLQYLAMGAHFSKDVVNRPGFAQLFFDAASEEREHAMKLIEYLLMRGELTNDVSSLLQVRPPTRSSWKG GVEALEHALSMESDVTKSIRNVIKACEDDSEFNDYHLVDYLTGDFLEEQYKGQRDLAGKASTLKKLMDRHEALGEFIFDK KLLGIDV | 25 |

TABLE 2-continued (SEQUENCE TABLE): DESCRIPTION OF THE SEQUENCES

| Description | Sequences | SEQ ID NO |
|---|---|---|
| SIB 17397 leader sequence gp220-T. ni ferritin light chain | MDSKGSSQKGSRLLLLLVVSNLLLPQGVLAEAALLVCQYTIQSLIHLTGEDPGFFNVEIPEFPFYPTCNVCTA DVNVTINFDVGGKKHQLDLDFGQLTPHTKAVYQPRGAFGGSENATNLFLLELLGAGELALTMRSKKLPIN VTTGEEQQVSLESVDVYFQDVFGTMWCHHAEMQNPVYLIPETVPYIKWDNCNSTNITAVVRAQGLDVTL PLSLPTSAQDSNFSVKTEMLGNEIDIECIMEDGEISQVLPGDNKFNITCSGYESHVPSGGILTSTSPVAT PIPGTGYAYSLRLTPRPVSRFLGNNSILYVFYSGNGPKASGGDYCIQSNIVFSDEIPASQDMPTNTTDIT YVGDNATYSVPMVTSEDANSPNVTVTAFWAWPNNTETDFKCKWTLTSGTPSGCENISGAFASNRTFDI TVSGLGTAPKTLIITRTATNATTTTHKVIFSKAPEGSADTCYNDVALDCGITSNSLALPR CNAVYGEYGSHGNVATELQAYAKLHLERSYDYLLSAAYFNNYQTNRAGFSKLFKKLSDEAWSKTIDIIKHVTKRGDKMNF DQHSTMKTERKNYTAENHELEALAKALDTQKELAERAFYIHREATRNSQHLHDPEIAQYLEEEFIEDHAEKIRTLAGHTS DLSLALYVFDEYLQKTV | 26 |
| SIB 17398 leader sequence gL_linker_gH-T. ni ferritin light chain | MRAVGVFLAICLVTIFVLPTWGNWAYPCCHVTQLRACHLLALENISDIYLVSNQTCDGFSLASLNSPKNGSNQLVISRCA NGLNVVSFFISILKRSSSALTGHLRELLTTLETLYGSFSVEDLFGANLNRYAWHRGGGGSGSASSGASASGSSNGSGSGS GSNSSASSGASSGGASGGSGSGAASLSEVKLHLDIEGHASHYTIPWTELMAKVPGLSPEALWREANVTEDLASMLNRYK LIYKTSGTLGIALAEPVDIPAVSEGSMQVDASKVHPGVISGLNSPACMLSAPLEKQLFYYIGTMLPNTRPHSYVFYQLRC HLSYVALSINGDKFQYTGAMTSKFLMGTYKRVTEKGDEHVLSLVFGKTKDLPDLRGPFSYPSLTSAQSGDYSLVIVTTFV HYANFHNYFVPNLKDMFSRAVTMTAASYARYVLQKLVLLEMKGGCREPELDTETLTTMFEVSVAFFKVGHAVGETGNGCV DLRWLAKSFFELTVLKDIIGICYGATVKGMQSYGLERLAAMLMATVKMEELGHLTTEKQEYALRLATVGYPKAGVYSGLI GGATSVLLSAYNRHPLFQPLHTVMRETLFIGSHVVLRELRLNVTTQGPNLALYQLLSTALCSALEIGEVLRGLALGTESG LFSPCYLSLRFDLTRDKLLSMAPQEATLDQAAVSNAVDGFLGRLSLEREDRDAWHLPAYKCVDRLDKVLMIIPLINVTFI ISSDREVRGSALYEASTTYLSSSLFLSPVIMNKCSQGAVAGEPRQIPKIQNFTRTQKSCIFCGFALLSYDEK EGLETTTYITSQEVQNSILSSNYFDFDNLHVHYLLLTTNGTVMEIAGLYEERASGSADTCYNDVALDCGITSNSLALPRC NAVYGEYGSHGNVATELQAYAKLHLERSYDYLLSAAYFNNYQTNRAGFSKLFKKLSDEAWSKTIDIIKHVTKRGDKMNFD QHSTMKTERKNYTAENHELEALAKALDTQKELAERAFYIHREATRNSQHLHDPEIAQYLEEEFIEDHAEKIRTLAGHTSD LKKFITANNGHDLSLALYVFDEYLQKTV | 27 |
| 16 amino acid linker | GGGGSGGGGSGGGGSG | 28 |
| 28 amino acid linker | GGSGSGSNSSASSGASSGGASGGSGGSG | 29 |
| 46 amino acid linker | GGSGSASSGASASGSSNGSGSGSGSNSSASSGASSGGASGGSGGSG | 30 |
| FR1 | GGSGSASAEAAAKEAAAKAGGSGGSG | 31 |
| FR2 | GGSGSASAEAAAKEAAAKEAAAKASGGSGGSG | 32 |
| 47 amino acid linker comprising a C for conjugation | SGGGSGSASSGASASGSSCSGSGSGSSSASSGASSGGASGGGSGGSG | 33 |
| Gp42 | DSKGSSQKGSRLLLLLVVSNLLLPQGVLAYFLPPRVGGGRVAAAAITWVPKPNVEVWPVDPPPPVNFNKTAEQEYGDKE TVKLPHWTPLHTFQVPQNYTKANCTYCNTREYTFSYKGCCFYFTKKKHTWNGCFQACAELYPCTYFYGPTPDILPVVTRN LNAIESLWVGVYRVGEGNWTSLDGGTFKVYQIFGSHCTYVSKFSTVPVSHHECSFLKPCLCVSQRSNS | 34 |
| CpG (phosphorothioate modifications where * is shown) | T*G*A*C*T*G*A*A*C*G*T*T*C*G*A*G*A*T*G*A | 35 |
| Exemplary gL polypeptide | NWAYPCCHVTQLRAQHLLALENISDIYLVSNQTCDGFSLASLNSPKNGSNQLVISRCANGLNVVSFFISILKRSSSALTG HLRELLTTLETLYGSFSVEDLFGANLNRYAWHRGG | 36 |
| Exemplary gH polypeptide | AASLSEVKLHLDIEGHASHYTIPWTELMAKVPGLSPEALWREANVTEDLASMLNRYKLIYKTSGTLGIALAEPVDIPAVS EGSMQVDASKVHPGVISGLNSPACMLSAPLEKQLFYYIGTMLPNTRPHSYVFYQLRCHLSYVALSINGDKFQYTGAMTSK FLMGTYKRVTEKGDEHVLSLVFGKTKDLPDLRGPFSYPSLTSAQSGDYSLVIVTTFVHYANFHNYFVPNLKDMFSRAVTM TAASYARYVLQKLVLLEMKGGCREPELDTETLTTMFEVSVAFFKVGHAVGETGNGCVDLRWLAKSFFELTVLKDIIGICY GATVKGMQSYGLERLAAMLMATVKMEELGHLTTEKQEYALRLATVGYPKAGVYSGLIGGATSVLLSAYNRHPLFQPLHTV MRETLFIGSHVVLRELRLNVTTQGPNLALYQLLSTALCSALEIGEVLRGLALGTESGLFSPCYLSLRFDLTRDKLLSMAP QEATLDQAAVSNAVDGFLGRLSLEREDRDAWHLPAYKCVDRLDKVLMIIPLINVTFIISSDREVRGSALYEASTTYLSSS | 37 |

TABLE 2-continued (SEQUENCE TABLE): DESCRIPTION OF THE SEQUENCES

| Description | Sequences | SEQ ID NO |
|---|---|---|
| | LFLSPVIMNKCSQGAVAGEPRQIPKIQNFTRTQKSCIFCGFALLSYDEKEGLETTTYITSQEVQNSILSSNYFDFDNLHV HYLLLTTNGTVMEIAGLYEERA | |
| Exemplary gp220 polypeptide | EAALLVCQYTIQSLIHLTGEDPGFFNVEIPEFPFYPTCNVCTADVNVTINFDVGGKKHQLDLDFGQLTPHTKAVYQPRGA FGGSENATNLFLLELLGAGELALTMRSKKLPINVTTGEEQQVSLESVDVYFQDVFGTMWCHHAEMQNPVYLIPETVPYIK WDNCNSTNITAVVRAQGLDVTLPLSLPTSAQDSNFSVKTEMLGNEIDIECIMEDGEISQVLPGDNKFNITCSGYESHVPS GGILTSTSPVATPIPGTGYAYSLRLTPRPVSRFLGNNSILYVFYSGNGPKASGGDYCIQSNIVFSDEIPASQDMPTNTTD ITYVGDNATYSVPMVTSEDANSPNVTVTAFWAWPNNTETDFKCKWTLTSGTPSGCENISGAFASNRTFDITVSGLGTAPK TLIITRTATNATTTHKVIFSKAPE | 38 |
| Cysteine-Thrombin-His Linker | <u>C</u>LVPRGSLEHHHHHH | 39 |
| Lumazine synthase of Aquifex aeolicus (strain VF5) | MQIYEGKLTAEGLRFGIVASRFNHALVDRLVEGAIDCIVRHGGREEDITLVRVPGSWEIPVAAGELARKEDIDAVIAIGV LIRGATPHFDYIASEVSKGLANLSLELRKPITFGVITADTLEQAIERAGTKHGNKGWEAALSAIEMANLFKSLR | 40 |
| E. coli 6,7-dimethyl-8-ribityllumazine synthase | MNIIEANVATPDARVAITIARFNNFINDSLLEGAIDALKRIGQVKDENITVVWVPGAYELPLAAGALAKTGKYDAVIALG TVIRGGTAHFEYVAGGASNGLAHVAQDSEIPVAFGVLTTESIEQAIERAGTKAGNKGAEAALTALEMINVLKAIKA | 41 |
| | Not Used | 42-200 |
| bfpFerritin-N19Q/C31S/S26C | ESQVRQQFSKDIEKLLNEQVNKEMQSSNLYMCSSWSYTHSLDGAGLFLFDHAAEEYEHAKKLIIFLNENNVPVQLTSIS APEHKFEGLTQIFQKAYEHEQHISESINNIVDHAIKSKDHATFNFLQWYVAEQHEEEVLFKDILDKIELIGNENHGLYLA DQYVKGIAKSRKS | 201 |
| bfpFerritin-N19Q/C31S/S72C | ESQVRQQFSKDIEKLLNEQVNKEMQSSNLYMSMSSWSYTHSLDGAGLFLFDHAAEEYEHAKKLIIFLNENNVPVQLTCIS LAPEHKFEGTQIFQKAYEHEQHISESINNIVDHAIKSKDHATFNFLQWYVAEQHEEEVLFKDILDKIELIGNENHGLYLA DQYVKGIAKSRKS | 202 |
| bfpFerritin-N19Q/C31S/A75C | ESQVRQQFSKDIEKLLNEQVNKEMQSSNLYMSMSSWSYTHSLDGAGLFLFDHAAEEYEHAKKLIIFLNENNVPVQLTSIS CPEHKFEGLTQIFQKAYEHEQHISESINNIVDHAIKSKDHATFNFLQWYVAEQHEEEVLFKDILDKIELIGNENHGLYLA DQYVKGIAKSRKS | 203 |
| bfpFerritin-N19Q/C31S/K79C | ESQVRQQFSKDIEKLLNEQVNKEMQSSNLYMSMSSWSYTHSLDGAGLFLFDHAAEEYEHAKKLIIFLNENNVPVQLTSIS APEHCFEGLTQIFQKAYEHEQHISESINNIVDHAIKSKDHATFNFLQWYVAEQHEEEVLFKDILDKIELIGNENHGLYLA DQYVKGIAKSRKS | 204 |
| bfpFerritin-N19Q/C31S/S100C | ESQVRQQFSKDIEKLLNEQVNKEMQSSNLYMSMSSWSYTHSLDGAGLFLFDHAAEEYEHAKKLIIFLNENNVPVQLTSIS APEHKFEGLTQIFQKAYEHEQHISECINNIVDHAIKSKDHATFNFLQWYVAEQHEEEVLFKDILDKIELIGNENHGLYLA DQYVKGIAKSRKS | 205 |
| bfpFerritin-N19Q/C31S/S111C | ESQVRQQFSKDIEKLLNEQVNKEMQSSNLYMSMSSWSYTHSLDGAGLFLFDHAAEEYEHAKKLIIFLNENNVPVQLTSIS APEHKFEGLTQIFQKAYEHEQHISESINNIVDHAIKCKDHATFNFLQWYVAEQHEEEVLFKDILDKIELIGNENHGLYLA DQYVKGIAKSRKS | 206 |
| bfpFerritin-N19Q/C31S/E12C | ESQVRQQFSKDIEKLLNCQVNKEMQSSNLYMSMSSWSYTHSLDGAGLFLFDHAAEEYEHAKKLIIFLNENNVPVQLTSIS APEHKFEGLTQIFQKAYEHEQHISESINNIVDHAIKSKDHATFNFLQWYVAEQHEEEVLFKDILDKIELIGNENHGLYLA DQYVKGIAKSRKS | 207 |
| Exemplary H. pylori Ferritin with bullfrog linker | ESQVRQQFSKDIEKLLNEQVNKEMNSSNLYMSMSSWCYTHSLDGAGLFLFDHAAEEYEHAKKLIIFLNENNVPVQLTSIS APEHKFEGLTQIFQKAYEHEQHISESINNIVDHAIKSKDHATFNFLQWYVAEQHEEEVLFKDILDKIELIGNENHGLYLA DQYVKGIAKSRKS | 208 |
| Exemplary wild-type H. pylori ferritin (GenBank Accession AAD06160.1) (without bullfrog linker or N-terminal Met) | LSKDIIKLLNEQVNKEMNSSNLYMSMSSWCYTHSLDGAGLFLFDHAAEEYEHAKKLIIFLNENNVPVQLTSISAPEHKFE GLTQIFQKAYEHEQHISESINNIVDHAIKSKDHATFNFLQWYVAEQHEEEVLFKDILDKIELIGNENHGLYLADQYVKGI AKSRKS | 209 |

TABLE 2-continued (SEQUENCE TABLE): DESCRIPTION OF THE SEQUENCES

| Description | Sequences | SEQ ID NO |
|---|---|---|
| CpG (ISS-1018) | TGACTGTGAACGTTCGAGATGA | 210 |
| *Trichoplusia ni* heavy chain ferritin | TQCNVNPVQIPKDWITMHRSCRNSMRQQIQMEVGASLQYLAMGAHFSKDVVNRPGFAQLFFDAASEEREHAMKLIEYLLM RGELTNDVSSLLQVRPPTRSSWKGGVEALEHALSMESDVTKSIRNVIKACEDDSEFNDYHLVDYLTGDFLEEQYKGQRDL AGKASTLKKLMDRHEALGEF<br><br>IFDKKLLGIDV | 211 |
| *Trichoplusia ni* light chain ferritin | ADTCYNDVALDCGITSNSLALPRCNAVYGEYGSHGNVATELQAYAKLHLERSYDYLLSAAYFNNYQTNRAGFSKLFKKLS DEAWSKTIDIIKHVTKRGDKMNFDQHSTMKTERKNYTAENHELEALAKALDTQKELAERAFYIHREATRNSQHLHDPEIA QYLEEEFIEDHAEKIRTLAGHTSDLKKFITANNGHDLSLALYVFDEYLQKTV | 212 |
| *Pyrococcus furiosus* ferritin | MLSERMLKALNDQLNRELYSAYLYFAMAAYFEDLGLEGFANWMKAQAEEEIGHALRFYNY IYDRNGRVELDEIPKPPKEWESPLKAFEAAYEHEKFISKSIYELAALAEEEKDYSTRAFL EWFINEQVEEEASVKKILDKLKFAKDSPQILFMLDKELSARAPKLPGLLMQGGE | 213 |
| human heavy chain ferritin | MTTASTSQVRQNYHQDSEAAINRQINLELYASYVYLSMSYYFDRDDVALKNFAKYFLHQSHEEREHAEKLMKLQNQRGGR IFLQDIKKPDCDDWESGLNAMECALHLEKNVQQSLLELHKLATDKNDPHLCDFIETHYLNEQVKAIKELGDHVTNLRKMG APESGLAEYLFDKHTLGDSDQES | 214 |
| human light chain ferritin (signal peptide is underlined) | <u>MDSKGSSQKGSRLLLLLVVSNLLLPQGVLASS</u>QIRQNYSTDVEAAVNSLVNLYLQASYTYLSLGFYFDRDDVALEGVSHF FRELAEEKREGYERLLKMQNQRGGRALFQDIKKPAEDEWGKTPDAMKAAMALEKKLNQALLDLHALGSARTDPHLCDFLE THFLDEEVKLIKKMGDHLTNLHRLGGPEAGLGEYLFERLTLKHD | 215 |
| lumazine synthase from *Aquifex aeolicus* | MQIYEGKLTAEGLRFGIVASRFNHALVDRLVEGAIDCIVRHGGREEDITLVRVPGSWEIPVAAGELARKEDIDAVIAIGV LIRGATPHFDYIASEVSKGLANLSLELRKPITFGVITADTLEQAIERAGTKHGNKGWEAALSAIEMANLFKSLR | 216 |
| bullfrog linker | ESQVRQQF | 217 |
| Cysteine-Thrombin-His Linker | CLVPRGSLEHHHHHH | 218 |
| *E. coli* 6,7-dimethyl-8-ribityllumazine synthase | MNITEANVATPDARVAITIARFNNFINDSLLEGAIDALKRIGQVKDENITVVWVPGAYELPLAAGALAKTGKYDAVIALG TVIRGGTAHFEYVAGGASNGLAHVAQDSEIPVAFGVLTTESIEQATERAGTKAGNKGAEAALTALEMINVLKAIKA | 219 |
| 16 amino acid linker | GGGGSGGGGSGGGGSG | 220 |
| 28 amino acid linker | GGSGSGSNSSASSGASSGGASGGSGGSG | 221 |
| 46 amino acid linker | GGSGSASSGASASGSSNGSGSGSGSNSSASSGASSGGASGGSGGSG | 222 |
| FR1 | GGSGSASAEAAAKEAAAKAGGSGGSG | 223 |
| FR2 | GGSGSASAEAAAKEAAAKEAAAKASGGSGGSG | 224 |
| 47 amino acid linker comprising a C for conjugation | SGGGSGSASSGASASGSSCSGSGSGSSSASSGASSGGASGGGSGGSG | 225 |
| SIB 15007 gL/gH/gp42-His | <u>MRAVGVFLAICLVTIFVLPTWGN</u>WAYPCCHVTQLRACHLLALENISDIYLVSNQTCDGESLASLNSPKNGSNCLVISRCA NGLNVVSFFISILKRSSSALTGHLRELLTTLETLYGSFSVEDLFGANLNRYAWHRG<u>GGGSGSASSGASASGSSNGSGSGS GSNSSASSGASSGGASGGSGGSG</u>AASLSEVKLHLDIEGHASHYTIPWTELMAKVPGLSPEALWREANVTEDLASMLNRYK LIYKTSGTLGIALAEPVDIPAVSEGSMQVDASKVHPGVISGLNSPACMLSAPLEKQLFYYIGTMLPNTRPHSYVFYQLRA HLSYVALSINGDKFQYTGAMTSKFLMGTYKRVTEKGDEHVSLVFGKTKDLPDLRGPFSYPSLTSAQSGDYSLVIVTTFV HYANFHNYFVPNLKDMFSRAVTMTAASYARYVLQKLVLLEMKGGCREPELDTETLTTMFEVSVAFFKVGHAVGETGNGCV DLRWLAKSFFELTVLKDIIIGICYGATVKGMQSYGLERLAAMLMATVKMEELGHLTTEKQEYALRLATVGYPKAGVYSGLI GGATSVLLSAYNRHPLFQPLHTVMRETLFIGSHVVLRELRLNVTTQGPNLALYQLLSTALCSALEIGEVLRGLALGTESG LFSPCYLSLFRDLTRDKLLSMAPQEATLDQAAVSNAVDGFLGRLSLEREDRDAWHLPAYKCVDRLDKVLMIIPLINVTFI ISSDREVRGSALYEASTTYLSSSLFLSPVIMNKCSQGAVAGEPRQIPKIQNFTRTQKSCIFCGFALLSYDEKEGLETTTY ITSQEVQNSILSSNYFDEDNLHVHYLLLTTNGTVMEIAGLYEERA<i>SGGGSGSASSGASASGSSGSGSGSGSSSASSGLAY FLPPRVRGGGRVAAAITWVPKPNVEVWPVDPPPPVNENKTAEQEYGDKEVKLPHWTPTLHTFQVPQNYTKANCTYCNTR EYTESYKGCCFYFTKKKHTWNGCFQACAELYPCTYFYGPTPDILPVVTRNLNAIESLWVGVYRVGEGNWTSLDGGTEKVY QIFGSHCTYVSKFSTVPVSHHECSFLKPCLCVSQRSNSGSHHHHHH</i> | 226 |

TABLE 2-continued (SEQUENCE TABLE): DESCRIPTION OF THE SEQUENCES

| Description | Sequences | SEQ ID NO |
|---|---|---|
| SIB 15008 gH/gL/gp42 NP | MRAVGVFLAICLVTIFVLPTWGN*WAYPCCHVTQLRAQHLLALENISDIYLVSNQTCDGESLASLNSPKNGSNQLVISRCA NGLNVVSFFISILKRSSSALTGHLRELLTTLETLYGSFSVEDLFGANLNRYAWHRG*GGGSGSASSGASASGSSNGSGSGS GSNSSASSGASSGGASGGSGGSGAASLSEVKLHLDIEGHASHYTIPWTELMAKVPGLSPEALWREANVTEDLASMLNRYK LIYKTSGTLGIALAEPVDIPAVSEGSMQVDASKVHPGVISGLNSPACMLSAPLEKQLFYYIGTMLPNTRPHSYVFYQLRA HLSYVALSINGDKFQYTGAMTSKFLMGTYKRVTEKGDEHVLSLVFGKTKDLPDLRGPFSYPSLTSAQSGDYSLVIVTTFV HYANFHNYFVPNLKDMFSRAVTMTAASYARYVLQKLVLLEMKGGCREPELDTETLTTMFEVSAFFKVGHAVGETGNGCV DLRWLAKSFFELTVLKDIIGICYGATVKGMQSYGLERLAAMLMATVKMEELGHLTTEKQEYALRLATVGYPKAGVYSGLI GGATSVLLSAYNRHPLFQPLHTVMRETLFIGSHVVLRELRLNVTTQGPNLALYQLLSTALCSALEIGEVLRGLALGTESG LFSPCYLSLRFDLTRDKLLSMAPQEATLDQAAVSNAVDGFLRGLSLEREDRDAWHLPAYKCVDRLDKVLMIIPLINVTFI ISSDREVRGSALYEASTTYLSSSLFLSPVIMNKCSQGAVAGEPRQIPKIQNFTRTQKSCIFCGFALLSYDEKEGLETTTY ITSQEVQNSILSSNYFDEDNLHVYLLLTTNGTVMEIAGLYEERA*SGGGSGSASSGASASGSSGSGSGSGSSSASSGLAY FLPPRVRGGGRVAAAAITWVPKPNVEVWPVDPPPPVNENKTAEQEYGDKEVKLPHWTPTLHTFQVPQNYTKANCTYCNTR EYTESYKGCCFYFTKKKHTWNGCFQACAELYPCTYFYGPTPDILPVVTRNLNAIESLWVGVYRVGEGNWTSLDGGTEKVY QIFGSHCTYVSKFSTVPVSHHECSFLKPCLCVSQRSNSGGSGASSGASASGSSGSGSGSGSSSASSGASSGGASGGS GGSGGGSGASSGASASGSSGSGSGS GSSSASSGASSGGASGGSGGS*GESQVRQQFSKDIEKLLNEQVNKEMQSSNLYMSMSSWSYTHSLDGAGLFLFDHAAEEYE HAKKLIIFLNENNVPVQLTSISAPEHKFEGLTQIFQKAYEHEQHISESINNIVDHAIKCKDHATFNFLQWYVAEQHEEEV LFKDILDKIELIGNENHGLYLADQYVKGIAKSRKS | 227 |
| SIB 15009 gH/gL/ gp42_NP_C12 | MRAVGVFLAICLVTIFVLPTWGN*WAYPCCHVTQLRAQHLLALENISDIYLVSNQTCDGESLASLNSPKNGSNQLVISRCA NGLNVVSFFISILKRSSSALTGHLRELLTTLETLYGSFSVEDLFGANLNRYAWHRG*GGGSGSASSGASASGSSNGSGSGS GSNSSASSGASSGGASGGSGGSGAASLSEVKLHLDIEGHASHYTIPWTELMAKVPGLSPEALWREANVTEDLASMLNRYK LIYKTSGTLGIALAEPVDIPAVSEGSMQVDASKVHPGVISGLNSPACMLSAPLEKQLFYYIGTMLPNTRPHSYVFYQLRA HLSYVALSINGDKFQYTGAMTSKFLMGTYKRVTEKGDEHVLSLVEGKTKDLPDLRGPFSYPSLTSAQSGDYSLVIVTTFV HYANFHNYFVPNLKDMESRAVTMTAASYARYVLQKLVLLEMKGGCREPELDTETLTTMFEVSAFFKVGHAVGETGNGCV DLRWLAKSFFELTVLKDIIGICYGATVKGMQSYGLERLAAMLMATVKMEELGHLTTEKQEYALRLATVGYPKAGVYSGLI GGATSVLLSAYNRHPLFQPLHTVMRETLFIGSHVVLRELRLNVTTQGPNLALYQLLSTALCSALEIGEVLRGLALGTESG LFSPCYLSLRFDLTRDKLLSMAPQEATLDQAAVSNAVDGFLGRLSLEREDRDAWHLPAYKCVDRLDKVLMIIPLINVTFI ISSDREVRGSALYEASTTYLSSSLELSPVIMNKCSQGAVAGEPRQIPKIQNFTRTQKSCIFCGFALLSYDEKEGLETTTY ITSQEVQNSILSSNYFDEDNLHVYLLLTTNGTVMEIAGLYEERA*SGGGSGSASSGASASGSSGSGSGSGSSSASSGLAY FLPPRVRGGGRVAAAAITWVPKPNVEVWPVDPPPPVNENKTAEQEYGDKEVKLPHWTPTLHTFQVPQNYTKANCTYCNTR EYTFSYKGCCFYFTKKKHTWNGCFQACAELYPCTYFYGPTPDILPVVTRNLNAIESLWVGVYRVGEGNWTSLDGGTEKVY QIFGSHCTYVSKFSTV PVSHHECSFLKPCLCVSQRSNSGGSGASSGASASGSSGSGSGSGSSSASSGASSGGASGGSGGSGESQVRQQFSKDIEK LLNEQVNKEMQSSNLYMSMSSWSYTHSLDGAGLFLFDHAAEEYEHAKKLIIFLNENNVPVQLTSISAPEHKFEGLTQIF QKAYEHEQHISESINNIVDHAIKCKDHATFNFLQWYVAEQHEEEVLFKDILDKIELIGNENHGLYLADQYVKGIAKSRKS | 228 |
| SIB 15010 gH/gL/ gp42_NP_C13 | MRAVGVFLAICLVTIFVLPTWGN*WAYPCCHVTQLRAQHLLALENISDIYLVSNQTCDGESLASLNSPKNGSNQLVISRCA NGLNVVSFFISILKRSSSALTGHLRELLTTLETLYGSFSVEDLFGANLNRYAWHRG*GGGSGSASSGASASGSSNGSGSGS GSNSSASSGASSGGASGGSGGSGAASLSEVKLHLDIEGHASHYTIPWTELMAKVPGLSPEALWREANVTEDLASMLNRYK LIYKTSGTLGIALAEPVDIPAVSEGSMQVDASKVHPGVISGLNSPACMLSAPLEKQLFYYIGTMLPNTRPHSYVEYQLRA HLSYVALSINGDKFQYTGAMTSKFLMGTYKRVTEKGDEHVLSLVEGKTKDLPDLRGPFSYPSLTSAQSGDYSLVIVTTFV HYANFHNYFVPNLKDMESRAVTMTAASYARYVLQKLVLLEMKGGCREPELDTETLTTMFEVSAFFKVGHAVGETGNGCV DLRWLAKSFFELTVLKDIIGICYGATVKGMQSYGLERLAAMLMATVKMEELGHLTTEKQEYALRLATVGYPKAGVYSGLI GGATSVLLSAYNRHPLFQPLHTVMRETLFIGSHVVLRELRLNVTTQGPNLALYQLLSTALCSALEIGEVLRGLALGTESG LFSPCYLSLRFDLTRDKLLSMAPQEATLDQAAVSNAVDGFLGRLSLEREDRDAWHLPAYKCVDRLDKVLMIIPLINVTFI ISSDREVRGSALYEASTTYLSSSLELSPVIMNKCSQGAVAGEPRQIPKIQNFTRTQKSCIFCGFALLSYDEKEGLETTTY ITSQEVQNSILSSNYFDFDNLHVYLLLTTNGTVMEIAGLYEERA*SGGGSGSASSGASASGSSGSGSGSGSSSASSGLAY FLPPRVRGGGRVAAAAITWVPKPNVEVWPVDPPPPVNENKTAEQEYGDKEVKLPHWTPTLHTFQVPQNYTKANCTYCNTR EYTFSYKGCCFYFTKKKHTWNGCFQACAELYPCTYFYGPTPDILPVVTRNLNAIESLWVGVYRVGEGNWTSLDGGTEKVY QIFGSHCTYVSKFSTV PVSHHECSFLKPCLCVSQRSNSEPEPEPEPEPEPGESQVRQQFSKDIEKLLNEQVNKEMQSSNLYMSMSSWSYTHSLDGAG LFLFDHAAEEYEHAKKLIIFLNENNVPVQLTSISAPEHKFEGLTQIFQKAYEHEQHISESINNIVDHAIKCKDHATFNFL QWYVAEQHEEEVLFKDILDKIELIGNENHGLYLADQYVKGIAKSRKS | 229 |
| SIB 15011 gH/gL/ gp42_NP_C14 | MRAVGVFLAICLVTIFVLPTWGN*WAYPCCHVTQLRACHLLALENISDIYLVSNQTCDGESLASLNSPKNGSNQLVISRCA NGLNVVSFFISILKRSSSALTGHLRELLTTLETLYGSFSVEDLFGANLNRYAWHRG*GGGSGSASSGASASGSSNGSGSGS GSNSSASSGASSGGASGGSGGSGAASLSEVKLHLDIEGHASHYTIPWTELMAKVPGLSPEALWREANVTEDLASMLNRYK LIYKTSGTLGIALAEPVDIPAVSEGSMQVDASKVHPGVISGLNSPACMLSAPLEKQLFYYIGTMLPNTRPHSYVEYQLRA HLSYVALSINGDKFQYTGAMTSKFLMGTYKRVTEKGDEHVLSLVFGKTKDLPDLRGPFSYPSLTSAQSGDYSLVIVTTFV HYANFHNYFVPNLKDMFSRAVTMTAASYARYVLQKLVLLEMKGGCREPELDTETLTTMFEVSAFFKVGHAVGETGNGCV DLRWLAKSFFELTVLKDIIGICYGATVKGMQSYGLERLAAMLMATVKMEELGHLTTEKQEYALRLATVGYPKAGVYSGLI GGATSVLLSAYNRHPLFQPLHTVMRETLFIGSHVVLRELRLNVTTQGPNLALYQLLSTALCSALEIGEVLRGLALGTESG LFSPCYLSLRFDLTRDKLLSMAPQEATLDQAAVSNAVDGFLGRLSLEREDRDAWHLPAYKCVDRLDKVLMIIPLINVTFI | 230 |

TABLE 2-continued (SEQUENCE TABLE): DESCRIPTION OF THE SEQUENCES

| Description | Sequences | SEQ ID NO |
|---|---|---|
| | ISSDREVRGSALYEASTTYLSSSLELSPVIMNKCSQGAVAGEPRQIPKIQNFTRTQKSCIFCGFALLSYDEKEGLETTTY<br>ITSQEVQNSILSSNYFDEDNLHVHYLLLTTNGTVMEIAGLYEERASGGGSGSASSGASASGSSGSGSGSGSSSASSGLAY<br>FLPPRVRGGGRVAAAAITWVPKPNVEVWPVDPPPPVNENKTAEQEYGDKEVKLPHWTPTLHTFQVPCNYTKANCTYCNTR<br>EYTFSYKGCCFYFTKKKHTWNGCFQACAELYPCTYFYGPTPDILPVVTRNLNAIESLWVGVYRVGEGNWTSLDGGTEKVY<br>QIFGSHCTYVSKFSTV<br>PVSHHECSFLKPCLCVSQRSNSGGSESQVRQQFSKDIEKLLNEQVNKEMQSSNLYMSMSSWSYTHSLDGAGLFLFDHAA<br>EEYEHAKKLIIFLNENNVPVQLTSISAPEHKFEGLTQIFQKAYEHEQHISESINNIVDHAIKCKDHATFNFLQWYVAEQH<br>EEEVLFKDILDLIELIGNENHGLYLADQYVKGIAKSRKS | |
| SIB 15012<br>gH/gL/<br>gp42_NP_C16 | MDSKGSSQKGSRLLLLLVVSNLLLPQGVLANWAYPCCHVTQLRACHLLALENISDIYLVSNQTCDAFSLASLNSPKGGSN<br>CLVISRCANGLNVVSFFISILKRSSSALTGHLRELLTTLETLYGSFSVEDLFGAGLNRYAWHRGGGGSGSASSGASASG<br>SGGSGSGSGSGSSASSGASSGGASGGSGGSGAASLSEVKLHLDIEGHASHYTIPWTELLAKVPGLSPEALWREANVTED<br>LASMLNRYKLIYKTSGTLGIALAEPVDIPAVSEGSMQVDASKVHPGVISGLNSPACMLSAPLEKQLFYYIGTMLPNTRP<br>HSYVEYQLRCHLSYVALSINGDKFQYTGAMTSKFLMGTYKRVTEKGDEHVLSLVFGKTKDLPDLRGPFSYPSLTSAQSG<br>EYSLVIVTTFVHYANFHNYFVPNLKDMFSRAVTMTAASYARYVLQKLVLLEMKGGCREPELETETLTTMFEVSVAFFKV<br>GHAVGETGNGCVDLRWLAKSFFELTVLKDIIGICYGATVKGMQSYGLERLAAILMATVKMEELGHLTTEKQEYALRLAT<br>VGYPKAGVYSGLIGGATSVLLSAYNRHPLFQPLHTVMRETLFIGSHVVLRELRLNVTTQGPNLALYQLLSTALCSALEI<br>GEVLRGLALGTESGLFSPCYLSLRFDLTRDKLLSIAPQEATLDQAAVSQAVDGFLGRLSLEREDRDAWHLPAYKCVDRL<br>DKVLMIIPLINVTFIISSDREVRGSALYEASTTYLSSSLELSPVILNKCSQGAVAGEPRQIPKIQNFTRTQKSCIFCGF<br>ALLSYDEKEGLETTTYITSQEVQNSILSSNYFDEDNLHVHYLLLTTNGTVMEIAGLYEERASGGGSGSASSGASASGSS<br>SASSGAITWVPKPNVEVWPVDPPPPVNENKTAEQEYGDKEVKLPHWTPTLHTFQVPCNYTKANCTYCNTRE<br>YTFSYKGCCFYFTKKKHTWQGCFQACAELYPCTYFYGPTPDILPVVTRSLQAIESLWVGVYRVGEGNWTSLDGGTEKVY<br>QIFGSHCTYVSKFSTVPVSHHECSFLKPCLCVSQRSNSGGSGSASSGASASGSSGSGSGSGSSSASSGASSGGASGGSG<br>GSGGGSGSASSGASASGSSGSGSGSGSSSASSGAS<br>SGGASGGSGGSGESQVRSQFSKDIEKLLNEQVNKEMQSSNLYMSMSSWSYTHSLDGAGLFLFDHAAEEYEHAKKLIIFLN<br>ENNVPVQLTSISAPEHKFEGLTQIFQKAYEHEQHISESINQIVDHAIKCKDHATFNFLQWYVAEQHEEEVLFKDILDKIE<br>LIGQENHGLYLADQYVKGIAKSRKS | 231 |
| SIB 15013<br>gH/gL_rigid_NP | MRAVGVFLAICLVTIFVLPTWGNWAYPCCHVTQLRAQHLLALENISDIYLVSNQTCDGFSLASLNSPKNGSNQLVISRCA<br>NGLNVVSFFISILKRSSSALTGHLRELLTTLETLYGSFSVEDLFGANLNRYAWHRGGGGSGSASSGASASGSSNGSGSGS<br>GSNSSASSGASSGGASGGSGGSGAASLSEVKLHLDIEGHASHYTIPWTELMAKVPGLSPEALWREANVTEDLASMLNRYK<br>LIYKTSGTLGIALAEPVDIPAVSEGSMQVDASKVHPGVISGLNSPACMLSAPLEKQLFYYIGTMLPNTRPHSYVFYQLRA<br>HLSYVALSINGDKFQYTGAMTSKFLMGTYKRVTEKGDEHVLSLVFGKTKDLPDLRGPFSYPSLTSAQSGDYSLVIVTTFV<br>HYANFHNYFVPNLKDMFSRAVTMTAASYARYVLQKLVLLEMKGGCREPELDTETLTTMFEVSVAFFKVGHAVGETGNGCV<br>DLRWLAKSFFELTVLKDIIGICYGATVKGMQSYGLERLAAMLMATVKMEELGHLTTEKQEYALRLATVGYPKAGVYSGLI<br>GGATSVLLSAYNRHPLFQPLHTVMRETLFIGSHVVLRELRLNVTTQGPNLALYQLLSTALCSALEIGEVLRGLALGTESG<br>LFSPCYLSLRFDLTRDKLLSMAPQEATLDQAAVSNAVDGFLGRLSLEREDRDAWHLPAYKCVDRLDKVLMIIPLINVTTY<br>FIISSDREVRGSALYEASTTYLSSSLFLSPVIMNKCSQGAVAGEPRQIPKIQNFTRTQKSCIFCGFALLSYDEKEGLETT<br>ITSQEVQNSILSSNYFDEDNLHVHYLLLTTNGTVMEIAGLYEERASGPEPEPEPEPEPEPEPEPEPEPEPEPEPEPEPE<br>PEPEPEPEPEPEPEPEPESQVRQQFSKDIEKLLNEQVNKEMQSSNLYMSMSSWSYTHSLDGAGLFLFDHAAEEYEHAKKLII<br>FLNENNVPVQLTSISAPEHKFEGLTQIFQKAYEHEQHISESINNIVDHAIKCKDHATFNFLQWYVAEQHEEEVLFKDILD<br>KIELIGNENHGLYLADQYVKGIAKSRKS | 232 |
| 46 amino acid linker | GGSGASSGASASGSSGGSGSGSGSGSSASSGASSGGASGGSGGSG | 233 |
| 32 amino acid linker | SGGGSSGSASSGASASGSSGSGSGSGSSSASSG | 234 |
| 88 amino acid linker | GGSGSASSGASASGSSGSGSGSGSSSASSGASSGGASGGSGGSGGGSGSASSGASASGSSGSGSGSGSSSASSGASSGG<br>ASGGSGGSG<br>SGGSGGSG | 235 |
| 44 amino acid linker | GGSGSASSGASASGSSGSGSGSGSSSASSGASSGGASGGSGGSG | 236 |
| 12 amino acid rigid linker | EPEPEPEPEPGG | 237 |

TABLE 2-continued (SEQUENCE TABLE): DESCRIPTION OF THE SEQUENCES

| Description | Sequences | SEQ ID NO |
|---|---|---|
| 48 amino acid rigid linker | SGEPEPEPEPEPEPEPEPEPEPEPEPEPEPEPEPEPEPEPEPEPEPEP | 238 |
| gp42 fusion segment | LAYFLPPRVRGGGRVAAAAITWVPKPNVEVWPVDPPPPVNENKTAEQEYGDKEVKLPHWTPTLHTFQVPQNYTKANCTYC NTREYTESYKGCCFYFTKKKHTWNGCFQACAELYPCTYFYGPTPDILPVVTRNLNAIESLWVGVYRVGEGNWTSLDGGTE STVPVSHHECSFLKPCLCVSQRSNS | 239 |
| gp42 fusion segment 2 | AITWVPKPNVEVWPVDPPPPVNENKTAEQEYGDKEVKLPHWTPTLHTFQVPQNYTKANCTYCNTREYTESYKGCCFYFTK KKHTWQGCFQACAELYPCTYFYGPTPDILPVVTRSLQAIESLWVGVYRVGEGNWTSLDGGTFKVYQIFGSHCTYVSKEST VPVSHHECSFLKPCLCKVYQIFGSHCTYVSKFVSQRSNS | 240 |
| SIB 15014 gH/gL/ gp42_NP_C17 | MDSKGSSQKGSRLLLLLVVSNLLLPQGVLANWAYPCCHVTQLRAQHLLALENISDIYLVSNQTCDAFSLASLNSPKQGSN QLVISRCANGLNVVSFFISILKRSSSALTGHLRELLTTLETLYGSFSVEDLFGAQLNRYAWHRGGGGSGSASSGASASGS SGGSGSGSGSGSSASSNPGASSGGASGGAGGAGAASLSEVKLHLDIEGHASHYTIPWTELLAKVPGLSPEALWREANVTE DLASMLNRYKLIYKTSGTLGIALAEPVDIPAVSEGSMQVDASKVHPGVISGLNSPACMLSAPLEKQLFYYIGTMLPNTRP HSYVFYQLRCHLSYVALSINGDKFQYTGAMTSKFLMGTYKRVTEKGDEHVLSLVFGKTKDLPDLRGPFSYPSLTSAQSGE YSLVIVTTFVHYANFHNYFVPNLKDMFSRAVTMTAASYARYVLQKLVLLEMKGGCREPELETETLTTMFEVSVAFFKVGH AVGETGNGCVDLRWLAKSFFELTVLKDIIGICYGATVKGMQSYGLERLAAILMATVKMEELGHLTTEKQEYALRLATVGY PKAGVYSGLIGGATSVLLSAYNRHPLFQPLHTVMRETLFIGSHVVRELRLNVTTQGPNLALYQLLSTALCSALEIGEVL RGLALGTESGLFSPCYLSRFDLTRDKLLSIAPQEATLDQAAVSQAVDGFLGRLSLEREDRDAWHLPAYKCVDRLDKVLM IIPLINVTFIISSDREVRGSALYEASTTYLSSSLFLSPVIMNKCSQGAVAGEPRQIPKIQNFTRTQKSCIFCGFALLSYD EKEGLETTTYITSQEVQNSILSSNYFDFDNLHVHYLLLTTNGTVMEIAGLYEERASGGGSGSASSGASASGSSGSGSGSG SASSGAITWVPKPNVEVWPVDPPPPVNENKTAEQEYGDKEVKLPHWTPTLHTFQVPQNYTKANCTYCNTREYTESYKG CCFYFTKKKHTWQGCFQACAELYPCTYFYGPTPDILPVVTRNLNAIESLWVGVYRVGEGNWTSLDGGTEKVYQIFGSHCT YVSKESTVPVSHHECSFLKPCLCVSQRSNSGGGSASSGASASGSSGSGSGSGSSSASSGASSGGASGGSGGSGGGSGSA SSGASASGSSGSGSGSGSSSASSGASSSGASASGSSGSGSGSGSSSASSGAS SGGASGGSGGSGESQVRSQFSKDIEKLLNEQVNKEMQSSNLYMSMSSWSYTHSLDGAGLFLFDHAAEEYEHAKKLIIFLN ENNVPVQLTSISAPEHKFEGLTQIFQKAYEHEQHISESINQIVDHAIKCKDHATFNFLQWYVAEQHEEEVLFKDILDKIE LIGQENHGLYLADQYVKGIAKSRKS | 241 |
| SIB 15015 gH/ gL/gp42_NP_c18 | MDSKGSSQKGSRLLLLLVVSNLLLPQGVLANWAYPCCHVTQLRAQHLLALENISDIYLVSNQTCDAFSLASLNSPKQGSN QLVISRCANGLNVVSFFISILKRSSSALTGHLRELLTTLETLYGSFSVEDLFGAQLNRYAWHRGGGGSGSASSGASASGS SGGSGSGSGSGSSASSGASSGGASGGSGSGAASLSEVKLHLDIEGHASHYTIPWTELLAKVPGLSPEALWREANVTEDL ASMLNRYKLIYKTSGTLGIALAEPVDIPAVSEGSMQVDASKVHPGVISGLNSPACMLSAPLEKQLFYYIGTMLPNTRPHS YVFYQLRCHLSYVALSINGDKFQYTGAMTSKFLMGTYKRVTEKGDEHVLSLVFGKTKDLPDLRGPFSYPSLTSAQSGEYS LVIVTTFVHYANFHNYFVPNLKDMFSRAVTMTAASYARYVLQKLVLLEMKGGCREPELETETLTTMFEVSVAFFKVGHAV GETGNGCVDLRWLAKSFFELTVLKDIIGICYGATVKGMQSYGLERLAAMLMATVKMEELGHLTTEKQEYALRLATVGYPK AGVYSGLIGGATSVLLSAYNRHPLFQPLHTVMRETLFIGSHVVRELRLNVTTQGPNLALYQLLSTALCSALEIGEVLRG LALGTESGLFSPCYLSRFDLTRDKLLSMAPQEATLDQAAVSNAVDGFLGRLSLEREDRDAWHLPAYKCVDRLDKVLMII PLINVTFIISSDREVRGSALYEASTTYLSSSLFLSPVIMNKCSQGAVAGEPRQIPKIQNFTRTQKSCIFCGFALLSYDEK EGLETTTYITSQEVQNSILSSNYFDFDNLHVHYLLLTTNGTVMEIAGLYEERASGGGSGSASSGASASGSSGSGSGSGS SASSGAITWVPKPNVEVWPVDPPPPVNENKTAEQEYGDKEVKLPHWTPTLHTFQVPQNYTKANCTYCNTREYTESYKGCC FYFTKKKHTWNGCFQACAELYPCTYFYGPTPDILPVVTRNLNAIESLWVGVYRVGEGNWTSLDGGTEKVYQIFGSHCTYV SKESTVPVSHHECSFLKPCLCVSQRSNSGGGSASSGASASGSSGSGSGSGSSSASSGASSGGASGGSGGSGGGSGSASS GASASGSSGSGSGSSSASSGASGASASGSSGSGSGSGSSSASSGAS SGGASGGSGGSGESQVRSQFSKDIEKLLNEQVNKEMQSSNLYMSMSSWSYTHSLDGAGLFLFDHAAEEYEHAKKLIIFLN ENNVPVQLTSISAPEHKFEGLTQIFQKAYEHEQHISESINQIVDHAIKCKDHATFNFLQWYVAEQHEEEVLFKDILDKIE LIGQENHGLYLADQYVKGIAKSRKS | 242 |

Key for SEQ ID NOs: 1-41
Leader Sequence — underlined
gL — Italicized
Linker — double underlined
gH — Bold
bfpFerr (ferritin) — wavy underline
FR — Italicized and double underline
gp220 — Italicized and bold
gp42 — Italicized and underlined
T. ni ferritin heavy chain — double wavy underline
Foldon sequence: Italicized and wavy underline
Thrombin cleavage site: Italicized and dashed underline
6X His Tag (SEQ ID NO: 243): Bold, italicized and curvy underline

EXAMPLES

The following examples are provided to illustrate certain disclosed embodiments and are not to be construed as limiting the scope of this disclosure in any way.

1. Antigenic EBV Polypeptides for Eliciting Antibodies Against EBV

Antigenic polypeptides that elicit antibodies against EBV were developed. Self-assembling ferritin nanoparticles were developed that display EBV gT and gH polypeptides as a single-chain, and the immunogenicity of these nanoparticles in mice was evaluated.

Figure 1B:
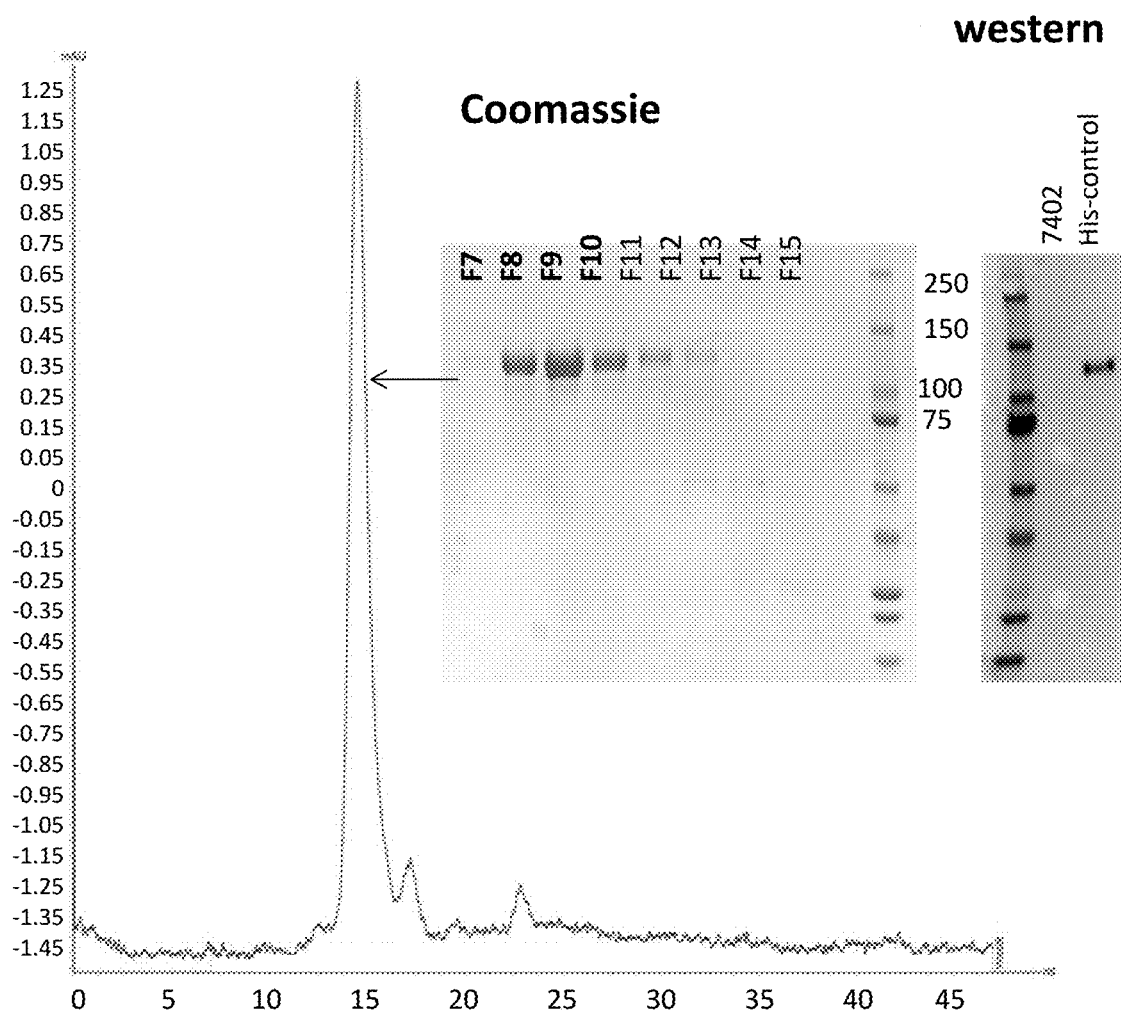
Figure 2A:
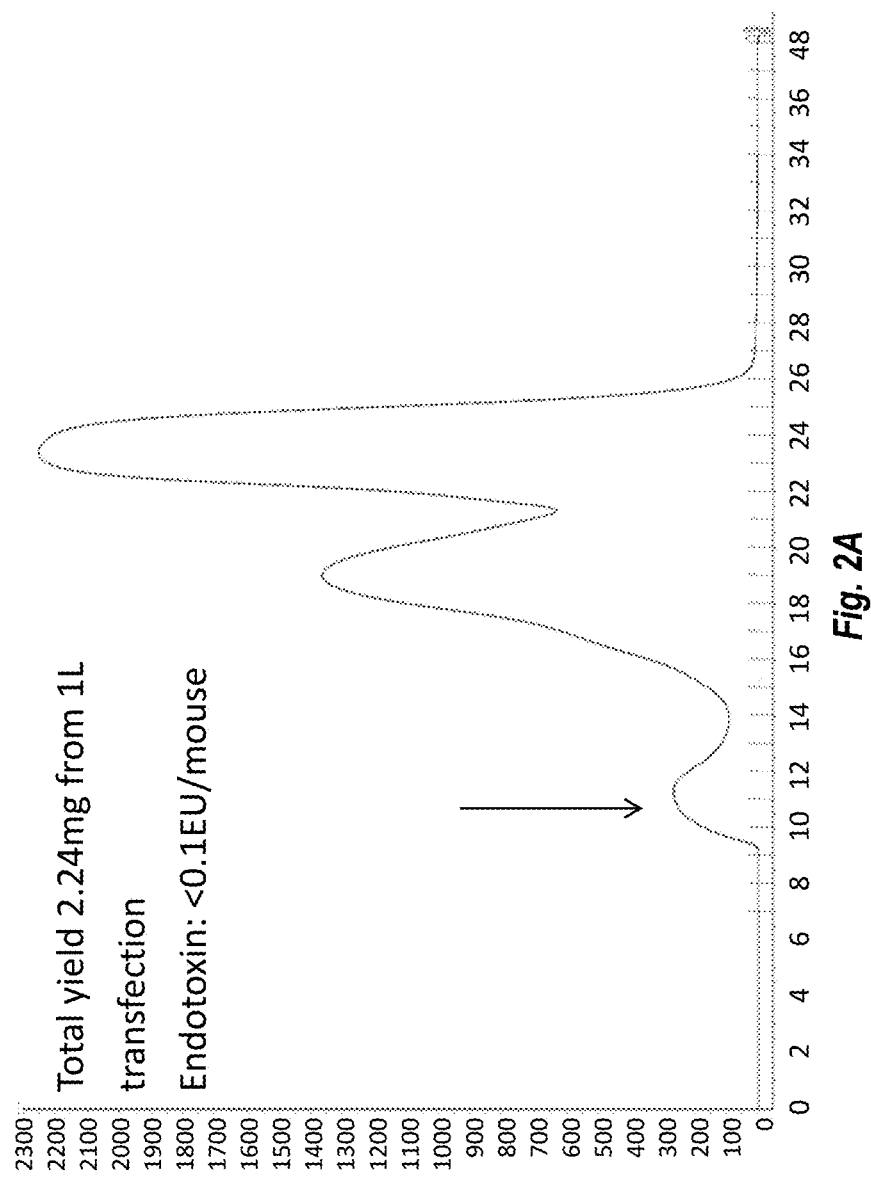
FIGS. 2A-2E shows purification and characterization of single-chain gL/gH-ferritin nanoparticles (SEQ ID NO: 14). A UV absorbance trace of Superose® 6 purification fractions is shown (FIG. 2A), as well as Coomassie (FIG. 2B) and Western blot (FIG. 2C) analysis of selected fractions from the purification (L indicates molecular weight ladder; the positions of the 150 and 250 kDa bands are indicated at right in FIG. 2B). Dynamic light scattering (FIG. 2D) and electron microscopy (FIG. 2E) analyses of the single-chain nanoparticles are also presented.
Figure 2B:
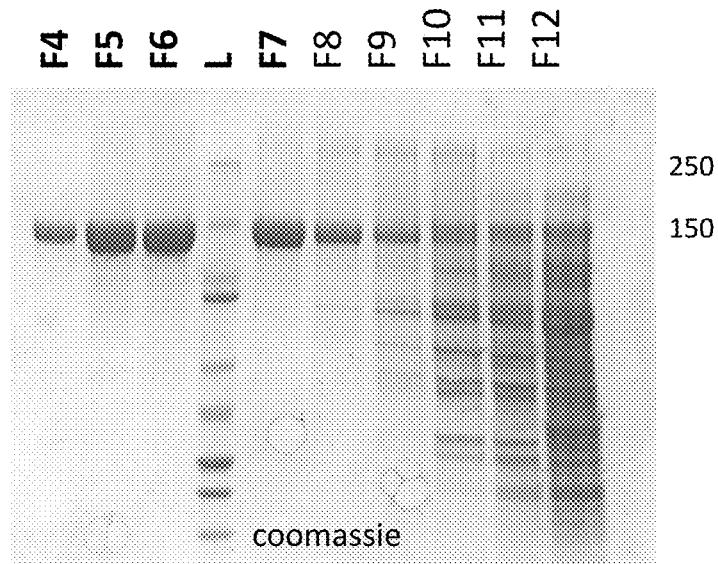
Figure 2C:
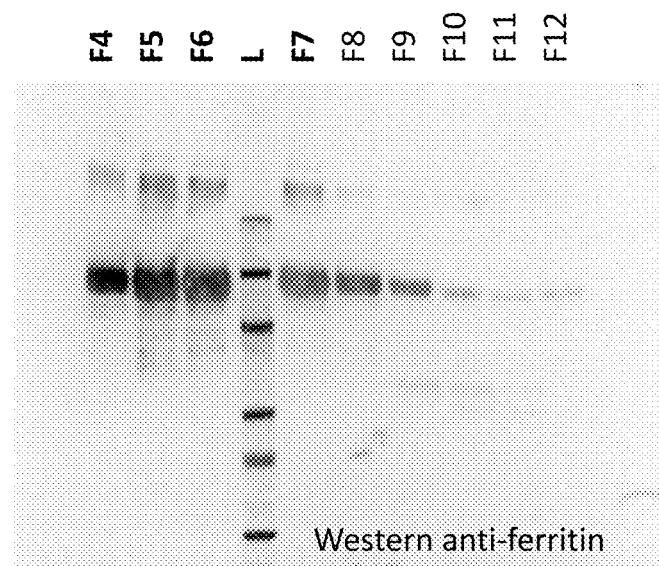
Figure 2D:
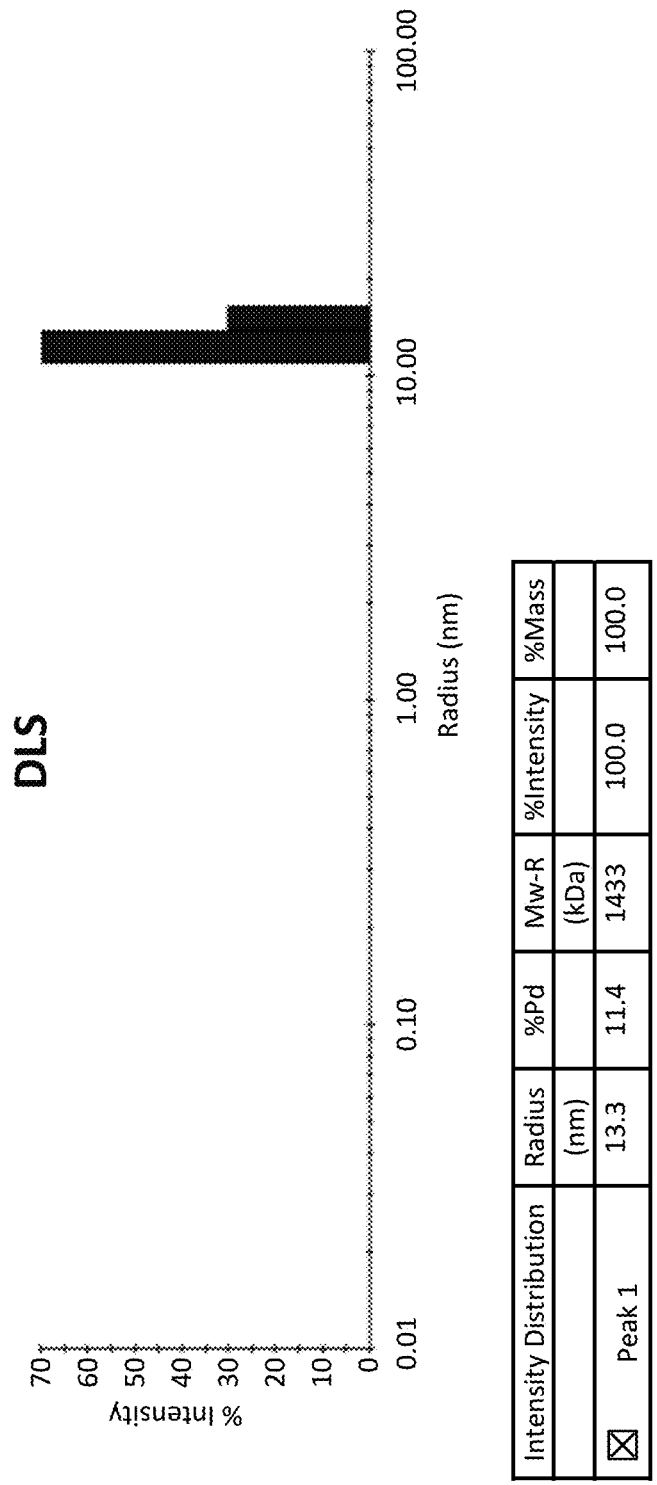
Figure 2E:
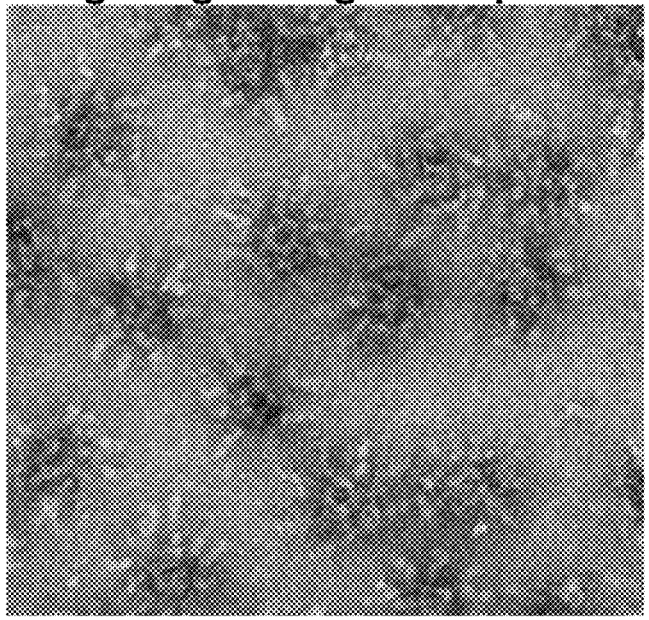

Monomeric and trimeric gL/gH constructs were expressed and purified. FIG. 1A shows single-chain gL and gH monomer (SEQ ID NO: 6)+/−His-tag cleavage by Coomassie and western blot (anti-His) analysis. FIG. 1B shows fractionation of a gL and gH trimer (SEQ ID NO: 11) on a Superose® SEC column as an absorbance trace and by Coomassie, along with a western blot to confirm His-tag cleavage by thrombin protease. The final concentration of samples was 1 mg/mL, the total volume was 15 mL, and the endotoxin level was 1.48 EU/mL for the SEQ ID NO: 6 construct.

Single-chain gL/gH ferritin nanoparticles (SEQ ID NO: 14) were expressed and purified. FIGS. 2A-2E show purification and characterization thereof by Superose® 6 SEC fractionation (2A), Coomassie of SEC fractions (2B), western blot of SEC fractions with anti-ferritin primary Ab (2C), dynamic light scattering (DLS, 2D), and electron microscopy (2E).

Figure 3:
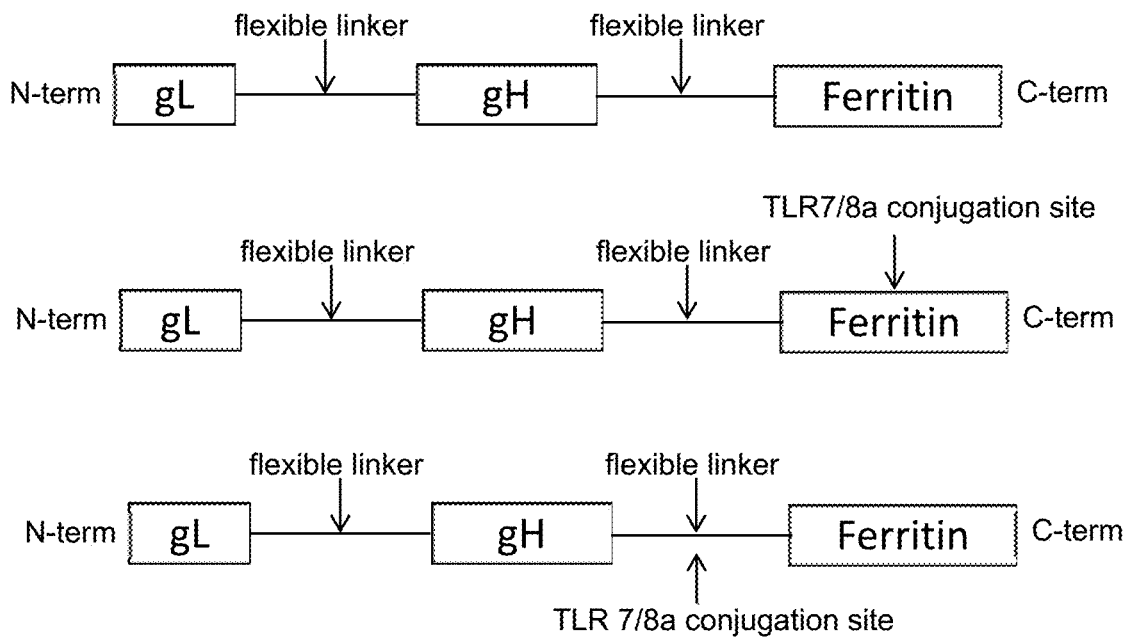
FIG. 3 shows different representative single-chain gL/gH-ferritin constructs.
Figure 4:
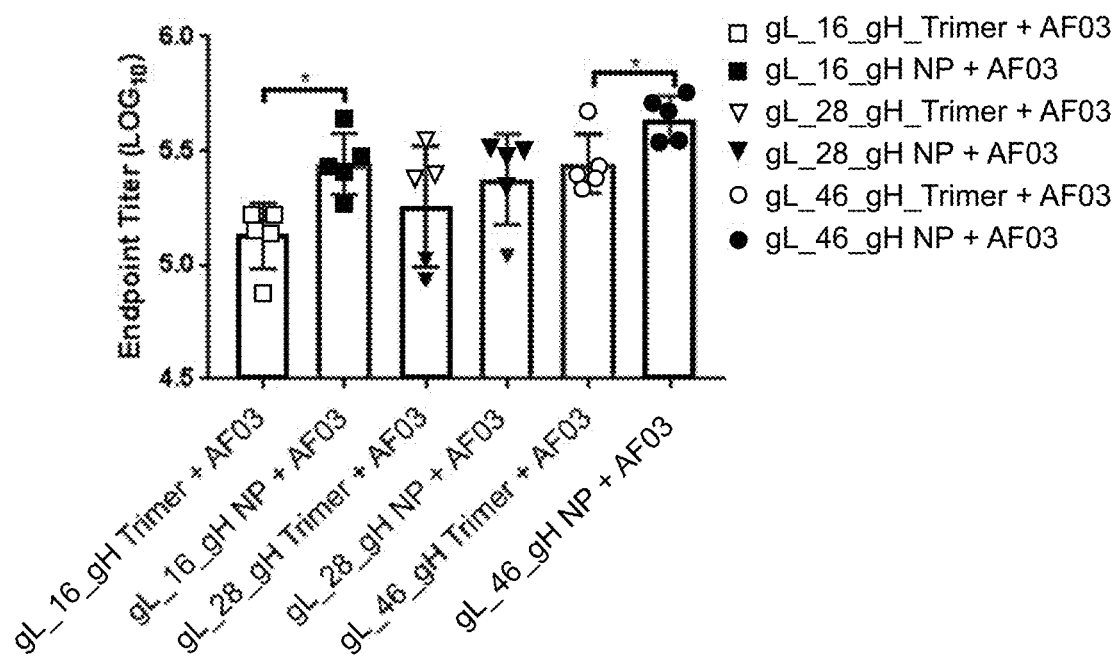
FIG. 4 shows antibody titers following immunization of mice with single-chain gL/gH trimers or nanoparticles (NP) admixed with AF03 adjuvant, which is a squalene emulsion-based adjuvant. *p-value=<0.05 when comparing the NP construct with its corresponding trimer construct. From left to right, constructs were SEQ ID NOs: 16, 10, 11, 13, 12, and 14.

Exemplary constructs of single-chain EBV gL and gH fused to ferritin are shown in FIG. 3. A conjugation site for an immune-stimulatory moiety, such as a toll-like receptor 7/8 agonist (TLR7/8a), can be present either on the ferritin or in the linker (see, e.g., SEQ ID NOS: 14, 19, 22, 20, 23, and 33 for exemplary sequences).

gL/gH trimers or nanoparticles with different linkers were injected into mice and immune sera were assessed (FIG. 4). Mice were given two 2-µg injections with adjuvant AF03, a squalene emulsion-based adjuvant, with a 3-week interval between doses. Anti-gL/gH antibody endpoint titers were measured by ELISA at week 6. For gH_16_gL, a nanoparticle (SEQ ID NO: 10) outperformed a trimer construct (SEQ ID NO: 16). The gL_28_gH nanoparticle (SEQ ID NO: 13) did not perform significantly differently from the trimer construct (SEQ ID NO: 11). The gL_46_gH nanoparticle (SEQ ID NO: 14) outperformed the gL_46_gH trimer (SEQ ID NO: 12).

These data indicate that single-chain gL/gH nanoparticles can elicit a robust immune response against EBV.

2. Bivalent Immunization Against gL/gH and Gp220

Figure 5A:
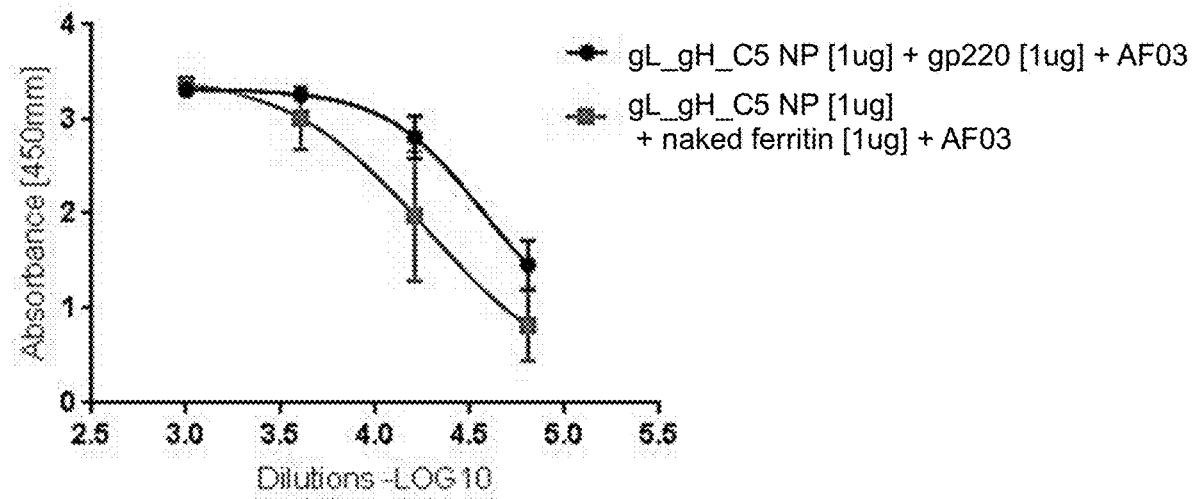
FIGS. 5A-5B show anti-gL/gH antibody response in mice to a bivalent composition comprising both gp220 nanoparticles (SEQ ID NO: 1) and a single-chain gL/gH nanoparticle ("gL_gH_C5 NP," SEQ ID NO: 19) compared to the single-chain gL/gH nanoparticle and negative control naked ferritin (i.e., ferritin not conjugated to any non-ferritin polypeptide or immune-stimulatory moiety). The results indicate that using the bivalent composition did not result in interference with the anti-gL/gH antibody response relative to the results with single-chain gL/gH with negative control naked ferritin. Both compositions included AF03 adjuvant. ELISA results at individual dilutions (FIG. 5A) and binding titer (FIG. 5B) are shown.
Figure 5B:
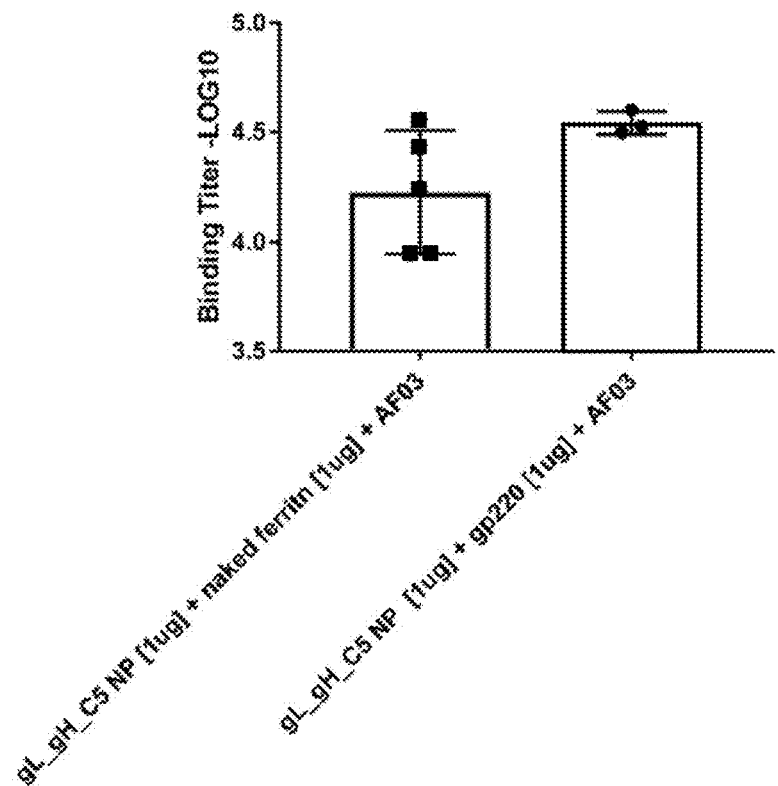
Figure 6A:
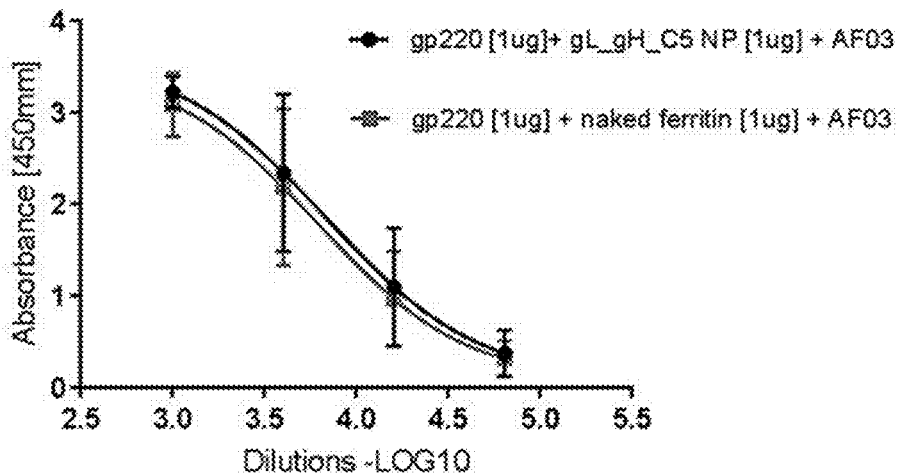
FIGS. 6A-6B show anti-gp220 antibody response to a bivalent composition comprising both gp220 nanoparticles and single-chain gL/gH nanoparticles as described for FIGS. 5A-B. The results indicate that using the bivalent composition did not result in interference with the anti-gp220 antibody response relative to the results with gp220 nanoparticles with negative control naked ferritin. Both compositions included AF03 adjuvant. ELISA results at individual dilutions (FIG. 6A) and binding titer (FIG. 6B) are shown.
Figure 6B:
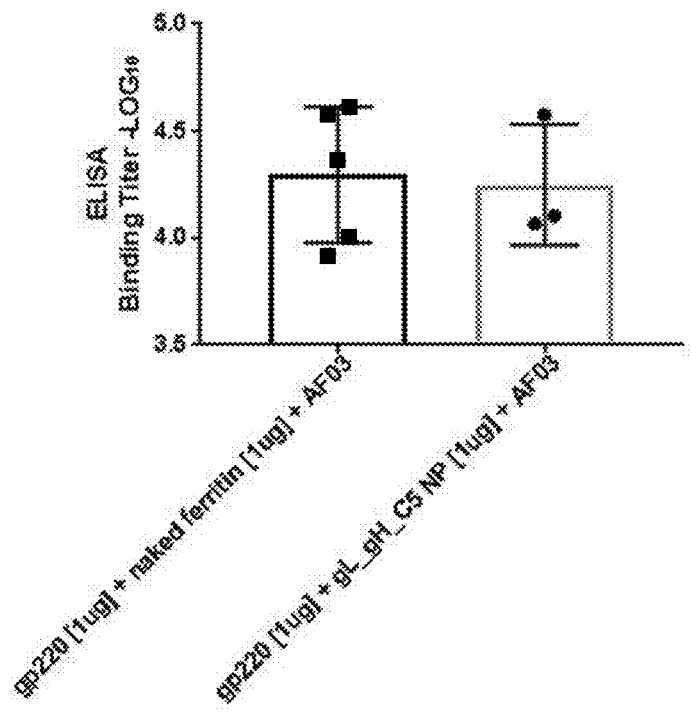

Bivalent immunization was performed using compositions comprising single-chain gL/gH nanoparticles and gp220 nanoparticles. Including the gp220 nanoparticles (SEQ ID NO: 1) had no significant interfering effect on the immune response elicited by single-chain gL/gH nanoparticles (gL-gH_C5 NP [SEQ ID NO: 19]), as measured by an ELISA binding assay using sera from mice vaccinated as described above (FIGS. 5A-5B, showing measurements at individual dilutions and binding titers, respectively). Similarly, no interference was observed in the response to the immune response to gp220 nanoparticles when administered in combination with the single-chain gL/gH nanoparticles, as measured by ELISA (FIGS. 6A-6B, showing measurements at individual dilutions and binding titers, respectively).

Thus, immunization with both a single-chain gL/gH nanoparticle and a gp220 nanoparticle did not decrease the immune response to either polypeptide.

3. Conjugation of Adjuvant to Ferritin Nanoparticles

Next, conjugation of adjuvants to ferritin nanoparticles was assessed. FIG. 7A illustrates a construct in which the ferritin comprises a mutation replacing a surface-exposed amino acid with a cysteine, which is available for conjugation. FIG. 7B shows an exemplary immune-stimulatory moiety (SM7/8a, a TLR-7/8 agonist) linked to a PEG4 linker and maleimide. This maleimide can be used to covalently conjugate the linker (itself attached to SM7/8a) to the surface-exposed cysteine of the ferritin. A polypeptide comprising a single-chain gL/gH polypeptide fused to ferritin conjugated to SM7/8a is shown in the electron micrograph of FIG. 7C.

Figure 8A:
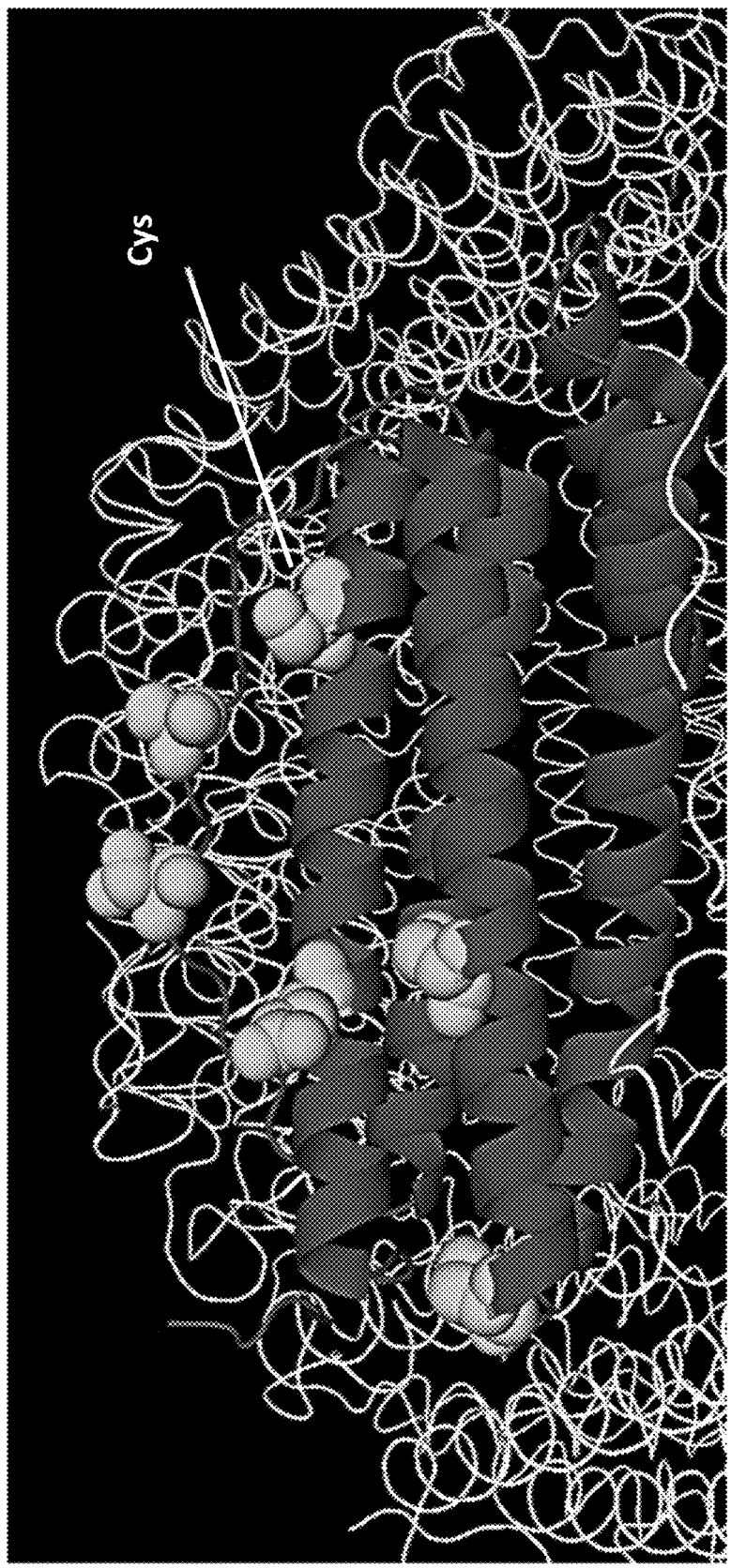
FIG. 8A shows a structure of part of a ferritin comprising a mutation replacing a surface-exposed amino acid with a cysteine, in which the location of the cysteine is indicated.
Figure 8B:
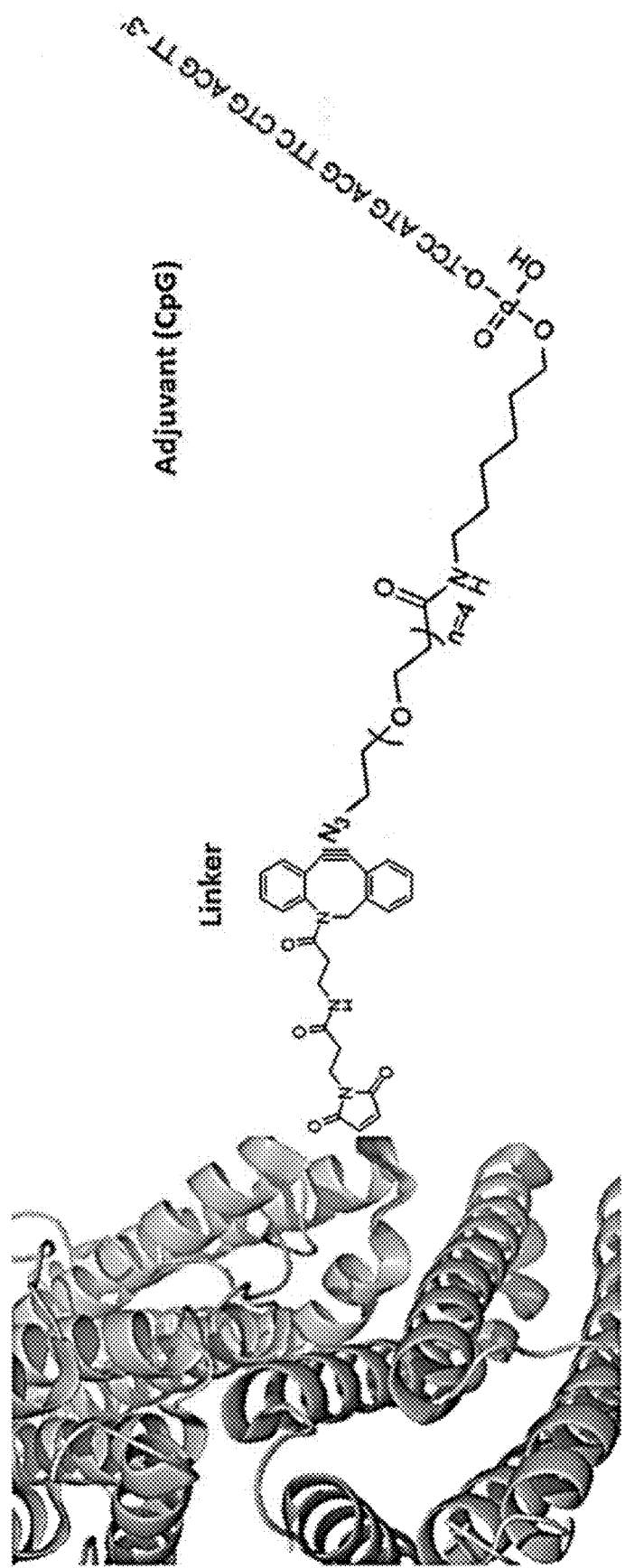
FIG. 8B illustrates conjugation of a CpG adjuvant (SEQ ID NO: 247) to ferritin by juxtaposing the ferritin, linker, and CpG adjuvant, oriented to show the parts of each moiety that become attached to each other in proximity.

A cysteine resulting from mutation of a surface-exposed amino acid is illustrated in the structure a ferritin molecule in FIG. 8A. Conjugation of a CpG adjuvant (SEQ ID NO: 230) to ferritin is illustrated in FIG. 8B by juxtaposing the ferritin, linker, and CpG adjuvant, oriented to show the parts of each moiety that become attached to each other in proximity.

Figure 9A:
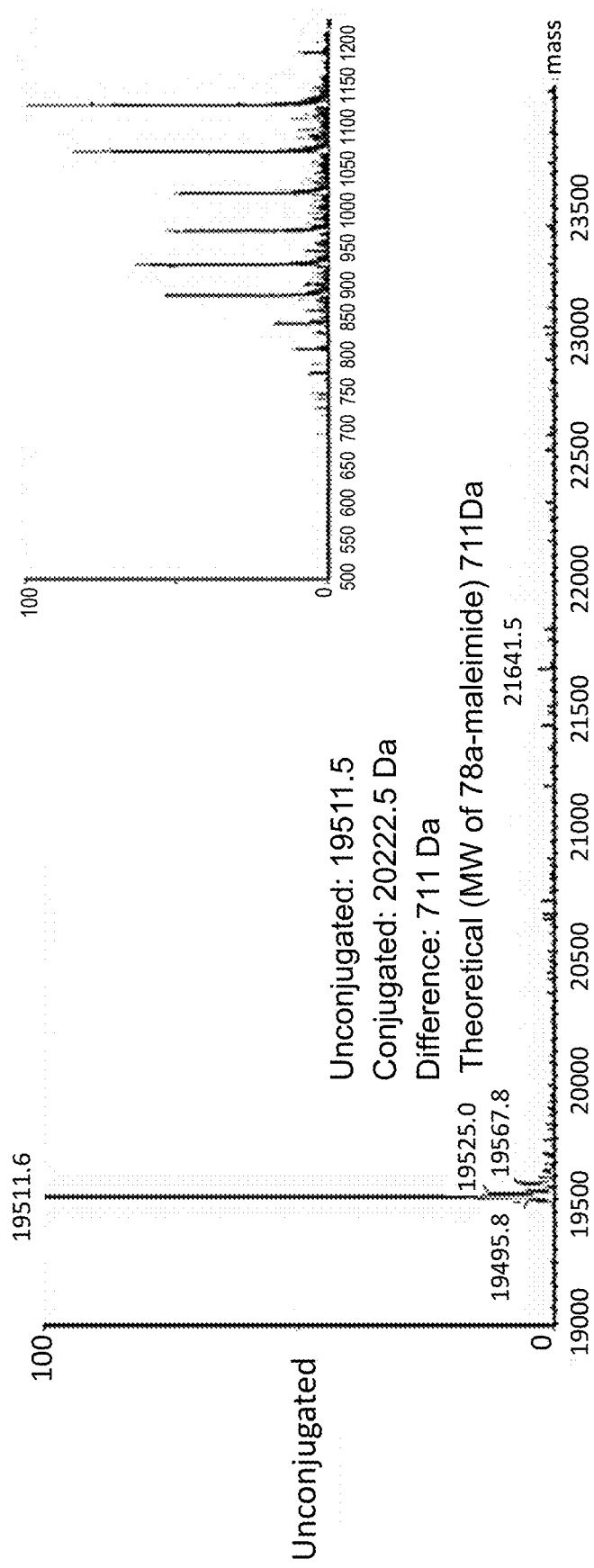
FIGS. 9A-9B show mass spectrometry (MS) spectra of the unconjugated (FIG. 9A) and SM7/8a-conjugated (FIG. 9B) forms of a gL/gH-ferritin. The difference in mass of the main peaks was 711 Da, which approximately corresponds to the predicted difference from conjugating the SM7/8a with linker.
Figure 9B:
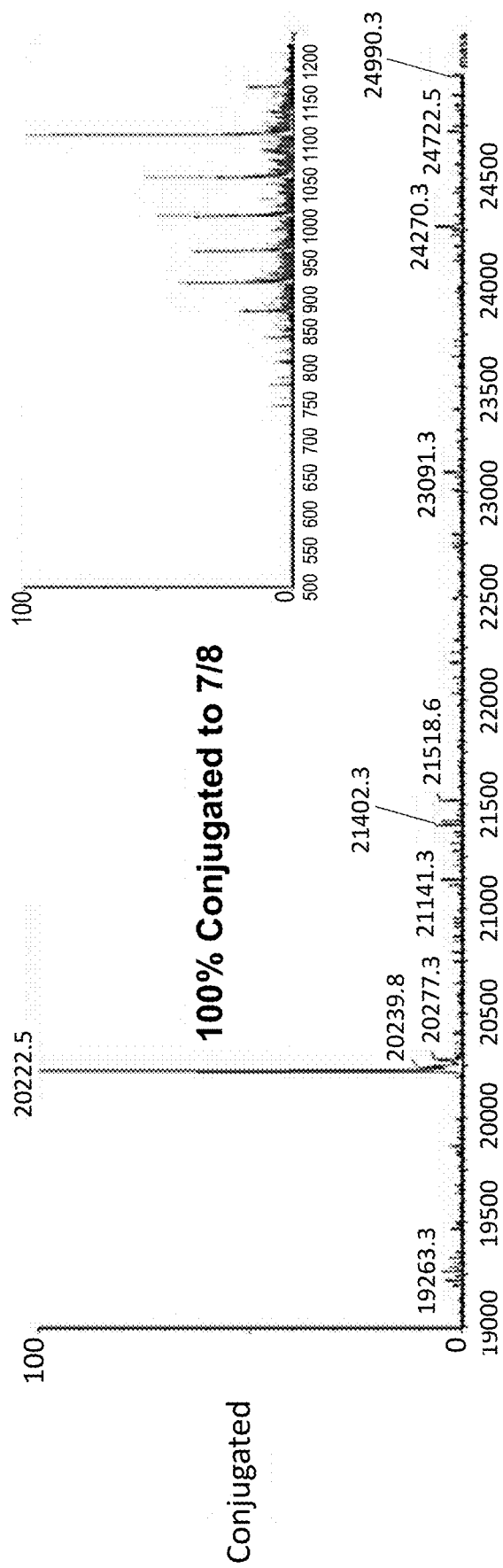

A gL/gH nanoparticle (SEQ ID NO: 19) was reduced using 2 mM TCEP and then oxidized via the addition of 1×PBS and using a 100 kD microspin column to remove TCEP. SM7/8a was then incubated with the gL/gH nanoparticle for conjugation. Excess SM7/8a was removed from the reaction via a 100 kD microspin column. Mass spectrometry (MS) data indicated that about 100% of the polypeptide comprising single-chain gL/gH and ferritin (SEQ ID NO: 19) was conjugated to SM7/8a (FIG. 9B) based on shift of the main MS peak relative to the spectrum of the unconjugated polypeptide (FIG. 9A). The difference between the mass of the conjugated and unconjugated polypeptide corresponds to the molecular weight of the SM7/8a-linker-maleimide adduct (711 Da).

Figure 10A:
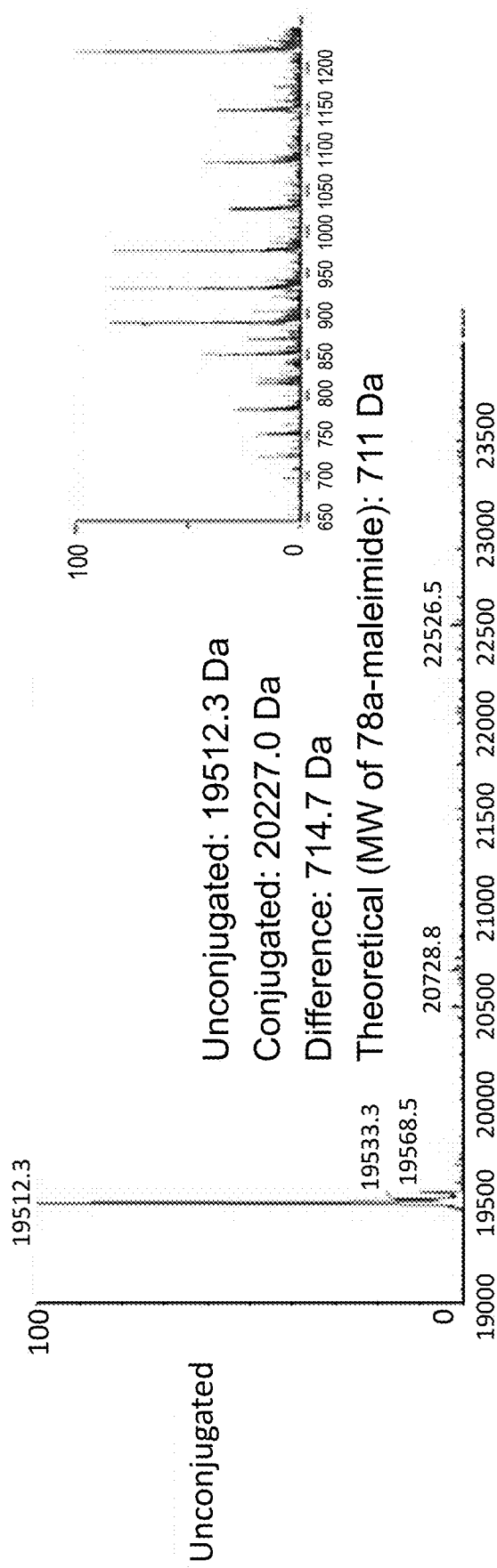
FIGS. 10A-10B show mass spectrometry (MS) spectra of the unconjugated (FIG. 10A) and SM7/8a-conjugated (FIG. 10B) forms of a gp220-ferritin. The difference in mass of the main peaks was 714.7 Da, which approximately corresponds to the predicted difference from conjugating the SM7/8a with linker.
Figure 10B:
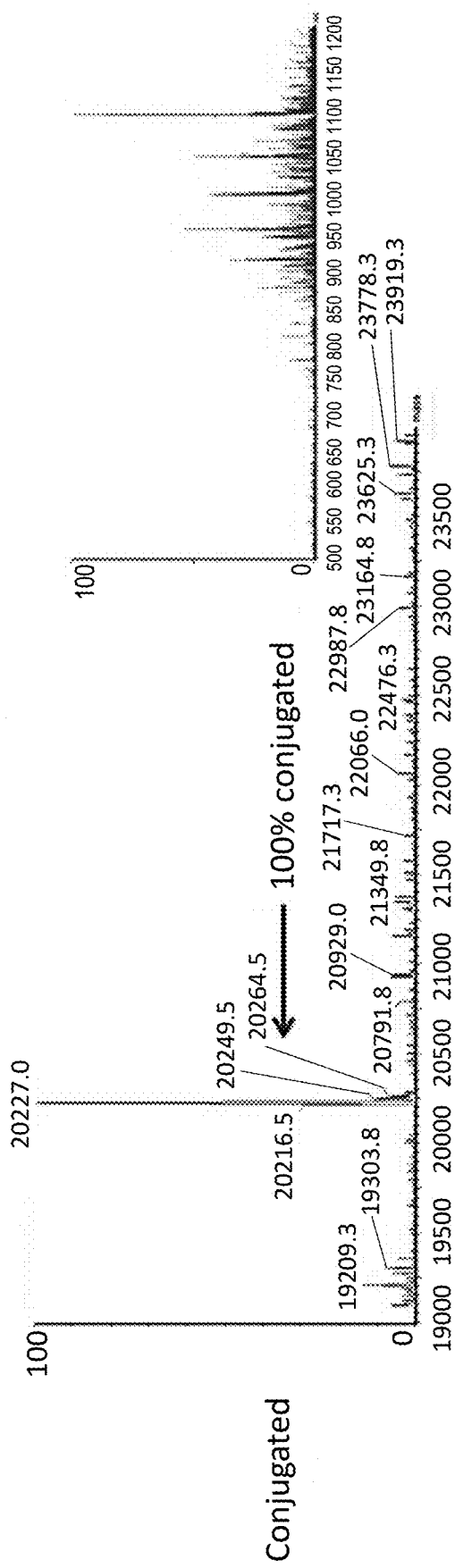

A gp220 nanoparticle (SEQ ID NO: 1) was reduced using 2 mM TCEP and then oxidized via the addition of 1×PBS and using a 100 kD microspin column to remove TCEP. The SM7/8a was then incubated with the gL/gH nanoparticle for conjugation. Excess SM7/8a was removed from the reaction via a 100 kD microspin column. MS data indicated that about 100% of a conjugated polypeptide comprising gp220 and ferritin (SEQ ID NO: 1) is conjugated to SM7/8a (FIG. 10B) based on shift of the main MS peak relative to the spectrum of the unconjugated polypeptide (FIG. 10A).

Electron microscopy (EM) data also confirmed that conjugation of SM7/8a to polypeptides comprising single-chain gL/gH and ferritin (FIG. 11B in comparison to unconjugated sample in FIG. 11A) or comprising gp220 and ferritin (FIG. 11D in comparison to unconjugated sample in FIG. 11C) did not disrupt nanoparticle assembly.

Figure 12A:
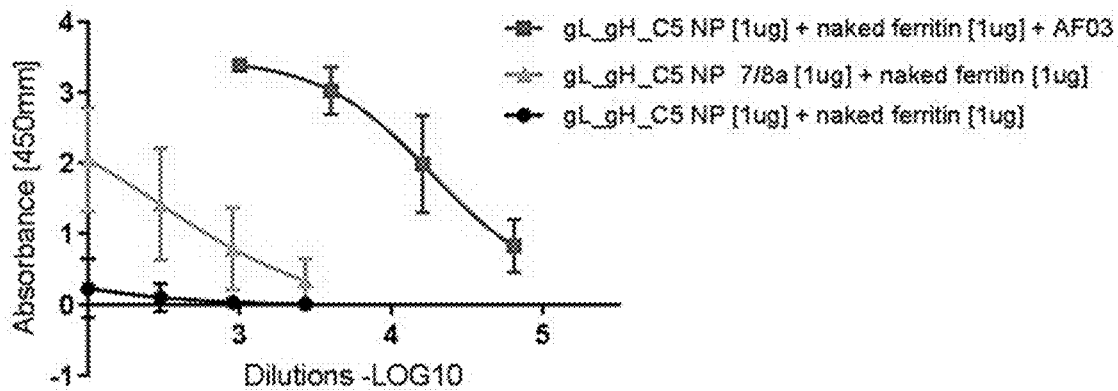
FIGS. 12A-12B show antibody responses in mice after treatment with ferritin nanoparticles comprising single-chain gL/gH either without conjugated SM7/8a or other adjuvant, with AF03 adjuvant as a separate molecule, or with conjugated SM7/8a. ELISA results are shown as individual dilutions (FIG. 12A) and binding titers (FIG. 12B).
Figure 12B:
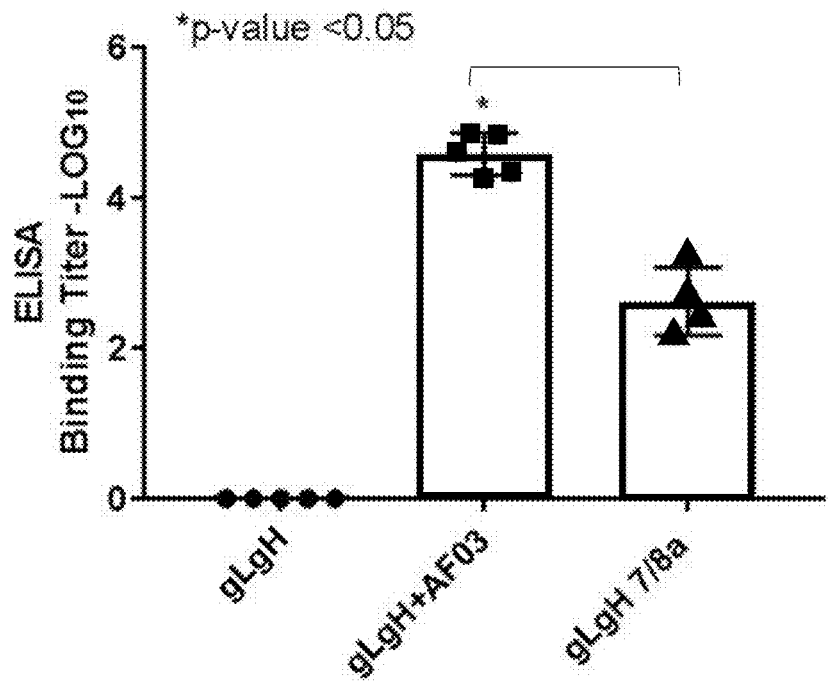
Figure 13A:
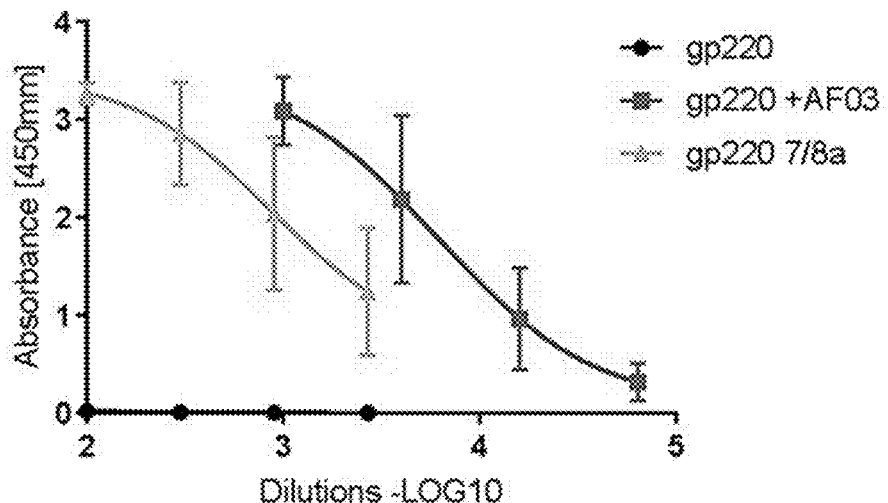
FIGS. 13A-13B show antibody responses in mice after treatment with nanoparticles comprising gp220 either alone, with AF03 adjuvant as a separate molecule, or with conjugated SM7/8a. ELISA results are shown as individual dilutions (FIG. 13A) and binding titers (FIG. 13B).
Figure 13B:
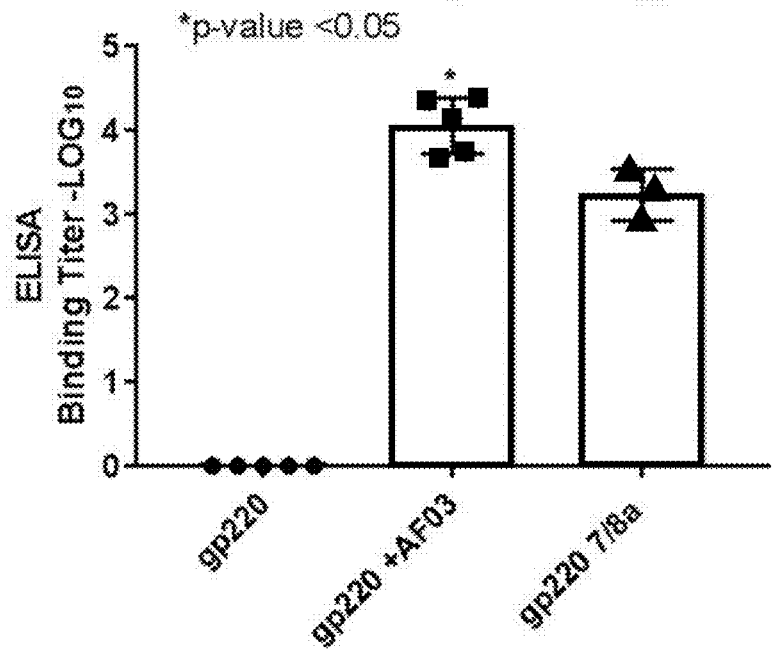
Figure 14A:
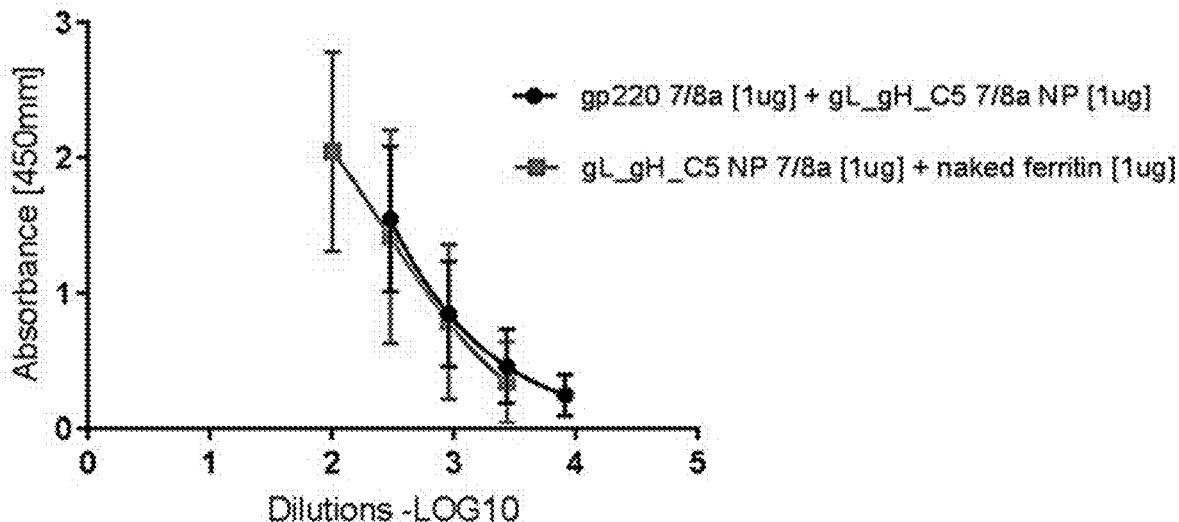
FIGS. 14A-14B show anti-gL/gH antibody responses in mice after treatment with gp220 nanoparticles conjugated to SM7/8a and single-chain gL/gH ferritin nanoparticles conjugated to SM7/8a compared to treatment with single-chain gL/gH ferritin nanoparticles conjugated to SM7/8a and naked ferritin, as measured by ELISA. Results are shown for experiments without (FIG. 14A) or with (FIG. 14B) admixed AF03.
Figure 14B:
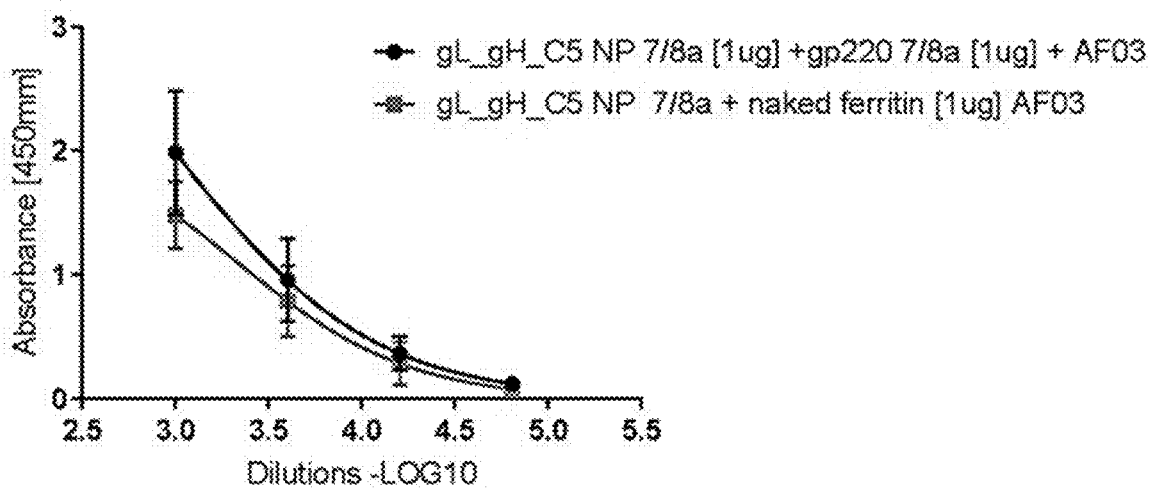
Figure 15A:
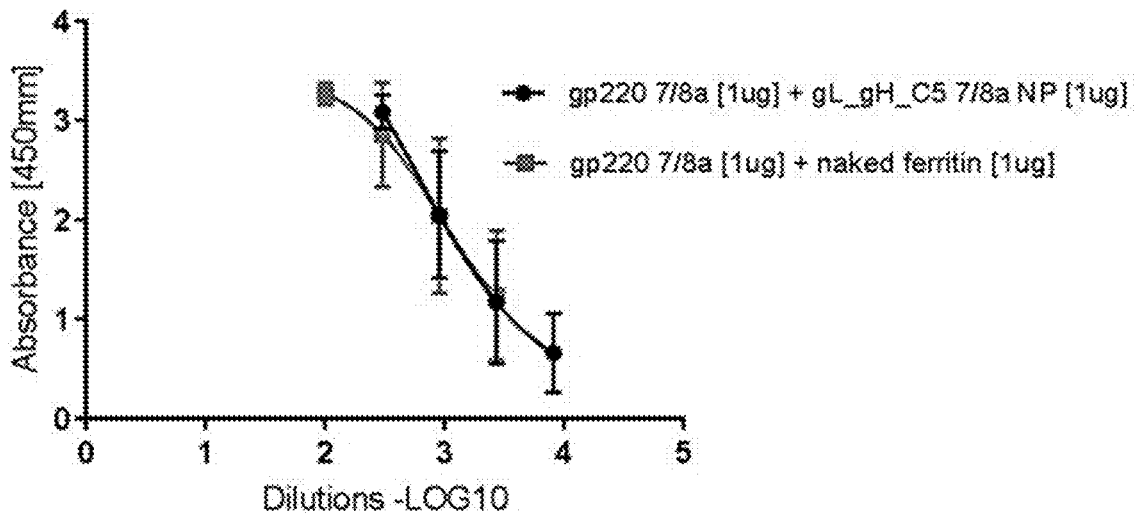
FIGS. 15A-15B show anti-gp220 antibody responses in mice after treatment with gp220 nanoparticles conjugated to SM7/8a and single-chain gL/gH nanoparticles conjugated to SM7/8a compared to treatment with gp220 nanoparticles conjugated to SM7/8a and naked ferritin, as measured by ELISA. Results are shown for experiments without (FIG. 15A) or with (FIG. 15B) admixed AF03.
Figure 15B:
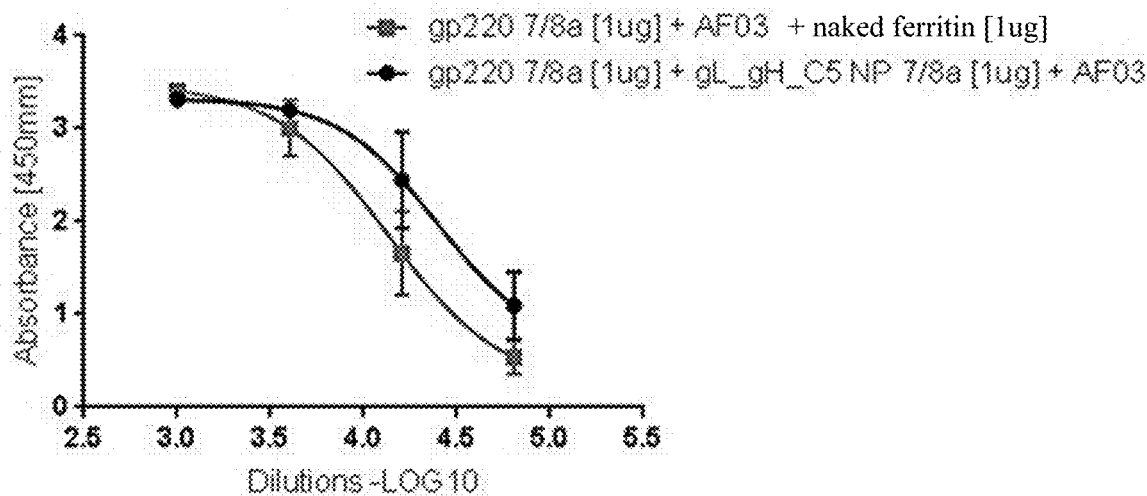
Figure 16:
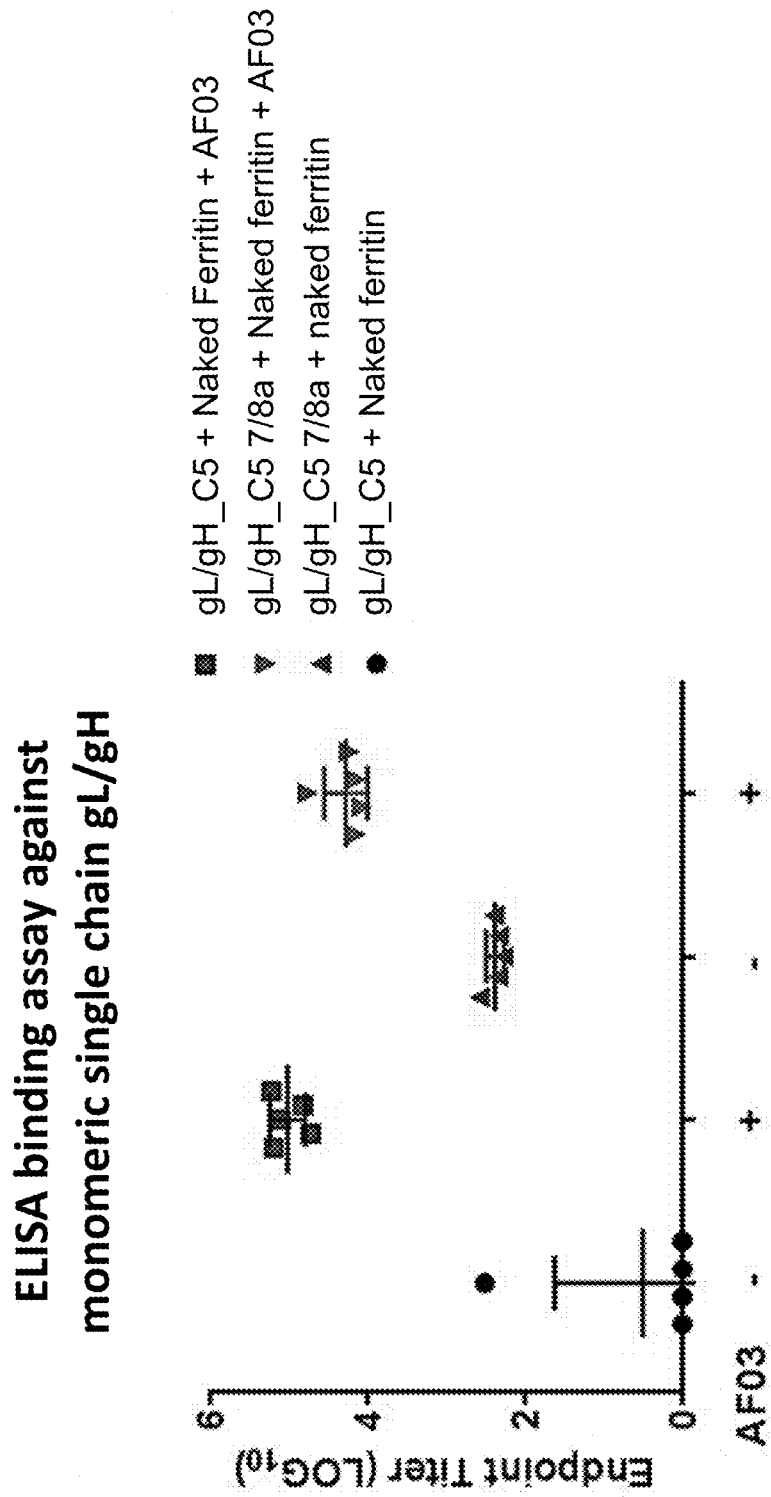
FIG. 16 shows anti-gL/gH antibody responses in mice after treatment with single-chain gL/gH nanoparticles (gL/gH_C5; SEQ ID NO: 19) and naked ferritin, with or without either or both of admixed AF03 adjuvant and/or SM7/8a conjugated to the single-chain gL/gH nanoparticles, as measured by ELISA endpoint titer.
Figure 17:
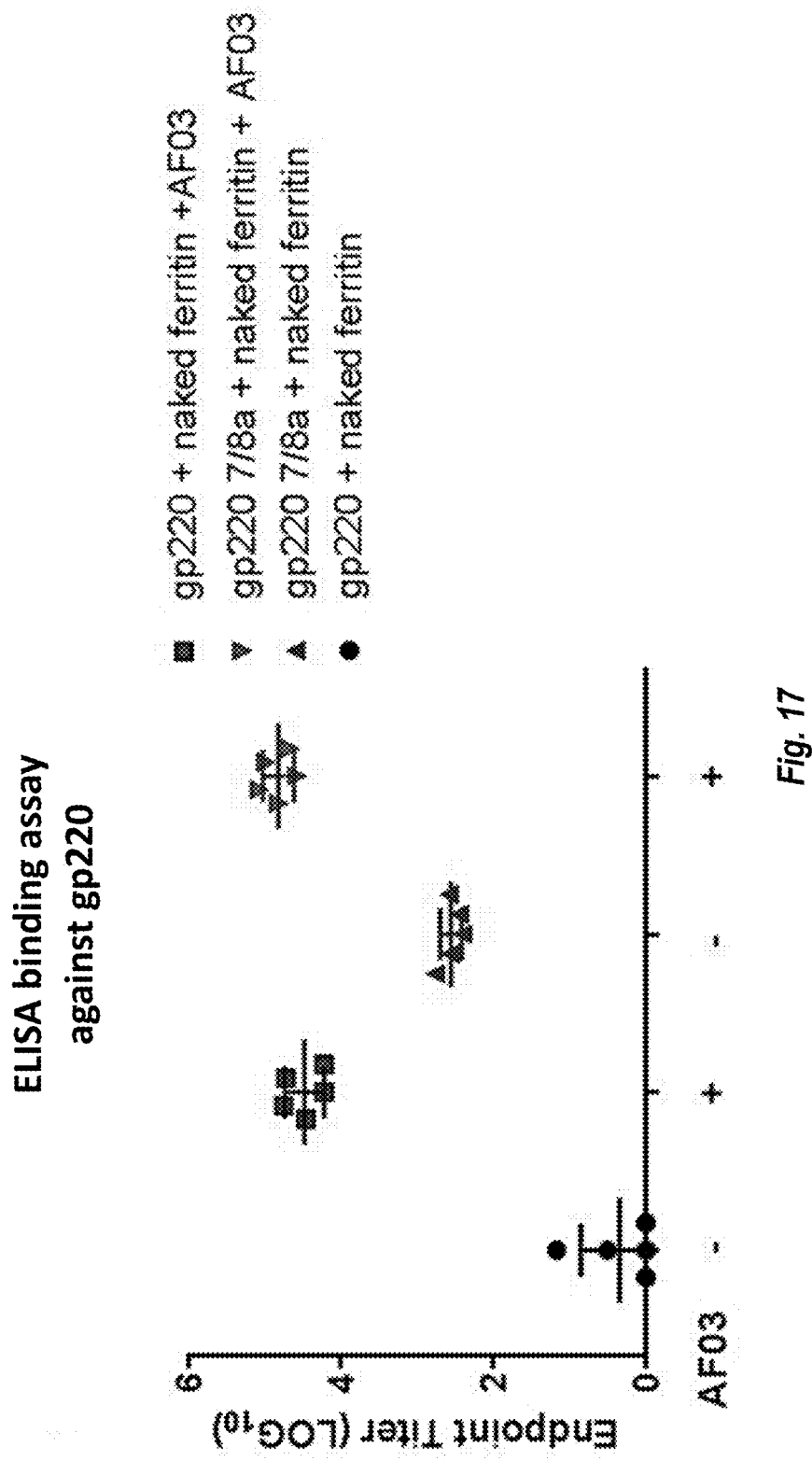
FIG. 17 shows anti-gp220 antibody responses in mice after treatment with gp220 nanoparticles and naked ferritin, with or without either or both of admixed AF03 adjuvant and/or SM7/8a conjugated to the gp220 nanoparticles.
Figure 18:
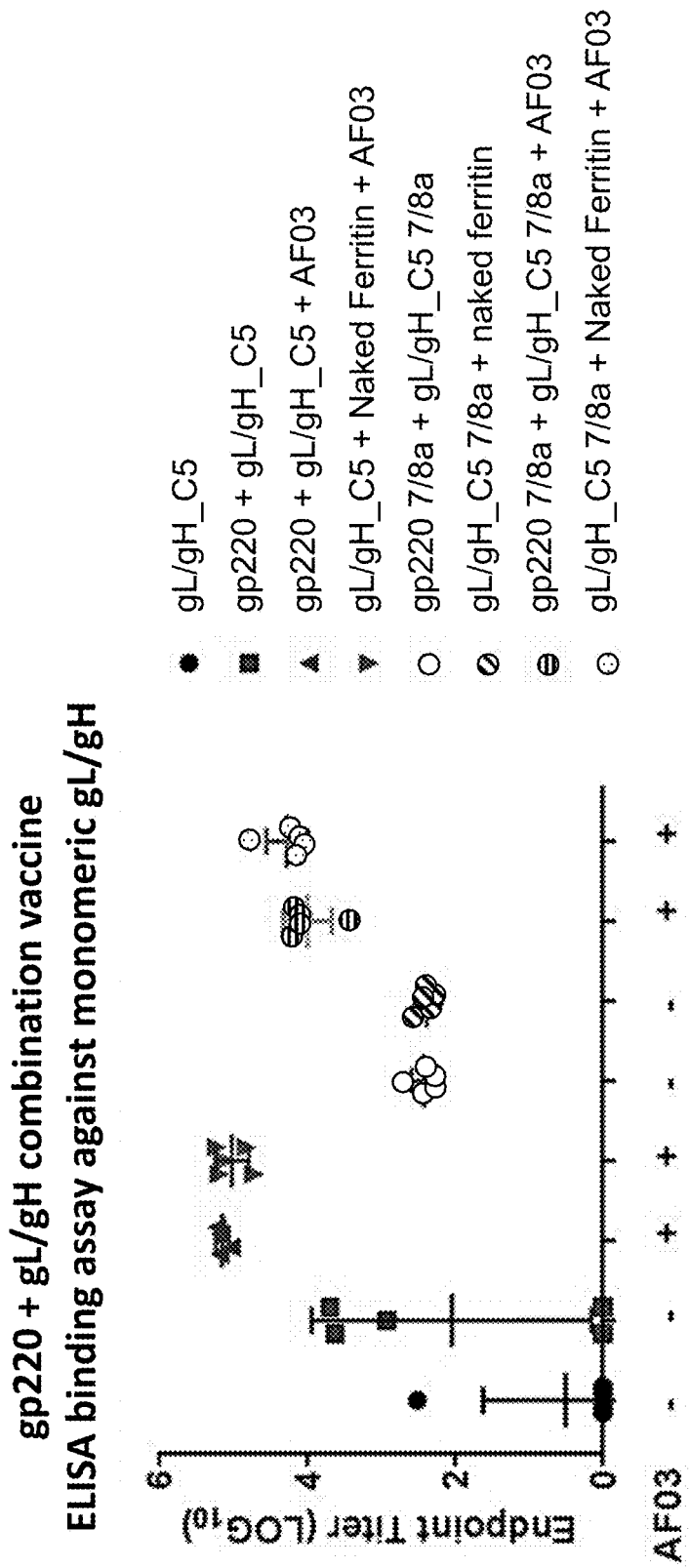
FIG. 18 shows anti-gL/gH antibody responses in mice after treatment with bivalent compositions comprising gp220 nanoparticles and single-chain gL/gH nanoparticles. As indicated in the legend, some nanoparticles were conjugated to SM7/8a, and some nanoparticles were admixed with AF03. The order of symbols from top to bottom in the key matches the order of symbols from left to right in the graph.
Figure 19:
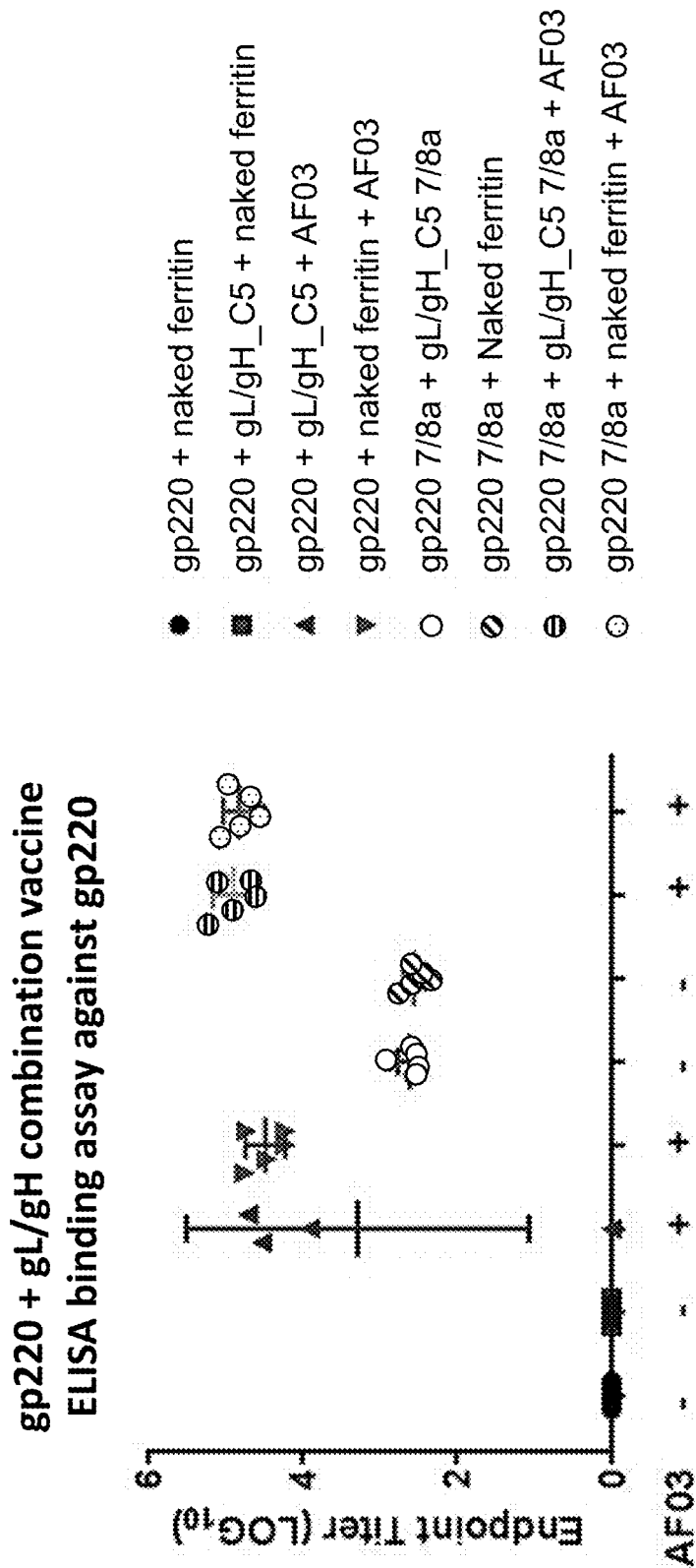
FIG. 19 shows anti-gp220 antibody responses in mice after treatment with bivalent compositions comprising single-chain gL/gH nanoparticles and gp220 nanoparticles and/or naked ferritin. As indicated in the legend, some nanoparticles were conjugated to SM7/8a, and some nanoparticles were admixed with AF03. The order of symbols from top to bottom in the key matches the order of symbols from left to right in the graph.
Figure 20A:
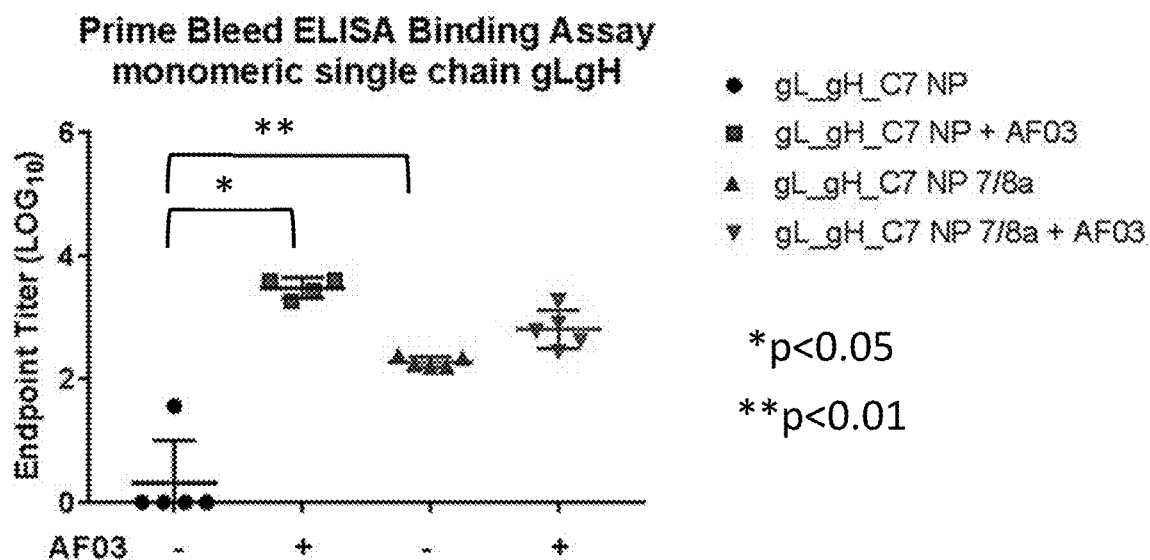
FIGS. 20A-20D show antibody responses in mice after treatment with gL_gH_C7 nanoparticle (SEQ ID NO: 20) with or without admixed AF03 adjuvant and/or conjugation to SM7/8a (FIG. 20A, 20C, or 20D) or CpG oligodeoxynucleotide (FIG. 20B). Shown are endpoint titer from prime bleed measured by ELISA (FIG. 20A), ELISA results at individual dilutions from booster bleed (FIG. 20B), and endpoint titers measured by ELISA from booster bleed (FIG nation with a gp220).
Figure 20B:
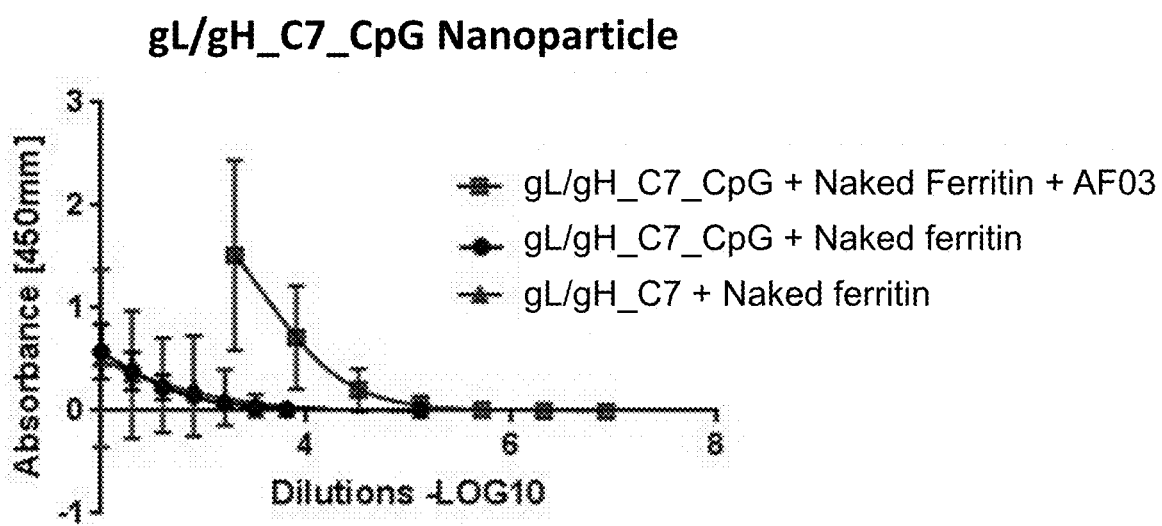
Figure 20C:
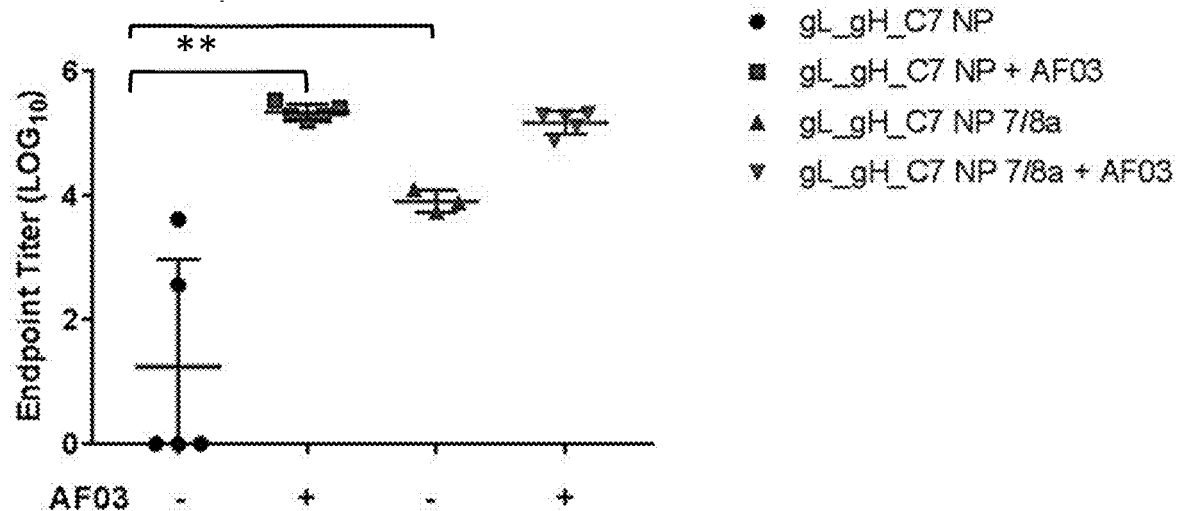
Figure 20D:
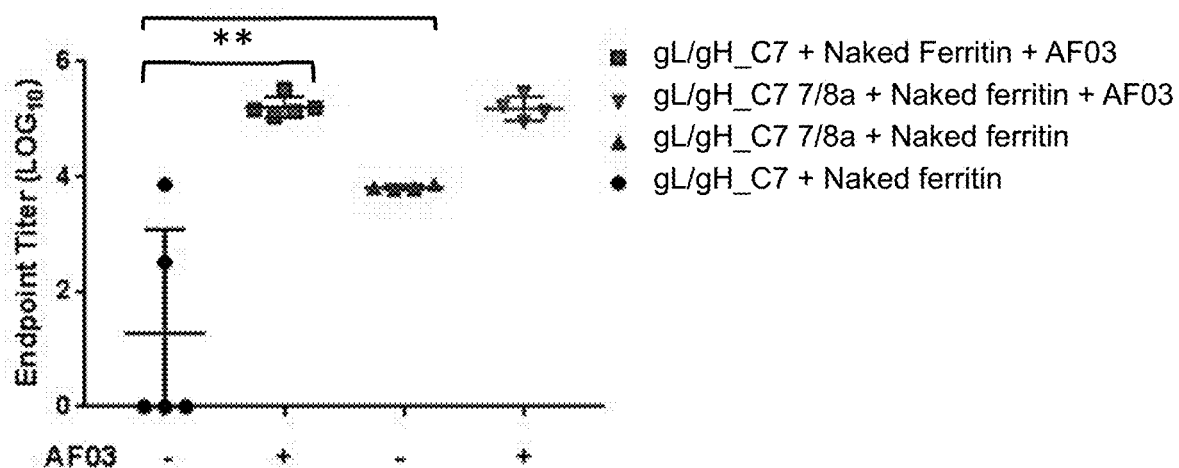
Figure 21:
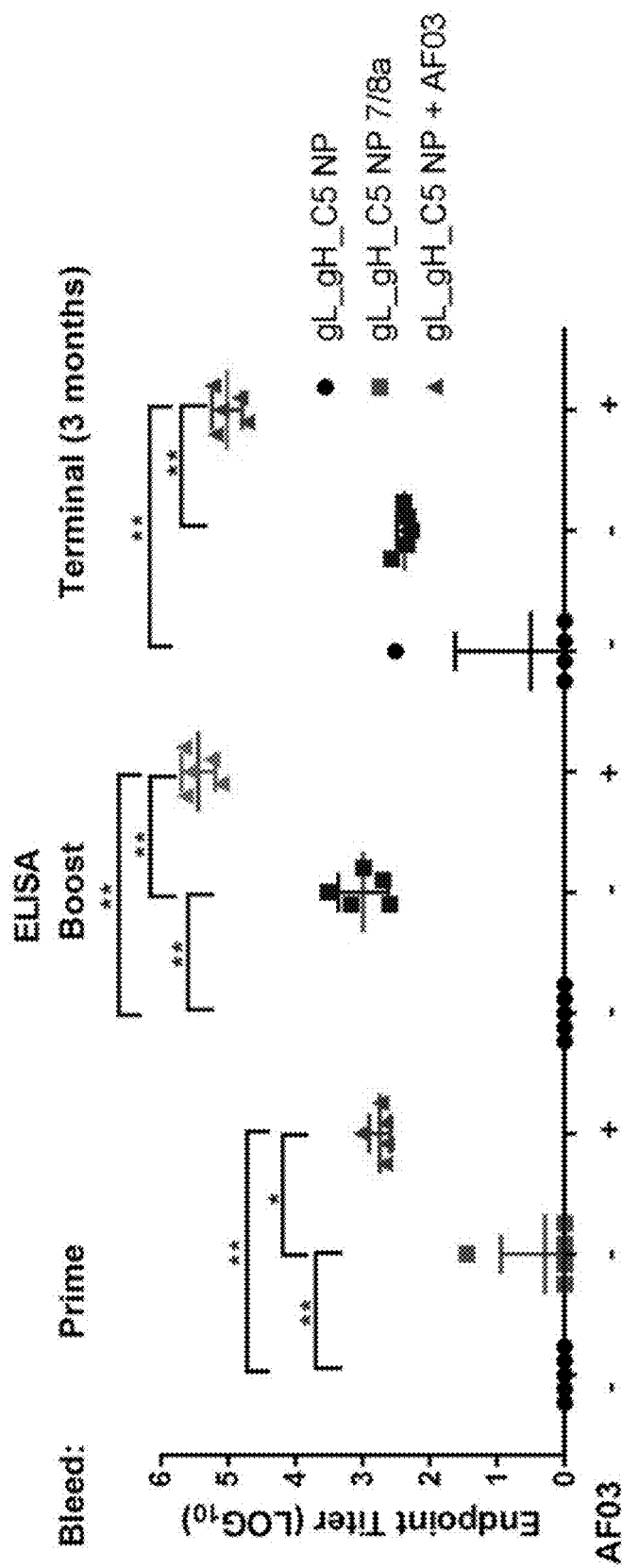
Figure 22:
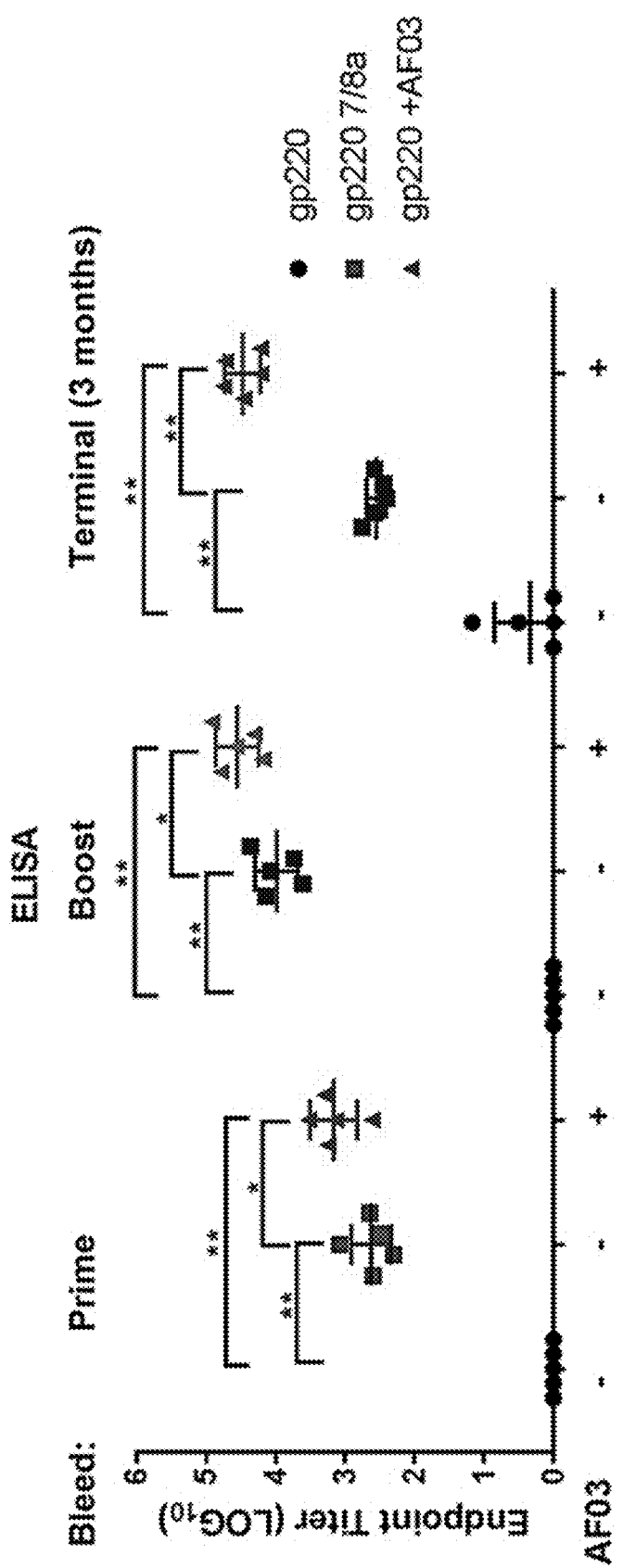
Figure 23A:
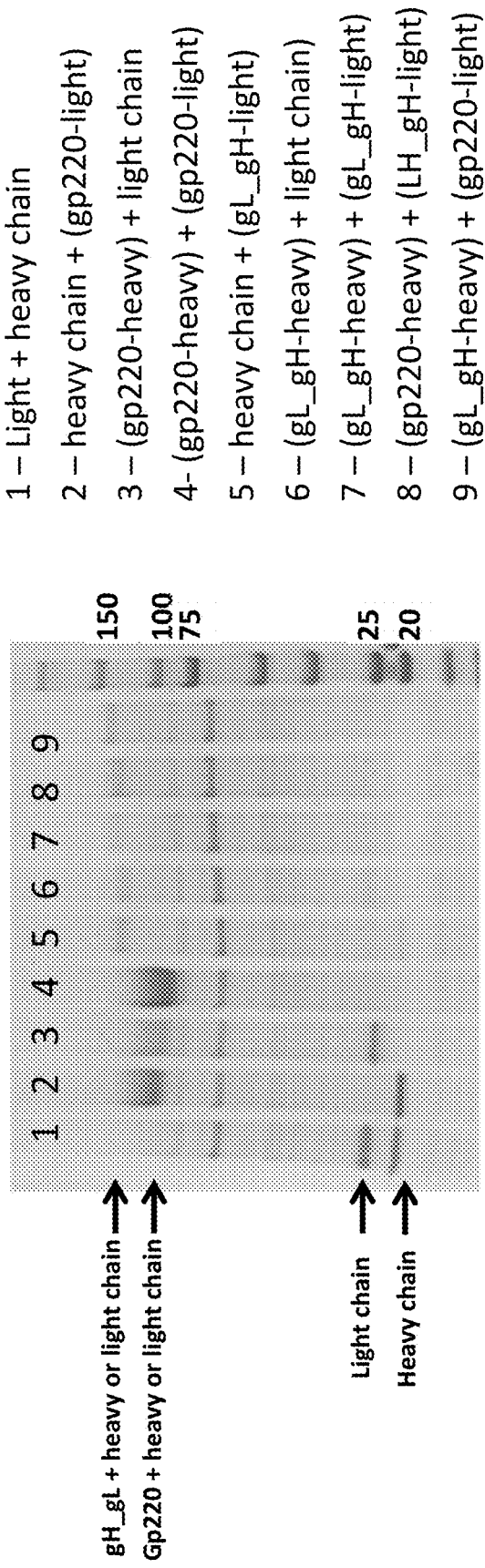
Figure 23B:
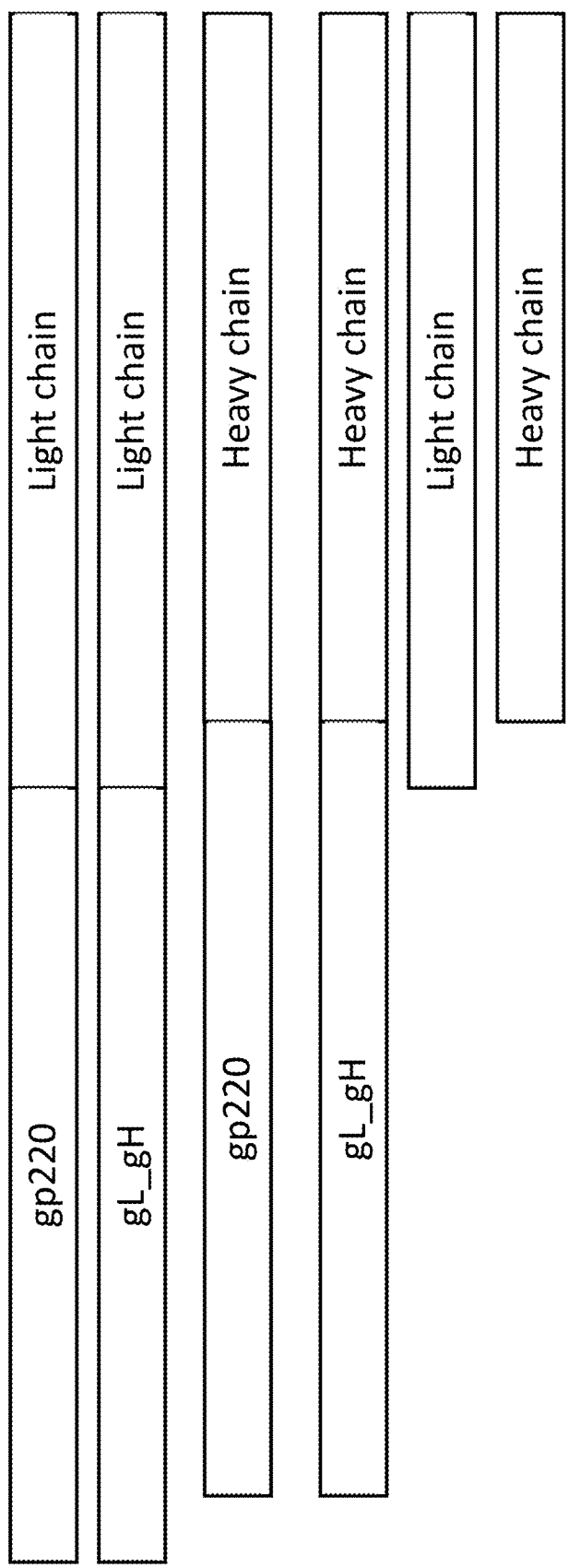

Antibody responses were assayed by ELISA following immunization with 1 µg of nanoparticles comprising single-chain gL/gH (gL_gH_C5 NP, FIGS. 12A and 12B) or nanoparticles comprising gp220 (FIGS. 13A and 13B). Nanoparticles were in combination with 1 µg of naked ferritin and were unconjugated or conjugated to SM7/8a. Unconjugated nanoparticles were administered with or without admixed AF03 adjuvant. Each mouse received 100 µL of the nanoparticle composition as described above. For mice receiving AF03 adjuvant, a 1:1 volume of AF03 was mixed with the nanoparticles. BALB/c mice (n=5/group) were immunized twice with a 3-week interval between doses. A bleed was taken for ELISA analysis at week 5. The most robust ELISA responses were seen for nanoparticles administered in the AF03 adjuvant. Conjugation to SM7/8a produced a more robust ELISA response compared to unconjugated nanoparticles without adjuvant.

Figure 24A:
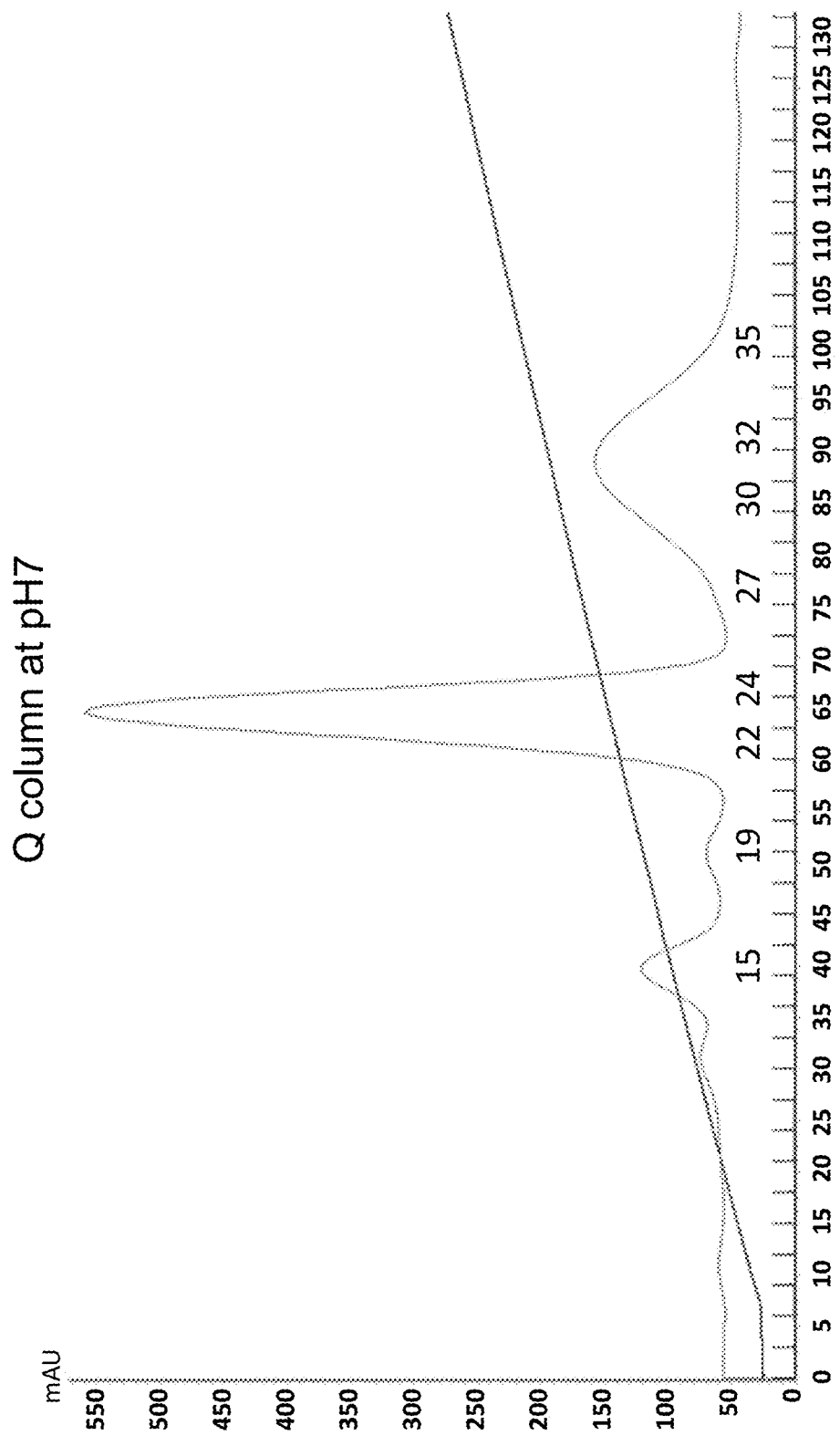
Figure 24B:
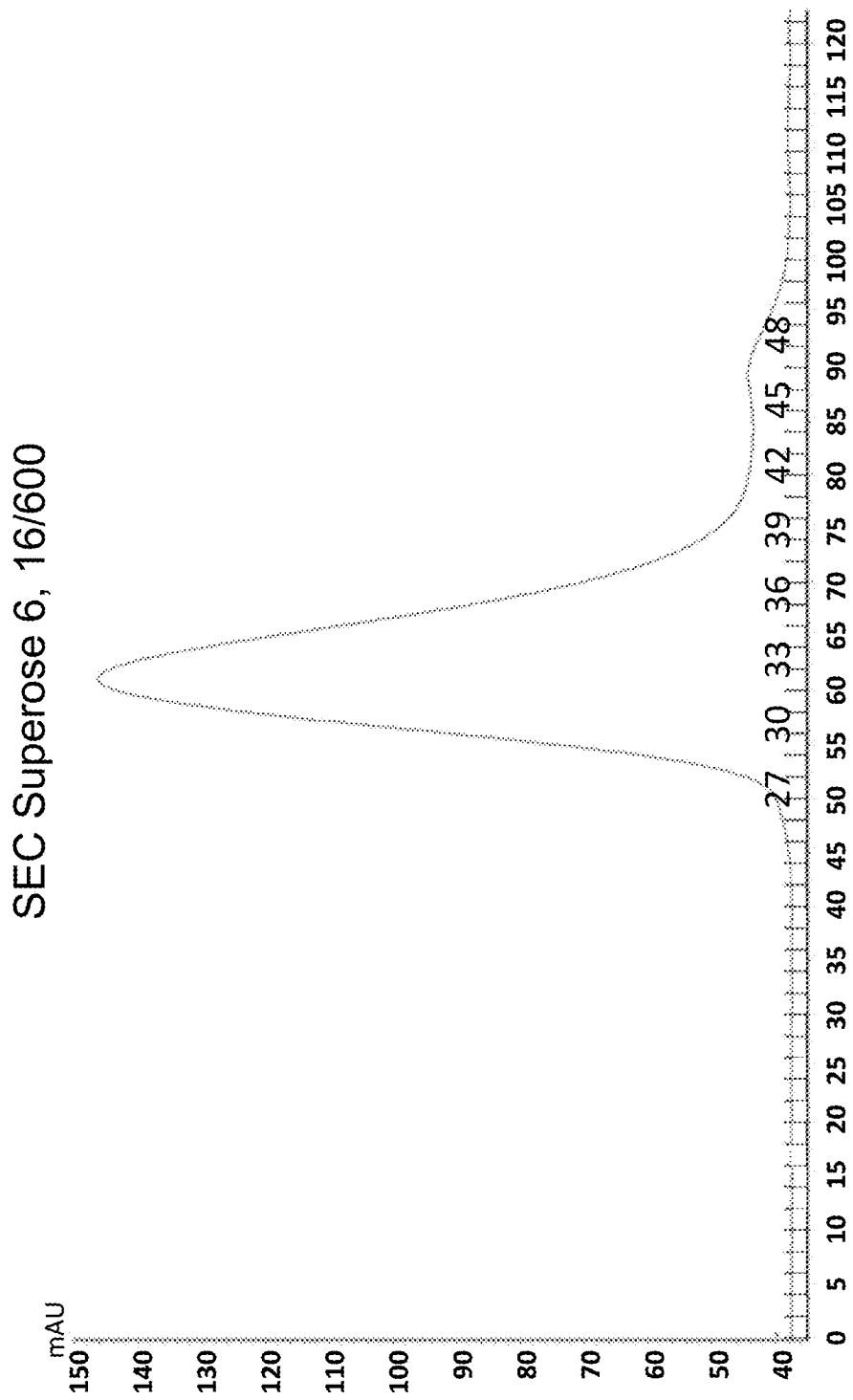
Figure 25A:
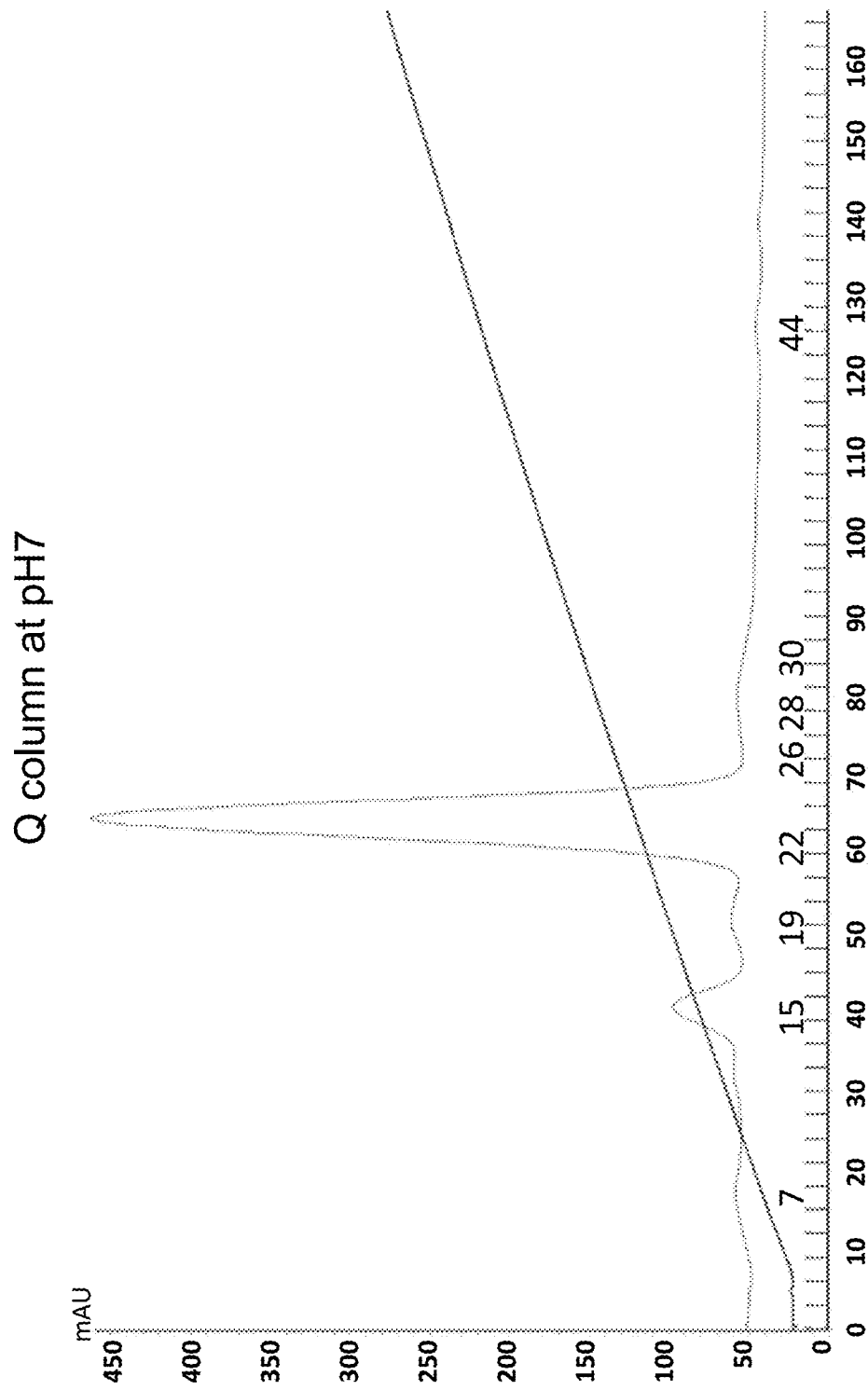
Figure 25B:
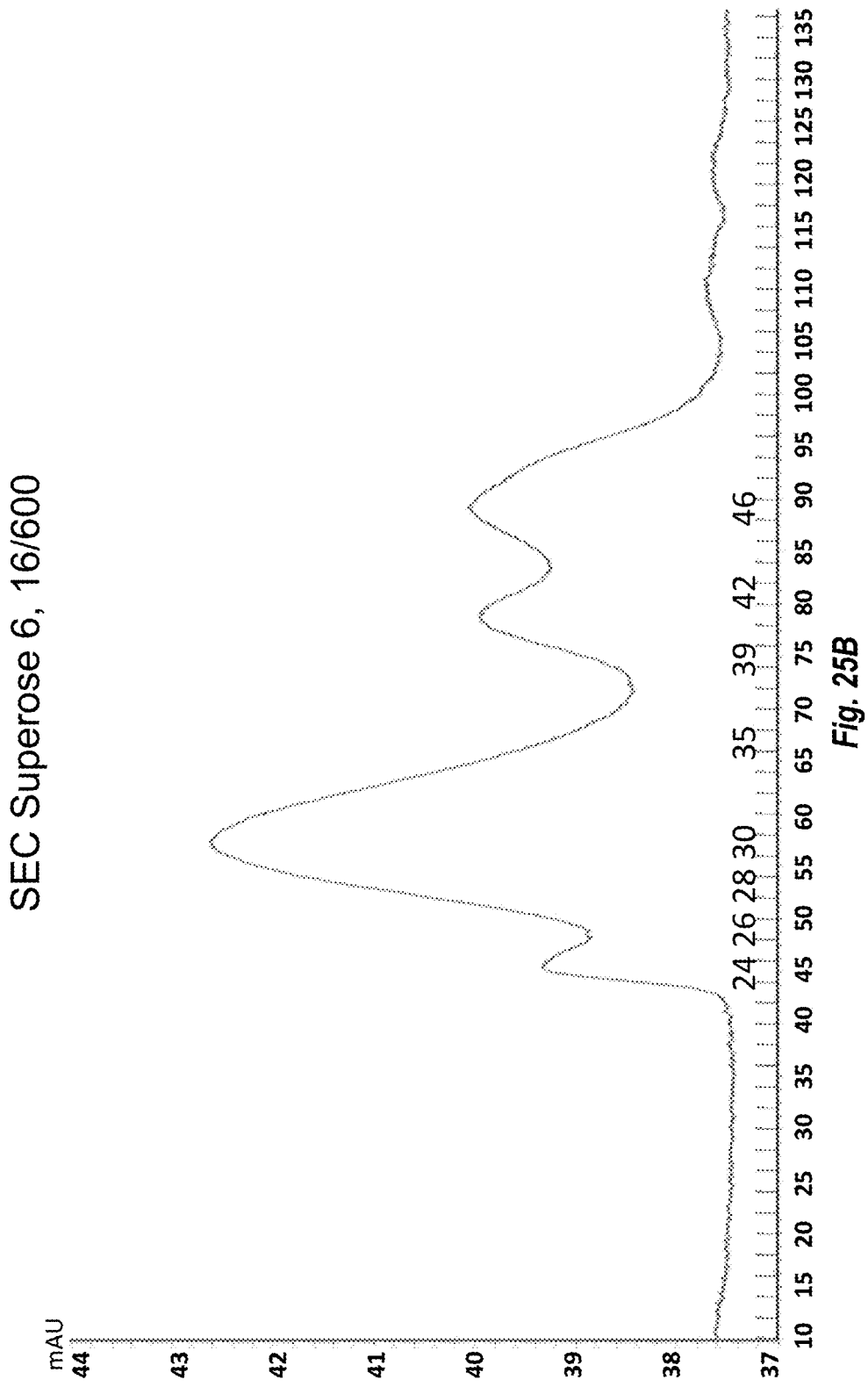

The effect of coadministration of 1 µg each of gL_gH_C5 nanoparticles conjugated to SM7/8a and gp220 nanoparticles conjugated to SM7/8a was also assessed, as compared to single administration of either nanoparticle accompanied by naked ferritin nanoparticles in FIGS. 14A-14B and 15A-15B. No interference was observed on the immune response to either single-chain gL/gH (FIGS. 14A-14B, without and with AF03, respectively) or gp220 (FIGS. 15A-15B, without and with AF03, respectively).

4. Long-Term Immunogenicity Studies

Studies were performed to assess immunogenicity at 3 months after dosing with nanoparticles comprising single-chain gL/gH (gL/gH_C5, SEQ ID NO: 19). BALB/c mice (n=5/group) were immunized twice with a 3-week interval between doses. Naked ferritin (i.e., ferritin not conjugated to any polypeptide or adjuvant) was administered at 1 μg with the 1 μg nanoparticles comprising single-chain gL/gH, and the nanoparticles were formulated in the presence or absence of admixed AF03 adjuvant. A bleed was taken for ELISA analysis at week 13. For mice receiving AF03 adjuvant, a 1:1 volume of AF03 was mixed with the nanoparticle composition. Each mouse received 100 μL of the nanoparticle composition described above. Some mice received nanoparticles comprising single-chain gL/gH in which the ferritin was conjugated to SM7/8a ("7/8a" in FIGS. 16-17).

As shown in FIG. 16, nanoparticles comprising single-chain gL/gH conjugated to SM7/8a produced the greatest immune response when formulated in AF03. A robust immune response was also seen for these nanoparticles without AF03.

A parallel experiment was performed using gp220 nanoparticles (SEQ ID NO: 1) (with or without conjugation to SM7/8a) in place of the nanoparticles comprising single-chain gL/gH. Similar results were seen for these nanoparticles, wherein the formulation including admixed AF03 produced the most robust response, and a robust immune response was also seen for these nanoparticles without AF03 (FIG. 17).

The immune response elicited by a bivalent composition comprising nanoparticles comprising single-chain gL/gH (gL/gH_C5; SEQ ID NO: 19) and nanoparticles comprising gp220 (SEQ ID NO: 1) was assessed. BALB/c mice (n=5/group) were immunized with a 3-week interval between doses. 100 μL of the nanoparticle composition containing 1 μg of each nanoparticle was administered. For mice receiving AF03 adjuvant, a 1:1 volume of AF03 was mixed with vaccine. A terminal week 13 bleed was taken for ELISA analysis. For immune responses against both single-chain gL/gH (FIG. 18) and gp220 (FIG. 19), no interference was seen due to administration of the nanoparticles in combination, as compared to administration of either nanoparticle in combination with naked ferritin.

Further experiments with the gL/gH_C5 nanoparticle (SEQ ID NO: 19) confirmed that long-term immune responses were seen when the nanoparticle was conjugated to SM7/8a (7/8a) or when the nanoparticle was formulated in AF03 (FIG. 21). BALB/c mice (n=5/group) were immunized with a 3-week interval between doses. 100 μL of the nanoparticle composition containing 1 μg of nanoparticles was administered. For mice receiving AF03 adjuvant, a 1:1 volume of AF03 was mixed with vaccine. Week 2 (Prime), 5 (Boost), and 13 (Terminal) bleeds were taken for ELISA analysis. A parallel experiment was performed using gp220 nanoparticles (SEQ ID NO: 1) and a similar long-term response was also seen for gp220 nanoparticles (FIG. 22).

A different nanoparticle comprising single-chain gL/gH (gL_gH_C7: SEQ ID NO: 20) was also assessed. The gL_gH_C7 construct comprises a flexible linker between the gH polypeptide and the ferritin with a cysteine as a conjugation site for an immune-stimulatory moiety. The linker may be used with a ferritin lacking a surface-exposed cysteine (as shown in SEQ ID NO: 20). SM7/8a was conjugated to gL_gH_C7 by reducing the protein using 2 mM TCEP and then oxidizing by adding 1×PBS and using a 100 kD microspin column to remove TCEP. The SM7/8a was then incubated with the gL/gH nanoparticle. Following conjugation, excess SM7/8a was removed from the reaction via a 100 kD microspin column.

Mice received 1 μg of these gL/gH nanoparticles, either conjugated to 7/8a or unconjugated, plus 1 μg of naked ferritin. 100 μL of the nanoparticle composition containing 1 μg of nanoparticles was administered. BALB/c mice (n=5/group) were immunized with a 3-week interval between doses. For mice receiving AF03 adjuvant, a 1:1 volume of AF03 was mixed with the nanoparticle composition. Week 2 (prime), 5 (booster), and 13 (terminal) bleeds were taken for ELISA analysis. These nanoparticles elicited immune responses when formulated in AF03 or when conjugated to SM7/8a as measured by ELISA endpoint titer at prime bleed (FIG. 20A). Similar results were seen with booster bleed (FIG. 20C) or terminal bleed (FIG. 20D) samples. These nanoparticles were also conjugated to a CpG oligodeoxynucleotide, and administered in the same way. Results for the CpG conjugate were similar to unconjugated nanoparticles (FIG. 20B) at week 5.

5. Characterization of Nanoparticles Comprising *Trichoplusia ni* Ferritin

Nanoparticles were also developed comprising *Trichoplusia ni* ferritin and gp220 and/or gL/gH polypeptides. *Trichoplusia ni* ferritin nanoparticles contain heavy and light chains self-assembled at a 1:1 ratio. It was found that combining one non-ferritin polypeptide with the light chain and another non-ferritin polypeptide on the heavy chain allowed presentation of two distinct polypeptides on the surface of individual nanoparticles. Thus, for example, a self-assembled *Trichoplusia ni* ferritin nanoparticle could present both gp220 and gL/gH.

A *Trichoplusia ni* ferritin nanoparticle was produced and purified with the heavy chain fused to either gp220 (SEQ ID NO: 24) or single-chain gL/gH (SEQ ID NO: 25) and the light chain fused to either gp220 (SEQ ID NO: 26) or single-chain gL/gH (SEQ ID NO: 27) (constructs illustrated in FIG. 23B and visualized by Coomassie gel staining in FIG. 23A, showing the expected increase in molecular weight relative to light and heavy chains alone). The combination of a light chain and a heavy chain fused to gL/gH and gp220, respectively or vice versa, generated an individual multivalent nanoparticle that can present two different EBV polypeptides.

Two *T. ni* ferritin nanoparticles with either only gp220 in both the heavy and light chains (as shown in FIG. 24E) or gp220 in the heavy chain and gH_gL in the light chain (as shown in FIG. 25E) were also produced. The purification followed two steps: The first purification step was an ion exchange chromatographic step (Q column, see FIG. 24A with Coomassie results in FIG. 24C and FIG. 25A with Coomassie results shown in FIG. 25C). This step was followed by size exclusion chromatography (see FIG. 24B with Coomassie results in FIGS. 24D and 25B with Coomassie results in FIG. 25D).

Figure 26B:
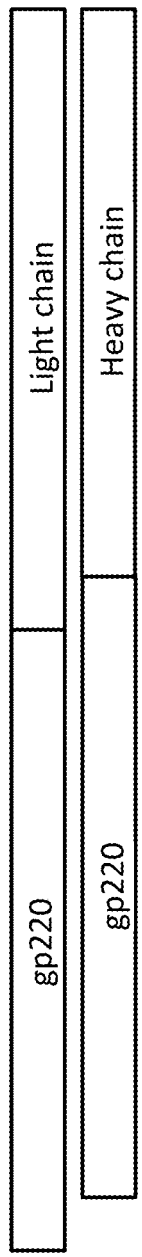
Figure 26C:
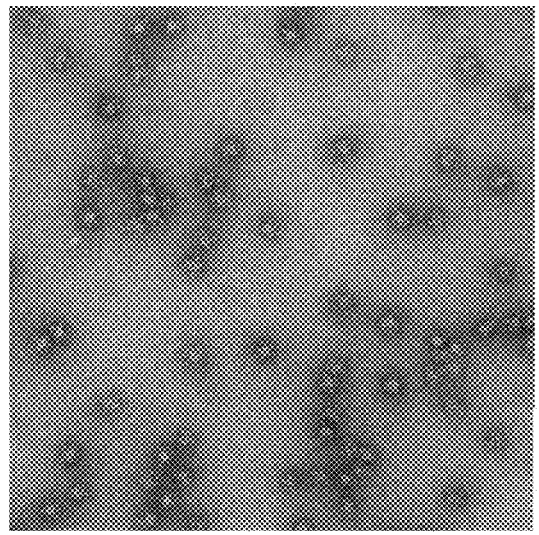
Figure 26A:
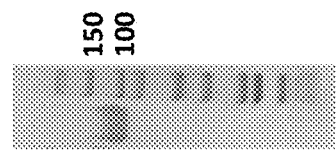
Figure 26D:
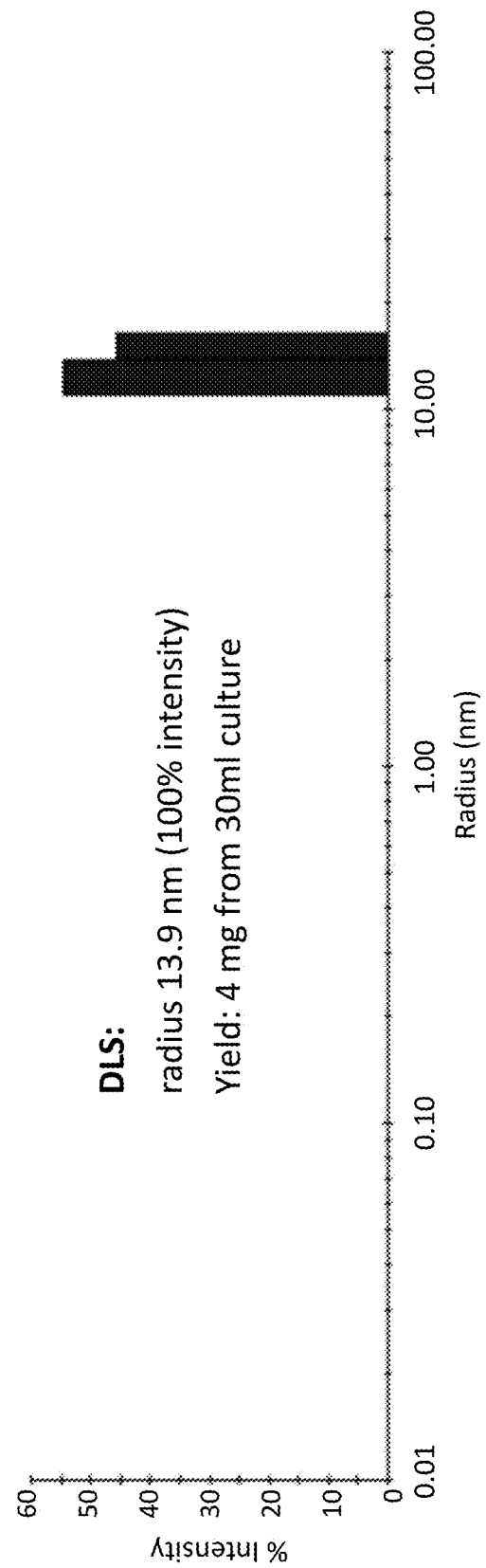
Figure 26H:
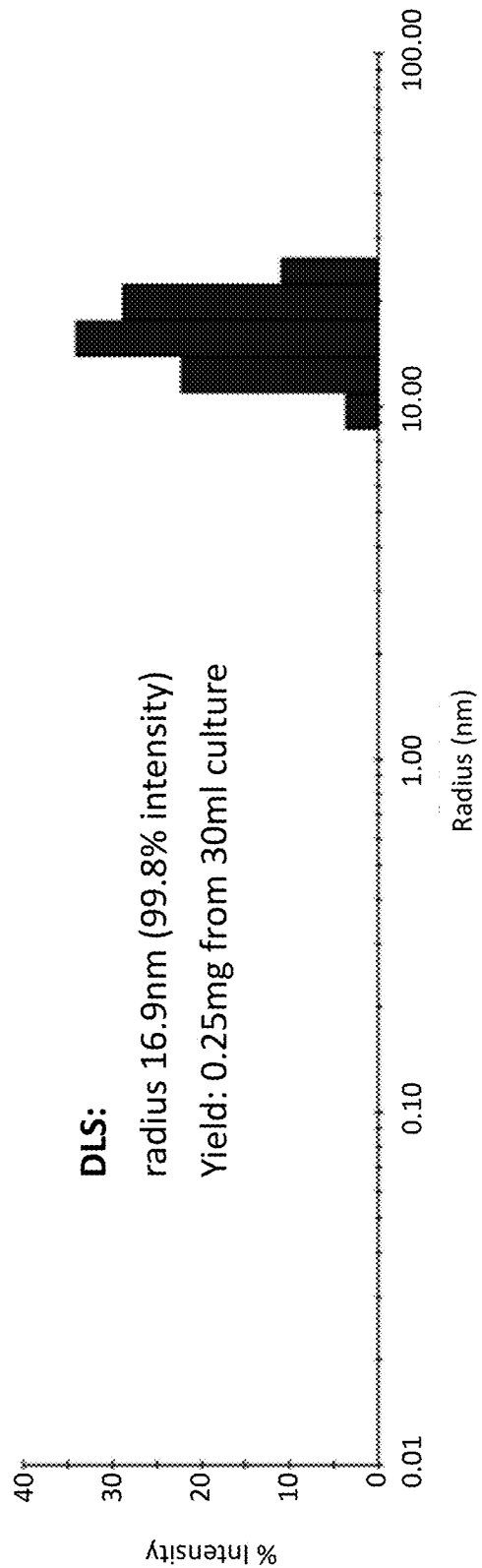
Figure 27B:
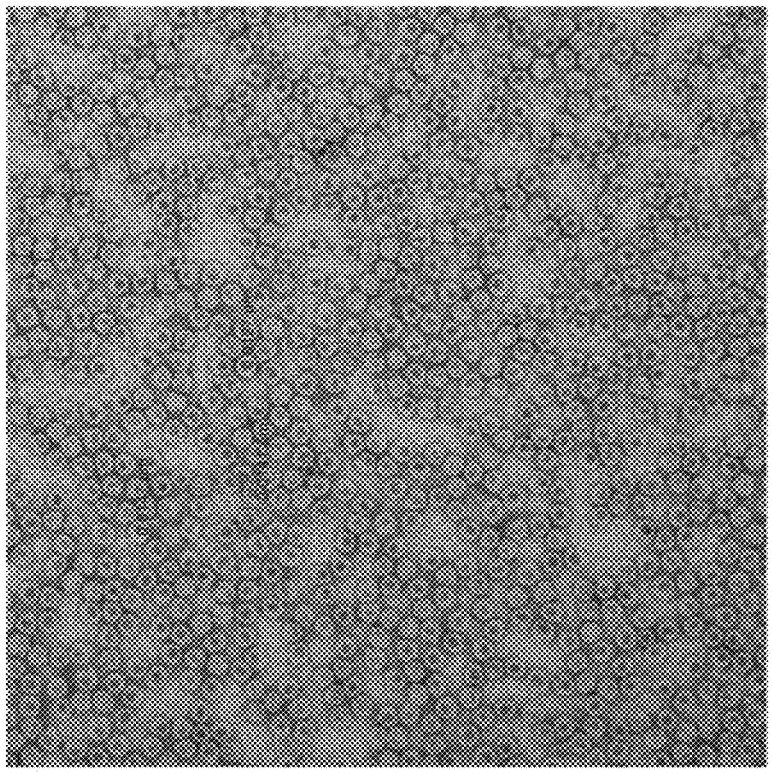
Figure 27A:
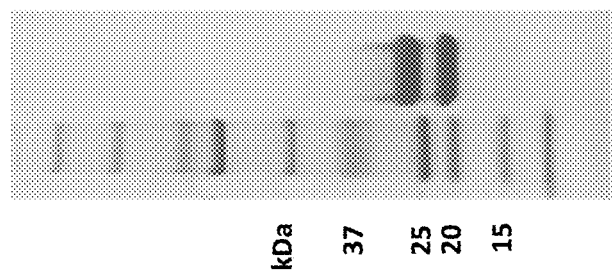
Figure 27C:
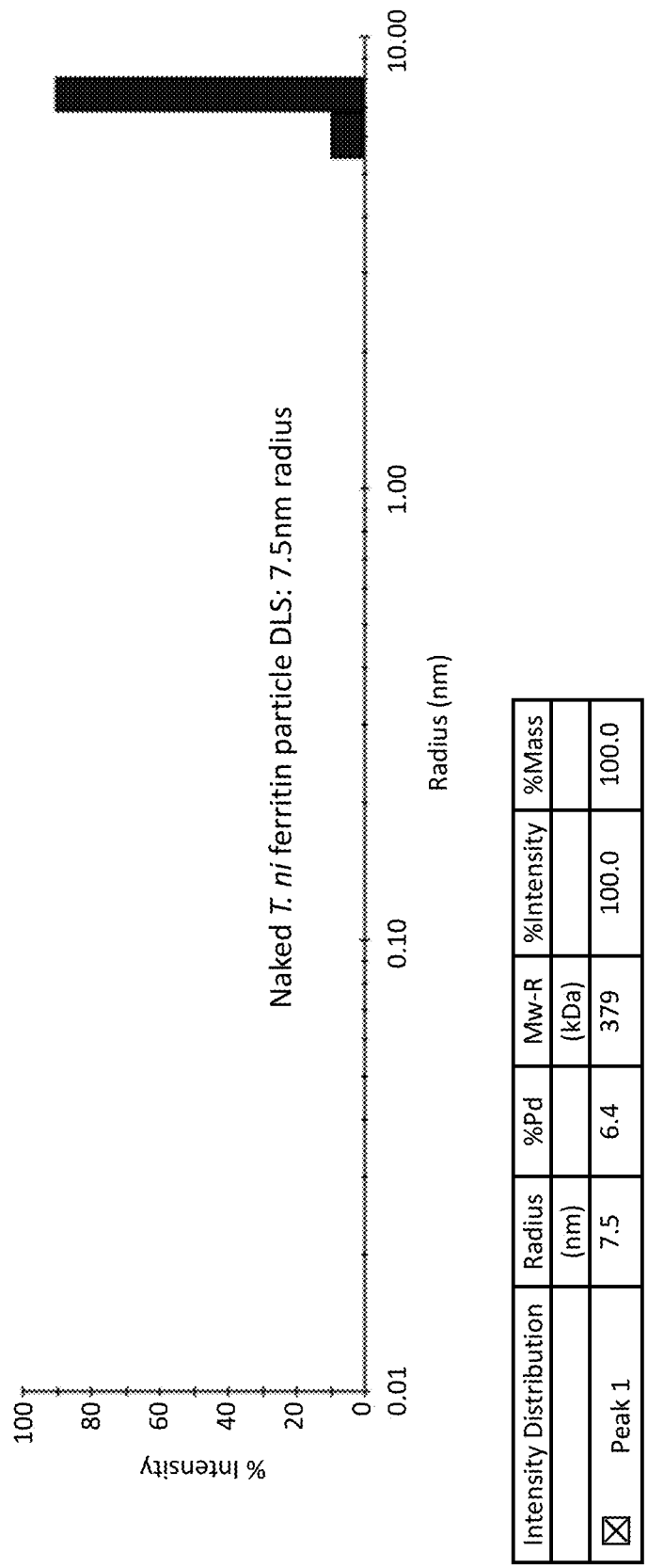

Nanoparticles comprising *Trichoplusia ni* light and heavy chain fused to gp220 (SEQ ID NOs: 24 and 26; illustrated in FIG. 26B) showed a profile consistent with formation of a nanoparticle comprising the heterologous gp220 polypeptide, based on Coomassie staining (FIG. 26A), an increase in DLS radius (FIG. 26D) relative to naked *T. ni* ferritin (FIG. 27C), and EM analysis (FIG. 26C) in which additional peripheral density around the nanoparticle core appeared relative to the naked nanoparticles (FIG. 27B). Similar results indicative of the presence of heterologous gL/gH and gp220 polypeptides in the nanoparticles were seen for SEQ ID NOs: 24 and 27 (*Trichoplusia ni* light chains with a gL/gH polypeptide and heavy chains with a gp220 polypeptide; see FIGS. 26E-26H for visualization by Coomassie staining, an illustration of the construct, an electron micrograph, and characterization by DLS, respectively). For comparison, FIGS. 27A-27C show Coomassie staining (FIG. 27A), DLS radius (FIG. 27B), and EM analysis (FIG. 27C) for naked *T. ni* ferritin (i.e., not conjugated to any polypeptide).

Thus, use of *T. ni* ferritin allows presentation of 2 polypeptides on individual nanoparticles.

6. gH/gL/gp42 Constructs

A cartoon of a single-chain construct of gH/gL/gp42 fused to ferritin (as in each of SEQ ID NOs: 227-231 and 241-242) is shown in FIG. 35A. The fusion between each protein is via a flexible amino acid linker or a rigid amino acid linker. The single-chain gH/gL/gp42 molecule provides a 1:1:1 ratio of heterotrimer formation on the nanoparticle.

Figure 34:
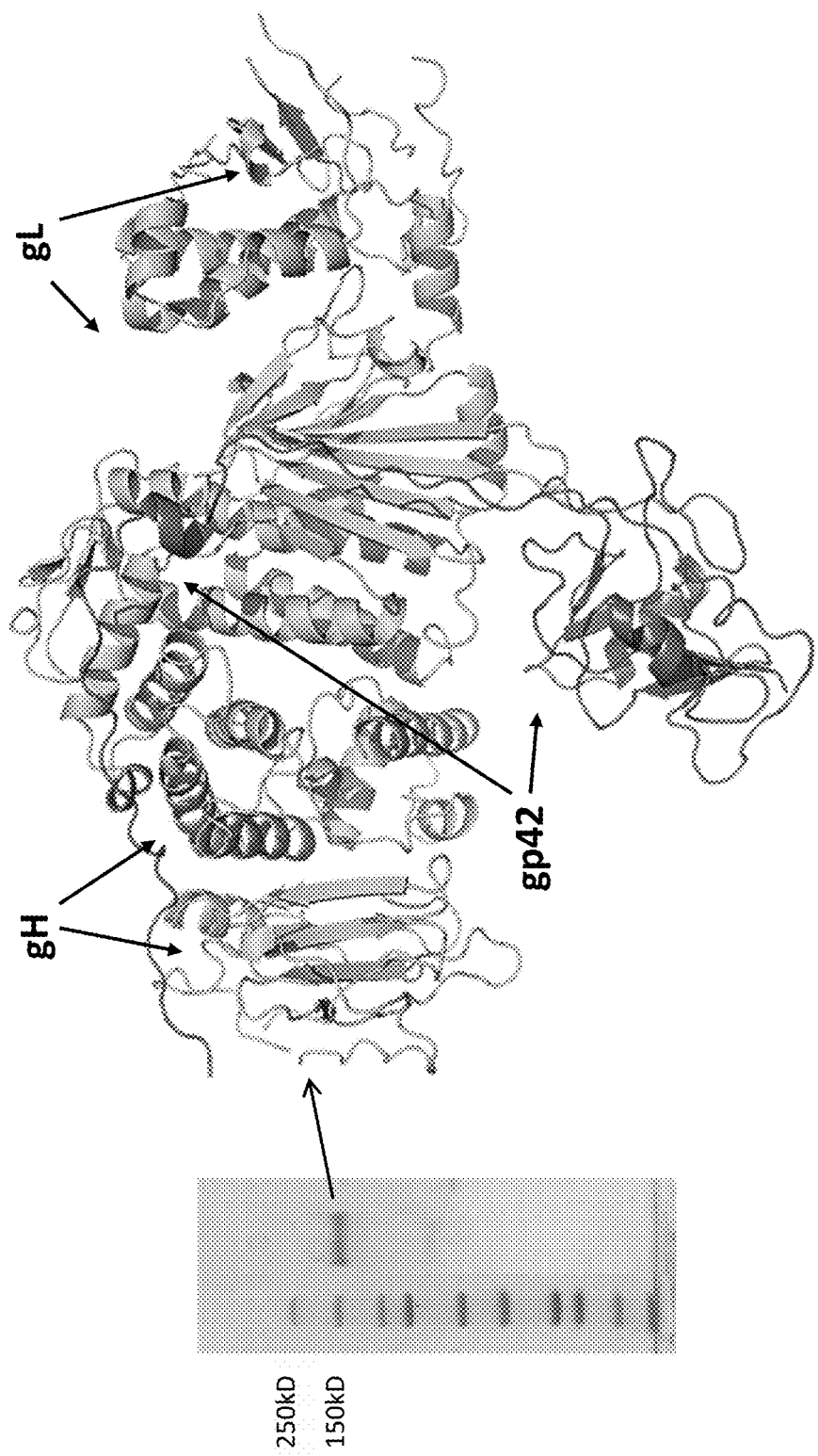
FIG. 34: An SDS reducing coomassie gel on the left shows the purified single-chain gH/gL/gp42-His product (SEQ ID NO: 226). The protein was purified using Nickel affinity chromatography. On the right is a 2.9 Angstrom crystal structure of the single-chain gH/gL/gp42-His product (SEQ ID NO: 226). Gp42 (in dark gray and indicated with arrows) interacts with the gH/gL heterodimer.

The crystal structure of a gH/gL/gp42 His-tagged fusion (SEQ ID NO: 226) has been solved to show that the single-chain gH/gL/gp42 can adopt a heterotrimer conformation similar to wild-type gH, gL, and gp42 proteins found in nature (FIGS. 34 and 35B). In FIGS. 34 and 35B, Gp42 (in dark gray and indicated with arrows in FIG. 34) interacts with the gH/gL heterodimer. FIG. 35C is a model of how this single-chain gH/gL/gp42 heterotrimer fused to ferritin is displayed on a nanoparticle. There are twenty-four copies of the single-chain gH/gL/gp42 that will be displayed on a single nanoparticle.

Figure 28A:
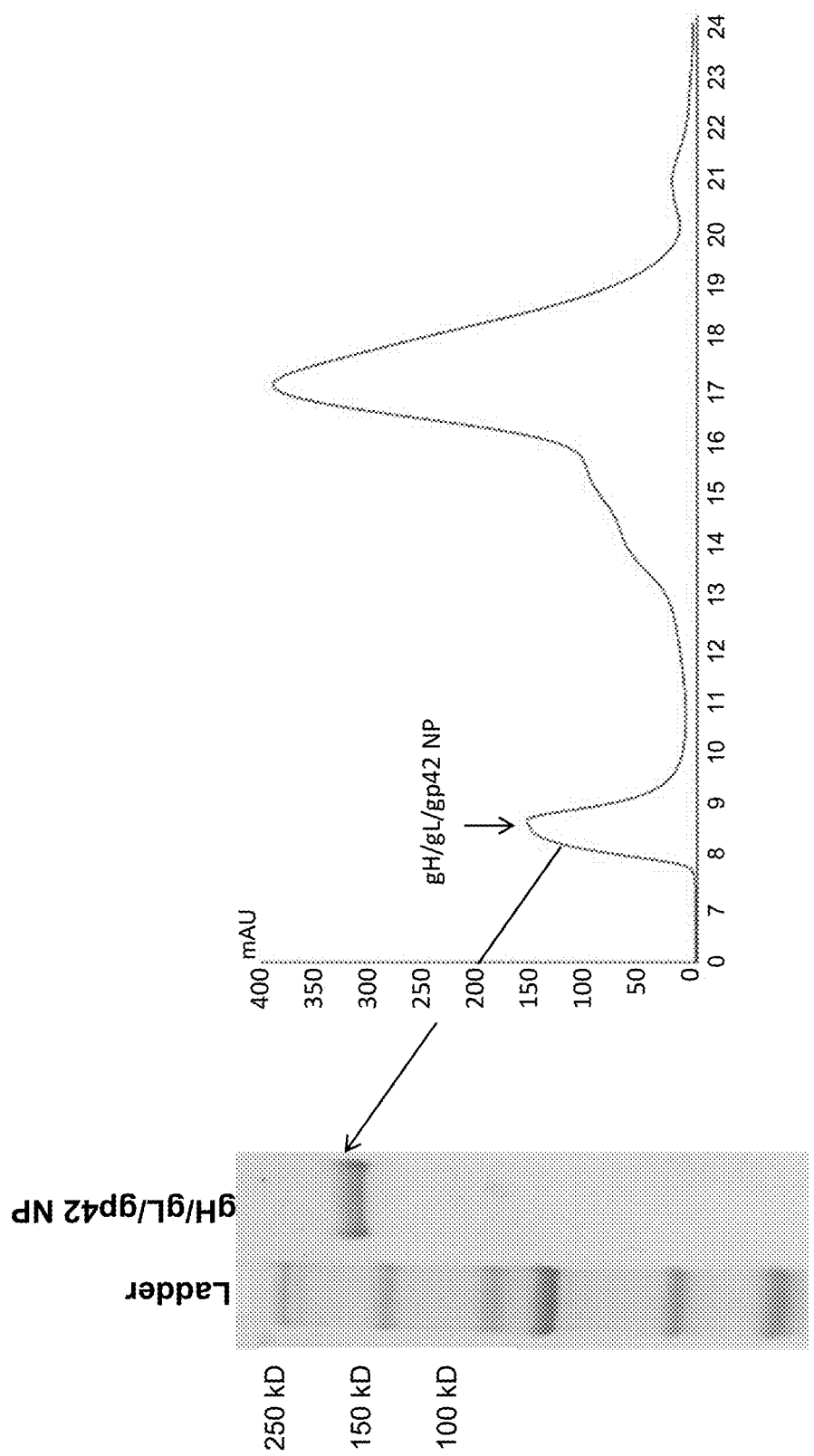
Figure 28B:
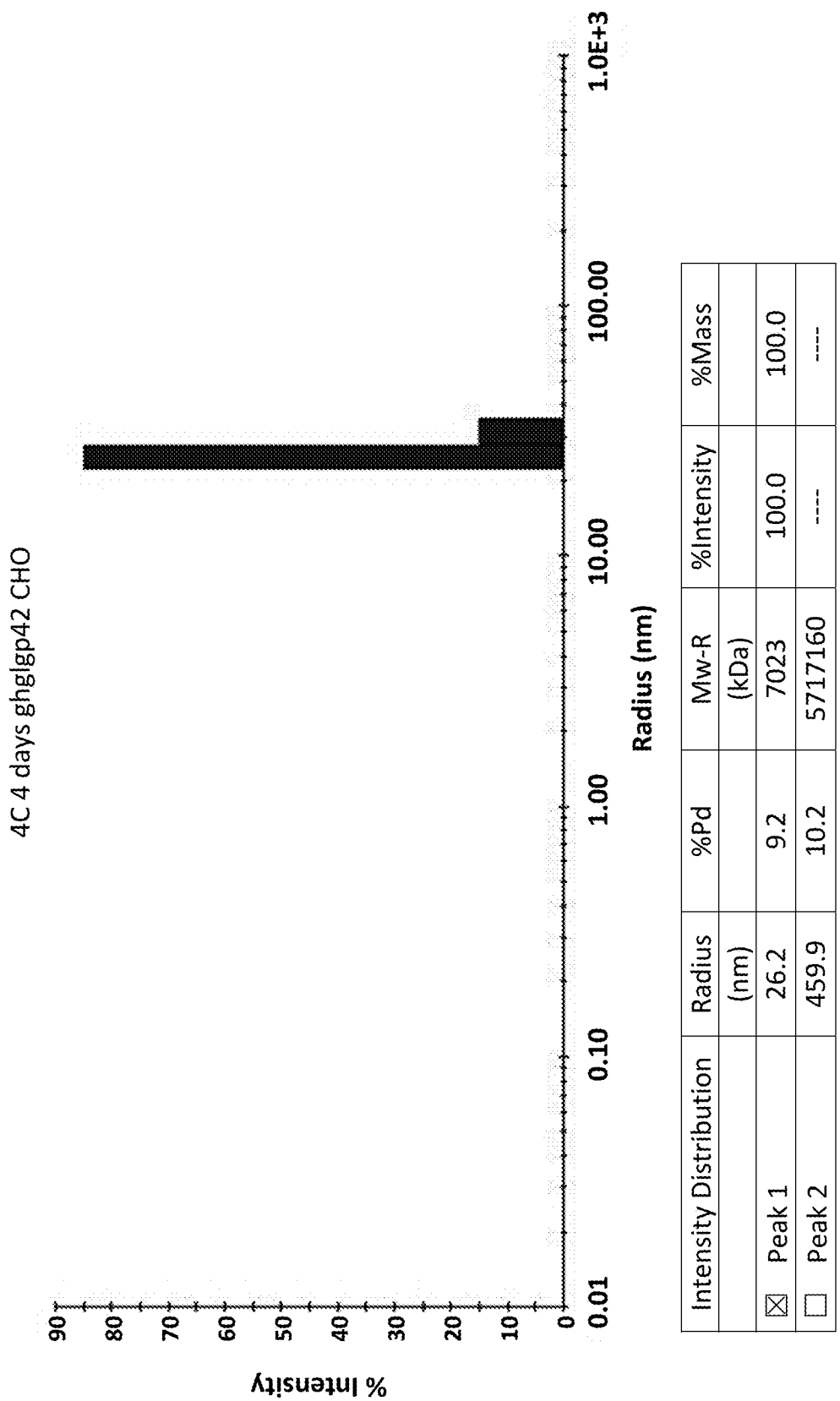

A gH/gL/gp42 NP construct (SEQ ID NO: 227) was expressed in 293 expi cells and purified (FIG. 28A). gH/gL/gp42 NP purified from CHO pools had a dynamic light scattering radius of around 26.2 nm (FIG. 28B).

Figures 29A, 29B:
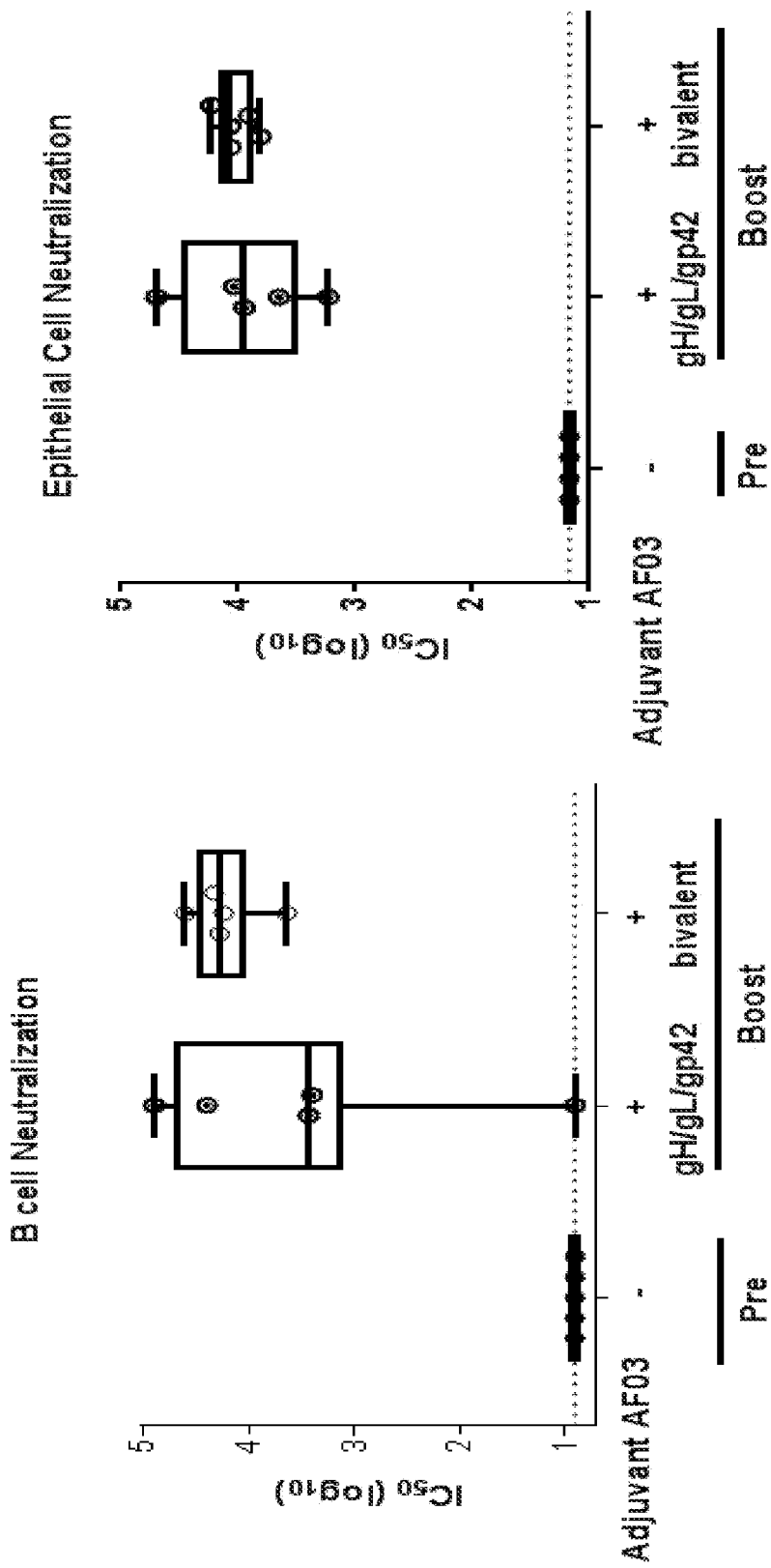
FIG. 29A shows B cell neutralization.
FIG. 29B shows epithelial cell neutralization.

The immune responses elicited by a monovalent (gH/gL/gp42 NP+naked ferritin nanoparticle) or bivalent (gH/gL/gp42 NP+gp220 NP) composition were assessed. The gH/gL/gp42 NP had the sequence of SEQ ID NO: 227 and the gp220 NP had the sequence of SEQ ID NO: 1. BALB/c mice (n=5/group) were immunized with a 3-week interval between doses. 100 μL of the nanoparticle composition containing 1 μg of each nanoparticle was administered with an AF03 adjuvant (1:1 volume of AF03 mixed with vaccine). The boost indicates the sera collected at week 5 after the second immunization. EBV viral neutralizing assay analysis in B cells (FIG. 29A) and in epithelial cells (FIG. 29B) was done using sera collected at week 5 from the mice. No interference was seen due to administration of the nanoparticles in bivalent formulation, as compared to administration of the monovalent form (gH/gL/gp42 with naked ferritin).

Figure 30A:
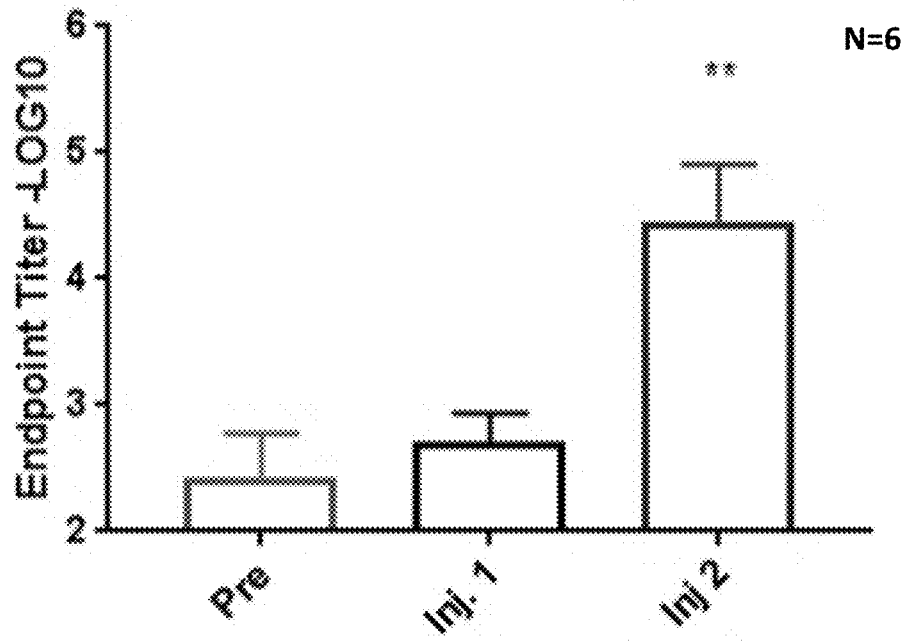
Figure 30B:
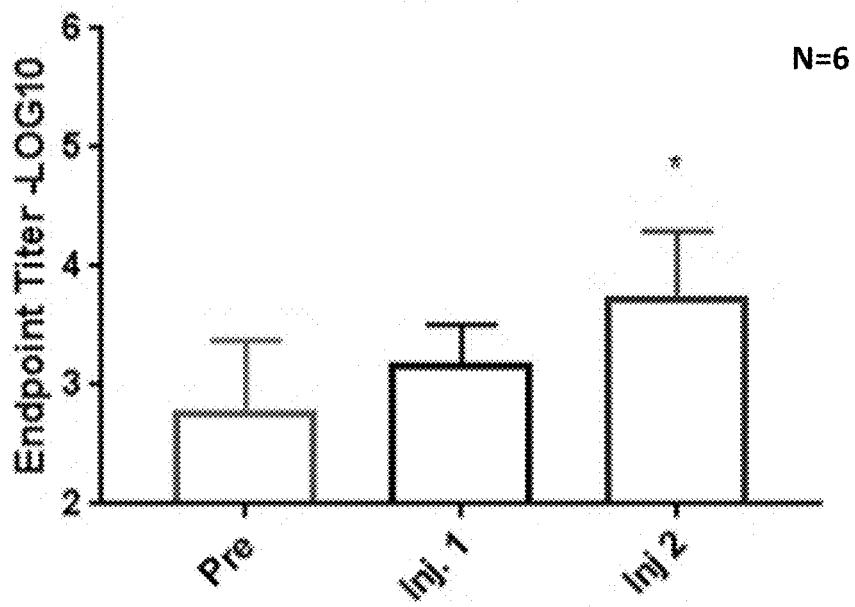
Figure 30E:
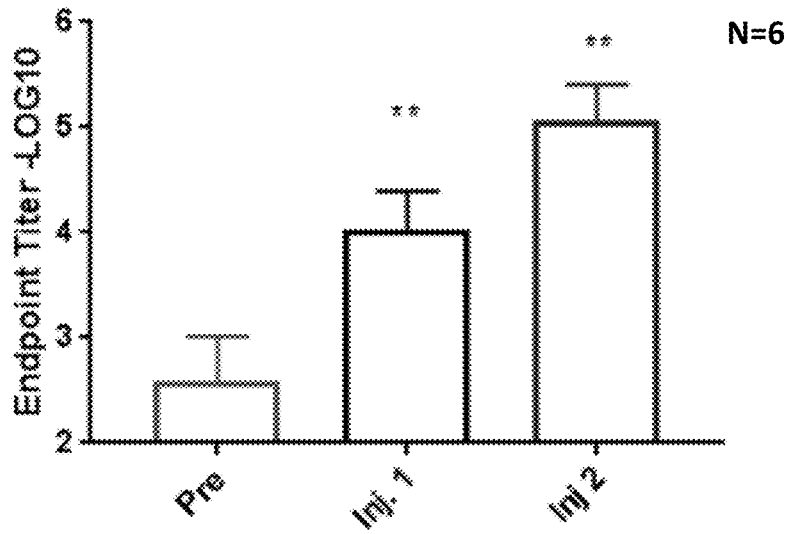
Figure 30F:
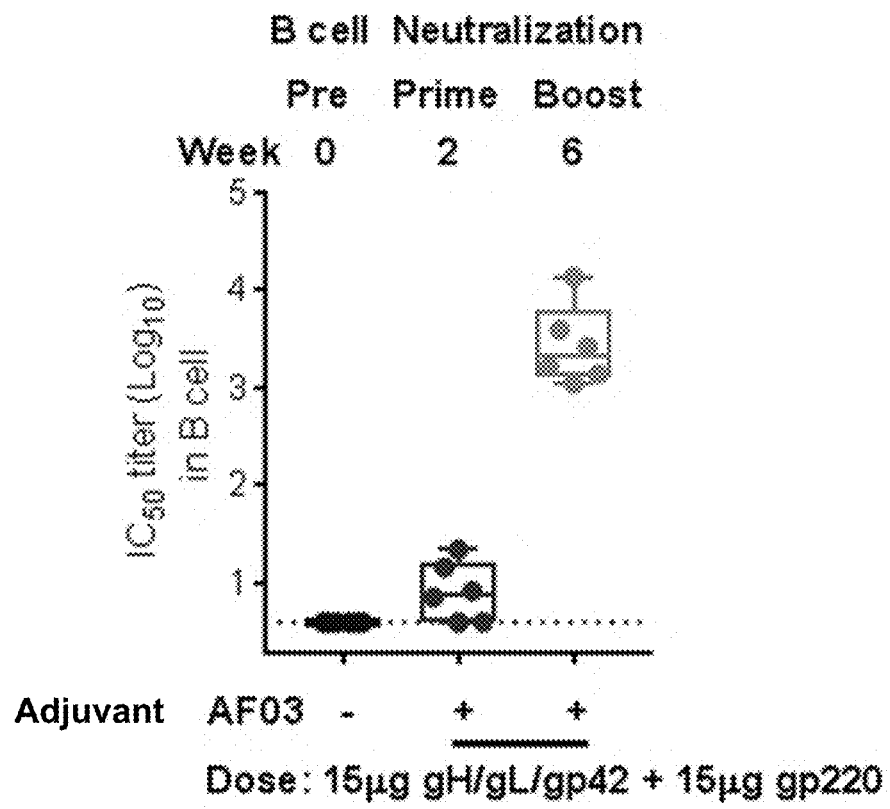
FIGS. 30F-G show an EBV viral neutralizing assay (in B cells and epithelial cells, respectively) of sera from ferrets vaccinated as indicated. Prime=Inj. 1 and Boost=Inj. 2.
Figure 30G:
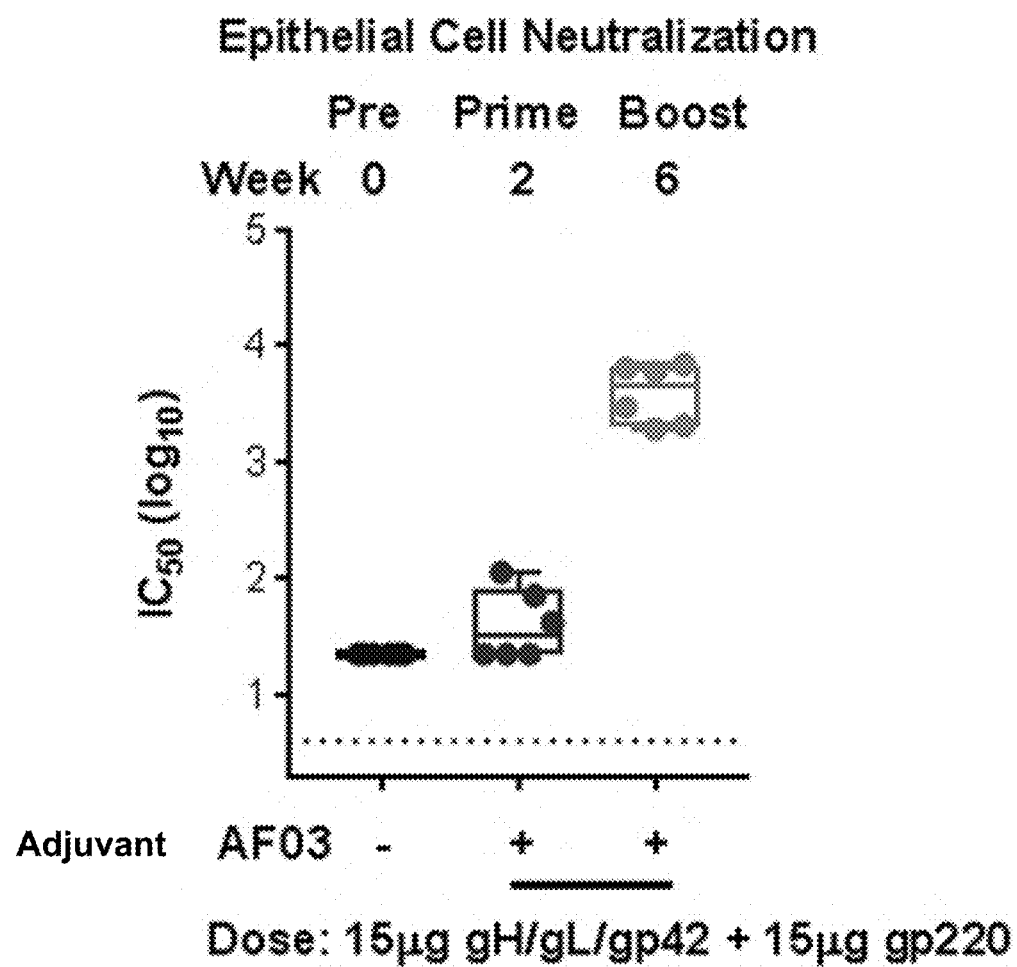
Figure 31A:
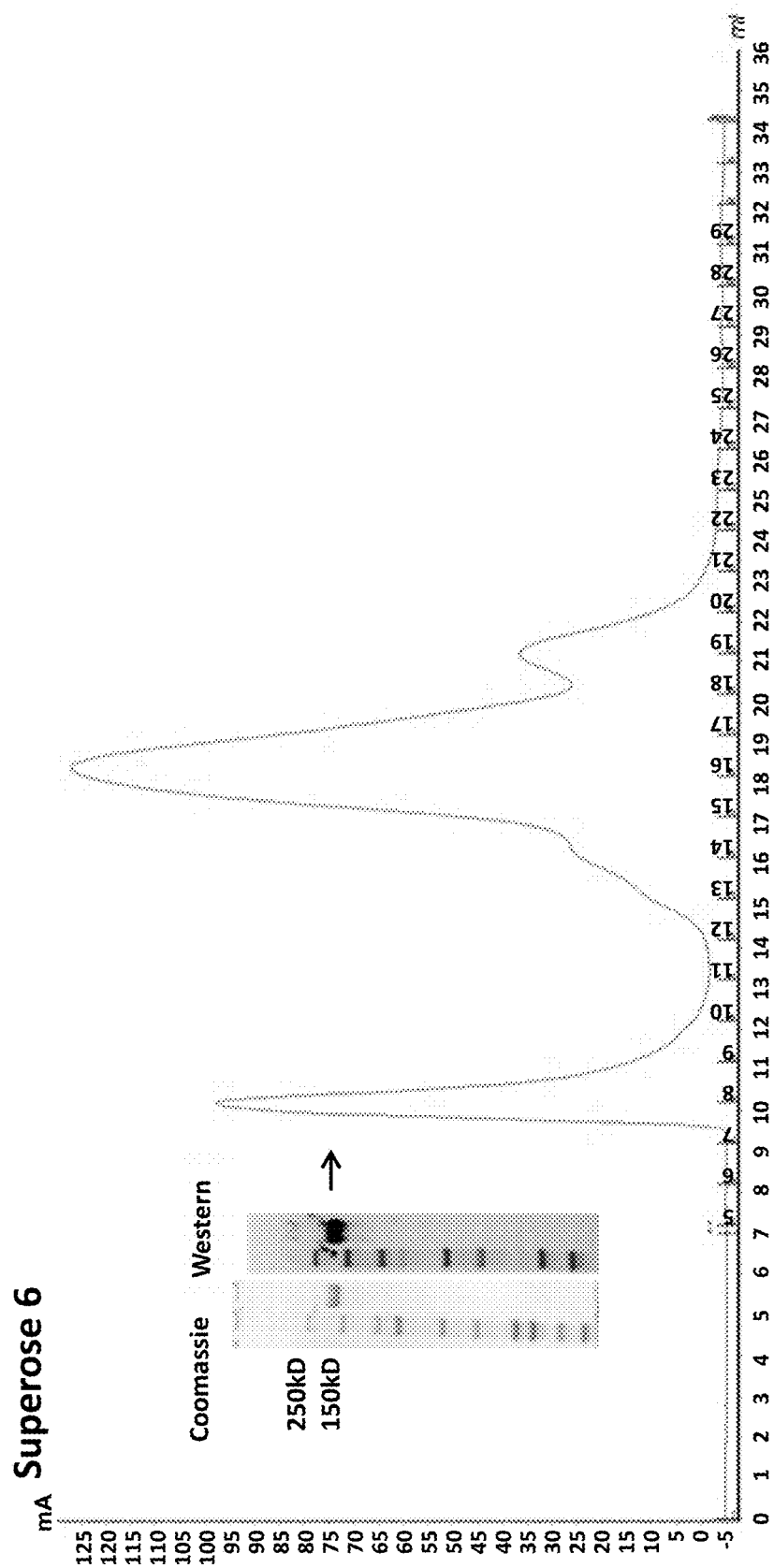
FIGS. 31A-B.
Figure 31B:
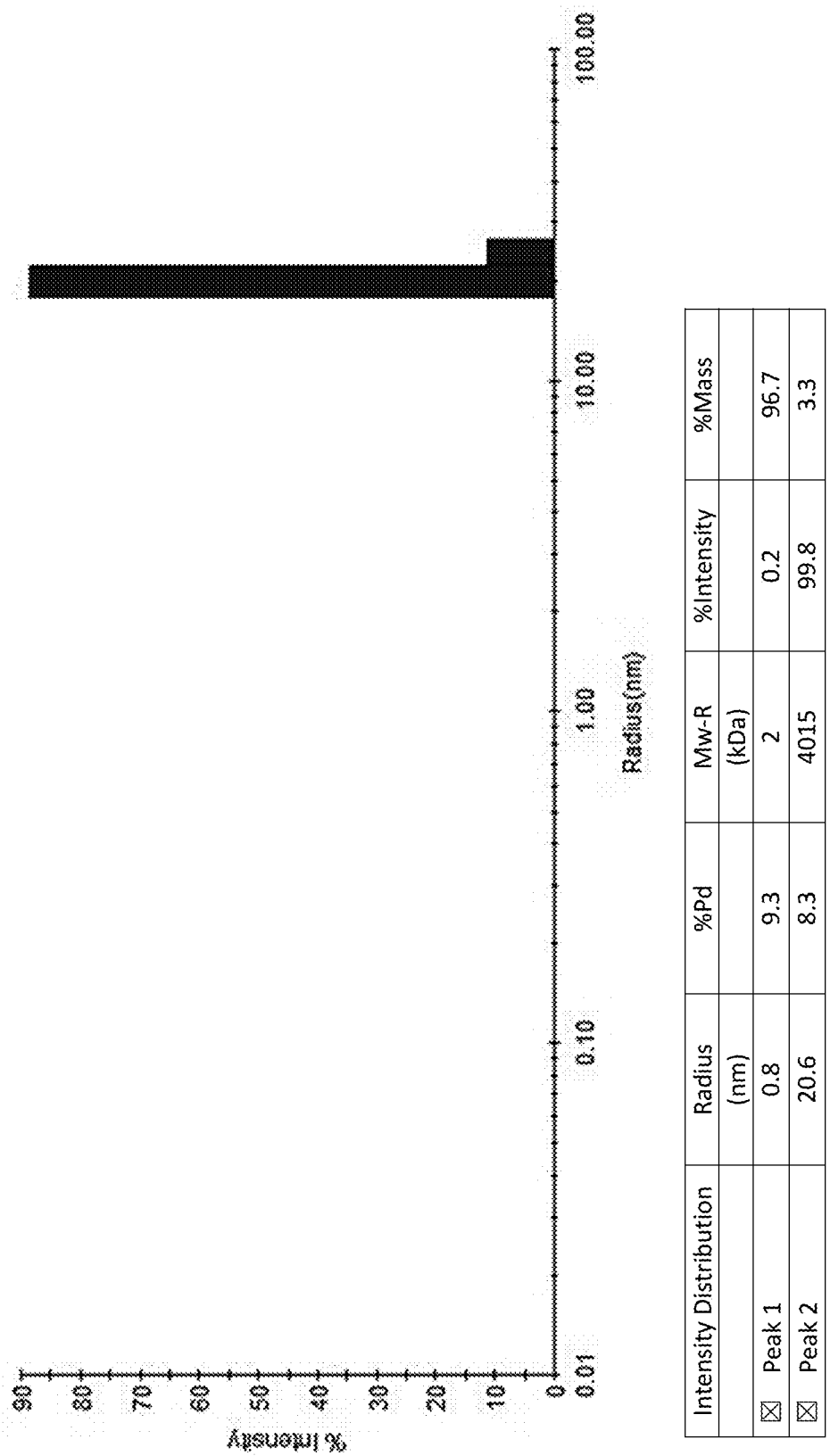
Figure 32A:
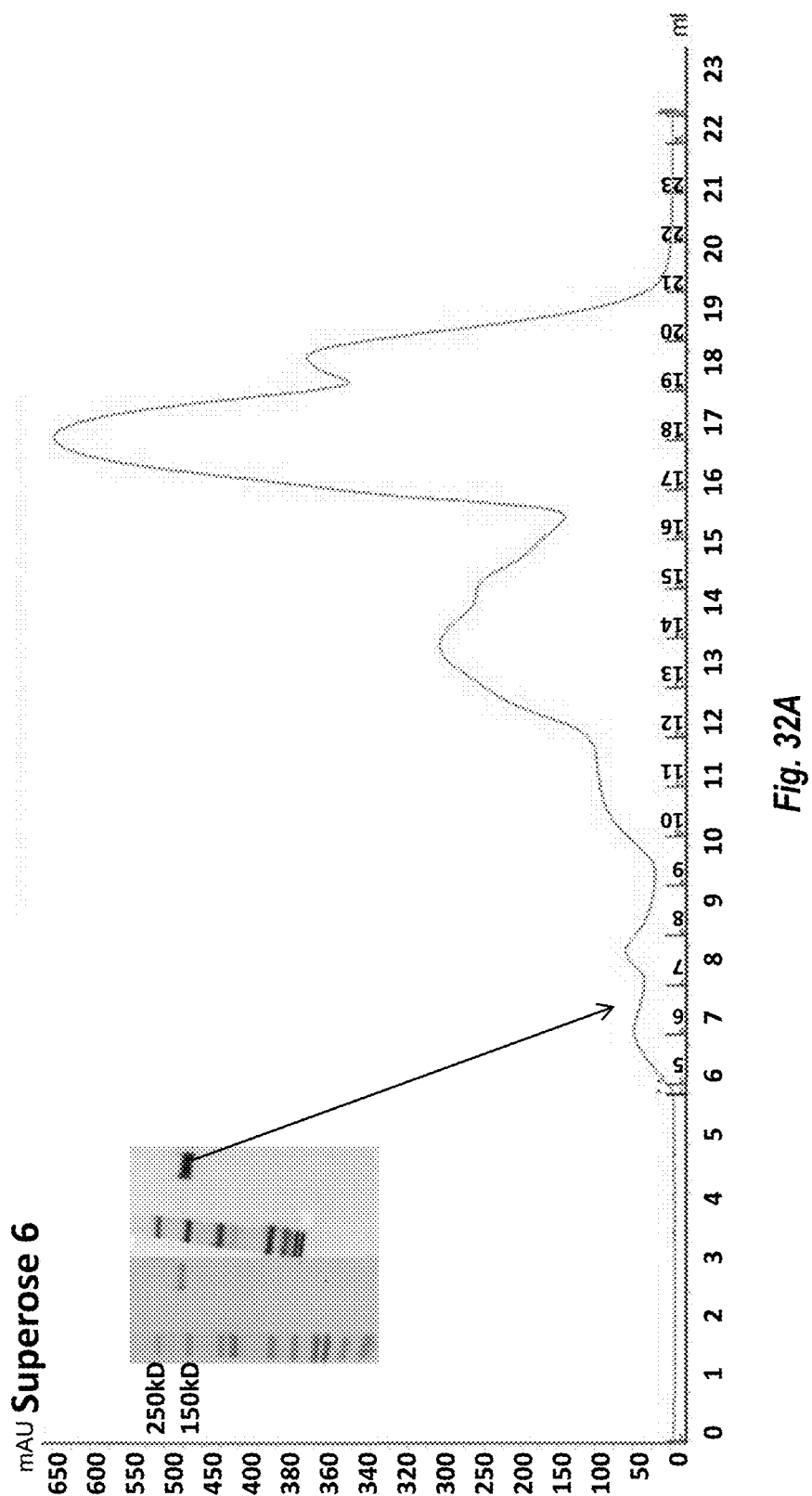
FIGS. 32A-B.
Figure 32B:
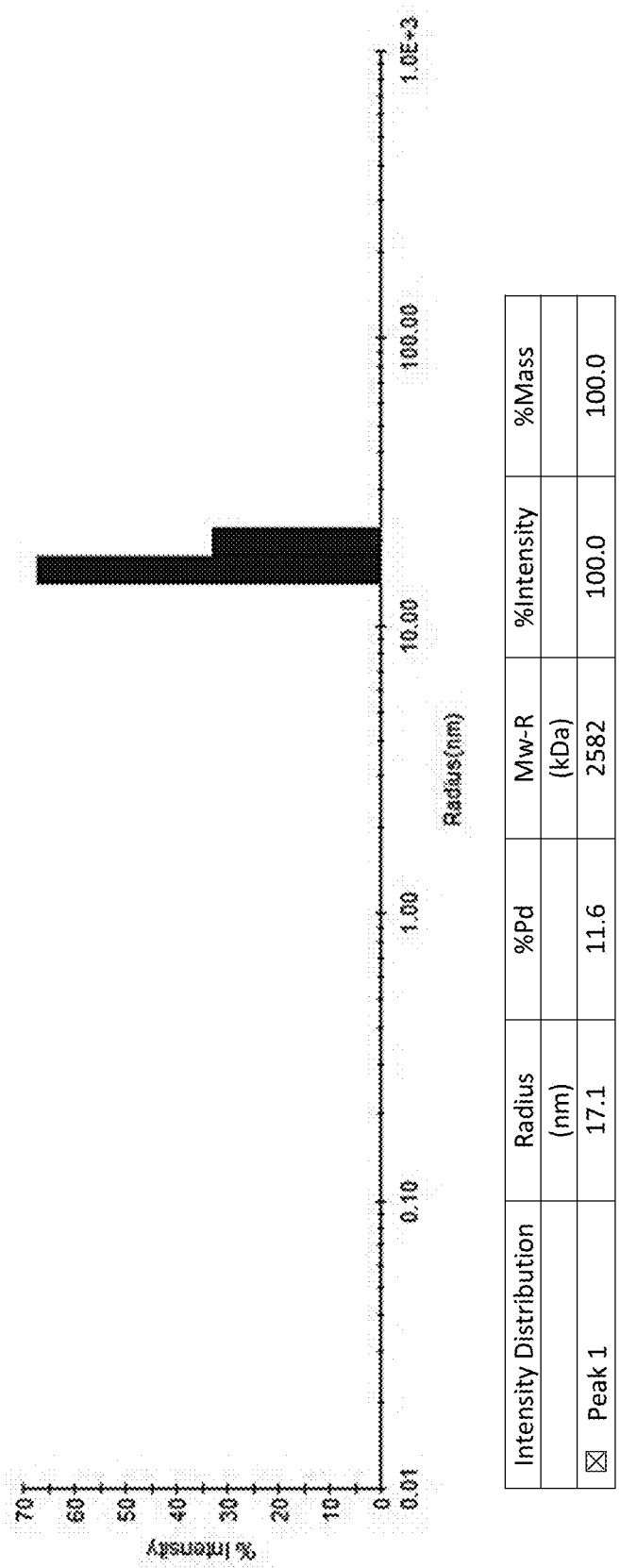
Figure 33A:
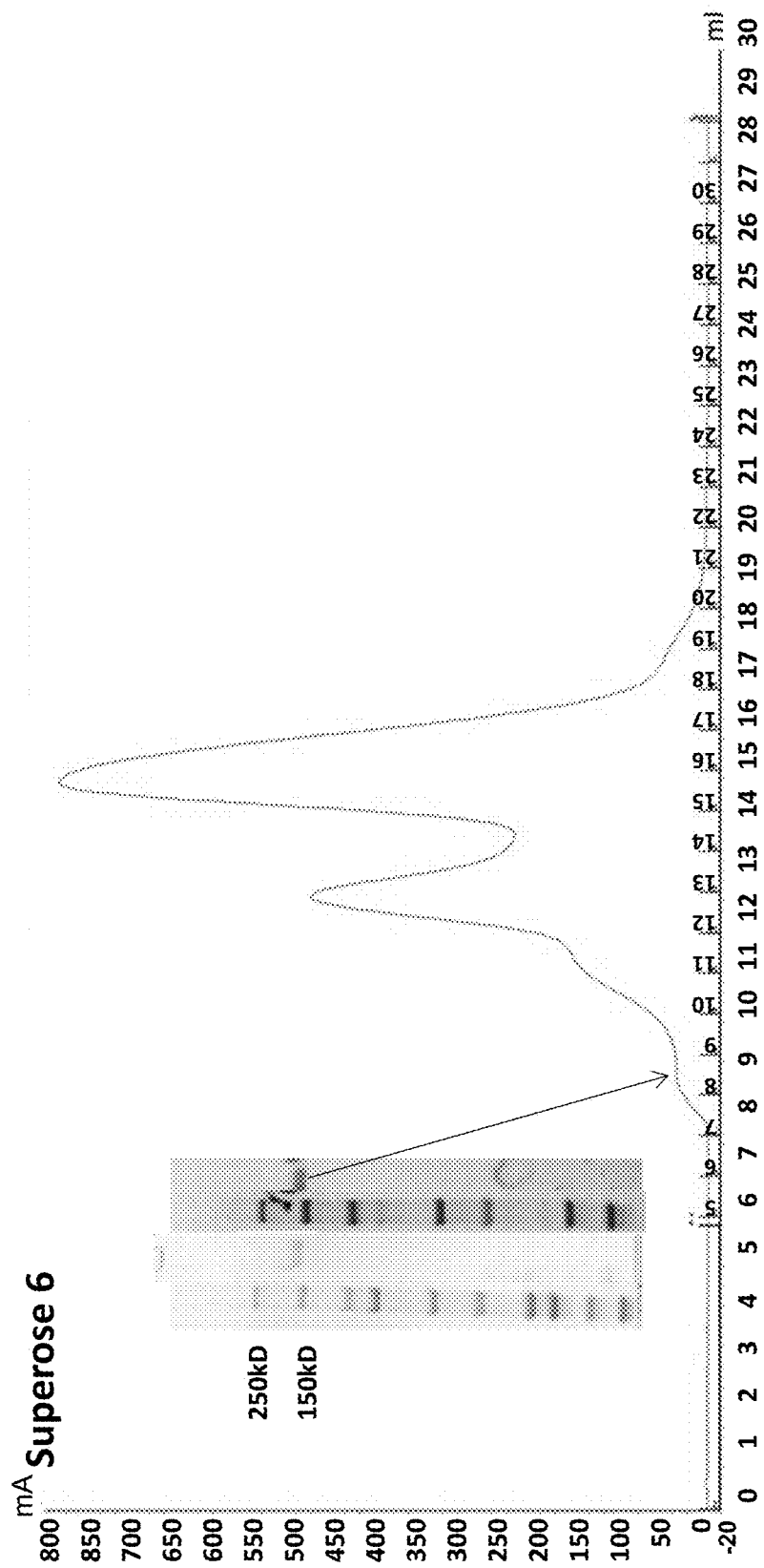
FIGS. 33A-B.
Figure 33B:
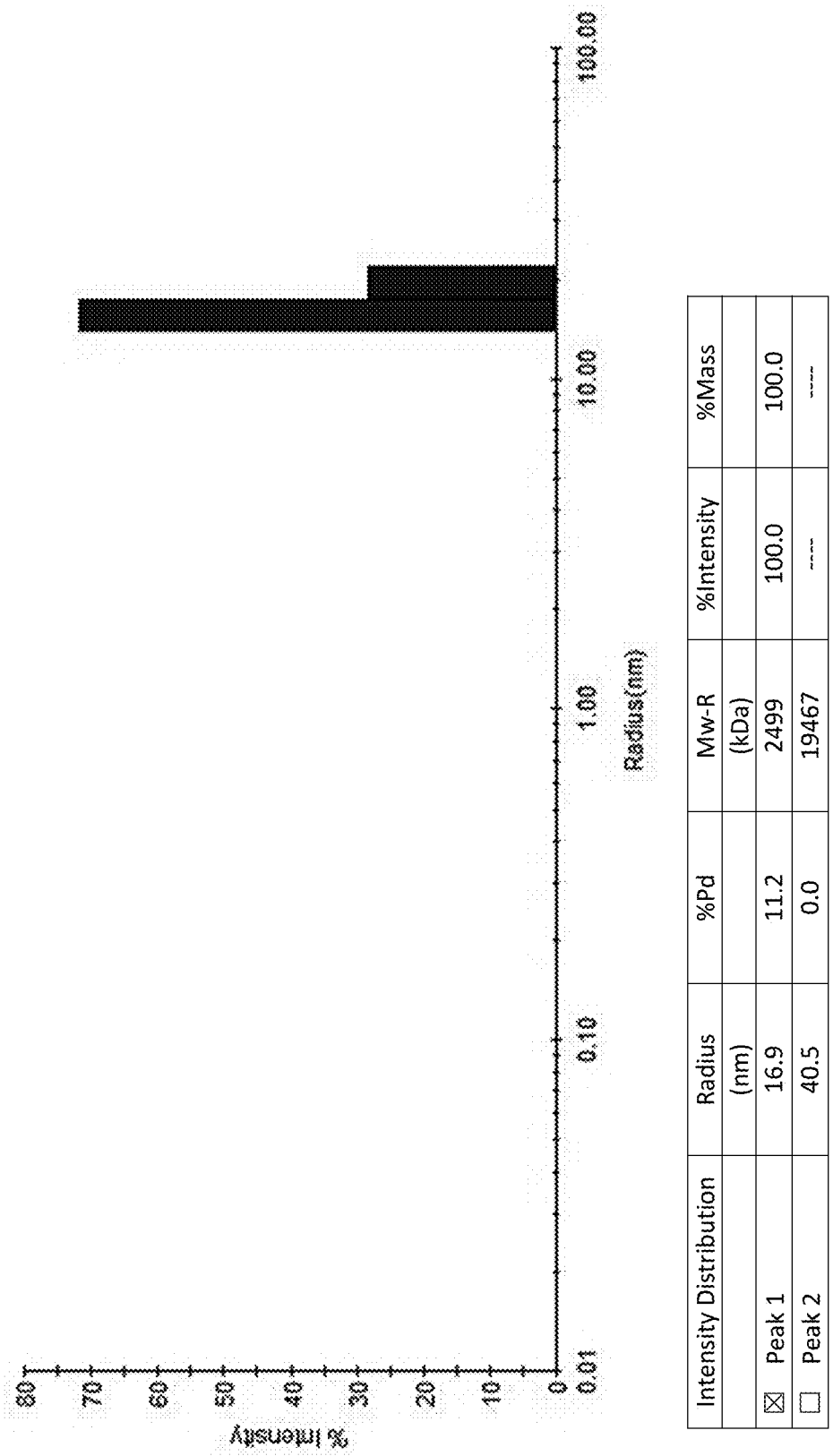

Bivalent immunization of ferrets was performed using compositions comprising single-chain gL/gH nanoparticles (gL_gH_C137A_bfpFerr Nanoparticle N19Q/C31S/S111C [SEQ ID NO: 22]) and gp220 nanoparticles (SEQ ID NO: 1) in the presence of adjuvant AF03 (FIGS. 30A-30B) or gL/gH/gp42 NP (SEQ ID NO: 227) and gp220 nanoparticles (SEQ ID NO: 1) in the presence of adjuvant AF03 (FIGS. 30C-30E). Inj. 1=injection one (sera collected from 6 ferrets at week 2 post Inj. 1). Inj. 2=injection 2 (sera collected from 6 ferrets at week 2 post Inj. 2). An ELISA binding assay measured endpoint binding titers against the antigens indicated in FIGS. 30A-30E. FIGS. 30F-G shows an EBV viral neutralizing assay (in B cells and epithelial cells, respectively) of sera from ferrets receiving bivalent vaccination of gL/gH/gp42 NP (SEQ ID NO: 227) and gp220 nanoparticles (SEQ ID NO: 1) in the presence of adjuvant AF03. Prime=Inj. 1 and Boost=Inj. 2.

gH/gL/gp42_NP_C12 (SEQ ID NO: 228) was expressed and purified using Superose 6 size exclusion chromatography (FIG. 31A). A dynamic light scattering analysis of the sample in FIG. 31A showed a particle size radius of 20.6 nm (FIG. 31B).

gH/gL/gp42_NP_C13 (SEQ ID NO: 229) was expressed and purified using Superose 6 size exclusion chromatography (FIG. 32A). A dynamic light scattering analysis of the sample in FIG. 32A showed a particle size radius of 17.1 nm (FIG. 32B).

gH/gL/gp42_NP_C14 (SEQ ID NO: 230) was expressed and purified using Superose 6 size exclusion chromatography (FIG. 33A). A dynamic light scattering analysis of the sample in FIG. 33A showed a particle size radius of 16.9 nm (FIG. 33B).

FIG. 35D shows the purification of SEQ ID NO: 227 after expression in 293Expi cells. A denaturing SDS coomassie gel shows the gH/gL/gp42 fused to ferritin to be above 150 kD with glycosylation. Negative stain electron microscopy analysis of the purified product shows the single-chain gH/gL/gp42 fused to ferritin can successfully form nanoparticles displaying the gH/gL/gp42 antigens on the surface (FIG. 35E). Through temperature, oxidation, and/or deamidation stress test on days 0, 3, 7, or 14, potential labile sequences have been identified via sequence analysis or mass spectrometry for the single-chain gH/gL/gp42 nanoparticle of SEQ ID NO: 227. To improve vaccine stability, expression, and/or immunogenicity of this vaccine construct, conservative amino acid substitution mutations will be made to SEQ ID NO: 227 in different combinations, particularly at the sites listed in Table 1. Conservative amino acid mutations at the respective location in the particular gene will also be tested in SEQ ID NOs: 228-230, which differ from SEQ ID NOs. 227 only by the linker sequence that fuses the C-terminus of gp42 with the N-terminus of the ferritin sequence.

We claim:

1. A polypeptide comprising an EBV gL polypeptide, an EBV gH polypeptide, an EBV gp42 polypeptide, and a ferritin, wherein a linker having a length of at least 40 amino acids and less than or equal to 50 amino acids separates the EBV gL polypeptide and the EBV gH polypeptide, and wherein the polypeptide comprises a sequence having at least 90% sequence identity to any one of SEQ ID NOs: 227-231, or to any one of SEQ ID NOs: 241-242 lacking the leader sequence.

2. A polypeptide comprising an EBV gL polypeptide, an EBV gH polypeptide, an EBV gp42 polypeptide, and a ferritin, wherein a linker having a length of 15 to 60 amino acids separates the EBV gH polypeptide and the EBV gp42 polypeptide, and wherein the polypeptide comprises a sequence having at least 90% sequence identity to any one of SEQ ID NOs: 227-231, or to any one of SEQ ID NOs: 241-242 lacking the leader sequence.

3. The polypeptide of claim 1, wherein a linker having a length of 15 to 60 amino acids separates the EBV gH polypeptide and the EBV gp42 polypeptide.

4. The polypeptide of claim 1, wherein the polypeptide comprises a sequence having at least 95% sequence identity to SEQ ID NO: 242 lacking the leader sequence.

5. The polypeptide of claim 1, wherein the polypeptide comprises a sequence having at least 98% sequence identity to SEQ ID NO: 242 lacking the leader sequence.

6. The polypeptide of claim 1, wherein the polypeptide comprises a sequence having at least 99% sequence identity to SEQ ID NO: 242 lacking the leader sequence.

7. The polypeptide of claim 1, wherein the polypeptide comprises the amino acid sequence of SEQ ID NO: 242 lacking the leader sequence.

8. The polypeptide of claim 1, wherein the polypeptide consists of the amino acid sequence of SEQ ID NO: 227 lacking the leader sequence.

9. The polypeptide of claim 1, wherein the EBV gL polypeptide comprises the amino acid sequence of amino acids 31-145 of SEQ ID NO: 242, the EBV gH polypeptide comprises the amino acid sequence of amino acids 192-853 of SEQ ID NO: 242, and the EBV gp42 polypeptide comprises the amino acid sequence of amino acids 886-1068 of SEQ ID NO: 242.

10. The polypeptide of claim 9, wherein the EBV gL polypeptide, the EBV gH polypeptide and the EBV gp42 polypeptide are in N- to C-terminal order within the polypeptide.

11. The polypeptide of claim 2, wherein a linker having a length of at least 40 amino acids and less than or equal to 50 amino acids separates the EBV gL polypeptide and the EBV gH polypeptide.

12. The polypeptide of claim 10, wherein a linker having a length of 46 or 47 amino acids separates the EBV gL polypeptide and the EBV gH polypeptide.

13. The polypeptide of claim 10, wherein a linker having a length of 15 to 60 amino acids separates the EBV gH polypeptide and the EBV gp42 polypeptide.

14. The polypeptide of claim 11, wherein a linker having a length of 30 to 50 amino acids separates the EBV gH polypeptide and the EBV gp42 polypeptide.

15. The polypeptide of claim 3, wherein (a) the linker that separates the EBV gL polypeptide and the EBV gH polypeptide, (b) the linker that separates the EBV gH polypeptide and the EBV gp42 polypeptide, or (c) the linker of (a) and the linker of (b) comprises one or more of glycine, asparagine, serine, and alanine.

16. The polypeptide of claim 13, wherein (a) the linker that separates the EBV gL polypeptide and the EBV gH polypeptide, (b) the linker that separates the EBV gH polypeptide and the EBV gp42 polypeptide, or (c) the linker of (a) and the linker of (b) comprises one or more of glycine, asparagine, serine, and alanine.

17. The polypeptide of claim 2, wherein the polypeptide comprises a sequence having at least 95% sequence identity to SEQ ID NO: 242 lacking the leader sequence.

18. The polypeptide of claim 2, wherein the polypeptide comprises a sequence having at least 98% sequence identity to SEQ ID NO: 242 lacking the leader sequence.

19. The polypeptide of claim 2, wherein the polypeptide comprises a sequence having at least 99% sequence identity to SEQ ID NO: 242 lacking the leader sequence.

20. A polypeptide comprising an EBV gL polypeptide, an EBV gH polypeptide, a linker having a length of 15 to 60 amino acids that separates the EBV gL polypeptide and the EBV gH polypeptide, an EBV gp42 polypeptide, a linker having a length of 15 to 60 amino acids that separates the EBV gH polypeptide and the EBV gp42 polypeptide, and a ferritin, wherein the EBV gL polypeptide has at least 95% sequence identity to the amino acid sequence of SEQ ID NO: 36, the EBV gH polypeptide has at least 95% sequence identity to the amino acid sequence of SEQ ID NO: 37, and the EBV gp42 polypeptide has at least 95% sequence identity to the amino acid sequence of SEQ ID NO: 239 or 240.

21. The polypeptide of claim 20, wherein the EBV gL polypeptide has at least 99% sequence identity to the amino acid sequence of SEQ ID NO: 36; the EBV gH polypeptide has at least 99% sequence identity to the amino acid sequence of SEQ ID NO: 37; the EBV gp42 polypeptide has at least 99% sequence identity to the amino acid sequence of SEQ ID NO: 239 or 240.

22. The polypeptide of claim 20, wherein the EBV gL polypeptide, the EBV gH polypeptide, and the EBV gp42 polypeptide are in N- to C-terminal order within the polypeptide.

23. The polypeptide of claim 22, wherein the linker that separates the EBV gL polypeptide and the EBV gH polypeptide has a length of 30 to 60 amino acids.

24. The polypeptide of claim 22, wherein the linker that separates the EBV gL polypeptide and the EBV gH polypeptide has a length of 40 to 50 amino acids.

25. The polypeptide of claim 23, wherein the linker that separates the EBV gH polypeptide and the EBV gp42 polypeptide has a length of 30 to 50 amino acids.

26. The polypeptide of claim 22, wherein the linker that separates the EBV gL polypeptide and the EBV gH polypeptide has the amino acid sequence of SEQ ID NO: 233 or 236; and the linker that separates the EBV gH polypeptide and the EBV gp42 polypeptide has the amino acid sequence of SEQ ID NO: 234.

27. The polypeptide of claim 23, wherein the linker that separates the EBV gL polypeptide and the EBV gH polypeptide has the amino acid sequence of SEQ ID NO: 233 or 236; and the linker that separates the EBV gH polypeptide and the EBV gp42 polypeptide has the amino acid sequence of SEQ ID NO: 234.

28. The polypeptide of claim 22, further comprising a linker that separates the EBV gp42 polypeptide and the ferritin, wherein the linker that separates the EBV gp42 polypeptide and the ferritin has at least 80% sequence identity to the amino acid sequence of SEQ ID NO: 235.

29. The polypeptide of claim 28, wherein the linker that separates the EBV gL polypeptide and the EBV gH polypeptide consists of an amino acid sequence that has at least 80% sequence identity to the amino acid sequence of any one of SEQ ID NOs: 222, 225, or 236; the linker that separates the EBV gH polypeptide and the EBV gp42 polypeptide consists of an amino acid sequence that has at least 80% sequence identity to the amino acid sequence of SEQ ID NO: 234; and the linker that separates the EBV gp42 polypeptide and the ferritin consists of an amino acid sequence that has at least 80% sequence identity to the amino acid sequence of SEQ ID NO: 235.

30. The polypeptide of claim 28, wherein the linker that separates the EBV gL polypeptide and the EBV gH polypeptide consists of an amino acid sequence that has at least 90% sequence identity to the amino acid sequence of SEQ ID NO: 233; the linker that separates the EBV gH polypeptide and the EBV gp42 polypeptide consists of an amino acid sequence that has at least 90% sequence identity to the amino acid sequence of SEQ ID NO: 234; and the linker that separates the EBV gp42 polypeptide and the ferritin consists of an amino acid sequence that has at least 90% sequence identity to the amino acid sequence of SEQ ID NO: 235.

31. The polypeptide of claim 28, wherein the linker that separates the EBV gL polypeptide and the EBV gH polypeptide consists of an amino acid sequence that has at least 95% sequence identity to the amino acid sequence of SEQ ID NO: 233; the linker that separates the EBV gH polypeptide and the EBV gp42 polypeptide consists of an amino acid sequence that has at least 95% sequence identity to the amino acid sequence of SEQ ID NO: 234; and the linker that separates the EBV gp42 polypeptide and the ferritin consists of an amino acid sequence that has at least 95% sequence identity to the amino acid sequence of SEQ ID NO: 235.

32. The polypeptide of claim 10, wherein the linker that separates the EBV gL polypeptide and the EBV gH polypeptide consists of an amino acid sequence that has at least 80% sequence identity to the amino acid sequence of any one of SEQ ID NOs: 222, 225, or 236; a linker that separates the EBV gH polypeptide and the EBV gp42 polypeptide consists of an amino acid sequence that has at least 80% sequence identity to the amino acid sequence of SEQ ID NO: 234; and a linker that separates the EBV gp42 polypeptide and the ferritin consists of an amino acid sequence that has at least 80% sequence identity to the amino acid sequence of SEQ ID NO: 235.

33. The polypeptide of claim 10, wherein the linker that separates the EBV gL polypeptide and the EBV gH polypeptide consists of an amino acid sequence that has at least 90% sequence identity to the amino acid sequence of SEQ ID NO: 233; a linker that separates the EBV gH polypeptide and the EBV gp42 polypeptide consists of an amino acid sequence that has at least 90% sequence identity to the amino acid sequence of SEQ ID NO: 234; and a linker that separates the EBV gp42 polypeptide and the ferritin consists of an amino acid sequence that has at least 90% sequence identity to the amino acid sequence of SEQ ID NO: 235.

34. The polypeptide of claim 10, wherein the linker that separates the EBV gL polypeptide and the EBV gH polypeptide consists of an amino acid sequence that has at least 95% sequence identity to the amino acid sequence of SEQ ID NO: 233; a linker that separates the EBV gH polypeptide and the EBV gp42 polypeptide consists of an amino acid sequence that has at least 95% sequence identity to the amino acid sequence of SEQ ID NO: 234; and a linker that separates the EBV gp42 polypeptide and the ferritin consists of an amino acid sequence that has at least 95% sequence identity to the amino acid sequence of SEQ ID NO: 235.

35. The polypeptide of claim 10, wherein the linker that separates the EBV gL polypeptide and the EBV gH polypeptide comprises the amino acid sequence of SEQ ID NO: 233; a linker that separates the EBV gH polypeptide and the EBV gp42 polypeptide comprises the amino acid sequence of SEQ ID NO: 234; and a linker that separates the EBV gp42 polypeptide and the ferritin comprises the amino acid sequence of SEQ ID NO: 235.

* * * * *